(12) United States Patent
Sun et al.

(10) Patent No.: US 8,999,917 B2
(45) Date of Patent: *Apr. 7, 2015

(54) VARIANT ACTIVIN RECEPTOR POLYPEPTIDES AND USES THEREOF

(71) Applicant: Amgen Inc., Thousand Oaks, CA (US)

(72) Inventors: Jeonghoon Sun, Thousan Oaks, CA (US); Lei-Ting Tony Tam, Thousand Oaks, CA (US); Huiquan Han, Thousand Oaks, CA (US); Keith Soo-Nyung Kwak, Thousand Oaks, CA (US); Xiaolan Zhou, Thousand Oaks, CA (US); John Lu, Culver City, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/932,421

(22) Filed: Jul. 1, 2013

(65) Prior Publication Data
US 2013/0288983 A1   Oct. 31, 2013

Related U.S. Application Data

(60) Continuation of application No. 13/329,897, filed on Dec. 19, 2011, now Pat. No. 8,501,678, which is a continuation-in-part of application No. 13/080,515, filed on Apr. 5, 2011, now Pat. No. 8,716,459, which is a division of application No. 12/074,877, filed on Mar. 5, 2008, now Pat. No. 7,947,646.

(60) Provisional application No. 61/065,474, filed on Feb. 11, 2008, provisional application No. 60/905,459, filed on Mar. 6, 2007.

(51) Int. Cl.
| | |
|---|---|
| *A61K 38/00* | (2006.01) |
| *A61P 35/00* | (2006.01) |
| *C07K 14/705* | (2006.01) |
| *C07K 14/71* | (2006.01) |
| *A61K 38/45* | (2006.01) |
| *A61K 31/513* | (2006.01) |
| *A61K 31/655* | (2006.01) |
| *A61K 38/17* | (2006.01) |
| *A61K 38/19* | (2006.01) |
| *A61K 38/20* | (2006.01) |
| *A61K 38/21* | (2006.01) |
| *A61K 38/50* | (2006.01) |

(52) U.S. Cl.
CPC .............. *C07K 14/705* (2013.01); *C07K 14/71* (2013.01); *A61K 38/45* (2013.01); *A61K 31/513* (2013.01); *A61K 31/655* (2013.01); *A61K 38/177* (2013.01); *A61K 38/179* (2013.01); *A61K 38/193* (2013.01); *A61K 38/2013* (2013.01); *A61K 38/212* (2013.01); *A61K 38/50* (2013.01); *C12Y 305/01001* (2013.01)

(58) Field of Classification Search
None
See application file for complete search history.

(56) References Cited

U.S. PATENT DOCUMENTS

| | | | |
|---|---|---|---|
| 3,773,919 | A | 11/1973 | Boswell et al. |
| 4,411,993 | A | 10/1983 | Gillis |
| 4,543,439 | A | 9/1985 | Frackelton, Jr. et al. |
| RE32,011 | E | 10/1985 | Zimmerman et al. |
| 4,816,567 | A | 3/1989 | Cabilly et al. |
| 4,902,614 | A | 2/1990 | Wakabayashi et al. |
| 5,567,584 | A | 10/1996 | Sledziewski et al. |
| 5,595,898 | A | 1/1997 | Robinson et al. |
| 5,693,493 | A | 12/1997 | Robinson et al. |
| 5,750,375 | A | 5/1998 | Sledziewski et al. |
| 5,827,733 | A | 10/1998 | Lee et al. |
| 5,863,738 | A | 1/1999 | Dijke et al. |
| 5,885,794 | A | 3/1999 | Mathews et al. |
| 5,994,618 | A | 11/1999 | Lee et al. |
| 6,096,506 | A | 8/2000 | Lee et al. |
| 6,162,896 | A | 12/2000 | Mathews |
| 6,300,129 | B1 | 10/2001 | Lonberg et al. |
| 6,465,239 | B1 | 10/2002 | Lee et al. |
| 6,468,535 | B1 | 10/2002 | Lee et al. |
| 6,472,179 | B2 | 10/2002 | Stahl et al. |
| 6,500,664 | B1 | 12/2002 | Lee et al. |
| 6,599,876 | B2 | 7/2003 | Kojima |
| 6,607,884 | B1 | 8/2003 | Lee et al. |
| 6,656,475 | B1 | 12/2003 | Lee et al. |
| 6,812,339 | B1 | 11/2004 | Venter et al. |
| 6,858,208 | B2 | 2/2005 | Lee et al. |
| 6,891,082 | B2 | 5/2005 | Lee et al. |

(Continued)

FOREIGN PATENT DOCUMENTS

| | | |
|---|---|---|
| CA | 1219215 | 3/1987 |
| EP | 0036676 | 9/1981 |

(Continued)

OTHER PUBLICATIONS

Office Action for U.S. Appl. No. 13/080,515, mailed on Sep. 26, 2013, 5 Pages.

(Continued)

*Primary Examiner* — Gyan Chandra
(74) *Attorney, Agent, or Firm* — Fenwick & West LLP

(57) ABSTRACT

The present invention provides variant activin IIB soluble receptor polypeptides and proteins capable of binding and inhibiting the activities of activin A, myostatin, or GDF-11. The present invention also provides polynucleotides, vectors and host cells capable of producing the variant polypeptides and proteins. Compositions and methods for treating muscle-wasting and other diseases and disorders are also provided.

19 Claims, 13 Drawing Sheets

(56) References Cited

U.S. PATENT DOCUMENTS

| | | |
|---|---|---|
| 7,166,707 B2 | 1/2007 | Feige |
| 7,189,827 B2 | 3/2007 | Feige |
| 7,399,848 B2 | 7/2008 | Lee et al. |
| 7,442,778 B2 | 10/2008 | Gegg et al. |
| 7,511,012 B2 | 3/2009 | Han et al. |
| 7,534,432 B2 | 5/2009 | Lee et al. |
| 7,645,861 B2 | 1/2010 | Gegg et al. |
| 7,655,764 B2 | 2/2010 | Gegg et al. |
| 7,655,765 B2 | 2/2010 | Gegg et al. |
| 7,662,931 B2 | 2/2010 | Gegg et al. |
| 7,709,605 B2 | 5/2010 | Knopf et al. |
| 7,736,653 B2 | 6/2010 | Kim et al. |
| 7,737,260 B2 | 6/2010 | Kim et al. |
| 7,750,127 B2 | 7/2010 | Gegg et al. |
| 7,750,128 B2 | 7/2010 | Gegg et al. |
| 7,803,923 B2 | 9/2010 | Han et al. |
| 7,842,663 B2 | 11/2010 | Knopf et al. |
| 7,928,075 B2 | 4/2011 | Han et al. |
| 7,947,646 B2 | 5/2011 | Sun et al. |
| 8,058,229 B2 | 11/2011 | Seehra et al. |
| 8,067,562 B2 | 11/2011 | Han et al. |
| 8,071,538 B2 | 12/2011 | Han et al. |
| 8,110,665 B2 | 2/2012 | Kim et al. |
| 8,124,094 B2 | 2/2012 | Kim et al. |
| 8,138,142 B2 | 3/2012 | Seehra et al. |
| 8,178,488 B2 | 5/2012 | Knopf et al. |
| 8,216,997 B2 | 7/2012 | Seehra et al. |
| 8,252,900 B2 | 8/2012 | Knopf |
| 8,343,933 B2 | 1/2013 | Knopf |
| 8,361,957 B2 | 1/2013 | Seehra |
| 2004/0223966 A1 | 11/2004 | Wolfman et al. |
| 2005/0186593 A1 | 8/2005 | Mathews et al. |
| 2006/0034831 A1 | 2/2006 | Tobin |
| 2006/0068468 A1 | 3/2006 | Knopf et al. |
| 2007/0117130 A1 | 5/2007 | Han et al. |
| 2008/0089897 A1 | 4/2008 | Wolfman et al. |
| 2009/0005308 A1 | 1/2009 | Knopf et al. |
| 2009/0087433 A1 | 4/2009 | Wolfman et al. |
| 2009/0118188 A1 | 5/2009 | Knopf et al. |
| 2009/0227497 A1 | 9/2009 | Sun et al. |
| 2011/0034372 A1 | 2/2011 | Lee et al. |
| 2011/0183897 A1 | 7/2011 | Sun et al. |
| 2011/0243933 A1 | 10/2011 | Poradosu et al. |
| 2011/0281796 A1 | 11/2011 | Han et al. |
| 2012/0148588 A1 | 6/2012 | Knopf |
| 2012/0156204 A1 | 6/2012 | Seehra |
| 2012/0295814 A1 | 11/2012 | Cramer et al. |
| 2012/0328595 A1 | 12/2012 | Sun et al. |
| 2013/0030159 A1 | 1/2013 | Han et al. |
| 2013/0071393 A1 | 3/2013 | Seehra |

FOREIGN PATENT DOCUMENTS

| | | |
|---|---|---|
| EP | 0058481 | 8/1982 |
| EP | 0088046 | 9/1983 |
| EP | 0133988 | 3/1985 |
| EP | 0143949 | 6/1985 |
| JP | 2006-516886 | 7/2006 |
| JP | 2009-513162 | 4/2009 |
| JP | 2009513162 A | 4/2009 |
| JP | 2010-519931 | 6/2010 |
| JP | 2010519931 A | 6/2010 |
| WO | WO 93/15722 | 8/1993 |
| WO | WO 94/09817 | 5/1994 |
| WO | WO 94/10332 | 5/1994 |
| WO | WO 94/20069 | 9/1994 |
| WO | WO 99/38890 | 8/1999 |
| WO | WO 00/29581 | 5/2000 |
| WO | WO 00/43781 | 7/2000 |
| WO | WO 00/43781 A3 | 7/2000 |
| WO | WO 2004/039948 A2 | 5/2004 |
| WO | WO 2004/039948 A3 | 5/2004 |
| WO | WO 2006/012627 A2 | 2/2006 |
| WO | WO 2006/020884 A2 | 2/2006 |
| WO | WO 2006/020884 A3 | 2/2006 |
| WO | WO 2007/053775 A1 | 5/2007 |
| WO | WO 2008/097541 A2 | 8/2008 |
| WO | WO 2008/109167 A2 | 9/2008 |
| WO | WO 2008/113185 | 9/2008 |
| WO | WO 2010/019261 A1 | 2/2010 |
| WO | WO 2010/062383 A2 | 6/2010 |

OTHER PUBLICATIONS

Office Action for Korean Patent Application No. 2012-7008467, mailed Oct. 18, 2013, 4 Pages.
Office Action for Taiwanese Patent Application No. 097107642 mailed on Feb. 17, 2014, 3 Pages.
Office Action for Chinese Patent Application No. CN 200880007116.0, Feb. 22, 2013, 13 Pages.
Communication Pursuant to Article 94(3) EPC for European Patent Application No. EP 08742032.9, Apr. 18, 2013, 4 pages.
Office Action for Canadian Patent Application No. 2,679,841, Apr. 8, 2013, 2 Pages.
Notice of Preliminary Rejection Office Action Summary for Korean Patent Application No. 2012-7008467, Apr. 18, 2013, 3 pages.
Office Action for Egypt Patent Application No. PCT13142009, May 1, 2013, 11 Pages.
Office Action for Philippine Patent Application No. 1-2009-501698, Jul. 10, 2013, 2 Pages.
Final Rejection Office Action for Japanese Patent Application No. 2009-552758, Aug. 1, 2013, 5 Pages.
Geisse, S., et al., "Eukaryotic Expression Systems: A Comparison," Protein Expression and Purification, Nov. 1996, pp. 271-282, vol. 8, Is. 3, Academic Press, Inc.
Examination Report for Malaysia Patent Application No. Pl20093636, Dec. 31, 2013, 3 Pages.
Office Action for Japanese Patent Application No. JP 2009-552758, Feb. 20, 2013, 2 Pages.
International Search Report and Written Opinion for PCT/US2012/070571, Mar. 19, 2013, 12 Pages.
Search Report for Gulf Cooperation Council Application No. GCC/P/2008/10291, Aug. 10, 2011, 11 Pages.
Examination Report for Gulf Cooperation Council Application No. GCC/P/2008/10291, Sep. 7, 2012, 6 Pages.
First Office Action for Eurasian Patent Application No. EA 2009708/28, Sep. 15, 2011, 2 Pages.
Second Office Action for Eurasian Patent Application No. EA 200970810/28, Nov. 21, 2012, 2 Pages.
Decision on Examination for Taiwan Patent Application No. TW 097107642, Aug. 29, 2012, 4 Pages.
Office Action issued by Intellectual Property Office of the Philippines, Patent Application No. 1-2009-501698, Oct. 25, 2012, 2 Pages.
Notice of Final Rejection for Korean Patent Application No. KR 2009-7020320, Sep. 4, 2012, 2 Pages.
PCT Written Opinion for PCT/US2008/003119, Sep. 6, 2009, 10 Pages.
PCT Search Report and Written Opinion for PCT/US2008/003119, Sep. 6, 2009, 16 Pages.
Attisano et al., "Novel Activin Receptors: Distinct Genes and Alternative mRNA Splicing Generate a Repertoire of Serine/Threonine Kinase Receptors," *Cell* 68:97-108, Jan. 1992.
Bowie et al. "Deciphering the Message in Protein Sequences: Tolerance to Amino Acid Substitutions," Science, 247:1306-1310, 1990.
Database Geneseq Accession No. AAW86245, Feb. 16, 1999, "Mouse ActRIIB4 receptor protein."
Database EMBL Accession No. AY421275, Dec. 13, 2003, "*Homo sapiens* ACVR2B gene, Virtual Transcript, partial sequence, genomic survey sequence."
Database Geneseq Accession No. AD043580, Jul. 29, 2004, "Amino acid sequence of ActRIIB."
Donaldson et al., "Activin and Inhibin Binding to the Soluble Extracellular Domain of Activin Receptor II," *Endocrinoloqv* 140(4):1760-1766, 1999.

(56) References Cited

OTHER PUBLICATIONS

Gray et al., "Identification of a Binding Site on the Type II Activin Receptor for Activin and Inhibin," J. Biol. Chem. 275(5):3206-3212, 2000.
Harrison et al., "An Activin Mutant with Disrupted ALK4 Binding Blocks Signaling via Type II Receptors," J. Biol. Chem. 279(27):28036-28044, 2004.
Harrison et al., "Antagonists of activin signaling: mechanisms and potential biological applications," TRENDS in Endocrinoloqy and Metabolism 16(2):73-78, Mar. 2005.
Hilden et al., "Expression of Type II Activin Receptor Genes During Differentiation of Human K562 Cells and cDNA Cloninq of the Human Type IIB Activin Receptor," Blood 83(8):2163-2170, Apr. 1994.
Lee, S. and McPherron, A.C., "Regulation of myostatin activity and muscle growth," Proc. Natl. Acad. Sci. USA 98(16):9306-9311, Jul. 2001.
Lee et al., "Regulation of muscle growth by multiple ligands signaling through activin type II receptors," Proc. Natl. Acad. Sci. USA 102(50):18117-18122, Dec. 2005.
Oh et al., "Activin type IIA and IIB receptors mediate Gdf11 signaling in axial vertebral patterning," Genes & Development 16:2749-2754, 2002.
Thompson et al., "Structures of an ActRIIB:activin A complex reveal a novel binding mode for TGF-~liqand:receptor interactions," The EMBO Journal 22(7): 1555-1566, 2003.
Tobin, J.F., and Celeste, A.J., "Myostatin, a negative regulator of muscle mass: implications for muscle deqenerative diseases," Current Opinion in Pharmacoloqy, Elsevier Science Publishers 5(3):328-332, 2005.
Wells, "Aditivity of Mutational Effects in Proteins," Biochemistry, 29:8509-8517, 1990.
Office Action for U.S. Appl. No. 13/080,515, May 17, 2012, 7 Pages.
Office Action for U.S. Appl. No. 13/080,515, Sep. 15, 2011, 10 Pages.
Office Action for U.S. Appl. No. 13/074,877, Feb. 1, 2013, 12 Pages.
Office Action for Canadian Patent Application No. CA 2,743,850, Oct. 24, 2013, 2 Pages.
Office Action for Mexico Patent Application No. MX/a/2011/005505, May 28, 2013, 9 Pages.
Office Action for Columbian Patent Application No. CO 11-79058-8, Jun. 17, 2013, 11 Pages.
Office Action for Colombian Patent Application No. 11-79058-5, Nov. 15, 2012, 15 Pages.
First Office Action for Chinese Patent Application No. 200980147945.3, Mar. 21, 2013, 13 Pages.
Second Office Action for Chinese Patent Application No. 200980147945.3, Nov. 29, 2013, 9 Pages.
Patent Examination Report No. 2 for Australian Patent Application No. 2011237541, mailed Oct. 22, 2012, 2 pages.
Patent Examination Report No. 1 for Australian Patent Application No. 2011237541, mailed Aug. 10, 2012, 3 pages.
Notification of Reasons for Rejection for Japanese Patent Application No. JP 2008-539077, Feb. 2, 2012, 3 Pages.
Notification of Reasons for Rejection for Japanese Patent Application No. JP 2008-539077, Dec. 19, 2012, 5 Pages.
Communication Pursuant to Article 94(3) EPC for European Patent Application No. EP 06827481.0, May 30, 2011, 3 pages.
Communication Pursuant to Article 94(3) EPC for European Patent Application No. EP 06827481.0, Jul. 20, 2010, 2 pages.
Communication Pursuant to Article 94(3) EPC for European Patent Application No. EP 06827481.0, Sep. 9, 2008, 2 pages.
PCT Written Opinion for PCT/US2006/043044, Mar. 15, 2007, 6 Pages.
International Search Report, PCT/US2006/043044, mailed Mar. 15, 2007, 4 Pages.
Examiner's First Report for Canadian Patent Application No. CA 2,627,200, Jun. 7, 2010, 3 pages.
Examiner's Second Report for Canadian Patent Application No. CA 2,627,200, Nov. 2, 2011, 2 pages.
Examiner's Third Report for Canadian Patent Application No. CA 2,627,200, May 28, 2012, 1 page.
Office Action for Eurasian Patent Application No. 201100832/28 Mailed on Feb. 27, 2014, 3 Pages.
Office Action for Japanese Patent Application No. 2012-171705 Mailed on Apr. 2, 2014, 8 Pages.
Office Action for New Zealand Patent Application No. 604818 Mailed on Apr. 2, 2014, 2 Pages.
Office Action for Colombian Patent Application No. 1239-2011 Mailed on Jun. 18, 2013, 34 Pages.
Office Action for Japanese Patent Application No. 2011-538599 Mailed Apr. 17, 2014, 6 Pages.
First Examination Report for New Zealand Patent Application No. 604818, Jan. 8, 2013, 2 Pages.
Office Action for Ukrainian Patent Application No. a 2011 07872, Oct. 25, 2012, 4 Pages.
Office Action for Taiwan Patent Application No. 098140431, Apr. 25, 2013, 3 Pages.
Communication pursuant to Article 94(3) EPC for European Patent Application No. EP 09761055.4, Sep. 13, 2013, 2 Pages.
Office Action for Canadian Patent Application No. CA 2,743,850, Sep. 5, 2012, 4 pages.
Invitation to Response to Written Opinion, Singapore Patent Application No. 201103777-7, Aug. 1, 2012, 5 pages.
Examination Report From the Intellectual Property Office for Taiwan Patent Application No. 098140431, Jun. 18, 2012, 11 pages.
Examiner's first report on Australian Patent Application No. AU 2009320364, Nov. 30, 2011, 2 pages.
PCT International Search Report and Written Opinion, PCT/US2009/006252, Jun. 17, 2010, 15 pages.
Opposition by AG Pharmaceutical Laboratories Industrial Association against Amgen Patent Application No. 1239-2011 in Chile, papers stamped by the Institution Nacional de Propiedad Industrial on Nov. 17, 2011 (Spanish with English translation), 15 Pages.
Akerstrom, B et al., "Protein G: A Powerful Tool for Binding and Detection of Monoclonal and Polyclonal Antibodies," Journal of Immunology, 135(4):2589-2592, 1985.
Attisano, L., et al., "Activation of Signalling by the Activin Receptor Complex," Molecular and Cellular Biology, Mar. 1996, p. 1066-1073, vol. 16. No. 3.
Barany, et al., "Solid-phase peptide synthesis," Ch. 1, The Peptides: Analysis, Synthesis, Biology, vol. 2, Gross and Meienhofer, eds., (Academic Press, New York, 1980), pp. 1-284.
Barany, et al., "Solid-phase peptide syntheses: a silver anniversary report," Int. J. Peptide Protein Res., 30:705-739, 1987.
Bogdanovish, S., et al., "Myostatin blockade improves function but not histopathology in a murine model of limb-girdle muscular dystrophy 2C," Muscle Nerve, Mar. 2008, pp. 308-316, vol. 37, No. 3.
Campbell, K., et al., "Totipotency of Multipotentiality of Cultured Cells: Applications and Progress," Theriogenology, Jan. 1, 1997, vol. 47, Issue 1, pp. 63-72.
Chaubert, et al., "Simultaneous Double Immunoenzymatic Labeling: A New Procedure for the Histopathologic Routine," Modern Pathology, 10(6):585-591, 1997.
Cipriano, S., et al., "Follistatin Is a Modulator of Gonadal Tumor Progression and the Activin-Induced Wasting Syndrome in Inhibin-Deficient Mice," Endocrinology, 2000, vol. 141, No. 7, pp. 2319-2327.
Coerver, K., et al., "Activin Signaling through Activin Receptor Type II Causes the Cachexia-Like Symptions in Inhibin-Deficient Mice," Molecular Endocrinology, 1996, vol. 10, No. 5, pp. 534-543.
Eppstein, et al., "Biological activity of liposome-encapsulated murine interferon .gamma. is mediated by a cell membrane receptor," Proc. Natl. Acad. Sci. USA, 82:3688-3692, 1985.
Ethier, J-F., et al., "Bovine Activin Receptor Type IIB Messenger Ribonucleic Acid Displays Alternative Splicing Involving a Sequence Homologous to Src-Homology 3 domain Binding Sites," Endocrinology, Jun. 1997, vol. 138, No. 6, p. 2425-2434.
Dennler, et al., "Direct binding of Smad3 and Smad4 to critical TGF.beta.-inducible elements in the promoter of human plasminogen activator inhibitor-type 1 gene," The EMBO Journal, 17(11):3091-3100, 1998.

(56) References Cited

OTHER PUBLICATIONS

Derynck, R., et al., "Smads: Transcriptional Activators of TGF-β Responses," Cell, Dec. 11, 1998, vol. 95, pp. 737-740.

Durocher, et al., "High-level and high-throughput recombinant protein production by transient transfection of suspension-growing human 293-EBNA1 cells," Nucleic Acids Research, 30(2e9) 2002, 9 Pages.

Gamer, L., et al., "A Novel BMP Expressed in Developing Mouse Limb, Spinal Cord, and Tail Bud Is a Potent Mesoderm Inducer in Xenopus Embryos," Developmental Biology, 1999, vol. 208, No. 1, pp. 222-232.

Gibbs, R., et al., "Evolutionary and Biomedical Insights from the Rhesus Macaque Genome," Science, Apr. 13, 2007, pp. 222-234, vol. 316.

Gluzman, et al., "SV40-Transformed Simian Cells Support the Replication of Early SV40 Mutants," Cell, 23:175-182, 1981.

Gonzalez-Cadavid, N., et al., "Organization of the human myostatin gene and expression in healthy men and HIV-infected men with muscle wasting," PNAS USA, 1998, vol. 95, pp. 14938-14943.

Hamrick, M., et al., "Bone Mineral Content and Density in the Humerus of Adult Myostatin-Deficient Mice," Calcif Tissue Int, 2002, vol. 71, No. 1, pp. 63-68.

Holzbaur, E.L., et al., Myostatin inhibition slows muscle atrophy in rodent models of amyotrophic lateral sclerosis, Neurobiology of Disease, 2006, pp. 697-707, vol. 23.

Ito, et al., "Presence of activin signal transduction in normal ovarian cells and epithelial ovarian carcinoma," British Journal of Cancer, 82(8):1415-1420, 2000.

Kaufman, R., et al., "Transgenic Analysis of a 100-kb Human β-Globin Cluster-Containing DNA Fragment Propagated as a Bacterial Artificial Chromosome," Blood, Nov. 1, 1999, vol. 94, No. 9, pp. 3178-3184.

Kinglsey, D., et al., "The TGF-β superfamily: new members, new receptors, and new genetic tests of function in different organisms," Genes Dev., 1994, vol. 8, pp. 133-146.

Kostelny, et al., "Formation of a Bispecific Antibody by the Use of Leucine Zippers," Journal of Immunology, 148(5):1547-1553, 1992.

Lambert-Messerlian, et al., "Secretion of Activin a in Recurrent Epithelial Ovarian Carcinoma," Gynecologic Oncology, 74:93-97, 1999.

Lalani, R., et al., "Myostatin and insulin-like growth factor-I and -II expression in the muscle of rafts exposed to the microgravity environment of the NeuroLab space shuttle flight," Journal of Endocrinology, 2000, vol. 167, pp. 417-428.

Lang, C., et al., "Regulation of myostatin by glucocorticoids after thermal injury," FASEB, 2001, vol. 1, No. 15, pp. 1807-1809.

Langer, R., et al., "Biocompatibility of polymeric delivery systems for macromolecules," J. of Biomedical Materials Research, 15:267-277, 1981.

Langer, R., "Controlled release of macromolecules," ChemTech, 12:98-105, 1982.

Ling, N., et al., "Pituitary FSH is released by a heterodimer of the β-subunits from the two forms of inhibin," Nature, 1986, vol. 321, pp. 779-782.

Longfellow, C., et al., "Thermodynamic and Spectroscopic Study of Bulge Loops in Oligoribonucleotides," Biochemistry, 1990, vol. 29, pp. 278-285.

Macias-Silva, et al., "MADR2 Is a Substrate of the TGF.beta. Receptor and Its Phosphorylation Is Required for Nuclear Accumulation and Signaling," Cell, 87:1215-1224, 1996.

Mason, A., et al., "Complementary DNA sequences of ovarian follicular fluid inhibin show precursor structure and homology with transforming growth factor-β," Nature, Dec. 1985, pp. 659-663, vol. 318.

Massague, J., "How Cells Read TGF-β Signals," Nature Rev: Molecular Cell Biology, 2000, pp. 169-178, vol. 1.

Mathews, L.S., "Activin Receptors and Cellular Signaling by the Receptor Serine Kinase Family," Endocrine Review, 1994, vol. 15, pp. 310-325.

McMahan, et al., "A novel IL-1 receptor, cloned from B cells by mammalian expression, is expressed in many cell types," The EMBO Journal, 10(10):2821-2832, 1991.

McPherron, A., et al., "Double muscling in cattle due to mutations in the myostatin gene," PNAS USA 1997, vol. 94, pp. 12457-12461.

McPherron, A., et al., "Regulation of anterior/posterior patterning of the axial skeleton by growth/differentiation factor 11," Natr Genet, 1999, vol. 22, No. 93, pp. 260-264.

McPherron, A., et al., "Regulation of skeletal muscle mass in mice by a new TGF-β superfamily member," Nature (London), May 1997, vol. 387, pp. 83-90.

Mendez, et al., "Functional transplant of megabase human immunoglobulin loci recapitulates human antibody response in mice," Nature Genetics 15:146-156, 1997.

Merrifield, B., "Solid Phase Synthesis," Science, 232:341-347, 1986.

Mikaelian, et al., "Modification of the Overlap Extension Method for Extensive Mutagenesis on the Same Template," Methods in Molecular Biology, 57:193-202, 1996.

NCBI, "myostatin [*Homo sapiens*]," GenBank Accession No. AAB86694, Nov. 20, 1997, 1 page, [online] [retrieved on Mar. 20, 2013] Retrieved from the internet <URL: http://www.ncbi.nlm.nih.gov/protein/aab86694>.

NCBI, "*Homo sapiens* inhibin, beta A (INHBA), mRNA," GenBank Accession No. NM_002192, Mar. 10, 2013, 4 pages [online] [retrieved on Mar. 20, 2013] Retrieved from the internet <URL:http://www.ncbi.nlm.nih.gov/nuccore/nm_002192>.

NCBI, "activin receptor type-2B precursor [*Homo sapiens*]," GenBank accession No. NP 001097, 3 pages, [online] [retrieved on Mar. 20, 2013] Retrieved from the internet <URL:http://www.ncbi.nlm.nih.gov/protein/np_001097>.

EBI, Swissprot Accession No. O95390, GDFII.sub.-Human, Growth/differentiation factor 11, 2 pages., [online] [retrieved on Sep. 9, 2010] Retrieved from the internet <URL:http://www.ebi.ac.uk/uniprot/unisave/?help=0&session=/ebi/exterv/-old-work/SESSION14...>.

Ngo, J.T., et al., "Computational Complexity, Protein Structure Prediction, and the Levinthal Paradox," The Protein Folding Problem and Tertiary Structure Prediction, pp. 492-495, 1994.

Oh, S., et al., "The signaling pathway mediated by the type IIB activin receptor controls axial patterning and lateral asymmetry in the mouse," Genes Dev, 1997, vol. 11, pp. 1812-1826.

Phillips, A., "The challenge of gene therapy and DNA delivery," Journal of Pharmacy and Pharmacology, Mar. 6, 2001, vol. 53, pp. 1169-1174.

Rasmussen, et al., "Isolation, characterization and recombinant protein expression in Veggie-CHO: A serum-free CHO host cell line," Cytotechnology, 28:31-42, 1998.

Rosenzweig, B., et al., "Cloning and characterization of a human type II receptor for bone morphogenetic proteins," Proc. Natl. Acad. Sci., Aug. 1995, vol. 92, pp. 7632-7636.

Sharma, M., et al., "Myostatin, a Transforming Growth Factor-β Superfamily Member, Is Expressed in Heart Muscle and Is Upregulated in Cardiomyocytes After Infarct," Journal of Cell Physiology, 1999, vol. 180, No. 1, pp. 1-9.

Shou, W., et al., "Role of Androgens in Testicular Tumor Development in Inhibin-Deficient Mice," Endocrinology, 1997, vol. 138 No. 11 pp. 5000-5005.

Sidman, et al., "Controlled Release of Macromolecules and Pharmaceuticals from Synthetic Polypeptides Based on Glutamic Acid," Biopolymers, 22:547-556, 1983.

Songsivilai, et al., "Bispecific antibody: a tool for diagnosis and treatment of disease," Clin. Exp. Immunology, 79:315-321, 1990.

Tam, et al., "S.sub.N2 Deprotection of Synthetic Peptides with a Low Concentration of HF in Dimethyl Sulfide: Evidence and Application in Peptide Synthesis," J. American Chemical Society, 105:6442-6455, 1983.

Urlaub, et al., "Isolation of Chinese hamster cell mutants deficient in dihydrofolate reductase activity," Proc. Natl. Acad. Sci. USA, 77(7):4216-4220, 1980.

Vale, W., et al., "Purification and characterization of an FSH releasing protein from porcine ovarian follicular fluid," Nature, Jun. 1986, vol. 321, 776-779.

(56) References Cited

OTHER PUBLICATIONS

Wang, A., et al., "Rapid analysis of gene expression (RAGE) facilitates universal expression profiling," Nucl. Acids Res., 1999, vol. 27, pp. 4609-4618.
Wigley, P., et al., "Site-specific Transgene Insertion: an Approach" Reprod Fertil. Dev., 1994, vol. 6, pp. 585-588.
Yarasheski, K.E., et al., "Serum myostatin-immunoreactive protein is increased in 60-92 year old women and men with muscle wasting," Journal of Nutrition, Health and Aging, 2002, vol. 6, No. 5, pp. 343-348.
Yen, et al., "Obesity, diabetes, and neoplasia in yellow A.sup.vy/-mice: ectopic expression of the agouti gene," FASEBJ. 8:479-488, 1994.
Zachwieja, J., et al., "Plasma myostatin-immunoreactive protein is increased after prolonged bed rest with low-dose $T_3$ Administration," Journal of Gravitational Physiology, Oct. 1999, vol. 6 No. 2, pp. 11-15.
Zimmers, T., et al., "Induction of Cachexia in Mice by Systemically Administered Myostatin," Science, 2002, vol. 296, pp. 1486-1488.
Office Action for Canadian Patent Application No. CA 2,679,841, Apr. 28, 2014, 2 Pages.
Communication pursuant to Article 94(3) EPC for European Patent Application No. EP 09761055.4, Apr. 28, 2014, 3 Pages.
Office Action for Israeli Patent Application No. 200605, Aug. 7, 2014, 4 Pages.
Office Action for Costa Rica Patent Application No. 11054, Sep. 24, 2014, 9 Pages.
Berrondo, M., "Predicting the structure and function of protein mutants," A Dissertation submitted to Johns Hopkins University in conformity with the requirements for the degree of Doctor of Philosophy Baltimore, Maryland, Jan. 2010, 176 Pages, Can be retrieved at <URL:http://graylab.jhu.edu/publications/dissertations/Berrondo2010.pdf>.
Office Action for Chilean Patent Application No. 1239-2011, Apr. 22, 2014, 75 Pages.
Office Action for Columbian Patent Application No. 11.079.058, May 14, 2014, 12 Pages.
Office Action for Mexican Patent Application No. MX/a/2012/008808, May 2, 2014, 10 Pages.
Office Action for Mexican Patent Application No. MX/a/2012/014888, Jun. 27, 2014, 4 Pages.
Office Action for Peru Patent Application No. 000436.2008, May 21, 2014, 58 Pages.
Office Action for U.S. Appl. No. 13/775,756, Aug. 25, 2014, 9 Pages.
First Examination Report for New Zealand Patent Application No. 627111, Jul. 24, 2014, 1 page.
PCT International Search Report and Written Opinion for PCT/US2014/014490, Jun. 27, 2014, 20 Pages.
Robertson, D.M., et al., "Inhibin/activin and ovarian cancer," Endocrine-Related Cancer, 2004, pp. 35-49, vol. 11.
Tournier, I., et al., "Germline Mutations of Inhibins in Early-Onset Ovarian Epithelial Tumors," Human Mutation, Dec. 2, 2013, pp. 294-297, vol. 35, No. 3.
Wildi, S., et al., Overexpression of activin A in stage IV colorectal cancer, GUT, 2001, pp. 409-417, vol. 49.
Alibhai, SMH, et al., "Long-term side effects of androgen deprivation therapy in men with non-metastatic prostate cancer: a systematic literature review," Crit Rev Oncol/Hematol. 2006, vol. 60, pp. 201-215.
Augustin, H.G., et al., "Control of vascular morphogenesis and homeostasis through the angiopoietin-Tie system," Nature Reviews Molecular Cell Biology, 2009, vol. 10, pp. 165-177.
Chang, K.P., et al., "Overexpression of activin A in oral squamous cell carcinoma: association with poor prognosis and tumor progression," Ann Surg Oncol. 2010, vol. 17, pp. 1945-1956.
Choi, J.-H., et al., "Gonadotropins and ovarian cancer," Endocrine Reviews, 2007, vol. 28, pp. 440-461.
Cobellis, L., et al. "High concentrations of activin A in the peritoneal fluid of women with epithelial ovarian cancer," J Soc Gynecol Investig. 2004, vol. 11, pp. 203-206.

de Kretser DM, et al., "Activin A and follistatin: their role in the acute phase reaction and inflammation," Journal of Endocrinology. 1999, vol. 161, pp. 195-198.
Do TV, "The role of activin A and Akt/GSK signaling in ovarian tumor biology," Endocrinology. 2008, vol. 149, pp. 3809-3816.
Dvorak, H.F., et al., "Tumor microenvironment and progression," Journal of Surgical Oncology, 2011, vol. 103, pp. 468-474.
Ellis, L.M., et al., "VEGF-targeted therapy: mechanisms of antitumour activity," Nature Reviews Cancer, 2008, vol. 8, pp. 579-591.
Gabizon A, et al., "Polyethylene glycol-coated (pegylated) liposomal doxorubicin: rationale for use in solid tumours," Drugs. 1997, vol. 54 (suppl 4), pp. 15-21.
Harada K, et al., "Serum immunoreactive activin A levels in normal subjects and patients with various diseases," J Clin Endocrinol Metab. 1996, vol. 81, pp. 2125-2130.
Hubner G, et al., "Activin: a novel player in tissue repair processes," Histology & Histopathology. 1999, vol. 14, pp. 295-304.
Jones KL, et al., "Activin A and follistatin in systemic inflammation," Molecular & Cellular Endocrinology. 2004, vol. 225, pp. 119-125.
Konishi, I. "Gonadotropins and ovarian carcinogenesis: a new era of basic research and its clinical implications," Int J Gynecol Cancer, 2006, vol. 16, pp. 16-22.
Kwak, K.S., et al., "Regulation of protein catabolism by muscle-specific and cytokine-inducible ubiquitin ligase E3alpha-II during cancer cachexia," Cancer Res, 2004, vol. 64, pp. 8193-8198.
Lambert-Messerlian GM, et al., "Secretion of activin A in recurrent epithelial ovarian carcinoma," Gynecol Oncol. 1999, vol. 74, pp. 93-97.
Lee SJ, et al., "Regulation of muscle growth by multiple ligands signaling through activin type II receptors," Proc Natl Acad Sci USA. 2005, vol. 102, pp. 18117-18122.
Lee SJ, et al., "Regulation of myostatin activity and muscle growth," Proc Natl. Acad. Sci., USA. 2001, vol. 98, pp. 9306-9311.
Luisi S, et al., "Expression and secretion of activin A: possible physiological and clinical implications," European Journal of Endocrinology. 2001, vol. 145, pp. 225-236.
MacDonald N, et al., "Understanding and managing cancer cachexia," J Am Coll Surg. 2003, vol. 197, pp. 143-161.
Matzuk MM, et al., "α-inhibin is a tumour-suppressor gene with gonadal specificity in mice," Nature. 1992, vol. 360, pp. 313-319.
Matzuk MM, et al., "Development of cancer cachexia-like syndrome and adrenal tumors in inhibin-deficient mice," Proc Natl Acad Sci USA. 1994, vol. 91, pp. 8817-8821.
Morley JE, et al., "Cachexia: pathophysiology and clinical relevance," Am J Clin Nutr. 2006, vol. 83, pp. 735-743.
Muscaritoli M, et al., "Prevention and treatment of cancer cachexia: new insights into an old problem," Eur J Cancer. 2006, vol. 42, pp. 31-41.
Payne, S.J.L., et al., "Influence of the tumor microenvironment on angiogenesis," Future Oncology, 2011, vol. 7, pp. 395-408.
Provencher DM, et al., "Characterization of four novel epithelial ovarian cancer cell lines," In Vitro Cellular & Developmental Biology Animal, 2000, vol. 36, pp. 357-361.
Roth SM, et al., "Myostatin: A therapeutic target for skeletal muscle wasting," Curr Opin Clin Nutr Metab Care. 2004, vol. 7, pp. 259-263.
Roubenoff R., "Origins and clinical relevance of sarcopenia," Can. J Appl Phys. 2001, vol. 26, pp. 78-89.
Roubenoff R, et al., "Standardization of nomenclature of body composition in weight loss," Am J Clin Nutr. 1997, vol. 66, pp. 192-196.
Steller, M.C. et al., "Inhibin Resistance Is Associated with Aggressive Tumorigenicity of Ovarian Cancer Cells," Mol. Cancer Res., 2005, vol. 3, pp. 50-61.
Strassmann, G., et al., "Suramin interferes with interleukin-6 receptor binding in vitro and inhibits colon-26-mediated experimental cancer cachexia in vivo," J Clin Invest, vol. 92, 1993, pp. 2152-2159.
Tomayko MM, et al., "Determination of subcutaneous tumor size in athymic (nude) mice," Cancer Chemother Pharmacol. 1989, vol. 24, pp. 148-154.
Yoshinaga K, et al., "Clinical significance of the expression of activin A in esophageal carcinoma," Int J Oncol 2003, vol. 22, pp. 75-80.

(56) References Cited

OTHER PUBLICATIONS

Zhou X, et al., "Reversal of cancer cachexia and muscle wasting by ActRIIB antagonism leads to prolonged survival," *Cell*, 2010, vol. 142, pp. 531-543.

Zimmers TA, et al., "Induction of cachexia in mice by systemically administered myostatin," *Science*. 2002, vol. 296, pp. 1486-1488.

Eurasian Patent Office, Office Action, Eurasian Patent Application No. 201100832, Nov. 28, 2014, three pages.

Philippines Intellectual Property Office, Office Action, Philippine Patent Application No. 1/2009/501698, Nov. 18, 2014, one page.

Vietnam National Office of Intellectual Property, Office Action, Vietnamese Patent Application No. 1-2014-02367, Nov. 17, 2014, two pages.

Indian Office Action, Indian Application No. 6356/DELNP/2009, Jan. 20, 2015, 3 pages.

MTAPWVALALLWGSLWPGSGRGEAETRECIYYNANWELER
TNQSGLERCEGEQDKRLHCYASW(A/R)NSSGTIELVKKG
CWLDDFNCYDRQECVATEENPQVYFCCCEGNFCNERFTHL
PEAGGPEVTYEPPPTAPTGGGGSVDKTHTCPPCPAPELLGG
PSVFLFPPKPKDTLMISRTPEVTCVVVDVSHEDPEVKFNWY
VDGVEVHNAKTKPREEQYNSTYRVVSVLTVLHQDWLNGKEY
KCKVSNKALPAPIEKTISKAKGQPREPQVYTLPPSRDELTK
NQVSLTCLVKGFYPSDIAVEWESNGQPENNYKTTPPVLDSD
GSFFLYSKLTVDKSRWQQGNVFSCSVMHEALHNHYTQKSLS
LSPGK
(SEQ ID NO: 98)

*Fig. 1*

MTAPWVALALLWGSLWPGSGRGEAETRECIYYNANWELER
TNGSGLERCEGEQDKRLHCYASW(A/R)NSSGTIELVKKG
CWLDDFNCYDRQECVATEENPQVYFCCCEGNFCNERFTHL
PEAGGPEGPWASTTIPSGGPEATAAAGDQGSGALWLCLEGP
AHEGGGGSVDKTHTCPPCPAPELLGGPSVFLFPPKPKDTLM
ISRTPEVTCVVVDVSHEDPEVKFNWYVDGVEVHNAKTKPRE
EQYNSTYRVVSVLTVLHQDWLNGKEYKCKVSNKALPAPIEK
TISKAKGQPREPQVYTLPPSRDELTKNQVSLTCLVKGFYPS
DIAVEWESNGQPENNYLTTPPVLDSDGSFFLYSKLTVDKS
WQQGNVFSCSVMHEALHNHYTQKSLSLSPGK
(SEQ ID NO: 99)

VARIANT ACTIVIN RECEPTOR POLYPEPTIDES AND USES THEREOF

CROSS-REFERENCE TO RELATED APPLICATIONS

This application is a continuation of U.S. Ser. No. 13/329,897, filed Dec. 19, 2011, which is a continuation-in-part of U.S. Ser. No. 13/080,515, filed Apr. 5, 2011, which is a divisional of U.S. Ser. No. 12/074,877, filed Mar. 5, 2008, now granted as U.S. Pat. No. 7,947,646, which claims the benefit of U.S. provisional application Ser. No. 61/065,474, filed Feb. 11, 2008, and U.S. provisional application Ser. No. 60/905,459, filed Mar. 6, 2007, the disclosures of which are relied upon and incorporated by reference herein.

REFERENCE TO THE SEQUENCE LISTING

The present application is being filed along with a Sequence Listing in electronic format. The Sequence Listing is provided as a file entitled A-1219-US-CIP_SeqList.txt which is 265,085 bytes in size, and was created Dec. 19, 2011. The information in the electronic format of the Sequence Listing is incorporated herein by reference in its entirety

FIELD OF THE INVENTION

The technical field of this invention relates to transforming growth factor-β (TGF-β) family members and soluble TGF-β receptors, as well as methods of modulating the activities of TGF-β family members for the treatment of various disorders.

BACKGROUND OF THE INVENTION

The transforming growth factor 13 (TGF-β) family of proteins includes the transforming growth factors-β (TGF-β), activins, bone morphogenic proteins (BMP), nerve growth factors (NGFs), brain-derived neurotrophic factor (BDNF), and growth/differentiation factors (GDFs). These family members are involved in the regulation of a wide range of biological processes including cell proliferation, differentiation, and other functions.

Growth/differentiation factor 8 (GDF-8), also referred to as myostatin, is a TGF-β family member expressed for the most part in the cells of developing and adult skeletal muscle tissue. Myostatin appears to play an essential role in negatively controlling skeletal muscle growth (McPherson et al., Nature (London) 387, 83-90 (1997)). Antagonizing myostatin has been shown to increase lean muscle mass in animals (McFerron et al., supra, Zimmers et al., Science 296:1486 (2002)).

Another member of the TGF-β family of proteins is a related growth/differentiation factor, GDF-11. GDF-11 has approximately 90% identity of the amino acid sequence of myostatin. GDF-11 has a role in the axial patterning in developing animals (Oh et al, Genes Dev 11:1812-26 (1997)), and also appears to play a role in skeletal muscle development and growth.

Activins A, B and AB are the homodimers and heterdimer respectively of two polypeptide chains, βA and βB (Vale et al. Nature 321, 776-779 (1986), Ling et al., Nature 321, 779-782 (1986)). Activins were originally discovered as gonadal peptides involved in the regulation of follicle stimulating hormone synthesis, and are now believed to be involved in the regulation of a number of biological activities. Activin A is a predominant form of activin.

Activin, myostatin, GDF-11 and other members of the TGF-β superfamily bind and signal through a combination of activin type II and activin type IIB receptors, both of which are transmembrane serine/threonine kinases (Harrison et al., J. Biol. Chem. 279, 28036-28044 (2004)). Cross-linking studies have determined that myostatin is capable of binding the activin type II receptors ActRIIA and ActRIIB in vitro (Lee et al., PNAS USA 98:9306-11 (2001)). There is also evidence that GDF-11 binds to both ActRIIA and ActRIIB (Oh et al., Genes Dev 16:2749-54 (2002)).

TGF-β protein expression is known to be associated with a variety of diseases and disorders. Therefore, therapeutic molecules capable of antagonizing several TGF-β proteins simultaneously may be particularly effective for these diseases and disorders.

In addition, the production of protein therapeutics can be complicated by problems occurring during the expression and purification of the protein. One problem is the aggregation of proteins during expression or purification. The accumulation of high levels of protein during cell culture conditions may lead to aggregation. Purification processes may expose the protein to additional factors promoting further aggregation (Cromwell, M. E. M. et al., The AAPS Journal 8:E572-E579, 2006). Attempts can be made to mitigate the factors that cause aggregation, however, a need exists for proteins designed to have a decreased tendency to form aggregates. The present invention fulfills the need for therapeutic molecules that bind to multiple ligands, and have reduced aggregation and thus improved manufacturability, in order to efficiently produce proteins useful for treating TGF-β related disease states.

SUMMARY OF THE INVENTION

The present invention provides an isolated protein comprising a variant human activin receptor IIB (designated vActRIIB or sActRIIB) polypeptide. As used herein the term vActRIIB polypeptide refers to both human vActRIIB polypeptides and human vActRIIB5 polypeptides. In one embodiment, the protein comprises a polypeptide having an amino acid sequence of SEQ ID NOS: 2 or 18 in which amino acids at either position E28 or R40, or both position E28 and R40 are substituted with another non-native amino acid, and wherein the polypeptide is capable of binding myostatin, activin A, or GDF-11. In one embodiment the protein comprises a polypeptide having an amino acid sequence of SEQ ID NOS: 2 or 18 in which the amino acids at positions E28 or R40, or both E28 and R40 are substituted with a non-native amino acid, and wherein the signal peptide is removed, and wherein the polypeptide is capable of binding myostatin, activin A, or GDF-11. In one embodiment the protein comprises a polypeptide having an amino acid sequence of SEQ ID NOS: 2 or 18 in which amino acids at positions E28 or R40, or both E28 and R40 are substituted with another amino acid, wherein the signal sequence is removed, and N-terminal of the mature polypeptide is truncated, and wherein the polypeptide is capable of binding myostatin, activin A, or GDF-11. In one embodiment the N-terminal mature truncated vActRIIB polypeptide lacks the N-terminal four amino acids or the N-terminal six amino acids of the mature sequence, wherein the polypeptide is capable of binding myostatin, activin A, or GDF-11. In one embodiment, the substitution at position E28 is selected from the group consisting of W, Y and A. In a further embodiment, the substitution at position E28 is selected from the group of amino acids consisting of A, F, Q, V, I, L, M, K, H, W and Y. In a further embodiment, the substitution at position R40 is selected from the group of amino acids consisting of G, Q, M, H, K and N. In a further embodiment the substitution at position E28 is selected from the group of amino acids consisting of A, F, Q, V, I, L, M, K, H, W and Y and the substitution at position R40 is selected from the group of amino acids consisting of A, G, Q, M, H, K and N. In a further embodiment the polypeptide further comprises a heterologous protein. In one embodiment, the heterologous protein is an Fc domain. In a further embodiment, the Fc domain is a human IgG Fc domain.

In one embodiment, the protein comprises polypeptides having an amino acid sequence set forth in SEQ ID NOS: 4, 6, 8, 10, 12, 14, 16, 20, 22, 24, 26, 28, 30, 32, 34, 36, 38, 40, 42, 44, 46, 52, 54, 56, 60, 62, 64, 66, 70, 72, 87, 88, 91, 93, 95, and 97.

In another embodiment, the protein comprises a polypeptide encoded by the polynucleotide having the sequence set forth in SEQ ID NOS: 3, 5, 7, 9, 11, 13, 15, 19, 21, 23, 25, 27, 29, 31, 33, 35, 37, 39, 41, 43, 45, 51, 53, 55, 59, 61, 63, 65, 67, 69, 71, 92, 94, 96 or its complement.

In another aspect the present invention provides an isolated nucleic acid molecule comprising a polynucleotide encoding a vActRIIB polypeptide. In one embodiment, the nucleic acid molecule comprises a polynucleotide having the nucleic acid sequence set forth in SEQ ID NOS: 3, 5, 7, 9, 11, 13, 15, 19, 21, 23, 25, 27, 29, 31, 33, 35, 37, 39, 41, 43, 45, 51, 53, 55, 59, 61, 63, 65, 69, 71, 92, 94, 96 or its complement.

In another embodiment, the nucleic acid molecule comprises a polynucleotide encoding a polypeptide consisting of the amino acid sequence set forth in the group consisting of SEQ ID NOS: 4, 6, 8, 10, 12, 14, 16, 20, 22, 24, 26, 28, 30, 32, 34, 36, 38, 40, 42, 44, 46, 52, 54, 56, 60, 62, 64, 66, 68, 70, 72, 87, 88, 91, 93, 95, and 97. In a further embodiment, the nucleic acid molecule further comprises a transcriptional or translational regulatory sequence.

In another aspect a recombinant vector comprising the vActRIIB nucleic acid molecule is provided. In another aspect, host cells comprising the recombinant vectors are provided, and methods of producing the vActRIIB polypeptides are provided.

The present invention further provides a composition containing at least one vActRIIB polypeptide or protein of the present invention. In one embodiment, the composition is a pharmaceutical composition containing the vActRIIB polypeptide or protein in admixture with a pharmaceutically acceptable carrier.

In another aspect, the present invention provides a method of treating or preventing a muscle wasting disease in a subject suffering from such a disorder by administering a therapeutic composition containing a vActRIIB polypeptide or protein to the subject. The muscle wasting disease includes or results from, but is not limited to, the following conditions: cancer cachexia, muscular dystrophy, amyotrophic lateral sclerosis, congestive obstructive pulmonary disease, chronic heart failure, chemical cachexia, cachexia from HIV/AIDS, renal failure, uremia, rheumatoid arthritis, age-related sarcopenia, age-related frailty, organ atrophy, carpal tunnel syndrome, androgen deprivation, and muscle-wasting due to inactivity from prolonged bed rest, spinal chord injury, stroke, bone fracture, and aging. The muscle wasting may also result from weightlessness due to space flight, insulin resistance, muscle wasting due to burns, androgen deprivation, and other disorders. In another aspect, the present invention provides a method of treating a disease correlated to expression of activin A. In one embodiment, the disease is cancer. In another aspect, the present invention provides a method of treating a metabolic disorder comprising administering a therapeutic composition to a subject in need of such treatment, wherein the metabolic disorder is selected from bone loss, diabetes, obesity, impaired glucose tolerance, hyperglycemia, androgen deprivation, and metabolic syndrome. In another aspect, the present invention provides a method of gene therapy comprising administering a vector encoding a vActRIIB polypeptide or protein of the present invention to a subject in need thereof, wherein the vector is capable of expressing the vActRIIB polypeptide or protein in the subject.

In another embodiment, a pharmaceutical composition is provided comprising i) a variant activin IIB receptor polypeptide (vActRIIB) wherein said polypeptide comprises the polypeptide sequence of SEQ ID NO: 18 except for a single amino acid substitution at position 28, wherein the polypeptide is capable of binding myostatin, activin A, or GDF-11, and ii) a chemotherapeutic agent. The variant activin IIB receptor of the pharmaceutical composition can have a substitution at position 28 of the vActRIIB polypeptide that is selected from the group consisting of A, F, Q, V, I, L, M, K, H, W and Y for E. In another embodiment the substitution at position 28 of the vActRIIB polypeptide is selected from the group of amino acids consisting of A, W and Y for E or the substitution at position 28 of the vActRIIB polypeptide is W. In yet other embodiments, the vActRIIB polypeptide lacks the N-terminal signal sequence. In yet other embodiments, the pharmaceutical also comprises a pharmaceutically acceptable carrier, a chemotherapeutic and the activin IIB receptor polypeptide variant.

In another aspect, the chemotherapeutic agent of the pharmaceutical composition is a nucleoside analogue. In other embodiments, the chemotherapeutic agent can be 5-fluorouracil or dacarbazine.

In another embodiment, a method of inhibiting myostatin activity in a subject in need of such treatment is provided comprising administering to the subject a therapeutically effective amount of a pharmaceutical composition comprising i) a variant activin IIB receptor polypeptide (vActRIIB) wherein said polypeptide comprises the polypeptide sequence of SEQ ID NO: 18 except for a single amino acid substitution at position 28, wherein the polypeptide is capable of binding myostatin, activin A, or GDF-11, and ii) a chemotherapeutic agent. The variant activin IIB receptor of the pharmaceutical composition can have a substitution at position 28 of the vActRIIB polypeptide that is selected from the group consisting of A, F, Q, V, I, L, M, K, H, W and Y for E. In other embodiment the substitution at position 28 of the vActRIIB polypeptide is selected from the group of amino acids consisting of A, W and Y for E or the substitution at position 28 of the vActRIIB polypeptide is W. In yet other embodiments, the vActRIIB polypeptide lacks the N-terminal signal sequence.

In another aspect, a method of treating a disease in which activin is overexpressed in a subject in need of such treatment is provided comprising administering to a subject a therapeutically effective amount of the composition comprising i) a variant activin IIB receptor polypeptide (vActRIIB) wherein said polypeptide comprises the polypeptide sequence of SEQ ID NO: 18 except for a single amino acid substitution at position 28, wherein the polypeptide is capable of binding myostatin, activin A, or GDF-11, and ii) a chemotherapeutic agent. The variant activin IIB receptor of the pharmaceutical composition can have a substitution at position 28 of the vActRIIB polypeptide that is selected from the group consisting of A, F, Q, V, I, L, M, K, H, W and Y for E. In other embodiment the substitution at position 28 of the vActRIIB polypeptide is selected from the group of amino acids consisting of A, W and Y for E or the substitution at position 28 of the vActRIIB polypeptide is W. In yet other embodiments, the vActRIIB polypeptide lacks the N-terminal signal sequence.

In an aspect of the invention, the above method can be used to treat cancers. The cancers can be testicular cancer, ovarian cancer or melanoma.

In another embodiment, a method of reducing the size of a tumor mass in a subject in need of such treatment is provided comprising administering an effective amount of a pharmaceutical composition comprising i) a variant activin IIB receptor polypeptide (vActRIIB) wherein said polypeptide comprises the polypeptide sequence of SEQ ID NO: 18 except for a single amino acid substitution at position 28, wherein the polypeptide is capable of binding myostatin, activin A, or GDF-11, and ii) a chemotherapeutic agent. The variant activin IIB receptor of the pharmaceutical composition can have a substitution at position 28 of the vActRIIB polypeptide that is selected from the group consisting of A, F, Q, V, I, L, M, K, H, W and Y for E. In other embodiment the substitution at position 28 of the vActRIIB polypeptide is selected from the group of amino acids consisting of A, W and Y for E or the substitution at position 28 of the vActRIIB polypeptide is W. In yet other embodiments, the vActRIIB polypeptide lacks the N-terminal signal sequence. The tumor mass can result from testicular or ovarian cancer or a melanoma.

In yet another embodiment, a method of treating melanoma, in a subject in need of such treatment is provided comprising administering to said subject a therapeutically effective amount of a pharmaceutical composition comprising a variant activin IIB receptor polypeptide (vActRIIB) wherein said polypeptide comprises the polypeptide sequence of SEQ ID NO: 18 except for a single amino acid substitution at position 28, wherein the polypeptide is capable of binding myostatin, activin A, or GDF-11.

In another embodiment, a method of treating a condition having overexpression of angiogenesis factors, in a subject in need of such treatment is provided comprising administering to said subject a therapeutically effective amount of a pharmaceutical composition comprising a variant activin IIB receptor polypeptide (vActRIIB) wherein said polypeptide comprises the polypeptide sequence of SEQ ID NO: 18 except for a single amino acid substitution at position 28, wherein the polypeptide is capable of binding myostatin, activin A, or GDF-11. The condition can be cancer and the cancer can be ovarian cancer. VEGF-A or Ang-1 can be overexpressed.

BRIEF DESCRIPTION OF THE DRAWINGS

FIG. 1. FIG. 1 shows the amino acid sequence of wild-type soluble ActRIIB-human IgG1Fc (SEQ ID NO: 98). The signal peptide sequence is in bold, followed by the mature ActRIIB extracellular domain, and the human IgG 1 Fc in italics, including a partial hinge region. Amino acids E28 and R40 are underlined. The linker sequence GGGGS (SEQ ID NO: 75) is in italics and underlined.

FIG. 2. FIG. 2 shows the amino acid sequence of soluble ActRIIB5-human IgG1Fc (SEQ ID NO: 99). The signal peptide sequence is in bold, followed by the mature ActRIIB5 soluble domain, and the human IgG1 Fc, including a partial hinge region, is in italics. E28 and R40 are underlined. The linker sequence (GGGGS) (SEQ ID NO: 75) is in italics and underlined.

FIG. 3 shows the effect of soluble vActRIIB-Fc E28W treatment on testicular (FIG. 3A) and ovarian (FIG. 3B) mass in inhibin-α knockout mice.

FIG. 4 shows the effect of soluble vActRIIB-Fc E28W treatment on survival rates in male (FIG. 4A) and female (FIG. 4B) inhibin-α knockout mice.

FIG. 5 shows the effect of soluble vActRIIB-Fc E28W treatment on body weight in colon 26 tumor-bearing mice.

FIG. 6 shows the effect of soluble vActRIIB-Fc E28W treatment on the survival of colon 26 tumor bearing mice.

FIG. 7A shows levels of activin in normal and ovarian cancer. *$P<0.001$, Student t-test; n=20. FIG. 7B shows the effect of sActRIIB on activin levels. Values are mean±SEM. *:$P<0.001$ vs. WT control. n=6-12. FIG. 7C shows changes in ovarian mass with sActRIIB. Values are mean±SEM. ***:$P<0.001$ vs. WT control. n=6-10. FIG. 7D shows ovarian tumors in treated and non-treated mice. Scale bar=10 mm FIG. 8—Values are mean SEM. *:$P<0.05$; Student t-test. n=10. FIG. 8B—**$P<0.01$, Student t-test.

FIG. 9A shows the effect of sActRIIB and 5-Fu on TOV-21G tumor growth inhibition in nude mice. Changes in tumor volumes were recorded longitudinally. ***:$P<0.001$ vs. PBS; #:$P<0.05$ vs. 5-Fu; ¶:$P<0.01$ vs. sActRIIB; Repeated measures ANOVA; n=12. FIG. 9B shows the effect of sActRIIB and dacarbazine on the growth of G361 human melanoma xenografts in nude mice. Results of tumor volume (mm3) are expressed as the mean±SEM. *:$P<0.05$ vs. PBS group. Statistics based on repeated measures ANOVA. n=8.

DETAILED DESCRIPTION

Figure 3A:
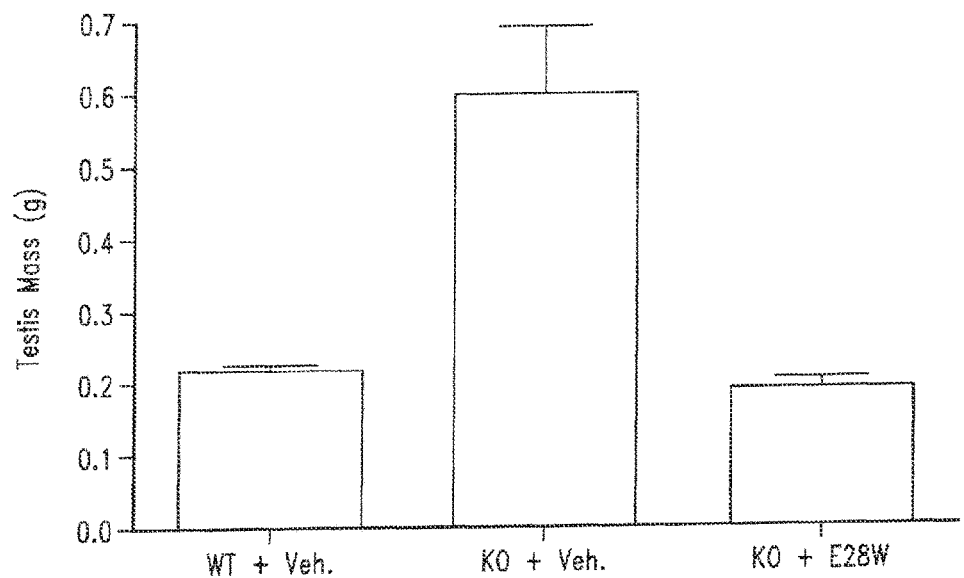
FIG. 3.

Proteins comprising variant human activin IIB receptor (vActRIIB; also referred to as sActRIIB) polypeptides are disclosed. These proteins and polypeptides are characterized by their ability to bind to at least one of three TGF-β proteins, myostatin (GDF-8), activin A, and GDF-11, and to inhibit the activities of these proteins. These proteins and polypeptides also exhibit a reduced tendency to aggregate compared to polypeptides not containing the modifications disclosed herein. The modifications consist of amino acid substitutions at positions 28, 40, or both 28 and 40 with reference to wild type ActRIIB of accession number NP_001097 (SEQ ID NO: 47), and the extracellular domain of ActRIIB (SEQ ID NO: 18) or ActRIIB5 (SEQ ID NO: 2).

As used herein the term "TGF-β family members" or "TGF-β proteins" refers to the structurally related growth factors of the transforming growth factor family including activins, and growth and differential factor (GDF) proteins (Kingsley et al. Genes Dev. 8: 133-146 (1994), McPherron et al. Growth factors and cytokines in health and disease, Vol. 1B, D. LeRoith and C. Bondy. ed., JAI Press Inc., Greenwich, Conn., USA: pp 357-393).

GDF-8, also referred to as myostatin, is a negative regulator of skeletal muscle tissue (McPherson et al. PNAS USA 94:12457-12461 (1997)). Myostatin is synthesized as an inactive protein complex approximately 375 amino acids in length, having GenBank Accession No: AAB86694 (SEQ ID NO: 49) for human. The precursor protein is activated by proteolytic cleavage at a tetrabasic processing site to produce an N-terminal inactive prodomain and an approximately 109 amino acid C-terminal protein which dimerizes to form a homodimer of about 25 kDa. This homodimer is the mature, biologically active protein (Zimmers et al., Science 296, 1486 (2002)).

As used herein, the term "prodomain" or "propeptide" refers to the inactive N-terminal protein which is cleaved off to release the active C-terminal protein. As used herein the term "myostatin" or "mature myostatin" refers to the mature, biologically active C-terminal polypeptide, in monomer, dimer or other form, as well as biologically active fragments or related polypeptides including allelic variants, splice variants, and fusion peptides and polypeptides. The mature myostatin has been reported to have 100% sequence identity among many species including human, mouse, chicken, porcine, turkey, and rat (Lee et al., PNAS 98, 9306 (2001)).

As used herein GDF-11 refers to the BMP (bone morphogenic protein) having Swissprot accession number O95390 (SEQ ID NO: 50), as well as variants and species homologs of that protein. GDF-11 has approximately 90% identity to myostatin at the amino acid level. GDF-11 is involved in the regulation of anterior/posterior patterning of the axial skeleton (McPherron et al, Nature Genet. 22 (93): 260-264 (1999); Gamer et al, Dev. Biol. 208 (1), 222-232 (1999)) but postnatal functions are unknown.

Activin A is the homodimer of the polypeptide chains BA. As used herein the term "activin A" refers to the activin protein having GenBank Accession No: NM_002192 (SEQ ID NO: 48), as well as variants and species homologs of that protein.

Activin Receptors

As used herein, the term activin type IIB receptors (ActRIIB) refers to human activin receptors having accession number NP_001097 (SEQ ID NO: 47). The term soluble ActRIIB encompasses the extracellular domain of ActRIIB (SEQ ID NO: 18), ActRIIB5 (SEQ ID NO: 2) and these sequences wherein the arginine at position 64 is substituted with alanine, as well as.

Variant soluble ActRIIB polypeptides

The present invention provides isolated proteins comprising human variant soluble ActIIB receptor polypeptides (referred to herein as vActRIIB polypeptides, or variant polypeptides or sActRIIB). As used herein the term "vActRIIB protein" refers to a protein comprising a vActRIIB polypeptide. As used herein the term "isolated" refers to a protein or polypeptide molecule purified to some degree from endogenous material. These polypeptides and proteins are characterized as having the ability to bind and inhibit the activity of any one of activin A, myostatin, or GDF-11. In some embodiments, the binding affinity of the variant polypeptides for activin A, myostatin, or GDF-11 is improved compared to wild-type polypeptides.

In one embodiment, the vActRIIB polypeptide has the amino acid sequence of SEQ ID NOS: 2 or 18 in which amino acids at either position E28 or R40, or both position E28 and R40 are substituted with another non-native amino acid, and wherein the polypeptide is capable of binding myostatin, activin A, or GDF-11. In another embodiment, the vActRIIB polypeptides are the mature versions, or the truncated mature versions of these sequences. As used herein the term "mature vActRIIB polypeptide" refers to the polypeptide having the amino acid signal sequence removed. In one embodiment, the mature sequences are, for example, amino acids 19 through 160 of SEQ ID NO: 2, and amino acids 19 through 134 of SEQ ID NO: 18, wherein one or both amino acids at positions 28 and 40 are substituted with another non-native amino acid and the polypeptides retain the ability to bind to activin A, myostatin, or GDF-11. As used herein the term truncated mature vActRIIB polypeptide refers to the polypeptide having the signal sequence and in addition amino acids from the N-terminal of the mature polypeptide removed. In one embodiment, the mature N-terminal 4 amino acids or the N-terminal 6 amino acids of the mature polypeptide are removed. In this embodiment, the truncated mature sequences are, for example, amino acids 23 through 160 of SEQ ID NO: 2, or amino acids 25 through 160 of SEQ ID NO: 2; and amino acids 23 through 134 of SEQ ID NO: 18, or amino acids 25 through 134 of SEQ ID NO: 18 wherein one or both amino acids at positions 28 and 40 are substituted with non-wild type amino acids which retain the ability to bind to activin A, myostatin, or GDF-11. As used herein, the term "position 28" and "position 40" (that is, E28 and R40) refers to the amino acid position with reference to the sequences SEQ ID NOS: 2 and 18 that include an 18 amino acid signal sequence. For consistency, if mature vActRIIB polypeptides have substitutions at position 10 and/or position 22, or truncated mature polypeptides have substitutions at position 6 and/or position 18, or substitutions at positions 4 and/or position 16 with respect to the mature or truncated mature sequences, these variants will still be referred to with respect to the full length SEQ ID NOS: 2 and 18, or as shown in FIG. 1 or 2, i.e., the amino acid substitution at position E28 and/or R40. Such mature embodiments or N-terminal truncated embodiments are exemplified below.

In one embodiment, the substitution at position E28 is selected from the group of amino acids consisting of W, Y and A. In one embodiment, the substitution at position 28 is W. In a further embodiment the substitution at position 28 is selected from the group of amino acids consisting of A, F, Q, V, I, L, M, K, H, W and Y. In a further embodiment, the substitution at position 40 is selected from the group of amino acids consisting of G, Q, M, H, K and N. In a further embodiment the substitution at position 28 is selected from the group of amino acids consisting of A, F, Q, V, I, L, M, K, H, W and Y and the substitution at position 40 is selected from the group of amino acids consisting of A, G, Q, M, H, K, and N. In one embodiment, the protein comprises polypeptides having an amino acid sequence selected from the group consisting of SEQ ID NOS: 4, 6, 8, 10, 12, 14, 16, 20, 22, 24, 26, 28, 30, 32, 34, 36, 38, 40, 42, 44, 46, 52, 54, 56, 60, 62, 64, 66, 68, 70, 72, 87, 88, 91, 93, 95, and 97. In another embodiment, the protein comprises a polypeptide encoded by the polynucleotide having the sequence set forth in the group consisting of SEQ ID NOS: 3, 5, 7, 9, 11, 13, 15, 19, 21, 23, 25, 27, 29, 31, 33, 35, 37, 39, 41, 43, 45, 51, 53, 55, 59, 61, 63, 65, 67, 69, 71, 92, 94, 96 or its complement.

In one embodiment, the signal sequences are removed from the vActRIIB polypeptide, leaving the mature variant polypeptides. Various signal peptides can be used in the preparation of the polypeptides of the instant application. The signal peptides can have the sequence shown in FIGS. 1 and 2 (SEQ ID NO: 73), or alternative signal sequences such as SEQ ID NO: 74, the signal sequence for SEQ ID NOS: 2 and 18. Any other signal peptides useful for expressing vActRIIB or vActRIIB5 polypeptides may be used.

In another embodiment, the vActRIIB polypeptides have sequences that are substantially similar to SEQ ID NOS: 2 and 18. As used herein the term "substantially similar" refers to polypeptides having at least about 80% identity, at least about 85% identity, at least about 90% identity, at least about 95% identity, at least about 98% identity, or at least about 99% identity to the amino acid sequence set forth in SEQ ID NOS: 2 and 18, and wherein one or both amino acids at positions 28 and/or 40 are substituted with non-wild type amino acids, wherein the polypeptide retains the activity of the polypeptide of SEQ ID NOS: 2 and 18, that is the ability to bind and inhibit myostatin, activin A or GDF-11. In addition, the term vActRIIB polypeptide encompasses fragments of SEQ ID NOS: 2 or 18 such as N and C terminal truncations containing the substitutions at position 28 and/or 40 described herein, wherein the polypeptide is capable of binding and inhibiting myostatin, activin A or GDF-11.

As used herein the term "derivative" of the vActRIIB and vActRIIB5 polypeptides refers to the attachment of at least one additional chemical moiety, or at least one additional polypeptide to form covalent or aggregate conjugates such as glycosyl groups, lipids, acetyl groups, or C-terminal or N-terminal fusion polypeptides, conjugation to PEG molecules, and other modifications which are described more fully below. Variant ActRIIB receptor polypeptides (vActRIIB) can also include additional modifications and derivatives, including modifications to the C and N termini which arise from processing due to expression in various cell types such as mammalian cells, E. coli, yeasts and other recombinant host cells. Further included are vActRIIB polypeptide fragments and polypeptides comprising inactivated N-glycosylation site(s), inactivated protease processing site(s), or conservative amino acid substitution(s), of the polypeptide sequences set forth in SEQ ID NOS: 4, 6, 8, 10, 12, 14, 16, 20, 22, 24, 26, 28, 30, 32, 34, 36, 38, 40, 42, 44, 46, 52, 54, 56, 60, 62, 64, 66, 68, 70, 72, 87, 88, 91, 93, 95, and 97.

As used herein, the term a "vActRIIB or vActRIIB5 polypeptide activity" or "a biological activity of a soluble ActRIIB or ActRIIB5 polypeptide" refers to one or more in vitro or in vivo activities of the vActRIIB and vActRIIB5 polypeptides including but not limited to those demonstrated in the Example below. Activities of the vActRIIB polypeptides include, but are not limited to, the ability to bind to myostatin or activin A or GDF-11, and the ability to reduce or neutralize an activity of myostatin or activin A or GDF-11. As used herein, the term "capable of binding" to myostatin, activin A, or GDF-11 refers to binding measured by methods known in the art, such as the Biacore method described in Example 2 below. Also, in Example 2, the pMARE C2C12 cell-based assay measures activin A neutralizing activity, myostatin neutralizing activity, and GDF-11 neutralizing activity. In vivo activities include but are not limited to increasing body weight, increasing lean muscle mass, increasing skeletal muscle mass, decreasing fat mass as demonstrated in animal models below and as known in the art. Biological activities further include reducing or preventing cachexia caused by certain types of tumors, preventing the growth of certain types of tumors, and increasing survival of certain animal models. Further discussion of the vActRIIB polypeptide activities is provided below.

The polypeptides of the present invention further comprise heterologous polypeptides attached to the vActRIIB polypeptide either directly or through a linker sequence to form a fusion protein. As used herein the term "fusion protein" refers to a protein having a heterologous polypeptide attached via recombinant DNA techniques. Heterologous polypeptides include but are not limited to Fc polypeptides, His tags, and leucine zipper domains to promote oligomerization and stabilization of the variant ActRIIB polypeptides as described in, for example, WO 00/29581, which is herein incorporated by reference. In one embodiment, the heterologous polypeptide is an Fc polypeptide or domain. In one embodiment, the Fc domain is selected from a human IgG1, IgG2, and IgG4 Fc domain. These are provided in SEQ ID NOS: 80, 82 and 84. The vActRIIB can further comprise all or a portion of the hinge sequence of the IgG1, IgG2, or IgG4 adjacent to its respective IgG Fc region. The full hinge sequence for IgG1, IgG2, and IgG4 are provided in SEQ ID NOS: 76, 77, and 78 respectively.

The vActRIIB polypeptide can optionally further comprise a "linker" sequence. Linkers serve primarily as a spacer between a polypeptide and a second heterologous polypeptide or other type of fusion or between two or more variant ActRIIB polypeptides. In one embodiment, the linker is made up of amino acids linked together by peptide bonds, preferably from 1 to 20 amino acids linked by peptide bonds, wherein the amino acids are selected from the 20 naturally occurring amino acids. One or more of these amino acids may be glycosylated, as is understood by those in the art. In one embodiment, the 1 to 20 amino acids are selected from glycine, alanine, proline, asparagine, glutamine, and lysine. Preferably, a linker is made up of a majority of amino acids that are sterically unhindered, such as glycine and alanine. Exemplary linkers are polyglycines (particularly $(Gly)_5$, $(Gly)_8$, poly(Gly-Ala), and polyalanines. One exemplary suitable linker as shown in the Examples below is $(Gly)_4Ser$ (SEQ ID NO: 75). In a further embodiment, vActRIIB can comprise a hinge linker, that is a linker sequence are provided adjacent to the hinge region, as exemplified in SEQ ID NO: 79.

The linkers are also non-peptide linkers. For example, alkyl linkers such as —NH—(CH2)s-C(O)—, wherein s=2-20 can be used. These alkyl linkers may further be substituted by any non-sterically hindering group such as lower alkyl (e.g., C1-C6) lower acyl, halogen (e.g., Cl, Br), CN, NH2, phenyl, etc.

In one embodiment the vActRIIB polypeptides can be attached to an Fc polypeptide, directly or via a linker, or via a hinge linker. In one embodiment, the Fc is a human IgG Fc. vActRIIB attached to Fc include for example, vActRIIB-IgG1Fc, E28A (SEQ ID NO: 60); vActRIIB-IgG1Fc, E28W (SEQ ID NO: 62), vActRIIB-IgG1Fc, E28Y (SEQ ID NO: 64), vActRIIB-IgG Fc, R40G (SEQ ID NO: 66), vActRIIB5-IgG1Fc, E28A (SEQ ID NO: 70), and vActRIIB5-IgG1Fc E28W (SEQ ID NO: 72), as shown in Tables 1 and 2, and described in the Examples herein. Further embodiments include vActRIIB-IgG2 Fc, E28W (SEQ ID NO: 91), vActRIIB-IgG2 Fc, E28Y (SEQ ID NO: 93), and vActRIIB-IgG2 Fc (SEQ ID NO: 95). The variants have been demonstrated to produce less aggregation compared to the wild type ActRIIB-IgG2 IgG2, as demonstrated in the Examples below.

The vActRIIB polypeptides disclosed herein can also be attached to a non-polypeptide molecule for the purpose of conferring desired properties such as reducing degradation and/or increasing half-life, reducing toxicity, reducing immunogenicity, and/or increasing the biological activity of the ActRIIB polypeptides. Exemplary molecules include but are not limited to linear polymers such as polyethylene glycol (PEG), polylysine, a dextran; a lipid; a cholesterol group (such as a steroid); a carbohydrate, or an oligosaccharide molecule.

In another aspect, the present invention provides isolated nucleic acid molecules comprising polynucleotides encoding the vActRIIB polypeptides of the present invention. As used herein the term "isolated" refers to nucleic acid molecules purified to some degree from endogenous material. In one embodiment, the nucleic acid molecule of the present invention comprises a polynucleotide encoding the polypeptides of SEQ ID NOS: 4, 6, 8, 10, 12, 14, 16, 20, 22, 24, 26, 28, 30, 32, 34, 36, 38, 40, 42, 44, 46, 52, 54, 56, 60, 62, 64, 66, 68, 70, 72, 87, 88, 91, 93, 95, and 97. Due to the known degeneracy of the genetic code, wherein more than one codon can encode the same amino acid, a DNA sequence can vary from that shown in SEQ ID NOS: 3, 5, 7, 9, 11, 13, 15, 19, 21, 23, 25, 27, 29, 31, 33, 35, 37, 39, 41, 43, 45, 51, 53, 55, 59, 61, 63, 65, 67, 69, 71, 92, 94, and 96 or the complementary strand of SEQ ID NOS: 3, 5, 7, 9, 11, 13, 15, 19, 21, 23, 25, 27, 29, 31, 33, 35, 37, 39, 41, 43, 45, 51, 53, 55, 59, 61, 63, 65, 67, 69, 71, 92, 94, and 96, and still encode a polypeptide having the amino acid sequence of SEQ ID NOS: 4, 6, 8, 10, 12, 14, 16, 20, 22, 24, 26, 28, 30, 32, 34, 36, 38, 40, 42, 44, 46, 52, 54, 56, 60, 62, 64, 66, 68, 70, 72, 87, 88, 91, 93, 95, and 97. Such variant DNA sequences can result from silent mutations occurring during production, or can be the product of deliberate mutagenesis of these sequences.

In another embodiment the nucleic acid molecule of the present invention comprises a polynucleotide having the polynucleotide sequence set forth in SEQ ID NOS: 3, 5, 7, 9, 11, 13, 15, 19, 21, 23, 25, 27, 29, 31, 33, 35, 37, 39, 41, 43, 45, 51, 53, 55, 59, 61, 63, 65, 67, 69, 71, 92, 94, and 96 or the complementary strand of SEQ ID NOS: 3, 5, 7, 9, 11, 13, 15, 19, 21, 23, 25, 27, 29, 31, 33, 35, 37, 39, 41, 43, 45, 51, 53, 55, 59, 61, 63, 65, 67, 69, 71, 92, 94, and 96. In another embodiment, the present invention provides nucleic acid molecules which hybridize under stringent or moderate conditions with the polypeptide-encoding regions of SEQ ID NOS: 3, 5, 7, 9, 11, 13, 15, 19, 21, 23, 25, 27, 29, 31, 33, 35, 37, 39, 41, 43, 45, 51, 53, 55, 59, 61, 63, 65, 67, 69, 71, 92, 94, and 96 wherein the encoded polypeptide comprises an amino acid sequence as set forth in SEQ ID NOS: 4, 6, 8, 10, 12, 14, 16, 20, 22, 24, 26, 28, 30, 32, 34, 36, 38, 40, 42, 44, 46, 52, 54, 56, 60, 62, 64, 66, 68, 70, 72, 87, 88, 91, 93, 95, and 97 and wherein the encoded polypeptide maintains an activity of a vActRIIB polypeptide.

Nucleic acid molecules of the invention include DNA in both single-stranded and double-stranded form, as well as the RNA complement thereof. DNA includes, for example, cDNA, genomic DNA, synthetic DNA, DNA amplified by PCR, and combinations thereof. Genomic DNA may be isolated by conventional techniques, such as by using the DNA of SEQ ID NOS:1 or 17, or a suitable fragment thereof, as a probe. Genomic DNA encoding ActRIIB polypeptides is obtained from genomic libraries which are available for a number of species. Synthetic DNA is available from chemical synthesis of overlapping oligonucleotide fragments followed by assembly of the fragments to reconstitute part or all of the coding regions and flanking sequences. RNA may be obtained from procaryotic expression vectors which direct high-level synthesis of mRNA, such as vectors using T7 promoters and RNA polymerase. cDNA is obtained from libraries prepared from mRNA isolated from various tissues that express ActRIIB. The DNA molecules of the invention include full length genes as well as polynucleotides and fragments thereof. The full length gene may also include sequences encoding the N-terminal signal sequence.

In another aspect of the present invention, expression vectors containing the nucleic acid sequences are also provided, and host cells transformed with such vectors and methods of producing the vActRIIB polypeptides are also provided. The term "expression vector" refers to a plasmid, phage, virus or vector for expressing a polypeptide from a polynucleotide sequence. Vectors for the expression of the vActRIIB polypeptides contain at a minimum sequences required for vector propagation and for expression of the cloned insert. An expression vector comprises a transcriptional unit comprising an assembly of (1) a genetic element or elements having a regulatory role in gene expression, for example, promoters or enhancers, (2) a sequence that encodes vActRIIB polypeptides to be transcribed into mRNA and translated into protein, and (3) appropriate transcription initiation and termination sequences. These sequences may further include a selection marker. Vectors suitable for expression in host cells are readily available and the nucleic acid molecules are inserted into the vectors using standard recombinant DNA techniques. Such vectors can include promoters which function in specific tissues, and viral vectors for the expression of vActRIIB in targeted human or animal cells. An exemplary expression vector suitable for expression of vActRIIB is the pDSRa, (described in WO 90/14363, herein incorporated by reference) and its derivatives, containing vActRIIB polynucleotides, as well as any additional suitable vectors known in the art or described below.

The application further provides methods of making vActRIIB polypeptides. A variety of other expression/host systems may be utilized. These systems include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells useful in recombinant protein production include but are not limited to VERO cells, HeLa cells, Chinese hamster ovary (CHO) cell lines, or their derivatives such as Veggie CHO and related cell lines which grow in serum-free media (see Rasmussen et al., 1998, Cytotechnology 28:31) or CHO strain DX-B11, which is deficient in DHFR (see Urlaub et al., 1980, Proc. Natl. Acad. Sci. USA 77:4216-20) COS cells such as the COS-7 line of monkey kidney cells (ATCC CRL 1651) (see Gluzman et al., 1981, Cell 23:175), W138, BHK, HepG2, 3T3 (ATCC CCL 163), RIN, MDCK, A549, PC12, K562, L cells, C127 cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Mammalian expression allows for the production of secreted or soluble polypeptides which may be recovered from the growth medium.

Using an appropriate host-vector system, vActRIIB polypeptides are produced recombinantly by culturing a host cell transformed with an expression vector containing the nucleic acid molecules of the present invention under conditions allowing for production. Transformed cells can be used for long-term, high-yield polypeptide production. Once such cells are transformed with vectors that contain selectable markers as well as the desired expression cassette, the cells can be allowed to grow for 1-2 days in an enriched media before they are switched to selective media. The selectable marker is designed to allow growth and recovery of cells that successfully express the introduced sequences. Resistant clumps of stably transformed cells can be proliferated using tissue culture techniques appropriate to the cell line employed. An overview of expression of recombinant proteins is found in Methods of Enzymology, v. 185, Goeddell, D. V., ed., Academic Press (1990).

In some cases, such as in expression using procaryotic systems, the expressed polypeptides of this invention may need to be "refolded" and oxidized into a proper tertiary structure and disulfide linkages generated in order to be biologically active. Refolding can be accomplished using a number of procedures well known in the art. Such methods include, for example, exposing the solubilized polypeptide to a pH usually above 7 in the presence of a chaotropic agent. The selection of chaotrope is similar to the choices used for inclusion body solubilization, however a chaotrope is typically used at a lower concentration. Exemplary chaotropic agents are guanidine and urea. In most cases, the refolding/oxidation solution will also contain a reducing agent plus its oxidized form in a specific ratio to generate a particular redox potential which allows for disulfide shuffling to occur for the formation of cysteine bridges. Some commonly used redox couples include cysteine/cystamine, glutathione/dithiobisGSH, cupric chloride, dithiothreitol DTT/dithiane DTT, and 2-mercaptoethanol (bME)/dithio-bME. In many instances, a co-solvent may be used to increase the efficiency of the refolding. Commonly used cosolvents include glycerol, polyethylene glycol of various molecular weights, and arginine.

In addition, the polypeptides can be synthesized in solution or on a solid support in accordance with conventional techniques. Various automatic synthesizers are commercially available and can be used in accordance with known protocols. See, for example, Stewart and Young, Solid Phase Peptide Synthesis, 2d. Ed., Pierce Chemical Co. (1984); Tam et al., J Am Chem Soc, 105:6442, (1983); Merrifield, Science 232:341-347 (1986); Barany and Merrifield, The Peptides, Gross and Meienhofer, eds, Academic Press, New York, 1-284; Barany et al., Int Pep Protein Res, 30:705-739 (1987).

The polypeptides and proteins of the present invention can be purified according to protein purification techniques are well known to those of skill in the art. These techniques involve, at one level, the crude fractionation of the proteinaceous and non-proteinaceous fractions. Having separated the peptide polypeptides from other proteins, the peptide or polypeptide of interest can be further purified using chromatographic and electrophoretic techniques to achieve partial or complete purification (or purification to homogeneity). The term "isolated polypeptide" or "purified polypeptide" as used herein, is intended to refer to a composition, isolatable from other components, wherein the polypeptide is purified to any degree relative to its naturally-obtainable state. A purified polypeptide therefore also refers to a polypeptide that is free from the environment in which it may naturally occur. Generally, "purified" will refer to a polypeptide composition that has been subjected to fractionation to remove various other components, and which composition substantially retains its expressed biological activity. Where the term "substantially purified" is used, this designation will refer to a peptide or polypeptide composition in which the polypeptide or peptide forms the major component of the composition, such as constituting about 50%, about 60%, about 70%, about 80%, about 85%, or about 90% or more of the proteins in the composition.

Various techniques suitable for use in purification will be well known to those of skill in the art. These include, for example, precipitation with ammonium sulphate, PEG, antibodies (immunoprecipitation) and the like or by heat denaturation, followed by centrifugation; chromatography such as affinity chromatography (Protein-A columns), ion exchange, gel filtration, reverse phase, hydroxylapatite, hydrophobic interaction chromatography; isoelectric focusing; gel electrophoresis; and combinations of these techniques. As is generally known in the art, it is believed that the order of conducting the various purification steps may be changed, or that certain steps may be omitted, and still result in a suitable method for the preparation of a substantially purified polypeptide. Exemplary purification steps are provided in the Examples below.

Various methods for quantifying the degree of purification of polypeptide will be known to those of skill in the art in light of the present disclosure. These include, for example, determining the specific binding activity of an active fraction, or assessing the amount of peptide or polypeptide within a fraction by SDS/PAGE analysis. A preferred method for assessing the purity of a polypeptide fraction is to calculate the binding activity of the fraction, to compare it to the binding activity of the initial extract, and to thus calculate the degree of purification, herein assessed by a "-fold purification number." The actual units used to represent the amount of binding activity will, of course, be dependent upon the particular assay technique chosen to follow the purification and whether or not the polypeptide or peptide exhibits a detectable binding activity.

Variant activin type IIB polypeptides bind to ligands that activate muscle-degradation cascades. vActRIIB polypeptides capable of binding and inhibiting the activity of the ligands activin A, myostatin, and/or GDF-11, have therapeutic potential against the diseases that involve muscle atrophy, as well as the treatment of certain cancers, e.g. ovarian tumors prostate tumors and melanoma, and other diseases as shown in the Examples below.

However, aggregation can occur when expressing or purifying wild-type ActRIIB or ActRIIB5 polypeptides. This aggregation includes structured oligomer formation during expression and non-structured aggregate generation both during expression and after polypeptide purification.

The combined approaches of structure analysis, molecular modeling, and mass spectrometry have indicated that multimerization may arise in ActRIIB polypeptides via intermolecular disulfide bond formation aided by electrostatic and hydrogen bonding interactions between nonglycosylated ActRIIB polypeptides. Significant hydrogen bonds exist at the interface of two ActRIIB molecules; between E28 side chain in one ActRIIB and R40 side chain in the other ActRIIB, for example. In addition, critical electrostatic interactions exist between E28 in one ActRIIB and R40 in the other ActRIIB.

These electrostatic interactions may significantly contribute to increase the population of temporal ActRIIB dimers, resulting in promotion of noncovalent and/or covalent bond formation between ActRIIB units. The interaction between residues 28 and 40 is the most critical among these interactions as these two residues are involved in double hydrogen bonds and a strong electrostatic interaction. The residues 28 and 40 are involved in ActRIIB:ActRIIB interactions and not in ActRIIB:ligand interactions. Thus, residues 28 and 40 can be substituted with non-native amino acids according to invention, to improve the solubility, and reduce the aggregation of the receptor polypeptides. Therefore, E28 and R40 were substituted respectively with other possible natural amino acids, expressed, and tested by Biacore as shown below. Biacore determined binding are shown in Tables 1A and 1B in Example 2 below. Furthermore, percent aggregation of the vActRIIB polypeptides are determined below.

The results in the Examples below show reduced aggregation for vActRIIB polypeptides and proteins having the amino acid substitutions described herein, while retaining the ability to bind and neutralize myostatin, activin A, or GDF-11.

Antibodies

The present invention further includes antibodies which bind to variant ActRIIB polypeptides, including those that specifically bind to the vActRIIB polypeptides of the present invention. As used herein the term "specifically binds" refers to antibodies having a binding affinity (Ka) for vActRIIB polypeptides of 106 M−1 or greater. As used herein, the term "antibody" refers to intact antibodies including polyclonal antibodies (see, for example Antibodies: A Laboratory Manual, Harlow and Lane (eds), Cold Spring Harbor Press, (1988)), and monoclonal antibodies (see, for example, U.S. Pat. Nos. RE 32,011, 4,902,614, 4,543,439, and 4,411,993, and Monoclonal Antibodies: A New Dimension in Biological Analysis, Plenum Press, Kennett, McKearn and Bechtol (eds.) (1980)). As used herein, the term "antibody" also refers to a fragment of an antibody such as F(ab), F(ab'), F(ab')2, Fv, Fc, and single chain antibodies which are produced by recombinant DNA techniques or by enzymatic or chemical cleavage of intact antibodies. The term "antibody" also refers to bispecific or bifunctional antibodies, which are an artificial hybrid antibody having two different heavy/light chain pairs and two different binding sites. Bispecific antibodies can be produced by a variety of methods including fusion of hybridomas or linking of Fab' fragments. (See Songsivilai et al, Clin. Exp. Immunol. 79:315-321 (1990), Kostelny et al., J. Immunol. 148:1547-1553 (1992)).

As used herein the term "antibody" also refers to chimeric antibodies, that is, antibodies having a human constant antibody immunoglobin domain coupled to one or more non-human variable antibody immunoglobin domain, or fragments thereof (see, for example, U.S. Pat. No. 5,595,898 and U.S. Pat. No. 5,693,493). Antibodies also refers to "humanized" antibodies (see, for example, U.S. Pat. No. 4,816,567 and WO 94/10332), minibodies (WO 94/09817), maxibodies, and antibodies produced by transgenic animals, in which a transgenic animal containing a proportion of the human antibody producing genes but deficient in the production of endogenous antibodies are capable of producing human antibodies (see, for example, Mendez et al., Nature Genetics 15:146-156 (1997), and U.S. Pat. No. 6,300,129). The term "antibodies" also includes multimeric antibodies, or a higher order complex of proteins such as heterdimeric antibodies, and anti-idiotypic antibodies. "Antibodies" also includes anti-idiotypic antibodies. The antibodies against v ActRIIB can be used, for example, to identify and quantitate vActRIIB in vitro and in vivo.

Also included are polyclonal antibodies from any mammal, for example mouse and rat antibodies, and rabbit antibodies, that bind specifically to the vActRIIB polypeptides described herein, including SEQ ID NOS: 4, 6, 8, 10, 12, 14, 16, 20, 22, 24, 26, 28, 30, 32, 34, 36, 38, 40, 42, 44, 46, 52, 54, 56, 60, 62, 64, 66, 68, 70, 72, 87, 88, 91, 93, 95, and 97.

Such antibodies find use as research tools and in quantitative assays for detecting and assaying the polypeptides disclosed herein. Such antibodies are made using methods described above and as known in the art.

Pharmaceutical Compositions

Pharmaceutical compositions containing the vActRIIB proteins and polypeptides of the present invention are also provided. Such compositions comprise a therapeutically or prophylactically effective amount of the polypeptide or protein in admixture with pharmaceutically acceptable materials, and physiologically acceptable formulation materials. The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company, 1990).

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the polypeptide. For example, suitable compositions may be water for injection, physiological saline solution for parenteral administration.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute thereof. In one embodiment of the present invention, compositions may be prepared for storage by mixing the selected composition having the desired degree of purity with optional formulation agents (Remington's Pharmaceutical Sciences, supra) in the form of a lyophilized cake or an aqueous solution. Further, the therapeutic composition may be formulated as a lyophilizate using appropriate excipients such as sucrose.

The formulations can be delivered in a variety of methods, for example, by inhalation therapy, orally, or by injection. When parenteral administration is contemplated, the therapeutic compositions for use in this invention may be in the form of a pyrogen-free, parenterally acceptable aqueous solution comprising the desired polypeptide in a pharmaceutically acceptable vehicle. A particularly suitable vehicle for parenteral injection is sterile distilled water in which a polypeptide is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In another aspect, pharmaceutical formulations suitable for injectable administration may be formulated in aqueous solutions, preferably in physiologically compatible buffers such as Hanks' solution, Ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions. In another embodiment, a pharmaceutical composition may be formulated for inhalation. Inhalation solutions may also be formulated with a propellant for aerosol delivery. In yet another embodiment, solutions may be nebulized. Pulmonary administration is further described in PCT Application No. PCT/US94/001875, which describes pulmonary delivery of chemically modified proteins.

It is also contemplated that certain formulations may be administered orally. In one embodiment of the present invention, molecules that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and presystemic degradation is minimized. Additional agents can be included to facilitate absorption of the therapeutic molecule. Diluents, flavorings, low melting point waxes, vegetable oils, lubricants, suspending agents, tablet disintegrating agents, and binders may also be employed. Pharmaceutical compositions for oral administration can also be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally also include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Additional pharmaceutical compositions will be evident to those skilled in the art, including formulations involving polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT/US93/00829 that describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate (Sidman et al., Biopolymers, 22:547-556 (1983), poly (2-hydroxyethyl-methacrylate) (Langer et al., J. Biomed. Mater. Res., 15:167-277, (1981); Langer et al., Chem. Tech., 12:98-105 (1982)), ethylene vinyl acetate (Langer et al., supra) or poly-D(−)-3-hydroxybutyric acid (EP 133,988). Sustained-release compositions also include liposomes, which can be prepared by any of several methods known in the art. See e.g., Eppstein et al., PNAS (USA), 82:3688 (1985); EP 36,676; EP 88,046; EP 143,949.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the polypeptide is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. Polypeptide compositions may be preferably injected or administered intravenously. Long-acting pharmaceutical compositions may be administered every three to four days, every week, or biweekly depending on the half-life and clearance rate of the particular formulation. The frequency of dosing will depend upon the pharmacokinetic parameters of the polypeptide in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

The route of administration of the pharmaceutical composition is in accord with known methods, e.g. orally, through injection by intravenous, intraperitoneal, intracerebral (intraparenchymal), intracerebroventricular, intramuscular, intraocular, intraarterial, intraportal, intralesional routes, intramedullary, intrathecal, intraventricular, transdermal, subcutaneous, or intraperitoneal; as well as intranasal, enteral, topical, sublingual, urethral, vaginal, or rectal means, by sustained release systems or by implantation devices. Where desired, the compositions may be administered by bolus injection or continuously by infusion, or by implantation device. Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In some cases, the vActRIIB polypeptides of the present invention can be delivered by implanting certain cells that have been genetically engineered, using methods such as those described herein, to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the polypeptide product(s) but prevent the destruction of the cells by the patient's immune system or by other detrimental factors from the surrounding tissues.

vActRIIB gene therapy in vivo is also envisioned wherein a nucleic acid molecule encoding vActRIIB, or a derivative of vActRIIB is introduced directly into the subject. For example, a nucleic acid sequence encoding a vActRIIB is introduced into target cells via local injection of a nucleic acid construct with or without an appropriate delivery vector, such as an adeno-associated virus vector. Alternative viral vectors include, but are not limited to, retroviruses, adenovirus, herpes simplex, virus and papilloma virus vectors. Physical transfer of the virus vector may be achieved in vivo by local injection of the desired nucleic acid construct or other appropriate delivery vector containing the desired nucleic acid sequence, liposome-mediated transfer, direct injection (naked DNA), or microparticle bombardment (gene-gun).

Uses of vActRIIB compositions

The present invention provides methods and pharmaceutical compositions for reducing or neutralizing the amount or activity of myostatin, activin A, or GDF-11 in vivo and in vitro by contacting the polypeptides with vActRIIB polypeptide. vActRIIB polypeptides have a high affinity for myostatin, activin A, and GDF-11, and are capable of reducing and inhibiting the biological activities of at least one of myostatin, activin A and GDF-11. In some embodiments, the vActRIIB polypeptides exhibit improved activity compared with the wild type ActRIIB polypeptides. This is demonstrated in the Examples below.

In one aspect, the present invention provides methods and reagents for treating myostatin-related and/or activin A related disorders in a subject in need of such a treatment by administering an effective dosage of a vActRIIB composition to the subject. As used herein the term "subject" refers to any animal, such as mammals including humans.

The compositions of the present invention are used to increase lean muscle mass as a percentage of body weight and decrease fat mass as percentage of body weight.

The disorders that can be treated by a vActRIIB composition include but are not limited to various forms of muscle wasting, as well as metabolic disorders such as diabetes and related disorders, and bone degenerative diseases such as osteoporosis. The vActRIIB compositions have been demonstrated to be effective in treating muscle wasting disorders in various disease models set forth in Example 3 below. This demonstrated in the treatment of muscle wasting in inhibin-α knockout mice, treatment of muscle wasting in colon-26 cancer cachexia models, prevention of muscular atrophy in hind limb suspension model, treatment of OXV female showing increase in lean muscle mass, decrease in fat mass and increase in bone mineral content.

Muscle wasting disorders also include dystrophies such as Duchenne's muscular dystrophy, progressive muscular dystrophy, Becker's type muscular dystrophy, Dejerine-Landouzy muscular dystrophy, Erb's muscular dystrophy, and infantile neuroaxonal muscular dystrophy. Additional muscle wasting disorders arise from chronic diseases or disorders such as amyotrophic lateral sclerosis, congestive obstructive pulmonary disease, cancer, AIDS, renal failure, organ atrophy, androgen deprivation, and rheumatoid arthritis.

Over-expression of myostatin and/or activin may contribute to cachexia, a severe muscle and fat wasting syndrome. The effectiveness of the vActRIIB polypeptides in treating cachexias in animal models is shown in Example 3 below. Cachexia also arises due to rheumatoid arthritis, diabetic nephropathy, renal failure, chemotherapy, injury due to burns, as well as other causes. In another example, serum and intramuscular concentrations of myostatin-immunoreactive protein was found to be increased in men exhibiting AIDS-related muscle wasting and was inversely related to fat-free mass (Gonzalez-Cadavid et al., PNAS USA 95: 14938-14943 (1998)). Myostatin levels have also been shown to increase in response to burns injuries, resulting in a catabolic muscle effect (Lang et al, FASEB J 15, 1807-1809 (2001)). Additional conditions resulting in muscle wasting may arise from inactivity due to disability such as confinement in a wheelchair, prolonged bed rest due to stroke, illness, spinal chord injury, bone fracture or trauma, and muscular atrophy in a microgravity environment (space flight). For example, plasma myostatin immunoreactive protein was found to increase after prolonged bed rest (Zachwieja et al. J Gravit Physiol. 6(2):11 (1999). It was also found that the muscles of rats exposed to a microgravity environment during a space shuttle flight expressed an increased amount of myostatin compared with the muscles of rats which were not exposed (Lalani et al., J. Endocrin 167 (3):417-28 (2000)).

In addition, age-related increases in fat to muscle ratios, and age-related muscular atrophy appear to be related to myostatin. For example, the average serum myostatin-immunoreactive protein increased with age in groups of young (19-35 yr old), middle-aged (36-75 yr old), and elderly (76-92 yr old) men and women, while the average muscle mass and fat-free mass declined with age in these groups (Yarasheski et al. J Nutr Aging 6(5):343-8 (2002)). In addition, myostatin has now been found to be expressed at low levels in heart muscle and expression is upregulated in cardiomyocytes after infarct (Sharma et al., J Cell Physiol. 180 (1):1-9 (1999)). Therefore, reducing myostatin levels in the heart muscle may improve recovery of heart muscle after infarct.

Myostatin also appears to influence metabolic disorders including type 2 diabetes, noninsulin-dependent diabetes mellitus, hyperglycemia, and obesity. For example, lack of myostatin has been shown to improve the obese and diabetic phenotypes of two mouse models (Yen et al. FASEB J. 8:479 (1994). It has been demonstrated in U.S. application Ser. No. 11/590,962, U.S. application publication No: 2007/0117130, AAV-ActRIIB5 vectors increases the muscle to fat ratio in an animal, in particular for obese animal models. The vActRIIB polypeptides of the present disclosure, such as SEQ ID NOS: 4, 6, 8, 10, 12, 14, 16, 20, 22, 24, 26, 28, 30, 32, 34, 36, 38, 40, 42, 44, 46, 52, 54, 56, 60, 62, 64, 66, 68, 70, 72, 87, 88, 91, 93, 95 are suitable for such uses. Therefore, decreasing fat composition by administering the compositions of the present invention will improve diabetes, obesity, and hyperglycemic conditions in animals. In addition, compositions containing the vActRIIB polypeptides may decrease food intake in obese individuals, as demonstrated in U.S. application Ser. No. 11/590,962, U.S. application publication No: 2007/0117130 for the ActRIIB5 polypeptide.

Administering the ActRIIB polypeptides of the present invention may improve bone strength and reduce osteoporosis and other degenerative bone diseases. This has been demonstrated in the OVX mouse model described below. It has been also been found, for example, that myostatin-deficient mice showed increased mineral content and density of the mouse humerus and increased mineral content of both trabecular and cortical bone at the regions where the muscles attach, as well as increased muscle mass (Hamrick et al. Calcif Tissue Int 71(1):63-8 (2002)). In addition, the vActRIIB compositions of the present invention can be used to treat the effects of androgen deprivation such as androgen deprivation therapy used for the treatment of prostate cancer.

The present invention also provides methods and compositions for increasing muscle mass in food animals by administering an effective dosage of the vActRIIB proteins to the animal. Since the mature C-terminal myostatin polypeptide is identical in all species tested, vActRIIB polypeptides would be expected to be effective for increasing muscle mass and reducing fat in any agriculturally important species including cattle, chicken, turkeys, and pigs.

The vActRIIB polypeptides and compositions of the present invention also antagonize the activity of activin A. Activin A is known to be expressed in certain types of cancers, particularly gonadal tumors such as ovarian carcinomas, and to cause severe cachexia. (Ciprano et al. Endocrinol 141 (7):2319-27 (2000), Shou et al., Endocrinol 138 (11):5000-5 (1997); Coerver et al, Mol Endocrinol 10(5):534-43 (1996); Ito et al. British J Cancer 82(8):1415-20 (2000), Lambert-Messerlian, et al, Gynecologic Oncology 74:93-7 (1999). In Example 3 below, the vActRIIB polypeptides of the present invention have been demonstrated to be effective in treating severe cachexia, reducing tumor size, and prolonging survival in inhibin-α knockout mice models and colon-26 cancer cachexia mouse models. Therefore, the compositions of the present disclosure can be used to treat conditions related to activin A overexpression, as well as myostatin expression, such as cachexia from certain cancers and the treatment of certain gonadal type tumors and melanoma.

The compositions of the present disclosure may be used alone or in combination with other therapeutic agents to enhance their therapeutic effects or decrease potential side effects. These properties include increased activity, increased solubility, reduced degradation, increased half-life, reduced toxicity, and reduced immunogenicity. Thus the compositions of the present disclosure are useful for extended treatment regimes. In addition, the properties of hydrophilicity and hydrophobicity of the compounds of the invention are well balanced, thereby enhancing their utility for both in vitro and especially in vivo uses. Specifically, compounds of the disclosure have an appropriate degree of solubility in aqueous media that permits absorption and bioavailability in the body, while also having a degree of solubility in lipids that permits the compounds to traverse the cell membrane to a putative site of action, such as a particular muscle mass.

The vActRIIB polypeptides and compositions of the present invention can be used in combination with chemotherapeutic agents for treating cancer. Chemotherapeutics can include anti-neoplastic drugs. Chemotherapeutics can also include alkylating agents, antimetabolites, plant alkaloids and terpenoids.

Alkylating agents can comprise cisplatin and caroplatin. Anti-metabolites can include purines (e.g. azathiprine or mercaptopurine) or pyrimidines. Additionally, chemotherapeutic agents can be nucleoside analogues, e.g. 5-fluorocil. Vinca alkaloids, such as vincristine or vinblastine can also be used.

Additional anti-neoplastic agents can include, for example, alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; ppipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

In addition, the vActRIIB polypeptides of the present invention are useful for detecting and quantitating myostatin, activin A, or GDF-11 in any number of assays. In general, the ActRIIB polypeptides of the present invention are useful as capture agents to bind and immobilize myostatin, activin A, or GDF-11 in a variety of assays, similar to those described, for example, in Asai, ed., Methods in Cell Biology, 37, Antibodies in Cell Biology, Academic Press, Inc., New York (1993). The polypeptides may be labeled in some manner or may react with a third molecule such as an antibody which is labeled to enable myostatin to be detected and quantitated. For example, a polypeptide or a third molecule can be modified with a detectable moiety, such as biotin, which can then be bound by a fourth molecule, such as enzyme-labeled streptavidin, or other proteins. (Akerstrom, J Immunol 135: 2589 (1985); Chaubert, Mod Pathol 10:585 (1997)).

The invention having been described, the following examples are offered by way of illustration, and not limitation.

EXAMPLES

Example 1

Expression and Purification of vActRIIB Polypeptides

The following methods were used for expressing and purifying the variant ActRIIB polypeptides.

The cDNA of the human activin type IIB receptor was isolated from a cDNA library of human testis origin (Clontech, Inc.) and cloned as described in U.S. application Ser. No. 11/590,962, U.S. application publication No: 2007/0117130.

Determination of Amino Acid Substitutions

The combined approaches of structure analysis, molecular modeling, and mass spectrometry indicated that aggregation (oligomerization) may arise in ActRIIB through intermolecular disulfide bond formation triggered by electrostatic and H-bonding interactions between nonglycosylated ActRIIB molecules. The residues 28 and 40 were determined to be involved in ActRIIB:ActRIIB interactions and not in ActRIIB interactions with its ligands.

Initially, E28 and R40 on ActRIIB-Fc were substituted with A at each position. Light scattering and mass spectrometry analyses confirmed that the fraction of fully glycosylated vActRIIB-IgG1Fc, E28A, and vActRIIB-IgG1Fc R40A was significantly increased compared to wild-type protein. E28A and R40A vActRIIB-IgG1Fc were incubated at 37° C. for 6 days, resulting little or no aggregation compared to wild type. Amino acid substitutions at positions 28 and 40 (with respect to SEQ ID NOS: 2 and 18 with the signal sequence) were made to alleviate or prevent aggregation that can occur during expression or purification of the wild-type ActRIIB (SEQ ID NOS: 2 and 18). This aggregation has been identified as structured oligomer formation during expression and non-structured aggregate generation both during expression and after protein purification.

Aggregation at different stages of the production and purification processes was determined using size exclusion chromatography according to the procedure below.

The following exemplary method was used to produce the variant ActRIIB polypeptides (vActRIIB and vActRIIB5). Polynucleotides encoding the vActRIIB, E28W (SEQ ID NO: 23) were fused to polynucleotides encoding human IgG1 Fc domain (SEQ ID NO: 82) or polynucleotides encoding human IgG2 Fc (SEQ ID NO: 84), via a hinge linker sequence (nucleotides encoding SEQ ID NO: 79) using PCR overlap extension using primers containing the mutation resulting in E28W. The full polynucleotide sequence is SEQ ID NO: 61. Double stranded DNA fragments were subcloned into pTT5 (Biotechnology Research Institute, National Research Council Canada (NRCC), 6100 Avenue Royalmount, Montréal (Québec) Canada H4P 2R2), pDSRα (described in WO/9014363) and/or derivatives of pDSRα. In other embodiments, polynucleotides encoding vActRIIB polypeptides were attached to polynucleotides encoding linker GGGGS (SEQ ID NO: 75) or multimers thereof, and or hinge linkers (such as SEQ ID NO: 79).

Transient expression of engineered vActRIIB-Fc and vActRIIB5-Fc was carried out as follows.

The engineered variants of the above two molecules were expressed transiently in serum-free suspension adapted 293-6E cells (National Research Council of Canada, Ottawa, Canada) maintained in FreeStyle™ medium (Invitrogen Corporation, Carlsbad, Calif.) supplemented with 250 µg/ml geneticin (Invitrogen) and 0.1% Pluronic F68 (Invitrogen). Transfections were performed as 1 L cultures. Briefly, the cell inoculum was grown to 1.1×106 cells/ml in a 4 L fernbach shake flask (Corning, Inc.). The shake flask culture was maintained on an Innova 2150 shaker platform (News Brunswick Scientific, Edison, N.J.) at 65 RPM which was placed in a humidified incubator maintained at 37° C. and 5% CO2. At the time of transfection, the 293-6E cells were diluted to 1.0×106 cells/ml.

The transfection complexes were formed in 100 ml FreeStyle medium. 1 mg plasmid DNA was first added to the medium followed by 3 ml of FuGene HD transfection reagent (Roche Applied Science, Indianapolis, Ind.). The transfection complex was incubated at room temperature for approximately 15 minutes and then added to the cells in the shake flask. Twenty-hour hours post transfection, 20% (w/v) of peptone TN1 (OrganoTechnie S.A., TeknieScience, QC, Canada) was added to reach a final concentration of 0.5% (w/v). The transfection/expression was performed for 4-7 days, after which the conditioned medium was harvested by centrifugation at 4,000 RPM for 60 minutes at 4° C.

Stable transfection and expression was carried out as follows. The vActRIIB-human (hu) IgG2-Fc cell lines were created by transfecting stable CHO host cells with the expression plasmids pDC323-vActRIIB (E28W)-huIgG2 Fc and pDC324-vActRIIB (E28W)-huIgG2 Fc (according to Bianchi et al., Biotech and Bioengineering, 84(4):439-444 (2003)) using a standard electroporation procedure. After transfection of the host cell line with the expression plasmids the cells were grown in serum-free selection medium without GHT for 2-3 weeks to allow for selection of the plasmid and recovery of the cells. Cell are selected until they achieved greater than 85% viability. This pool of transfected cells was then cultured in medium containing 150 nM methotrexate.

Cell Line Cloning

A cell bank was made of selected clones according to the following procedure. An amplified pool of stable transfected cells was seeded in 96-well plates, and candidate clones were evaluated for growth and productivity performance in small-scale studies. Pre-master cell banks (PMCB) of approximately 60 vials were prepared from the chosen clone. All PMCBs were tested for sterility, mycoplasma and viruses.

A vActRIIB-Fc expressing cell line was scaled up using a typical fed-batch process. Cells were inoculated into a Wave bioreactor (Wave Biotech LLC). Culture was fed three times with bolus feeds. 10 L were harvested on day 10, the remainder was harvested on day 11; both harvests underwent depth filtration followed by sterile filtration. The conditioned media was filtered through a 10 inch 0.45/0.2 micron pre filter, followed by a filtration through a 6 inch 0.2 micron filter.

Protein Purification

Approximately 5 L of the conditioned medium containing ActRIIB-Fc (both IgG1 and IgG2), ActRIIB5-Fc (both IgG1 and IgG2), and variants of these were concentrated using a 5 ft2 10K membrane tangential flow filter (Pall). The concentrated material was applied to a 5 mL Protein A High Performance Column™ (GE Healthcare) which had been equilibrated with PBS (Dulbecco's with no magnesium chloride or calcium chloride). After washing the column with the equilibration buffer until the absorbance at 280 nm (OD280) was less than 0.1, the bound protein was eluted with 0.1 M glycine-HCl, pH 2.7, and immediately neutralized with 1 M Tris-HCl, pH 8.5. The neutralized eluted pool was concentrated to a volume of 1 ml and applied to a 320 ml Sephacryl-200 column (GE Healthcare) that was equilibrated in PBS (Dulbecco's with no magnesium chloride or calcium chloride. A 4-20% SDS PAGE gels (Invitrogen) were run to determine which fractions to pool. These polypeptides were tested for activity, and degree of aggregation, as shown below.

Optionally, the polypeptides can be further purified, using for example, using a Shp-Sepharose column. Concentration was determined using OD280.

Example 2

In Vitro Activity Assays

Samples of vActRIIB polypeptides purified as described above were diluted with phosphate-buffered saline (PBS: 2.67 mM potassium chloride, 138 mM sodium chloride, 1.47 mM potassium phosphate monobasic, 8.1 mM sodium phosphate dibasic, pH 7.4) to 0.2 mg/ml, incubated at 37° C. for 6 days, then applied to MALDI-MS (matrix-assisted laser desorption/ionization mass spectrometry), SEC and/or SEC-LS analyses. The aggregation of the wt and variant polypeptides after the protein A purification step were determined using SEC or SEC-LS, and the molecular weight of the molecules confirmed using the MALDI-MS procedure described below.

Size exclusion chromatography (SEC). Experiments were performed on an Agilent 1100 HPLC system with two columns (TOSOHAAS G3000swxl, 7.8×300 mm) in tandem. 2×PBS was used as the mobile phase at 0.5 ml/minute.

Size exclusion chromatography-light scattering (SEC-LS). Experiments were performed on an Agilent 1100 HPLC system with a Superdex-200 gel filtration column (Amersham Pharmacia, Waukesha, Wis.). The samples were then passed through a Wyatt miniDawn LS laser light scattering detector and Wyatt Optilab DSP Refractometer (Wyatt Technology Co., Santa Barbara, Calif.) to determine the molecular mass. PBS was used as the mobile phase at 0.4 ml/minute.

Matrix-Assisted laser Desorption/Ionization Mass Spectrometry. Samples were mixed (1:1) with sinapinic acid and applied to MALDI-MS (Applied Biosystems Voyager System 2009). This procedure was used to check molecular weight of the molecules.

Determination of binding affinity, and IC50 values for activin and myostatin were obtained as described below.

Qualitative BIAcore® Assay. E28 and R40 were substituted respectively with other natural amino acids in fusions with IgG1 Fc as described above. These were generated with or without linkers, as shown in the Tables below. Each vActRIIB-IgG1Fc sample from conditioned media was captured on goat anti-human IgG1 Fc antibody (Jackson Immuno Research, cat#109-005-098, lot 63550) coated CMS surface. 20 nM of Activin A was injected over captured sample surfaces using BIACore2000 (BIACore Life Sciences, Piscataway, N.J.). The resulting sensorgrams were normalized to the captured RL (500 RU) of vActRIIB-IgG1Fc variants. The normalized binding response (RU) for some variants are shown in Table 2, and is further described below. Relative binding affinity for activin was also determined by Biacore measurements using conditioned media obtained from mammalian cell expression. Activin A (20 nM) was used to capture soluble receptor polypeptide in the conditioned media and measured SPR signals were normalized. Normalized SPR of +++++: >60, ++++:40-60, +++:20-40, ++:10-20, +:5-10, −:<5.

Table 1A and Table 1B summarize the results of the relative binding data. The table below shows that certain embodiments of the vActRIIB-IgG1Fc in particular bound to activin A with higher affinity than wild type, or retained comparable affinity with the wild type.

TABLE 1A

Wild-type and Engineered ActRIIB-IgG1 Fc Binding (Stable Transfectants)

| CHO | Expression | Molecule | Res28 | Res40 | Linker (SEQ ID NO: 75) | Relative activin binding |
|---|---|---|---|---|---|---|
| CHO | Stable | ActRIIB5 | none (E28) | None | none | +++ |
| CHO | Stable | ActRIIB5 | E28A | None | none | +++ |
| CHO | Stable | ActRIIB5 | E28A | None | GGGGS | +++ |
| CHO | Stable | ActRIIB5 | none | R40A | GGGGS | +++ |
| CHO | Stable | ActRIIB5 | E28W | R40A | GGGGS | ++++ |
| CHO | Stable | ActRIIB | none (E28) | None | GGGGS | ++++ |

TABLE 1A-continued

Wild-type and Engineered ActRIIB-IgG1 Fc Binding
(Stable Transfectants)

| CHO | Expression | Molecule | Res28 | Res40 | Linker (SEQ ID NO: 75) | Relative activin binding |
|---|---|---|---|---|---|---|
| CHO | Stable | ActRIIB | E28A | None | GGGGS | +++ |
| CHO | Stable | ActRIIB | E28A | None | 2(GGGGS) | +++ |
| COS | Stable | ActRIIB | none (E28) | None | none | ++ |
| COS | Stable | ActRIIB | E28A | None | none | ++ |
| COS | Stable | ActRIIB | none (E28) | R40A | none | ++ |

TABLE 1B

Wild-type and Engineered ActRIIB-IgG1 Fc Binding
(Transient Transfectants)

| CHO | Expression | Molecule | Res28 | Res40 | Linker (SEQ ID NO: 75) | Relative activin binding |
|---|---|---|---|---|---|---|
| COS | Transient | ActRIIB | E28W | none | GGGGS | +++++ |
| COS | Transient | ActRIIB | E28Y | none | GGGGS | +++++ |
| COS | Transient | ActRIIB | none (E28) | R40G | GGGGS | +++ |
| COS | Transient | ActRIIB | E28F | none | GGGGS | +++ |
| COS | Transient | ActRIIB | none (E28) | none | GGGGS | + |
| COS | Transient | ActRIIB | none (E28) | none | GGGGS | + |
| CHO | Transient | ActRIIB | E28A | none | none | − |
| COS | Transient | ActRIIB | E28T | none | GGGGS | − |
| COS | Transient | ActRIIB | E28Q | none | GGGGS | + |
| COS | Transient | ActRIIB | E28S | none | GGGGS | − |
| COS | Transient | ActRIIB | E28D | none | GGGGS | − |
| COS | Transient | ActRIIB | E28V | none | GGGGS | + |
| COS | Transient | ActRIIB | E28I | none | GGGGS | ++ |
| COS | Transient | ActRIIB | E28L | none | GGGGS | + |
| COS | Transient | ActRIIB | E28C | none | GGGGS | − |
| COS | Transient | ActRIIB | E28G | none | GGGGS | − |
| COS | Transient | ActRIIB | E28P | none | GGGGS | − |
| COS | Transient | ActRIIB | E28R | none | GGGGS | − |
| COS | Transient | ActRIIB | E28N | none | GGGGS | − |
| COS | Transient | ActRIIB | E28A | none | GGGGS | + |
| COS | Transient | ActRIIB | E28M | none | GGGGS | ++ |
| COS | Transient | ActRIIB | E28K | none | GGGGS | + |
| COS | Transient | ActRIIB | E28H | none | GGGGS | + |
| COS | Transient | ActRIIB | none (E28) | R40Q | GGGGS | + |
| COS | Transient | ActRIIB | none (E28) | R40P | GGGGS | − |

TABLE 1B-continued

Wild-type and Engineered ActRIIB-IgG1 Fc Binding (Transient Transfectants)

| CHO | Expression | Molecule | Res28 | Res40 | Linker (SEQ ID NO: 75) | Relative activin binding |
|---|---|---|---|---|---|---|
| CHO | Transient | ActRIIB | none (E28) | R40A | GGGGS | + |
| COS | Transient | ActRIIB | none (E28) | R40L | GGGGS | − |
| COS | Transient | ActRIIB | none (E28) | R40T | GGGGS | − |
| COS | Transient | ActRIIB | none (E28) | R40F | GGGGS | − |
| COS | Transient | ActRIIB | none (E28) | R40Y | GGGGS | − |
| COS | Transient | ActRIIB | none (E28) | R40V | GGGGS | − |
| COS | Transient | ActRIIB | none (E28) | R40S | GGGGS | − |
| COS | Transient | ActRIIB | none (E28) | R40M | GGGGS | + |
| COS | Transient | ActRIIB | none (E28) | R40H | GGGGS | ++ |
| COS | Transient | ActRIIB | none (E28) | R40I | GGGGS | − |
| COS | Transient | ActRIIB | none (E28) | R40C | GGGGS | − |
| COS | Transient | ActRIIB | none (E28) | R40K | GGGGS | ++ |
| COS | Transient | ActRIIB | none (E28) | R40N | GGGGS | ++ |

C2C12 Cell Based Activity Assay vActRIIB5-IgG1Fc and vActRIIB-IgG1Fc variants were generated as described above. The ability of these variants to inhibit the binding of activin A or myostatin to the activin IIB receptor was tested using a cell based activity assay as described below.

A myostatin/activin/GDF-11-responsive reporter cell line was generated by transfection of C2C12 myoblast cells (ATCC No: CRL-1772) with a pMARE-luc construct. The pMARE-luc construct is made by cloning twelve repeats of the CAGA sequence, representing the myostatin/activin response elements (Dennler et al. EMBO 17: 3091-3100 (1998)) into a pLuc-MCS reporter vector (Stratagene cat #219087) upstream of the TATA box. The C2C12 cells naturally express activin receptor IIB on their cell surface. When myostatin/activinA/GDF-11 binds the cell receptors, the Smad pathway is activated, and phosphorylated Smad binds to the response element (Macias-Silva et al. Cell 87:1215 (1996)), resulting in the expression of the luciferase gene. Luciferase activity was then measured using a commercial luciferase reporter assay kit (cat #E4550, Promega, Madison, Wis.) according to manufacturer's protocol. A stable line of C2C12 cells that has been transfected with pMARE-luc (C2C12/pMARE) was used to measure activity according to the following procedure. Reporter cells were plated into 96 well cultures. Screening using dilutions of the wild type and variant ActRIIB-IgG1 Fc fusions constructed as described above was performed with the concentration fixed at 4 nM activin. Activin A was pre-incubated with the receptors at several concentrations. Activin activity was measured by determining the luciferase activity in the treated cultures. The IC50 values were determined for each polypeptide. These are shown in Table 2. The same procedure was followed for ActRIIB-huIgG2 Fc fusions produced as described above for the determination of myostatin. Protein A purified wt and variants were used in the determination of IC50 values for myostatin using the same methodology. For this determination, the polypeptides were pre-incubated with 4 nM myostatin. In addition, the degree of aggregation was determined using the procedures described above. These values are given in Table 3 below.

Out of the set of ActRIIB5-IgG1 Fc variants that are listed in Table 1A, several ActRIIB-IgG1 Fc variants and three ActRIIB5-IgG1 Fc variants together with the wild type polypeptides were further purified and analyzed by SPR (surface plasmon resonance) at 20 nM activin A. Table 2 shows the SPR binding affinity of selected vActRIIB-IgG1 Fc polypeptides for activin. Activin A (20 nM) was used to capture vActRIIB polypeptides in the samples and measured SPR signals were normalized. IC50 values were obtained from cell-based activin inhibition assays described above. Standard errors are less than 10% for all results.

TABLE 2

| Variant | SPR normalized RU (RU = response unit) | $IC_{50}$ (nM) Activin |
|---|---|---|
| ActRIIB-IgG1Fc (SEQ ID NO: 58) | 35 | 8.20 |
| vActRIIB-IgG1Fc, E28A (SEQ ID NO: 60) | 20 | 25.30 |
| vActRIIB-IgG1Fc, E28W (SEQ ID NO: 62) | 128 | 2.07 |
| vActRIIB-IgG1Fc, E28Y (SEQ ID NO: 64) | 115 | 2.10 |
| vActRIIB-IgG1Fc, R40G (SEQ ID NO: 66) | 18 | |
| ActRIIB5-IgG1Fc (SEQ ID NO: 68) | 37 | |
| vActRIIB5-IgG1Fc, E28A (SEQ ID NO: 70) | 8 | |
| vActRIIB5-IgG1Fc, E28W (SEQ ID NO: 72) | 45 | 16.86 |

As shown above in Table 2 above, the IC50 value of vActRIIB-IgG1Fc (E28W) for blocking activin was 2.07 nM and the IC50 value of vActRIIB-IgG1Fc (E28Y) was 2.1 nM compared to wild type. Furthermore, the E28W and E28Y variants of vActRIIB-IgG1Fc were stable and not aggregated once purified.

The IC50 value in a myostatin blocking cell based assay was determined for additional variant polypeptides as well. These variants were the mature truncated vActRIIB polypeptides lacking the signal sequence and the first six amino acids of the N-terminal. These sequences are shown in Table 3.

Table 3 shows the percent aggregation of the protein after protein A purification, and the IC50 value with respect to myostatin. It can be seen that the percent aggregation is much less for the variant polypeptides compared with the wild type. Similar results were obtained for mature truncated vActRIIB polypeptides without the signal sequence and the N-terminal four amino acids, and with identical substitutions as shown below.

TABLE 3

| ActRIIB-Fc Variant | ActRIIB | Linker-Hinge | IgG2 Fc | % aggregation | $IC_{50}$ (nM) for myostatin cell based assay |
|---|---|---|---|---|---|
| hActRIIB-$hIgG_2Fc$ (SEQ ID NO: 89) | ETRE[28]CIYYNANWELERTNQSGLERCEGEQDKRLHCYASWRNSSGTIELVKKGCWLDDFNCYDRQECVATEENPQVYFCCCEGNFCNERFTHLPEAGGPEVTYEPPPTAPT (SEQ ID NO: 86) | GGGGSVECPPCP (SEQ ID NO: 79) | APPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPEIKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK (SEQ ID NO: 80) | 13% | 1.1 |
| hActRIIB-$hIgG_2Fc$ (E28W) (SEQ ID NO: 91) | ETRW[28]CIYYNANWELERTNQSGLRCEGEQDKRLHCYASWRNSSGTIELVKKGCWLDDFNCYDRQECVATEENPQVYFCCCEGNFCNERFTHLPEAGGPEVTYEPPPTAPT (SEQ ID NO: 87) | GGGSVECPPCP (SEQ ID NO: 79) | APPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK (SEQ ID NO: 80) | 2% | 0.9 |
| hActRIIB-$hIgG_2Fc$ (E28Y) (SEQ ID NO: 93) | ETRY[28]CIYYNANWELERTNQSGLERCEGEQDKRLHCYASWRNSSGTIELVKKGCWLDDFCYDRQECVATEENPQVYFCCCEGNFCNERFTHLPEAGGPEVTYEPPPTAPT (SEQ ID NO: 88) | GGGGSVECPPCP (SEQ ID NO: 79) | APPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK (SEQ ID NO: 80) | 4% | 1.0 |

Table 4 identifies the sequences corresponding to SEQ ID NOS:1-99 in the sequence listing.

TABLE 4

| SEQ ID NO | Description |
|---|---|
| 1 | ActRIIB5 extracellular domain, polynucleotide |
| 2 | ActRIIB5 extracellular domain, polypeptide |
| 3 | vActRIIB5 E28A polynucleotide |
| 4 | vActRIIB5 E28A polypeptide |
| 5 | vActRIIB5 E28A and R40A polynucleotide |
| 6 | vActRIIB5 E28A and R40A polypeptide |
| 7 | vActRIIB5 E28W polynucleotide |
| 8 | vActRIIB5 E28W polypeptide |
| 9 | vActRIIB5 E28Y polynucleotide |
| 10 | vActRIIB5 E28Y polypeptide |
| 11 | vActRIIB5 E28X wherein X is A, F, Q, V, I, L, M, K, H, W or Y polynucleotide |
| 12 | vActRIIB5 E28X wherein X is A, F, Q, V, I, L, M, K, H, W or Y polypeptide |
| 13 | vActRIIB5 E28X and R40X, wherein X(28) is A, F, Q, V, I, L, M, K, H, W or Y wherein X(40) is A, G, Q, M, H, K or N polynucleotide |
| 14 | vActRIIB5 E28X and R40X, wherein X(28) is A, F, Q, V, I, L, M, K, H, W or Y wherein X(40) is A, G, Q, M, H, K or N polypeptide |
| 15 | vActRIIB5 R40X wherein X is G, Q, M, H, K or N polynucleotide |
| 16 | vActRIIB5 R40X wherein X is G, Q, M, H, K or N polypeptide |
| 17 | ActRIIB extracellular domain, polynucleotide |
| 18 | ActRIIB extracellular domain, polypeptide |
| 19 | vActRIIB E28A polynucleotide |
| 20 | vActRIIB E28A polypeptide |
| 21 | vActRIIB E28A and R40A polynucleotide |
| 22 | vActRIIB E28A and R40A polypeptide |
| 23 | vActRIIB E28W polynucleotide |
| 24 | vActRIIB E28W polypeptide |
| 25 | vActRIIB E28Y polynucleotide |
| 26 | vActRIIB E28Y polypeptide |
| 27 | vActRIIB E28X wherein X is A, F, Q, V, I, L, M, K, H, W or Y polynucleotide |
| 28 | vActRIIB E28X wherein X is A, F, Q, V, I, L, M, K, H, W or Y polypeptide |
| 29 | vActRIIB E28X and R40X, wherein X(28) is A, F, Q, V, I, L, M, K, H, Y or W wherein X(40) is A, G, Q, M, H, K or N polynucleotide |
| 30 | vActRIIB E28X and R40X, wherein X(28) is A, F, Q, V, I, L, M, K, H, Y or W wherein X(40) is A, G, Q, M, H, K or N polypeptide |
| 31 | vActRIIB R40X wherein X is G, Q, M, H, K or N polynucleotide |
| 32 | vActRIIB R40X wherein X is G, Q, M, H, K or N polypeptide |
| 33 | vActRIIB R64A, E28A polynucleotide |
| 34 | vActRIIB R64A, E28A polypeptide |
| 35 | vActRIIB R64A, E28A and R40A polynucleotide |
| 36 | vActRIIB R64A, E28A and R40A polypeptide |
| 37 | vActRIIB R64A, E28W polynucleotide |
| 38 | vActRIIB R64A, E28W polypeptide |
| 39 | vActRIIB R64A, E28Y polynucleotide |
| 40 | vActRIIB R64A, E28Y polypeptide |
| 41 | vActRIIB R64A, E28X wherein X is A, F, Q, V, I, L, M, K, H, Y or W polynucleotide |
| 42 | vActRIIB R64A, E28X wherein X is A, F, Q, V, I, L, M, K, H, Y or W polypeptide |
| 43 | vActRIIB R64A, E28X and R40X, wherein X(28) is A, F, Q, V, I, L, M, K, H, W or Y wherein X(40) is A, G, Q, M, H, K or N polynucleotide |
| 44 | vActRIIB R64A, E28X and R40X, wherein X(28) is A, F, Q, V, I, L, M, K, H, W or Y wherein X(40) is A, G, Q, M, H, K or N polypeptide |
| 45 | vActRIIB R64A, R40X wherein X is G, Q, M, H, K or N polynucleotide |
| 46 | vActRIIB R64A, R40X wherein X is G, Q, M, H, K or N polypeptide |
| 47 | Sequence Accession NP_001097 (Wild type ActRIIB) polypeptide |
| 48 | Sequence Accession NM_002192 (Activin A) polypeptide |
| 49 | Sequence Accession AAB86694 (Myostatin) polypeptide |
| 50 | Sequence Accession O95390 (GDF-11) polypeptide |
| 51 | vActRIIB5 E28X and R40X, wherein X = any amino acid polynucleotide |
| 52 | vActRIIB5 E28X and R40X, wherein X = any amino acid polypeptide |
| 53 | vActRIIB E28X and R40X, wherein X = any amino acid polynucleotide |
| 54 | vActRIIB E28X and R40X, wherein X = any amino acid polypeptide |
| 55 | vActRIIB R64A, E28X and R40X, wherein X = any amino acid polynucleotide |
| 56 | vActRIIB R64A, E28X and R40X, wherein X = any amino acid polypeptide |
| 57 | ActRIIB-IgG1Fc mature polynucleotide |
| 58 | ActRIIB-IgG1Fc mature polypeptide |
| 59 | vActRIIB-IgG1Fc E28A (E10A) mature polynucleotide |
| 60 | vActRIIB-IgG1Fc E28A (E10A) mature polypeptide |
| 61 | vActRIIB-IgG1Fc E28W (E10W) mature polynucleotide |
| 62 | vActRIIB-IgG1Fc E28W (E10W) mature polypeptide |
| 63 | vActRIIB-IgG1Fc E28Y (E10Y) mature polynucleotide |
| 64 | vActRIIB-IgG1Fc E28Y (E10Y) mature polypeptide |
| 65 | vActRIIB-IgG1Fc R40G (R22G) mature polynucleotide |
| 66 | vActRIIB-IgG1Fc mature R40G (R22G) mature polypeptide |
| 67 | vActRIIB5-IgG1Fc mature polynucleotide |
| 68 | vActRIIB5-IgG1Fc mature polypeptide |
| 69 | vActRIIB5-IgG1Fc E28A (E10A) mature polynucleotide |
| 70 | vActRIIB5-IgG1Fc E28A (E10A) mature polypeptide |
| 71 | vActRIIB5-IgG1Fc E28W (E10W) mature polynucleotide E10W |
| 72 | vActRIIB5-IgG1Fc E28W (E10W) mature polypeptide E10W |
| 73 | Signal sequence shown in FIGS. 1 and 2 |
| 74 | Alternative signal sequence |
| 75 | Linker |
| 76 | Complete hinge regions for IgG1 |
| 77 | Complete hinge region for IgG2 |
| 78 | Complete hinge region for IgG4 |
| 79 | Hinge linker |
| 80 | IgG2Fc polypeptide |
| 81 | IgG2Fc nucleotide degenerate |
| 82 | IgG1Fc polypeptide |
| 83 | IgG1Fc polynucleotide |
| 84 | IgG4Fc polypeptide |
| 85 | IgG4Fc polynucleotide-degenerate |
| 86 | ActRIIB mature truncated wt polypeptide |
| 87 | vActRIIB (E4W) (E28W) mature truncated polypeptide |
| 88 | vActRIIB (E4Y) (E28Y) mature truncated polypeptide |
| 89 | ActRIIB-IgG2Fc mature truncated polypeptide |
| 90 | ActRIIB-IgG2Fc mature truncated polynucleotide degenerate |
| 91 | vActRIIB-IgG2Fc (E4W) E28W mature truncated polypeptide |
| 92 | vActRIIB-IgG2Fc (E4W) E28W mature truncated polynucleotide |
| 93 | vActRIIB-IgG2Fc (E4Y) E28Y mature truncated polypeptide |
| 94 | vActRIIB-IgG2Fc (E4Y) E28Y mature truncated polynucleotide |
| 95 | vActRIIB-IgG2Fc (E4A) E28A mature truncated polypeptide |
| 96 | vActRIIB-IgG2Fc (E4A) E28A mature truncated polynucleotide degenerate |
| 97 | vActRIIB-IgG2Fc (E4X) E28X-wherein X is A, F, Q, V, I, L, M, K, H, W or Y mature truncated polypeptide |
| 98 | FIG. 1-ActRIIB-IgG1Fc |
| 99 | FIG. 2-ActRIIB5-IgG1Fc |

Example 3

In Vivo Treatments Using vActRIIB

All of the following animal studies were carried out using the mature truncated vActRIIB-IgG2 Fc (E28W) polypeptide, (SEQ ID NO: 91), according to the procedures described below.

Treatment of Muscle Wasting in Inhibin-α Deficient Mice

Inhibin-α is a naturally occurring inhibitor of activin A. Mice lacking inhibin-α show significantly elevated activin A levels in circulation and suffer from a lethal wasting syndrome which is associated with the spontaneous formation of tumors such as ovarian, testicular cancers and adrenal cancers (Matzuk et al., PNAS 91(19):8817-21 (1994), Cipriano et al. Endocrinology 121(7): 2319-27 (2000), Matzuk et al., Nature 360(6402):313-9 (1992)). For the following experiments, inhibin-α knockout mice (C57BL/6J) were obtained from Charles River Laboratories. The effects of the vActRIIB-IgG2 Fc E28W (SEQ ID NO: 91) (hereinafter E28W, or E28W polypeptide, or soluble receptor E28W) on body weight and muscle mass was examined in inhibin-α knockout mice. A 14-day single-injection study in 8-week-old male inhibin-α knockout mice was performed. At 8 weeks of age, the male inhibin-α knockout mice had lost more than 25% of body weight compared to age-matched wild-type littermate control mice. 5 of the knockout mice were given a single subcutaneous injection of E28W (30 mg/kg), while 5 knockout mice were subcutaneously administered an equal volume of PBS (vehicle) on day 0. As a baseline control, 5 age-matched wild-type mice were administered a single subcutaneous injection of vehicle on day 0. The mice were weighed at day 0, day 7 and day 14. At the end of day 14, all the mice were sacrificed, and their lean carcass weights and calf muscle mass were analyzed via necropsy. Over the 14-day study period, the average body weight of the vehicle-treated knockout mice dropped by approximately 1.1 g from 22.5 g on day 0 to 21.4 g on day 14. In contrast, the average body weight of the E28W-treated knockout mice showed a dramatic gain by 11 g from 22.1 g on day 0 to 33.1 g on day 14. Terminal necropsy analysis revealed that the E28W polypeptide virtually doubled the lean carcass weight and calf muscle mass in the inhibin-α knockout mice, as shown below. The average lean carcass weight of the E28W-treated knockout mice was approximately 14.9 g compared with approximately 8.0 g for the vehicle-treated knockout mice, and approximately 12.1 g for vehicle-treated wild-type control mice. The average calf muscle weight (from both legs) of the E28W-treated knockout mice was approximately 426 mg compared with approximately 209 mg for the vehicle-treated knockout mice, and approximately 324 mg for vehicle-treated wild-type control mice. These results demonstrate the effectiveness of the E28W polypeptide for the treatment of disease states of weight loss and muscle wasting and are summarized in the Table below.

|  | WT plus Vehicle | KO plus Vehicle | KO plus E28W |
| --- | --- | --- | --- |
| Body Weight | 28.64 +/− 1.11 | 21.36 +/− 0.99* | 33.10 +/− 1.56 *# |
| Lean Carcass (g) | 12.07 +/− 0.36 | 8.00 +/− 0.29* | 14.90 +/− 0.77 *# |
| Calf Muscle (g) | 0.324 +/− 0.014 | 0.209 +/− 0.012* | 0.426 +/− 0.024 *# |

*$P < 0.05$ vs. WT + Veh; #$P < 0.05$ vs. KO + Veh.

Figure 3B:
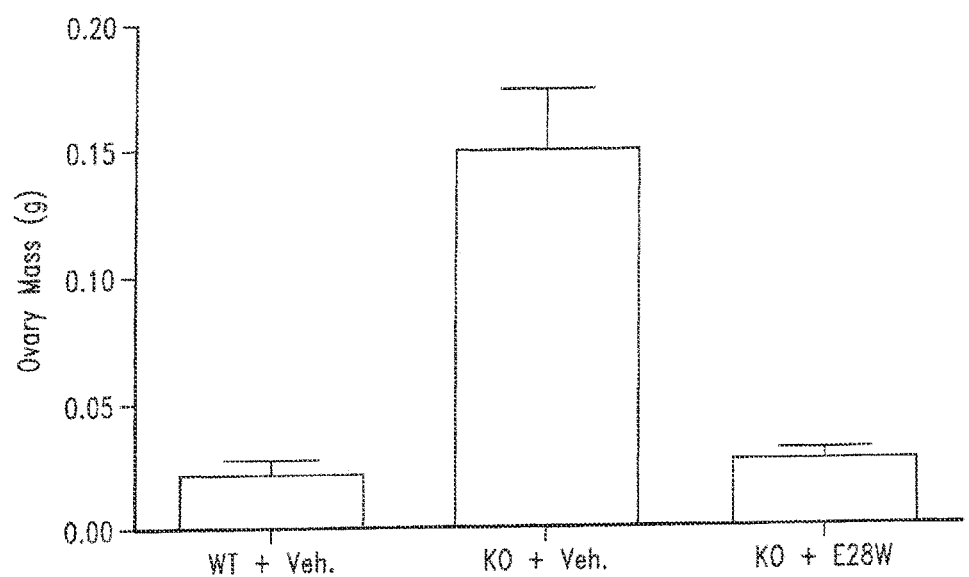

The effects of the administration of the E28W polypeptide on the rates of formation of testicular and ovarian tumors were examined in male and female inhibin-α KO mice, respectively. In this study, 11 of the inhibin-α knockout mice, including 8-week-old males (n=5) and 9-week-old females (n=6), were treated with a single subcutaneous injection of E28W (30 mg/kg), while another 11 of the inhibin-α knockout mice, including age-matched males (n=5) and females (n=6) received a single injection of an equal volume of PBS (vehicle). In addition, 11 of the wild-type littermate control mice, including age-matched males (n=5) and females (n=6) were administered a single injection of vehicle. Two weeks after the treatment, the mice were sacrificed and subjected to necropsy to examine the rates of formation of visually identifiable testicular and ovarian tumors. It was observed that 10 of the 11 vehicle-treated knockout mice developed identifiable tumors. Specifically, testicular and ovarian tumor formations were found in 5 out of the 5 males and 5 out of the 6 females examined, respectively. The sizes of these tumors were found to be 2-3 fold larger than the corresponding normal testis or ovary in wild-type control mice. This is shown in FIG. 3. Only 10% (1 out of 11) of the E28W-treated inhibin-α knockout mice showed visible tumor formation. Specifically, in females, 1 out of 6 of the E28W-treated knockout mice developed an identifiable ovarian tumor, whereas 5 out of the 6 of the untreated female knockouts had little or no change in the size or gross morphology of the ovary compared with age-matched wild-type controls. 5 out of 5 of the E28W-treated male knockout mice showed no visible tumors with little or no change in the size or gross morphology of the testis in comparison to the age-matched wild-type controls. These results demonstrate that E28W administration was effective in reducing the formation of testicular and ovarian tumors in the inhibin-α KO mice, and also in reducing the formation of melanoma s, suggesting a clinical utility for the soluble receptor therapy in cancer treatment.

The effectiveness of the E28W polypeptide in treating anorexia was examined in male inhibin-α knockout mice. In this study, food consumption in the inhibin-α knockout mice (n=5) was significantly reduced compared to that of the age-matched wild-type mice (n=10). It was observed that the food intake of the E28W treated inhibin-α knockout mice was significantly increased during a 3-week period examined. The average weekly food intake in the E28W-treated knockout mice increased to a level slightly higher than that in the age-matched wild-type control mice, and was about 50% greater than the average weekly food intake of the knockout mice treated with the vehicle. Thus, the data show that the E28W treatment was highly effective in ameliorating anorexia in the inhibin-α KO mice.

Figure 4A:
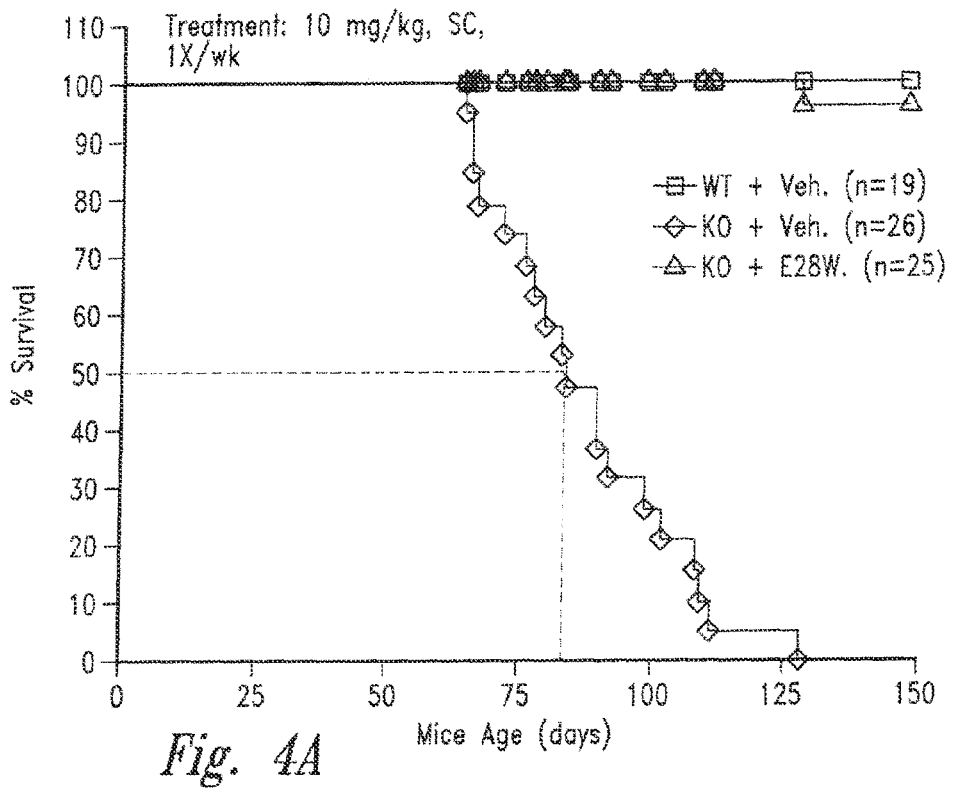
FIGS. 4A-4B.
Figure 4B:
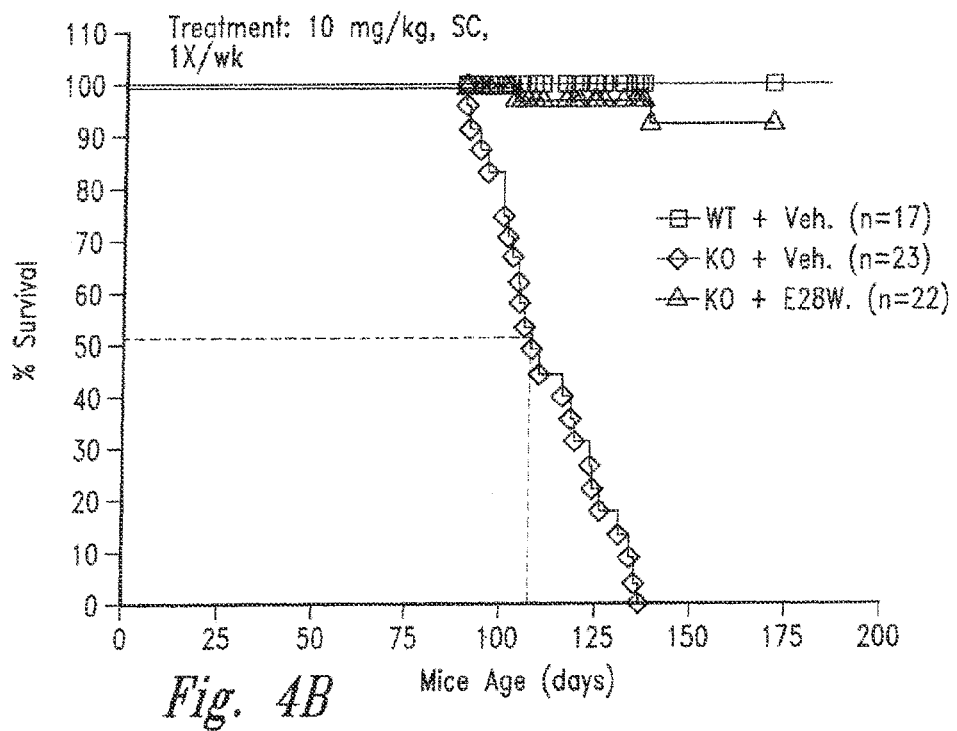

The effect of the E28W treatment on survival was examined in male and female inhibin-α KO mice, respectively. For males, 25 inhibin-α KO mice around 50 days of age were administered the E28W polypeptide (10 mg/kg/wk, SC), while 26 age-matched inhibin-α KO mice received vehicle (PBS). 19 aged-matched wild-type male mice received vehicle and were used as baseline control. The vehicle-treated knockout mice started dying on day 15 of the study (around 65 days of age). By day 34 of the experiment (around 84 days of age), 50% of the vehicle-treated knockout mice had died, and by day 78 (around 128 days of age), 100% of them had died. In contrast, none of the 25 knockout mice treated with the E28W polypeptide, or of the 19 wild-type control mice treated with vehicle, died before day 78 of the study (around 128 days of age). In the E28W-treated knockout mice, 1 out of 25 died on day 78 of the study (around 128 days of age) and 24 out of 25 survived beyond day 100 (around 150 days of age). No vehicle-treated wild type mice died during the 100-day study period. Similar survival results were obtained in female inhibin-α KO mice. 22 of female inhibin-α KO mice of approximately 50 days of age were treated with E28W (10 mg/kg/wk, SC), while 23 female inhibin-α KO mice of the same age were treated with PBS (vehicle). In the meantime, 17 of wild type female control mice were treated with vehicle. The vehicle-treated female knockout mice began dying on day 40 of the study (around 90 days of age). By day 58 of the experiment (around 108 days of age), 50% of the vehicle-treated female knockout mice had died, and by day 86 of the study (about 136 days of age) 100% of them had died. In contrast, only about 5% (1 out of 22) of the E28W-treated female knockout mice had died while about 90% (20 out of 22) survived beyond day 120 of the study (about 170 days of age). No vehicle-treated wild type mice died during the 120-day study period. Therefore, the data demonstrate that the E28W polypeptide therapy is effective in dramatically prolonging the survival of both male and female inhibin-α knockout mice. A schematic plot of the survival curves for both the male and female knockout mice is provided in FIG. 4.

Treatment of Muscle Wasting in Colon-26 Tumor Bearing Mice

Figure 5:
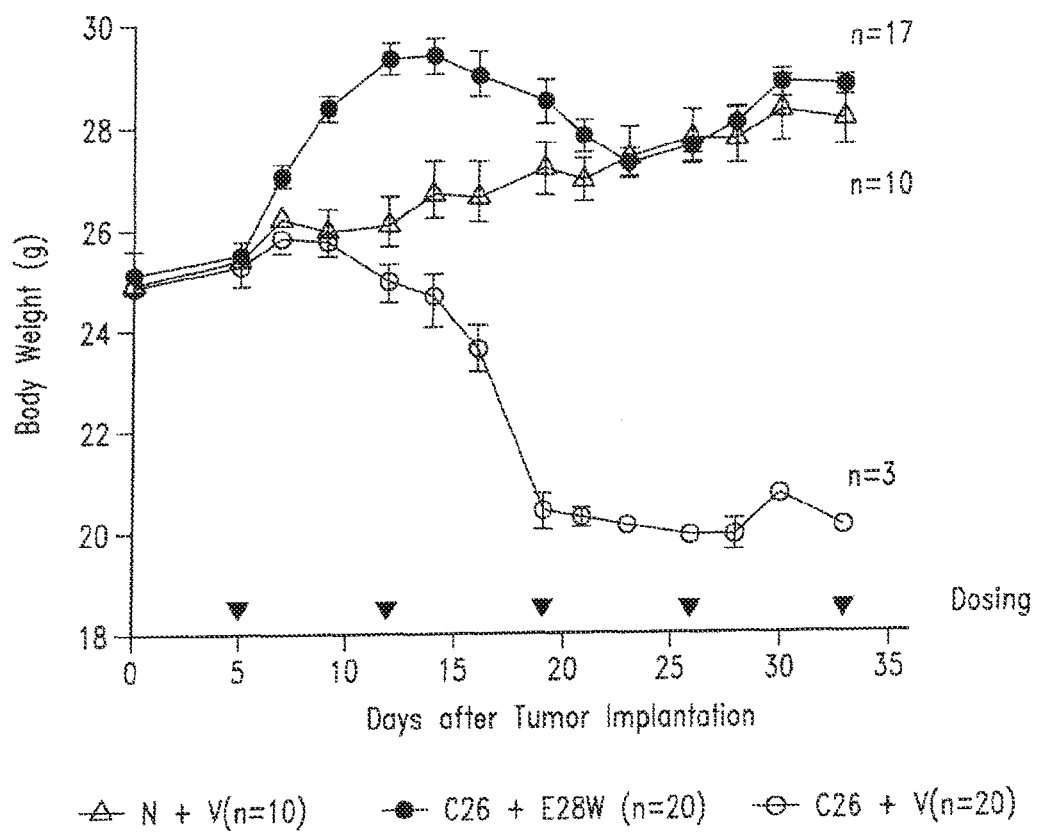
FIG. 5.

Colon-26 tumor bearing mice is a widely used preclinical animal model for studying cancer cachexia (Fujita et al., Int J Cancer 68(5):637-43 (1996), Kwak et al., Cancer Research 64(22):8193-8 (2004)). The effect of E28W polypeptide on body weight change, muscle mass and survival rate were studied in the tumor-bearing mice. Colon-26 (C-26) tumor cells were subcutaneously implanted into 40 10-week-old, male CDF1 mice at 0.5×106 cells per mouse. The tumor implantation was performed on day 0. Beginning on day 5 after tumor implantation, twenty C-26 mice were treated weekly with a subcutaneous injection of 10 mg/kg vActRIIB IgG2 Fc E28W (SEQ ID NO: 91), while twenty C-26 mice were treated with a vehicle (PBS). At the same time, 10 age and weight matched normal mice were treated with a vehicle (PBS) only. Body weight and food intake were determined 3 times per week. The tumor-bearing mice were inspected twice daily for survival. Tumor sizes were measured using calipers (Ultra-Cal IV IP65 electronic caliper, Fred V Fowler Co. Boston Mass.) connected to a PC computer and values were automatically recorded to a worksheet in a Microsoft Excel data file. As shown in FIG. 5, two weeks after tumor implantation, the mice bearing C-26 tumors developed severe cachexia and lost their body weight dramatically. E28W treatment effectively mitigated the body weight loss in the tumor-bearing mice. The average body weight of the tumor-bearing mice treated with E28W was significantly higher than that of the tumor-bearing mice treated with vehicle (p<0.001, from day 7 to day 33 after tumor-inoculation. Unpaired T test, Graph pad Software Inc. San Diego Calif.).

Figure 6:
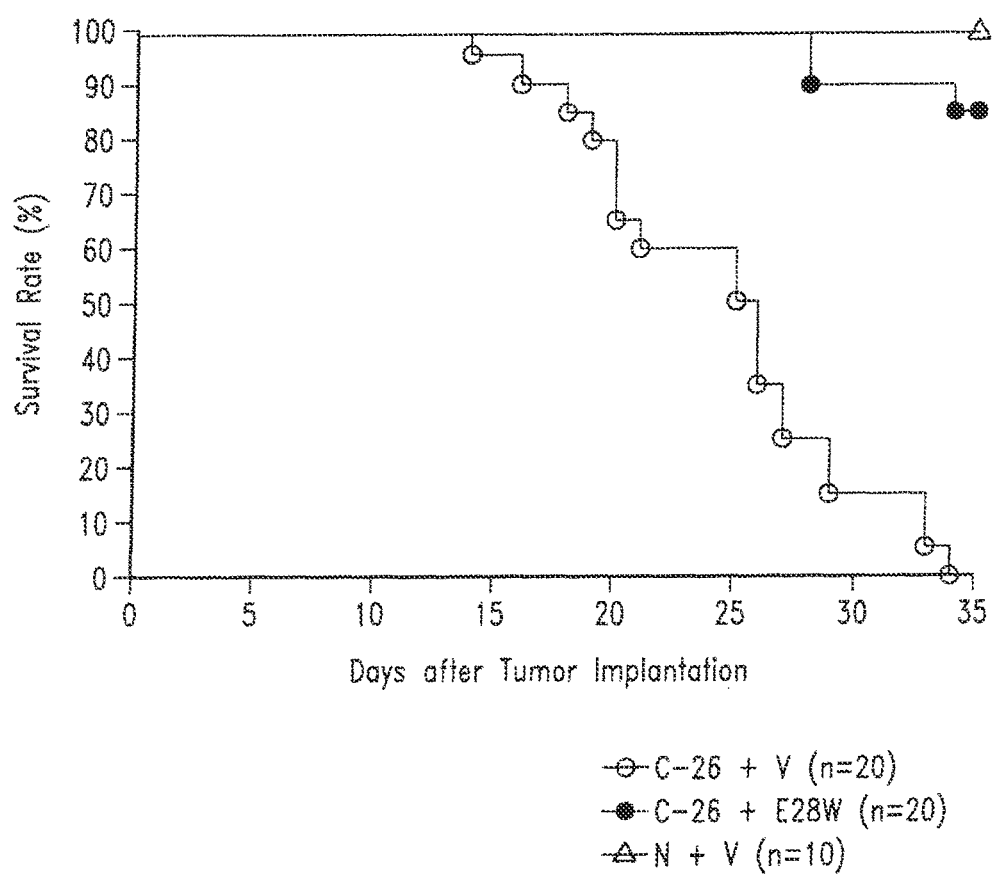
FIG. 6.

There was no difference in tumor size between the E28W polypeptide treated and vehicle treated groups indicating that the treatment had no effect on C-26 tumor growth. Terminal necropsy analysis showed that the average lean carcass mass and calf muscle weight of the E28W-treated C-26 tumor-bearing mice were significantly higher than those of the tumor-bearing mice treated with vehicle (p<0.001 for both lean carcass and calf muscle). The effect of the E28W on survival of the C-26 tumor-bearing mice is shown in FIG. 6. The vehicle treated mice began dying at about day 14 post tumor implantation. At day 35 post tumor implantation, all 20 vehicle treated C-26 tumor-bearing mice died; however 17 out of 20 C-26 tumor-bearing mice treated with E28W were still surviving. Thus, the E28W treatment led to a significant prolongation of survival of the C-26 tumor-bearing mice (p<0.0001, chi-square test). Therefore, the E28W polypeptide was not only effective in maintaining body weight and muscle mass but also in prolonging the survival of the C-26 tumor-bearing mice.

Treatment of Hindlimb Suspension Mice

The hindlimb suspension mouse model was used to examine the effect of the vActRIIB-IgG2 Fc E28W (SEQ ID NO: 91) on muscle mass in disuse state. Hindlimb suspension procedure is essentially the same as previously reported by Carlson C J et al (Carlson C J, Booth F W and Gordon S E: Am J Physiol Regul Integr Comp Physiol. 277: R601-RR606, 1999). Nine-week-old female C57BL/6 mice were used for the study. A total of 60 mice were divided into three groups as follows: 1. Non-suspended baseline control group (20 mice) treated with vehicle (PBS), 2. Hindlimb suspension group (20 mice) treated with vehicle, and 3. Hindlimb suspension mice group (20 mice) treated with vActRIIB-IgG2 Fc, E28W. Specifically, a single SC injection of either 30 mg/kg of vActRIIB-IgG 2 Fc E28W or vehicle was given to the above described groups respectively, at the time of the initiation of hindlimb suspension. Body weight changes were measured longitudinally 2-3 times per week. 5 mice from each group were sacrificed at the following 4 different time points: day 1, day 3, day 7 and day 14. Calf muscle weights were determined via necropsy.

As shown in the Table below, hindlimb suspension led to a significant loss in body weight up to 10%. Treatment of the hindlimb suspended mice with vActRIIB-IgG2 Fc E28W led to a significant body weight gain to a level higher than either the vehicle treated hindlimb suspension group or the non-suspended baseline control group as analyzed by ANOVA measurement. During the two-week study period, the average body weight gain of the vActRIIB-IgG2 Fc E28W (SEQ ID NO: 91) treatment group was 12.6% in comparison to the 0.2% drop in the vehicle-treated suspension group and 4.8% weight gain in the non-suspended baseline control group, respectively. Time-course necropsy results showed that the hindlimb muscle mass changed in parallel to the body weights. Treatment of the suspended mice with vActRIIB-IgG2 Fc (E28W) completely mitigated the muscle loss. Therefore, the results of this experiment show that E28W is effective in the treatment of muscle atrophy associated with disuse.

| Group/days (body weight change %) | day 3 (%) | day 7 (%) | day 14 (%) |
| --- | --- | --- | --- |
| Non-HS + PBS | 2.4% | 2.9% | 4.8% |
| HS + vehicle | −10.0% | −3.0% | −0.2% |
| HS + E28W, 30 mg/ml | −9.7% | 2.1% | 12.6% |

Treatment of OVX Mice

Ovariectomized female C57Bl6 mice (OVX) are considered to be a model for female hypogonadism and osteoporesis. 24 female C57Bl6 mice were ovariectomized at age 3 months and allowed to recover for 3 months. At age 6 months, 24 OVX mice as well as 24 age-matched sham operated control C57Bl6 mice were measured for longitudinal changes in body weight, muscle, and fat mass by NMR and bone mass (PIXImus—GE LUNAR Corporation) over a 3 month treatment period. At the end of the period, the animals were sacrificed, and the bone tissues harvested during terminal necropsy and subjected to Faxitron X-ray and microCT (Faxitron X-ray Corporation and GE Medical system) analysis. It was demonstrated to the E28W variant receptor (SEQ ID NO: 91) was effective at increasing body weight, specifically lean skeletal muscle mass, and bone mass, while decreasing fat content of the mice to the level seen in non-ovariectomized mice. Specifically, over a 12 week period, lean muscle mass was increased from 20 g to 27.0 g for OVX mice treated with E28W, compared with 20 g to 27.5 g for sham operated mice treated with E28W, compared with almost no increase in lean muscle mass for OVX plus vehicle or sham plus vehicle (about 19 grams for OVX plus vehicle and about 20 g for wild type plus vehicle). In the same study, OVX mice treated with E28W showed reduced fat mass from 8 g average per animal to about 4 g average per animal, comparable with the sham operated animals, by the end of the 12 week study. The OVX mice treated with the vehicle, in contrast, did not lose fat mass at any time during the study. Finally, bone mass was increased in the OVX mice treated with E28W compared with vehicle treated OVX mice. Analysis of femur/tibia BMC (Bone mineral content) of the dissected bone harvested during terminal necropsy was determined by pQCT analysis (Peripheral Quantitative Computed Tomography). The OVX mice treated with E28W increased BMC of about 0.045 g/cm to about 0.055 g/cm at the end of the 12 week study, which is comparable to the final BMC of sham operated vehicle treated animals. The OVX mice treated with vehicle showed about the same BMC of 0.045 g/cm at the end of the 12 week study. The E28W treated wild type mice showed an increase of BMC from about 0.054 g/cm to about 0.065 g/cm at the end of the 12 week study. These studies demonstrate the effectiveness of the E28W polypeptide as potential treatments of frailty, osteoporesis, and obesity in aging.

Example 4

Treatment of Cancer with sActRIIB (E28W—SEQ ID No. 91)

Figure 7A:
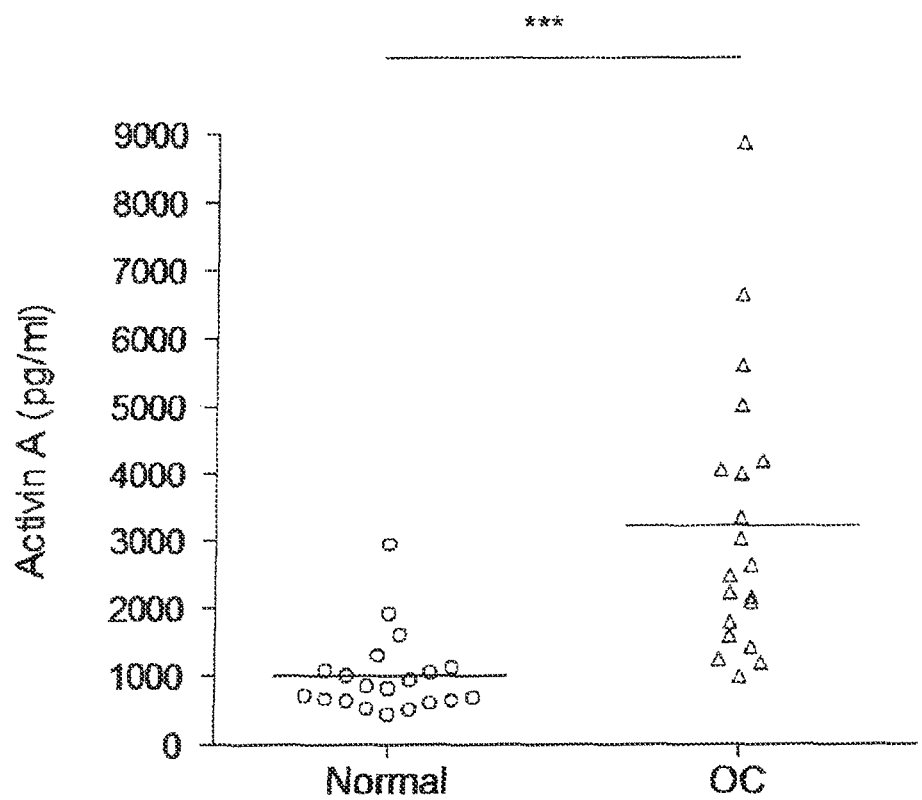
FIGS. 7A-7D show activin levels in mice (FIG. 7A) and the effect of sActRIIB (E28W) on ovarian cancer (OC) (FIGS. 7A-7D) in KO mice.
Figure 7B:
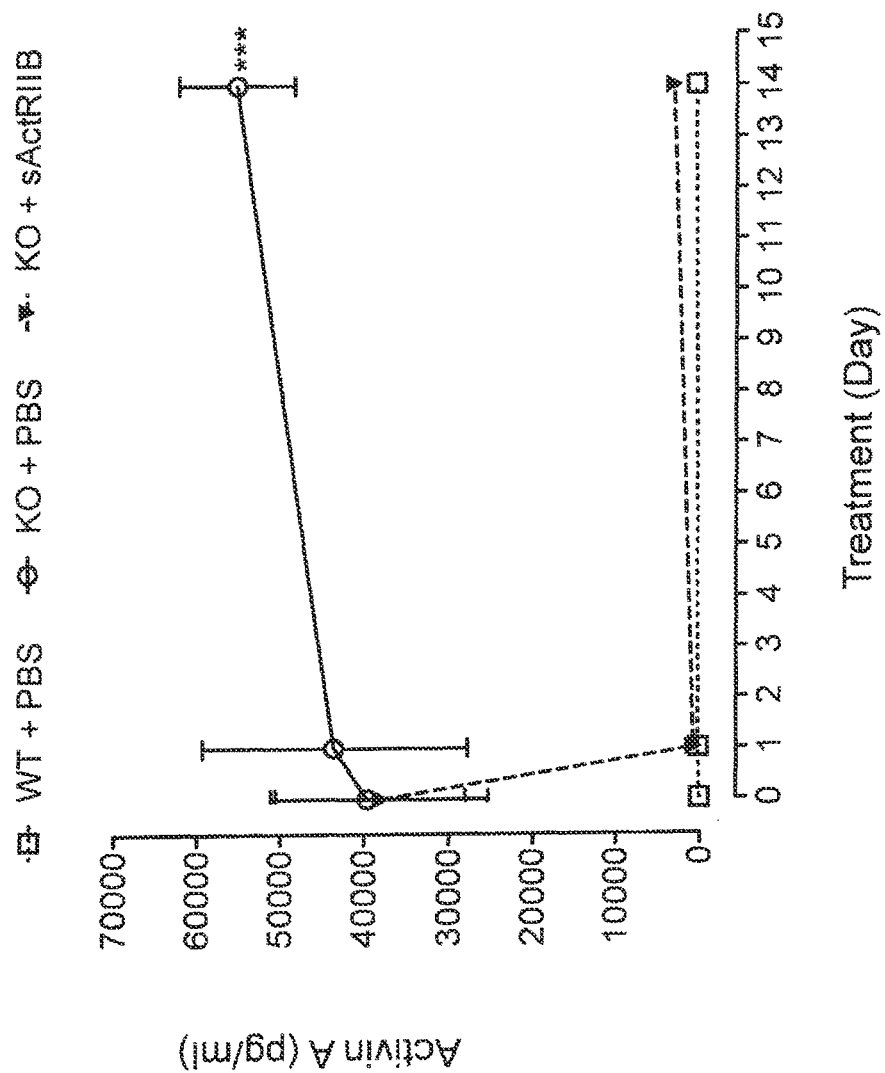
Figure 7C:
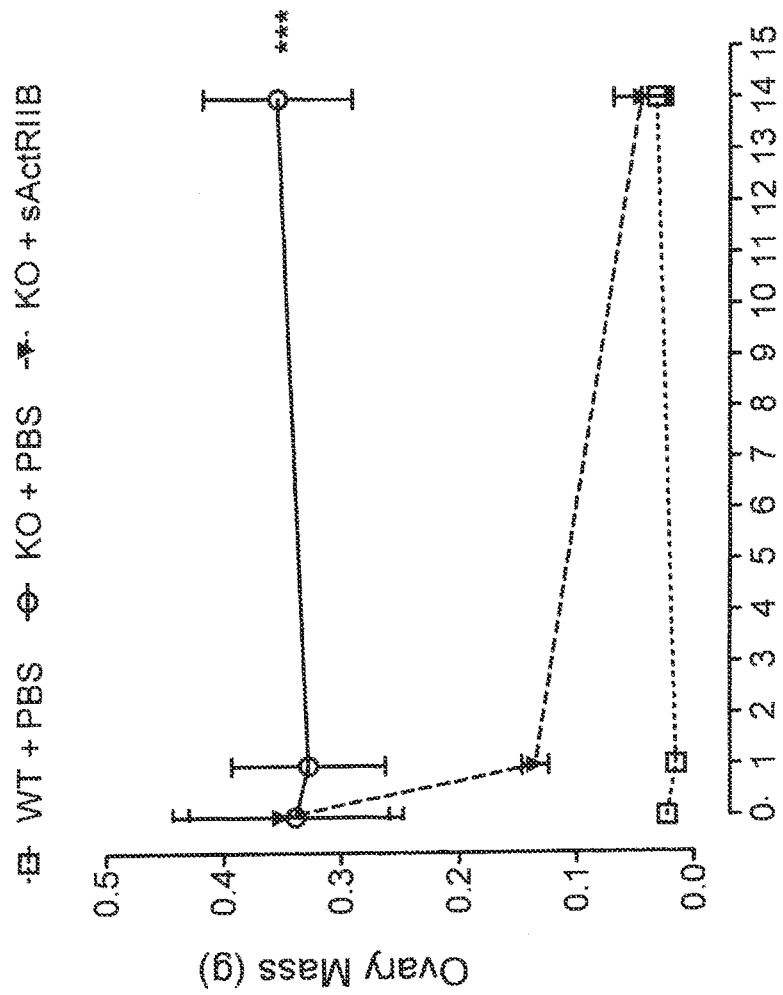
Figure 7D:
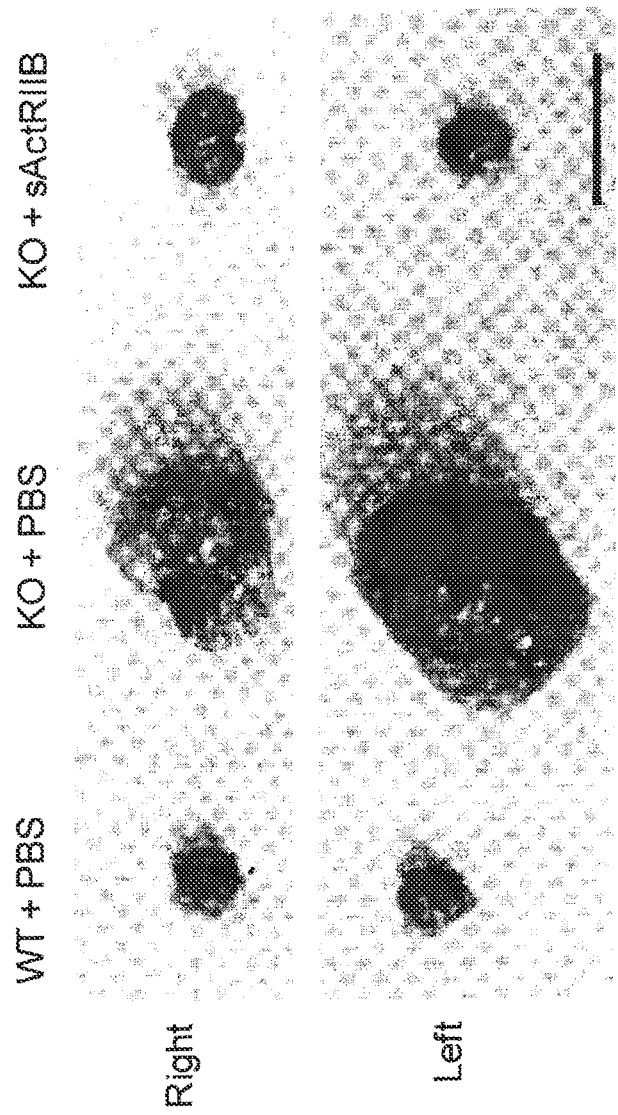

Activin levels in mice with ovarian cancer (OC) was investigated (FIG. 7A). Circulating activin A levels were significantly elevated in mice with ovarian cancer (OC) compared to normal control subjects (Normal). Serum activin A was measured by ELISA. The effect of ovarian cancer treatment with sActRIIB (E28W) (SEQ ID. NO: 91) is shown in FIGS. 7B-7D. 12-week-old female KO mice with established ovarian tumors were treated for 14 days with a single injection of sActRIIB or PBS. Control, age-matched female WT littermates received PBS. It can be seen in FIG. 7B that the elevated circulating levels of activin A in the KO mice was rapidly reduced to the WT control level by sActRIIB treatment. Serum activin A was measured by ELISA at day 0, 1 and 14 after treatment.

In FIG. 7C it can be seen that sActRIIB treatment rapidly reduced the ovarian tumor mass in the KO mice to the WT control level. The weights of ovaries (left and right) of individual animals were analyzed by cohorts via necropsy at day 0, 1 and 14 after treatment. Representative gross morphology images of ovaries depicting the dramatic regression of the advanced ovarian tumors in KO mice in response to 14-day sActRIIB treatment. (FIG. 7D)

Several additional observation were made in KO mice treated with sActRIIB (data not shown). Overexpression of Activin A mRNA was seen in ovarian tumors of KO mice. The overexpression was prevented by sActRIIB treatment. Additionally, sActRIIB treatment completely blocked the increase in phospho-Smad2 in ovarian tumors in KO mice. Also, the severe loss of E-cadherin in ovarian tumors of KO mice was reversed by sActRIIB treatment. Finally, representative immunohistochemical images showed the complete disappearance of E-cadherin immunoreactivity from ovarian sections of KO mice and the reappearance of strong E-cadherin staining after 14-day treatment with sActRIIB.

Figure 8A:
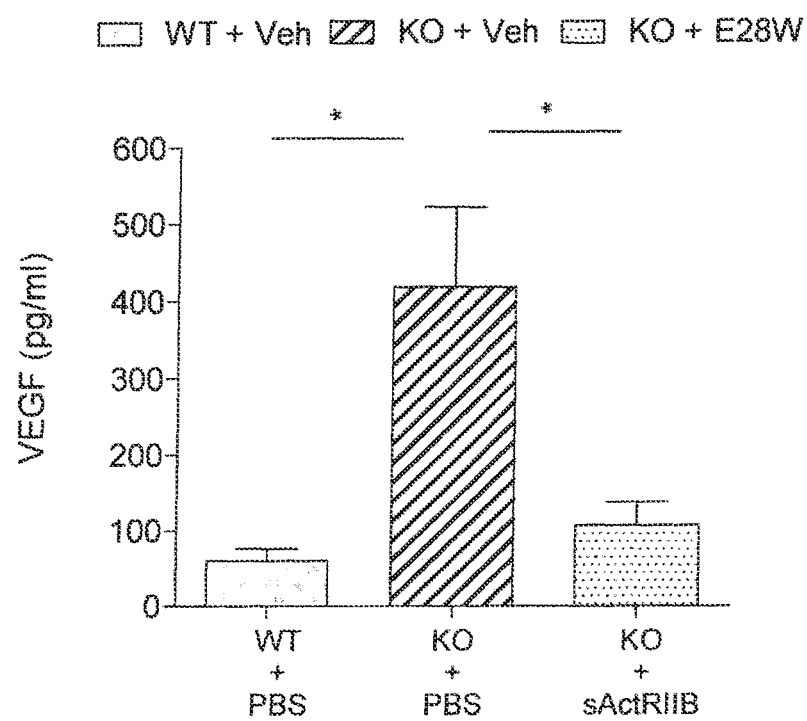
FIGS. 8A-8B show Activin A blockade abolishes overexpression of VEGF levels in ovarian tumors (FIG. 8A) and activation of caspase-3 in testicular tumors following treatment with sActRIIB (E28W) (FIG. 8B).

FIG. 8A shows that Activin A blockade can abolish the overexpression of VEGF in ovarian tumors in inhibin-α KO mice. 12-week-old female KO mice with established ovarian tumors were treated for 14 days with a single injection of sActRIIB or PBS. As controls, age-matched female WT littermates received PBS. ELISA data reveals that the serum VEGF levels are markedly elevated in the KO mice but are reduced to the WT control levels after sActRIIB treatment.

Additionally, in data not shown, it was observed that immunohistochemical staining images demonstrated dramatically increased VEGF and Ang-1 immunoreactivities in the ovarian tumor sections in KO mice, which were completely abolished by sActRIIB treatment. Western blot analysis also revealed that the expressions of tumor angiogenesis-related proteins Endoglin, Osteropontin, IGFBP-1 and IGFBP-2 were highly induced in ovarian tumors in KO mice but were decreased to the WT control levels after sActRIIB treatment.

Figure 8B:
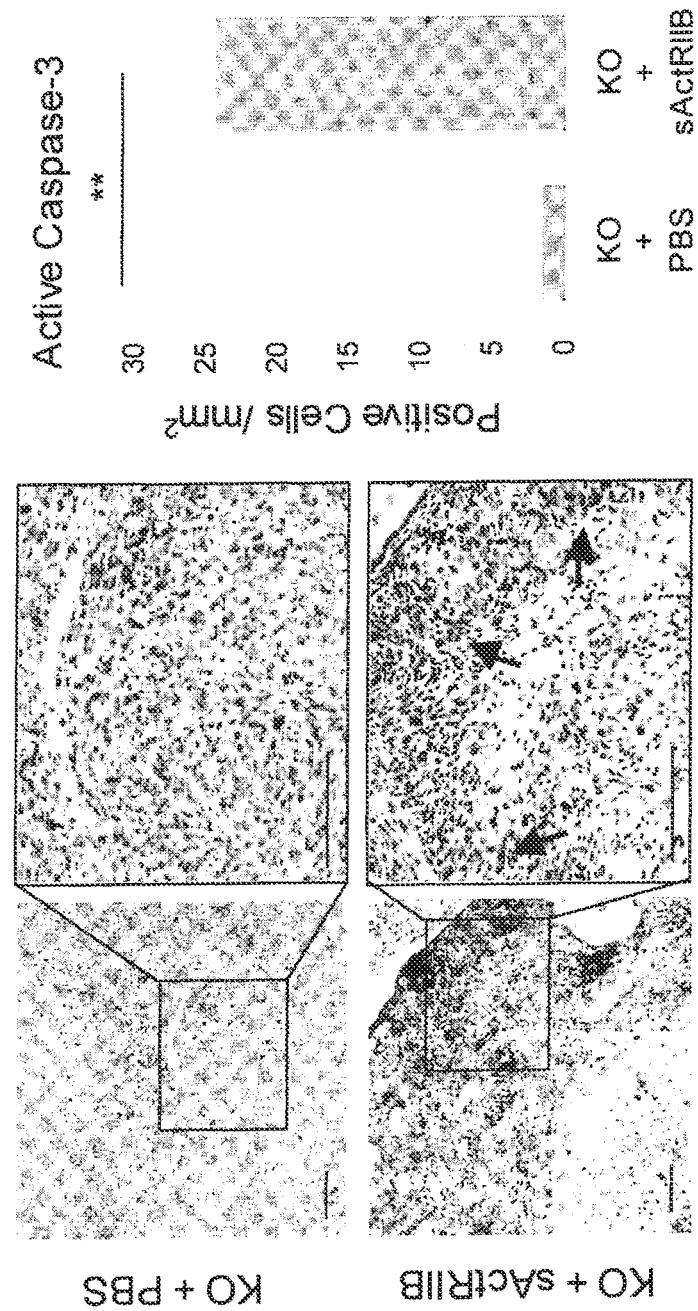

Immunohistochemical analysis shows that sActRIIB treatment leads to caspase-3 activation in testicular tumors in the KO mice. In FIG. 8B arrows point to the active caspase-3 immunoreactivity in the sActRIIB-treated ovarian tumor section where residual tumor cells are clustered. There was an absence of active caspase-3 immunostaining in the PBS-treated ovarian tumor section. The histogram on the right shows the quantitative analysis of active caspase-3 based on multiple ovarian sections from 3 animals in each group.

In another experiment, it was shown that activin A antagonism suppressed angiopoeitin-1 overexpression and prevented neovascularization in the tumor microenvironment in TOV-21G human ovarian cancer xenografts. Implantation of TOV-21G ovarian cancer xenografts resulted in elevated activin A in circulation in CD1 nude mice. Activin A was measured by ELISA. Administration of activin A antagonist, sActRIIB suppressedTOV-21G tumor growth in CD1 nude mice. The TOV-21G xenografts-bearing mice were treated with sActRIIB, or with PBS at day 12 post tumor implantation.

Blocking activin A had no direct effect on the proliferation in vitro of TOV-21G cells in cell cultures. Growth of TOV 21G cells was monitored "by real time in vitro micro-imaging" using the IncuCyte system. The activin A inhibitors were added at the time of cell seeding. Staurosporin, as a positive control for inhibition of cell growth, was used to demonstrate the reliability of the monitoring system.

Blocking activin A suppressed Ang-1 overexpression and inhibited tumor neovascularization in TOV-21G ovarian tumor xenografts. TOV-21G xenografts-bearing nude mice were treated with sActRIIB or PBS at day 12 post tumor implantation. The TOV-21G tumors were isolated at different time points after the treatment and then subjected to immunohistochemical staining for Ang-1 and CD31 as a marker of neovasculature. Cell nuclei were counterstained.

Caspase-3 activation and cancer cell apoptosis in TOV-21G xenograft tumors also followed blocking of activin A. TOV-21G tumor sections were immunohistochemically examined for caspase-3 activation using active caspase-3-specific antibody and for cell apoptosis using TUNEL staining. sActRIIB induced active caspase-3 and cell apoptosis.

The experiments demonstrate that activin A is capable of stimulating angiogenesis factor overexpression (e.g., VEGF-A and Ang-1) by multiple cell types (i.e., cancer, endothelial, fibroblast and monocytic cells), whereas blocking the elevated activin A in tumors prevented overexpression of angiogenic factors and as a consequence activated caspase-3 and cell apoptosis, leading to tumor suppression.

Example 5

Ovarian and Testicular Morphology

Histological examination of ovarian and testicular tumors in 10-week-old male and 14-week-old female inhibin-α KO mice that had been treated for two weeks with PBS or sActRIIB along with age-matched WT controls was performed. 8-week-old male and 12-week-old female inhibin-α KO mice received a single injection of sActRIIB or PBS. 14 days after the treatment, ovarian and testicular organs were collected by necropsy. Tissue sections were subjected to Periodic Acid-Schiff Staining for ovaries and Masson's Trichrome Staining for testes.

In the untreated female KO mice, the greatly enlarged ovaries were predominantly filled with solid cancer mass and large hemorrhages with hardly any recognizable follicles left. However, after the sActRIIB treatment, the ovaries were normal in size, and their morphology appeared relatively normal with many recognizable follicles, minimal cancer invasion and few hemorrhages. This microscopic analysis thus corroborates our findings on tumor weight and gross morphology and confirmed that the sActRIIB treatment caused a dramatic cancer regression in the testes and ovaries in the KO animals. In the untreated male KO mice, the normal testicular structures were no longer recognizable by light microscopy, as the seminiferous tubules were mostly replaced by a massive, undifferentiated cancer mass. However, after the sActRIIB treatment, the testicular structures appeared relatively normal with most of the seminiferous tubules largely intact, although a few small areas still contained residual cancer cells, and the number of spermatogonia cells in some tubules was reduced.

It was also noted that sActRIIB treatment rapidly reduced the testicular tumor mass in the KO mice to the WT control level. The weights of testes (left and right) of individual animals were analyzed by cohorts via necropsy immediately before and 14 days after treatment. For the experiment $P<0.001$ vs. WT control. n=6-12.

Additionally, it was noted that sActRIIB abolished VEGF and Ang-1 overexpression and induced caspase-3 activation in testicular tumors in inhibin-α KO-mice. Angiopoietin-2 transcripts were decreased toward control levels after sActRIIB treatment in both ovarian and testicular tumors.

Example 6

Effect of the Combination of sActRIIB and a Chemotherapeutic

Figure 9A:
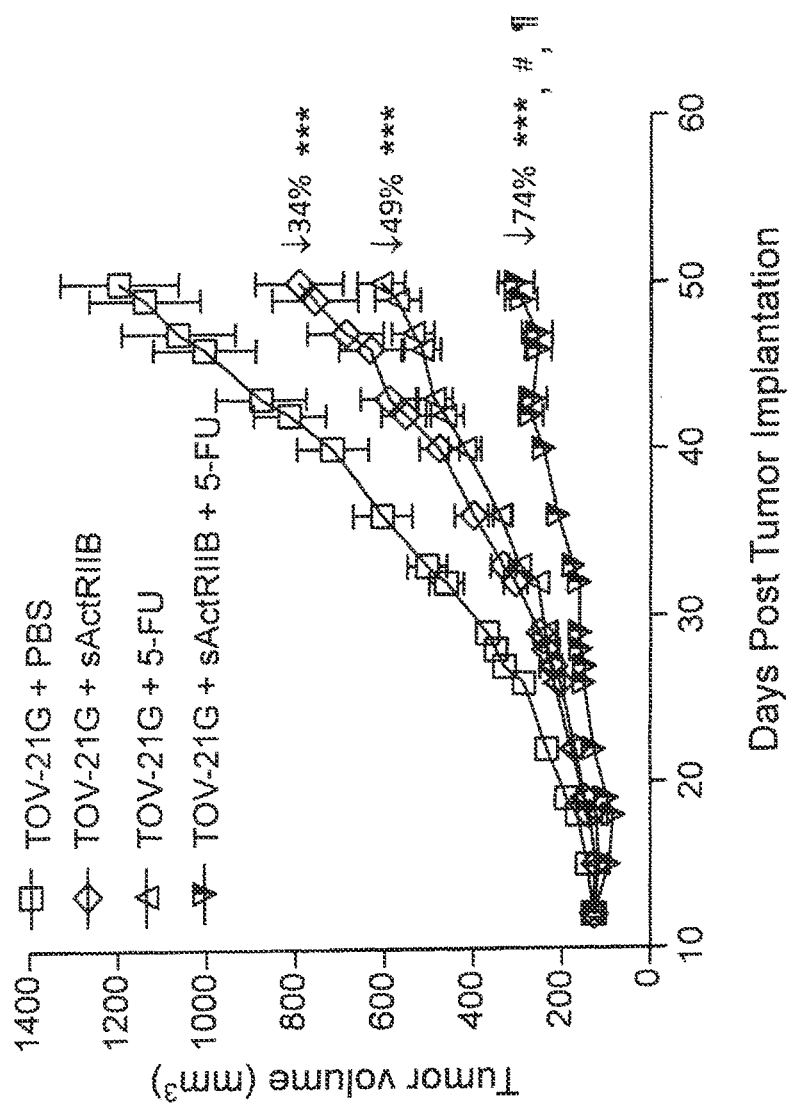
FIGS. 9A-9B show the effect of activin antagonist sActRIIB (E28W) and cytotoxic chemotherapeutic agents on tumor growth.

The effect of activin antagonist sActRIIB and cytotoxic chemotherapeutic agent 5-Fluorouracil on TOV-21G tumor growth inhibition in nude mice. (FIG. 9A) TOV-21G xenografts-bearing nude mice were treated at day 12 post tumor implantation with sActRIIB, 5-Fu, or combination of sActRIIB and 5-Fu, respectively. Changes in tumor volumes were recorded longitudinally. It can be observed in FIG. 9A that sActRIIB by itself reduces tumor volume 34% and 5-fluorouracil (5-FU) by itself reduces tumor volume by 49%. Combining the two together, however, decrease tumor volume by 74%.

Figure 9B:
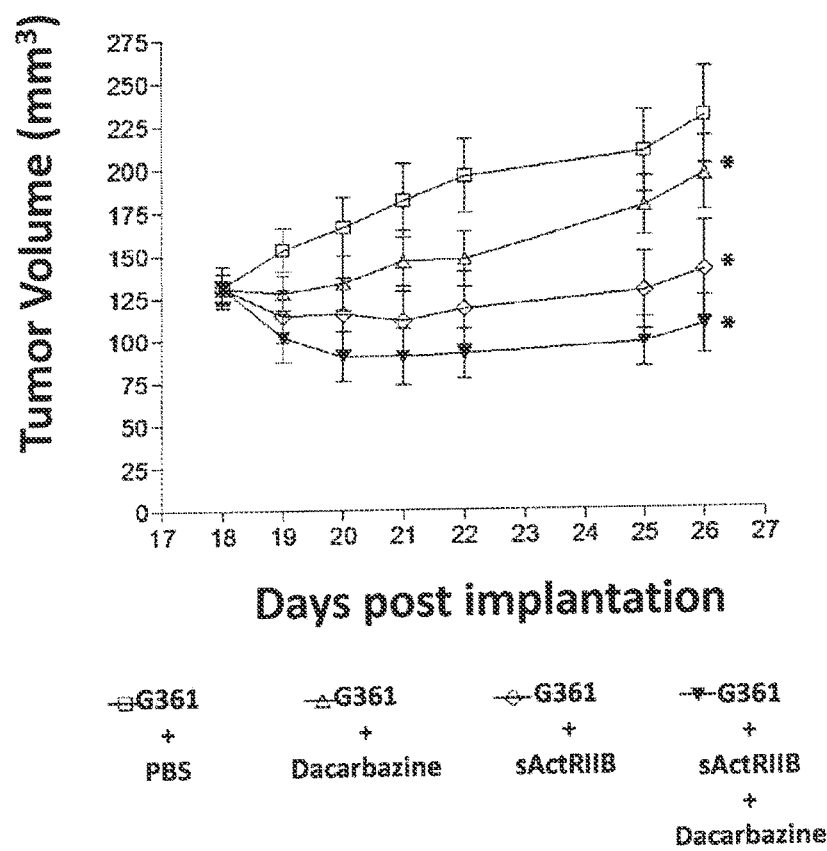

FIG. 9B shows the effects of sActRIIB and dacarbazine on growth inhibition of G361 human melanoma xenograft in nude mice. BALB/c nude mice were treated with sActRIIB, dacarbazine, or sActRIIB plus dacarbazine. For dacarbazine combination study, BALB/c nude mice implanted with G361 xenograft ($5\times10^6$ cells/mouse) were treated with sActRIIB only (10 mg/kg, SC, 1×/wk), dacarbazine only (4 consecutive days of daily IP injection at 5 mg/kg), or sActRIIB and 5-FU combination beginning at day 18 post tumor implantation. Tumor volumes were measured longitudinally by electronic caliper up to day 26 after implantation.

Given that the chemotherapeutic and sActRIIB presumably act by different mechanisms, it would not necessarily be expected that the demonstrated results, i.e. both agents in combination would affect overall tumor growth greater than either agent individually.

Ovarian cancer is the deadliest of all gynecologic cancers. Activin A, a gonadal cytokine that serves important functions in regulating the menstrual cycle, is expressed strongly in many malignancies including ovarian cancer. Neutralizing activin A eradicates ovarian tumors established in inhibin-deficient mice and markedly impedes the growth of multiple activin A-secreting ovarian xenograft tumors in nude mice. Blocking activin A appears to have no direct effect on the proliferation in vitro of ovarian cancer cells in cell cultures, but, in vivo, it completely abolishes the overexpression of angiogenesis factors (i.e., VEGF and angiopoietins) and inhibits neovascularization in the tumor microenvironment. It, thereby, induces caspase-3 activation and cancer cell apoptosis in ovarian tumors. This profound effect in vivo can be explained, at least in part, by the ability of tumor-derived activin A to trigger the overproduction of angiogenesis factors in the host's endothelial cells, which reside in the tumor microenvironment. In addition to the ovarian tumors, activin blockade was also found to inhibit the in vivo growth of at least two other cancer types (testicular tumors and melanoma) that secrete activin A. Importantly, the tumor-inhibitory effect of activin antagonism was found to be, at least, additive to that of 5-fluorouracil or dacarbazine chemotherapy. These findings demonstrate a function of activin A as a critical mediator of tumor angiogenesis and tumorigenesis. Blocking the elevated activin A with sActRIIB, therefore, appears to be a promising new approach to combat ovarian cancer, testicular cancer, melanoma and possibly other malignancies.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed:

1. A pharmaceutical composition comprising i) an isolated protein comprising a variant activin JIB receptor polypeptide (vActRIIB) wherein vActRIIB comprises a polypeptide sequence having at least 96% identity to the amino acid sequence set forth at amino acids 25 through 134 of SEQ ID NO: 18, wherein the polypeptide comprises an amino acid substitution at position 28, and wherein the polypeptide is capable of binding myostatin, activin A, or GDF-11, and ii) a chemotherapeutic agent.

2. The pharmaceutical composition of claim 1, wherein the substitution at position 28 of the vActRIIB polypeptide is selected from the group consisting of A, F, Q, V, I, L, M, K, H, W and Y for E.

3. The pharmaceutical composition of claim 1, wherein the substitution at position 28 of the vActRIIB polypeptide is selected from the group of amino acids consisting of A, W and Y for E.

4. The pharmaceutical composition of claim 1, wherein the substitution at position 28 of the vActRIIB polypeptide is W.

5. The pharmaceutical composition of claim 1, wherein the chemotherapeutic agent is a nucleoside analogue, 5-fluorouracil, and/or dacarbazine.

6. The pharmaceutical composition of claim 1, wherein the polypeptide sequence has at least 99% identity to the amino acid sequence set forth at amino acids 25 through 134 of SEQ ID NO: 18, wherein vActRIIB comprises a W amino acid substitution at position 28, wherein the isolated protein further comprises an Fc domain linked to vActRIIB via a linker, wherein the sequence of the Fc domain is shown in SEQ ID NO:80, and wherein the sequence of the linker is shown in SEQ ID NO:79.

7. The pharmaceutical composition of claim 1, wherein vActRIIB comprises a polypeptide sequence having at least 97% identity to the amino acid sequence set forth at amino acids 25 through 134 of SEQ ID NO: 18.

8. The pharmaceutical composition of claim 1, wherein vActRIIB comprises a polypeptide sequence having at least 98% identity to the amino acid sequence set forth at amino acids 25 through 134 of SEQ ID NO: 18.

9. A method of treating a gonadal cancer in a subject in need of such treatment comprising administering a therapeutically effective amount of the composition of claim 1 to the subject, wherein the substitution at position 28 is selected from the group of amino acids consisting of A, W, and Y for E.

10. The method of claim 9, wherein the cancer is ovarian cancer or testicular cancer.

11. A method of reducing the size of a gonadal tumor mass in a subject in need of such treatment comprising administering an effective amount of the composition of claim 1 to the subject, wherein the substitution at position 28 is selected from the group of amino acids consisting of A, W, and Y for E.

12. The method of claim 11, wherein the tumor mass is resulting from testicular or ovarian cancer.

13. The composition of claim 1, wherein the chemotherapeutic agent is an anti-neoplastic agent.

14. The composition of claim 13, wherein the anti-neoplastic agent is doxorubicin.

15. The composition of claim 1, wherein the composition is formulated for injection.

16. The composition of claim 1, wherein the composition is formulated in an aqueous solution.

17. The composition of claim 1, wherein the composition further comprises an excipient.

18. The composition of claim 1, wherein the composition further comprises a buffer.

19. The composition of claim 1, wherein the composition further comprises a polysorbate.

* * * * *

UNITED STATES PATENT AND TRADEMARK OFFICE
CERTIFICATE OF CORRECTION

PATENT NO. : 8,999,917 B2
APPLICATION NO. : 13/932421
DATED : April 7, 2015
INVENTOR(S) : Jeonghoon Sun et al.

It is certified that error appears in the above-identified patent and that said Letters Patent is hereby corrected as shown below:

Title page, item (72), delete "Jeonghoon Sun, Thousan Oaks, CA (US);", and insert --Jeonghoon Sun, Thousand Oaks, CA (US);--

In The Claims

Column 219, line 28, Claim 1, delete "JIB", and insert --IIB--

Signed and Sealed this
Fifteenth Day of March, 2016

Michelle K. Lee
*Director of the United States Patent and Trademark Office*

SEQUENCE LISTING

```
<160> NUMBER OF SEQ ID NOS: 99

<210> SEQ ID NO 1
<211> LENGTH: 480
<212> TYPE: DNA
<213> ORGANISM: Homo sapiens
<220> FEATURE:
<221> NAME/KEY: CDS
```

<222> LOCATION: (1)..(480)

<400> SEQUENCE: 1

```
atg acg gcg ccc tgg gtg gcc ctc gcc ctc ctc tgg gga tcg ctg tgc      48
Met Thr Ala Pro Trp Val Ala Leu Ala Leu Leu Trp Gly Ser Leu Cys
1               5                   10                  15 gcc ggc tct ggg cgt ggg gag gct gag aca cgg gag tgc atc tac tac      96
Ala Gly Ser Gly Arg Gly Glu Ala Glu Thr Arg Glu Cys Ile Tyr Tyr
            20                  25                  30 aac gcc aac tgg gag ctg gag cgc acc aac cag agc ggc ctg gag cgc     144
Asn Ala Asn Trp Glu Leu Glu Arg Thr Asn Gln Ser Gly Leu Glu Arg
        35                  40                  45 tgc gaa ggc gag cag gac aag cgg ctg cac tgc tac gcc tcc tgg cgc     192
Cys Glu Gly Glu Gln Asp Lys Arg Leu His Cys Tyr Ala Ser Trp Arg
    50                  55                  60 aac agc tct ggc acc atc gag ctc gtg aag aag ggc tgc tgg cta gat     240
Asn Ser Ser Gly Thr Ile Glu Leu Val Lys Lys Gly Cys Trp Leu Asp
65                  70                  75                  80 gac ttc aac tgc tac gat agg cag gag tgt gtg gcc act gag gag aac     288
Asp Phe Asn Cys Tyr Asp Arg Gln Glu Cys Val Ala Thr Glu Glu Asn
                85                  90                  95 ccc cag gtg tac ttc tgc tgc tgt gaa ggc aac ttc tgc aac gag cgc     336
Pro Gln Val Tyr Phe Cys Cys Cys Glu Gly Asn Phe Cys Asn Glu Arg
            100                 105                 110 ttc act cat ttg cca gag gct ggg ggc ccg gaa gga ccc tgg gcc tcc     384
Phe Thr His Leu Pro Glu Ala Gly Gly Pro Glu Gly Pro Trp Ala Ser
        115                 120                 125 acc acc atc ccc tct ggt ggg cct gaa gcc act gca gct gct gga gat     432
Thr Thr Ile Pro Ser Gly Gly Pro Glu Ala Thr Ala Ala Ala Gly Asp
    130                 135                 140 caa ggc tcg ggg gcg ctt tgg ctg tgt ctg gaa ggc cca gct cat gaa     480
Gln Gly Ser Gly Ala Leu Trp Leu Cys Leu Glu Gly Pro Ala His Glu
145                 150                 155                 160
```

<210> SEQ ID NO 2
<211> LENGTH: 160
<212> TYPE: PRT
<213> ORGANISM: Homo sapiens

<400> SEQUENCE: 2

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Gly Pro Trp Ala Ser
        115                 120                 125

Thr Thr Ile Pro Ser Gly Gly Pro Glu Ala Thr Ala Ala Ala Gly Asp
    130                 135                 140
```

-continued

```
Gln Gly Ser Gly Ala Leu Trp Leu Cys Leu Glu Gly Pro Ala His Glu
145                 150                 155                 160

<210> SEQ ID NO 3
<211> LENGTH: 480
<212> TYPE: DNA
<213> ORGANISM: Homo sapiens
<220> FEATURE:
<221> NAME/KEY: CDS
<222> LOCATION: (1)..(480)
<220> FEATURE:
<221> NAME/KEY: modified_base
<222> LOCATION: (84)..(84)
<223> OTHER INFORMATION: a, c, t, g, unknown or other

<400> SEQUENCE: 3 atg acg gcg ccc tgg gtg gcc ctc gcc ctc ctc tgg gga tcg ctg tgc      48
Met Thr Ala Pro Trp Val Ala Leu Ala Leu Leu Trp Gly Ser Leu Cys
1               5                   10                  15 gcc ggc tct ggg cgt ggg gag gct gag aca cgg gcn tgc atc tac tac      96
Ala Gly Ser Gly Arg Gly Glu Ala Glu Thr Arg Ala Cys Ile Tyr Tyr
            20                  25                  30 aac gcc aac tgg gag ctg gag cgc acc aac cag agc ggc ctg gag cgc     144
Asn Ala Asn Trp Glu Leu Glu Arg Thr Asn Gln Ser Gly Leu Glu Arg
        35                  40                  45 tgc gaa ggc gag cag gac aag cgg ctg cac tgc tac gcc tcc tgg cgc     192
Cys Glu Gly Glu Gln Asp Lys Arg Leu His Cys Tyr Ala Ser Trp Arg
 50                  55                  60 aac agc tct ggc acc atc gag ctc gtg aag aag ggc tgc tgg cta gat     240
Asn Ser Ser Gly Thr Ile Glu Leu Val Lys Lys Gly Cys Trp Leu Asp
65                  70                  75                  80 gac ttc aac tgc tac gat agg cag gag tgt gtg gcc act gag gag aac     288
Asp Phe Asn Cys Tyr Asp Arg Gln Glu Cys Val Ala Thr Glu Glu Asn
                85                  90                  95 ccc cag gtg tac ttc tgc tgc tgt gaa ggc aac ttc tgc aac gag cgc     336
Pro Gln Val Tyr Phe Cys Cys Cys Glu Gly Asn Phe Cys Asn Glu Arg
            100                 105                 110 ttc act cat ttg cca gag gct ggg ggc ccg gaa gga ccc tgg gcc tcc     384
Phe Thr His Leu Pro Glu Ala Gly Gly Pro Glu Gly Pro Trp Ala Ser
        115                 120                 125 acc acc atc ccc tct ggt ggg cct gaa gcc act gca gct gct gga gat     432
Thr Thr Ile Pro Ser Gly Gly Pro Glu Ala Thr Ala Ala Ala Gly Asp
130                 135                 140 caa ggc tcg ggg gcg ctt tgg ctg tgt ctg gaa ggc cca gct cat gaa     480
Gln Gly Ser Gly Ala Leu Trp Leu Cys Leu Glu Gly Pro Ala His Glu
145                 150                 155                 160

<210> SEQ ID NO 4
<211> LENGTH: 160
<212> TYPE: PRT
<213> ORGANISM: Homo sapiens

<400> SEQUENCE: 4

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Ala Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
 50                  55                  60

Asn Ser Ser Gly Thr Ile Glu Leu Val Lys Lys Gly Cys Trp Leu Asp
```

|                              |     |
| ---------------------------- | --- |
| 65                           |     |
|                         70   |     |
|                              70 |     |

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Gly Pro Trp Ala Ser
        115                 120                 125

Thr Thr Ile Pro Ser Gly Gly Pro Glu Ala Thr Ala Ala Ala Gly Asp
130                 135                 140

Gln Gly Ser Gly Ala Leu Trp Leu Cys Leu Glu Gly Pro Ala His Glu
145                 150                 155                 160

<210> SEQ ID NO 5
<211> LENGTH: 480
<212> TYPE: DNA
<213> ORGANISM: Homo sapiens
<220> FEATURE:
<221> NAME/KEY: CDS
<222> LOCATION: (1)..(480)
<220> FEATURE:
<221> NAME/KEY: modified_base
<222> LOCATION: (84)..(84)
<223> OTHER INFORMATION: a, c, t, g, unknown or other
<220> FEATURE:
<221> NAME/KEY: modified_base
<222> LOCATION: (120)..(120)
<223> OTHER INFORMATION: a, c, t, g, unknown or other

<400> SEQUENCE: 5

```
atg acg gcg ccc tgg gtg gcc ctc gcc ctc ctc tgg gga tcg ctg tgc      48
Met Thr Ala Pro Trp Val Ala Leu Ala Leu Leu Trp Gly Ser Leu Cys
1               5                   10                  15 gcc ggc tct ggg cgt ggg gag gct gag aca cgg gcn tgc atc tac tac      96
Ala Gly Ser Gly Arg Gly Glu Ala Glu Thr Arg Ala Cys Ile Tyr Tyr
                20                  25                  30 aac gcc aac tgg gag ctg gag gcn acc aac cag agc ggc ctg gag cgc     144
Asn Ala Asn Trp Glu Leu Glu Ala Thr Asn Gln Ser Gly Leu Glu Arg
            35                  40                  45 tgc gaa ggc gag cag gac aag cgg ctg cac tgc tac gcc tcc tgg cgc     192
Cys Glu Gly Glu Gln Asp Lys Arg Leu His Cys Tyr Ala Ser Trp Arg
        50                  55                  60 aac agc tct ggc acc atc gag ctc gtg aag aag ggc tgc tgg cta gat     240
Asn Ser Ser Gly Thr Ile Glu Leu Val Lys Lys Gly Cys Trp Leu Asp
65                  70                  75                  80 gac ttc aac tgc tac gat agg cag gag tgt gtg gcc act gag gag aac     288
Asp Phe Asn Cys Tyr Asp Arg Gln Glu Cys Val Ala Thr Glu Glu Asn
                85                  90                  95 ccc cag gtg tac ttc tgc tgc tgt gaa ggc aac ttc tgc aac gag cgc     336
Pro Gln Val Tyr Phe Cys Cys Cys Glu Gly Asn Phe Cys Asn Glu Arg
            100                 105                 110 ttc act cat ttg cca gag gct ggg ggc ccg gaa gga ccc tgg gcc tcc     384
Phe Thr His Leu Pro Glu Ala Gly Gly Pro Glu Gly Pro Trp Ala Ser
        115                 120                 125 acc acc atc ccc tct ggt ggg cct gaa gcc act gca gct gct gga gat     432
Thr Thr Ile Pro Ser Gly Gly Pro Glu Ala Thr Ala Ala Ala Gly Asp
130                 135                 140 caa ggc tcg ggg gcg ctt tgg ctg tgt ctg gaa ggc cca gct cat gaa     480
Gln Gly Ser Gly Ala Leu Trp Leu Cys Leu Glu Gly Pro Ala His Glu
145                 150                 155                 160
```

<210> SEQ ID NO 6
<211> LENGTH: 160

```
<212> TYPE: PRT
<213> ORGANISM: Homo sapiens

<400> SEQUENCE: 6

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Ala Cys Ile Tyr Tyr
            20                  25                  30

Asn Ala Asn Trp Glu Leu Glu Ala Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Gly Pro Trp Ala Ser
        115                 120                 125

Thr Thr Ile Pro Ser Gly Gly Pro Glu Ala Thr Ala Ala Ala Gly Asp
    130                 135                 140

Gln Gly Ser Gly Ala Leu Trp Leu Cys Leu Glu Gly Pro Ala His Glu
145                 150                 155                 160

<210> SEQ ID NO 7
<211> LENGTH: 480
<212> TYPE: DNA
<213> ORGANISM: Homo sapiens
<220> FEATURE:
<221> NAME/KEY: CDS
<222> LOCATION: (1)..(480)

<400> SEQUENCE: 7 atg acg gcg ccc tgg gtg gcc ctc gcc ctc ctc tgg gga tcg ctg tgc      48
Met Thr Ala Pro Trp Val Ala Leu Ala Leu Leu Trp Gly Ser Leu Cys
1               5                   10                  15 gcc ggc tct ggg cgt ggg gag gct gag aca cgg tgg tgc atc tac tac      96
Ala Gly Ser Gly Arg Gly Glu Ala Glu Thr Arg Trp Cys Ile Tyr Tyr
            20                  25                  30 aac gcc aac tgg gag ctg gag cgc acc aac cag agc ggc ctg gag cgc     144
Asn Ala Asn Trp Glu Leu Glu Arg Thr Asn Gln Ser Gly Leu Glu Arg
        35                  40                  45 tgc gaa ggc gag cag gac aag cgg ctg cac tgc tac gcc tcc tgg cgc     192
Cys Glu Gly Glu Gln Asp Lys Arg Leu His Cys Tyr Ala Ser Trp Arg
    50                  55                  60 aac agc tct ggc acc atc gag ctc gtg aag aag ggc tgc tgg cta gat     240
Asn Ser Ser Gly Thr Ile Glu Leu Val Lys Lys Gly Cys Trp Leu Asp
65                  70                  75                  80 gac ttc aac tgc tac gat agg cag gag tgt gtg gcc act gag gag aac     288
Asp Phe Asn Cys Tyr Asp Arg Gln Glu Cys Val Ala Thr Glu Glu Asn
                85                  90                  95 ccc cag gtg tac ttc tgc tgc tgt gaa ggc aac ttc tgc aac gag cgc     336
Pro Gln Val Tyr Phe Cys Cys Cys Glu Gly Asn Phe Cys Asn Glu Arg
            100                 105                 110 ttc act cat ttg cca gag gct ggg ggc ccg gaa gga ccc tgg gcc tcc     384
Phe Thr His Leu Pro Glu Ala Gly Gly Pro Glu Gly Pro Trp Ala Ser
        115                 120                 125 acc acc atc ccc tct ggt ggg cct gaa gcc act gca gct gct gga gat     432
Thr Thr Ile Pro Ser Gly Gly Pro Glu Ala Thr Ala Ala Ala Gly Asp
```

```
Thr Thr Ile Pro Ser Gly Gly Pro Glu Ala Thr Ala Ala Gly Asp
    130                 135                 140 caa ggc tcg ggg gcg ctt tgg ctg tgt ctg gaa ggc cca gct cat gaa      480
Gln Gly Ser Gly Ala Leu Trp Leu Cys Leu Glu Gly Pro Ala His Glu
145                 150                 155                 160
```

<210> SEQ ID NO 8
<211> LENGTH: 160
<212> TYPE: PRT
<213> ORGANISM: Homo sapiens

<400> SEQUENCE: 8

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Trp Cys Ile Tyr Tyr
                20                  25                  30

Asn Ala Asn Trp Glu Leu Glu Arg Thr Asn Gln Ser Gly Leu Glu Arg
            35                  40                  45

Cys Glu Gly Glu Gln Asp Lys Arg Leu His Cys Tyr Ala Ser Trp Arg
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Gly Pro Trp Ala Ser
        115                 120                 125

Thr Thr Ile Pro Ser Gly Gly Pro Glu Ala Thr Ala Ala Gly Asp
    130                 135                 140

Gln Gly Ser Gly Ala Leu Trp Leu Cys Leu Glu Gly Pro Ala His Glu
145                 150                 155                 160
```

<210> SEQ ID NO 9
<211> LENGTH: 480
<212> TYPE: DNA
<213> ORGANISM: Homo sapiens
<220> FEATURE:
<221> NAME/KEY: CDS
<222> LOCATION: (1)..(480)

<400> SEQUENCE: 9

```
atg acg gcg ccc tgg gtg gcc ctc gcc ctc ctc tgg gga tcg ctg tgc       48
Met Thr Ala Pro Trp Val Ala Leu Ala Leu Leu Trp Gly Ser Leu Cys
1               5                   10                  15 gcc ggc tct ggg cgt ggg gag gct gag aca cgg tac tgc atc tac tac       96
Ala Gly Ser Gly Arg Gly Glu Ala Glu Thr Arg Tyr Cys Ile Tyr Tyr
                20                  25                  30 aac gcc aac tgg gag ctg gag cgc acc aac cag agc ggc ctg gag cgc      144
Asn Ala Asn Trp Glu Leu Glu Arg Thr Asn Gln Ser Gly Leu Glu Arg
            35                  40                  45 tgc gaa ggc gag cag gac aag cgg ctg cac tgc tac gcc tcc tgg cgc      192
Cys Glu Gly Glu Gln Asp Lys Arg Leu His Cys Tyr Ala Ser Trp Arg
50                  55                  60 aac agc tct ggc acc atc gag ctc gtg aag aag ggc tgc tgg cta gat      240
Asn Ser Ser Gly Thr Ile Glu Leu Val Lys Lys Gly Cys Trp Leu Asp
65                  70                  75                  80 gac ttc aac tgc tac gat agg cag gag tgt gtg gcc act gag gag aac      288
Asp Phe Asn Cys Tyr Asp Arg Gln Glu Cys Val Ala Thr Glu Glu Asn
                85                  90                  95
```

```
ccc cag gtg tac ttc tgc tgt gaa ggc aac ttc tgc aac gag cgc      336
Pro Gln Val Tyr Phe Cys Cys Cys Glu Gly Asn Phe Cys Asn Glu Arg
            100                 105                 110 ttc act cat ttg cca gag gct ggg ggc ccg aaa gga ccc tgg gcc tcc  384
Phe Thr His Leu Pro Glu Ala Gly Gly Pro Glu Gly Pro Trp Ala Ser
        115                 120                 125 acc acc atc ccc tct ggt ggg cct gaa gcc act gca gct gct gga gat  432
Thr Thr Ile Pro Ser Gly Gly Pro Glu Ala Thr Ala Ala Ala Gly Asp
    130                 135                 140 caa ggc tcg ggg gcg ctt tgg ctg tgt ctg gaa ggc cca gct cat gaa  480
Gln Gly Ser Gly Ala Leu Trp Leu Cys Leu Glu Gly Pro Ala His Glu
145                 150                 155                 160
```

<210> SEQ ID NO 10
<211> LENGTH: 160
<212> TYPE: PRT
<213> ORGANISM: Homo sapiens

<400> SEQUENCE: 10

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Tyr Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Gly Pro Trp Ala Ser
        115                 120                 125

Thr Thr Ile Pro Ser Gly Gly Pro Glu Ala Thr Ala Ala Ala Gly Asp
    130                 135                 140

Gln Gly Ser Gly Ala Leu Trp Leu Cys Leu Glu Gly Pro Ala His Glu
145                 150                 155                 160
```

<210> SEQ ID NO 11
<211> LENGTH: 480
<212> TYPE: DNA
<213> ORGANISM: Homo sapiens
<220> FEATURE:
<221> NAME/KEY: CDS
<222> LOCATION: (1)..(480)
<220> FEATURE:
<221> NAME/KEY: modified_base
<222> LOCATION: (82)..(84)
<223> OTHER INFORMATION: a, c, t, g, unknown or other

<400> SEQUENCE: 11

```
atg acg gcg ccc tgg gtg gcc ctc gcc ctc ctc tgg gga tcg ctg tgc  48
Met Thr Ala Pro Trp Val Ala Leu Ala Leu Leu Trp Gly Ser Leu Cys
1               5                   10                  15 gcc ggc tct ggg cgt ggg gag gct gag aca cgg nnn tgc atc tac tac  96
Ala Gly Ser Gly Arg Gly Glu Ala Glu Thr Arg Xaa Cys Ile Tyr Tyr
            20                  25                  30 aac gcc aac tgg gag ctg gag cgc acc aac cag agc ggc ctg gag cgc  144
```

```
                                                  -continued

Asn Ala Asn Trp Glu Leu Glu Arg Thr Asn Gln Ser Gly Leu Glu Arg
                     35                  40                  45 tgc gaa ggc gag cag gac aag cgg ctg cac tgc tac gcc tcc tgg cgc              192
Cys Glu Gly Glu Gln Asp Lys Arg Leu His Cys Tyr Ala Ser Trp Arg
 50                  55                  60 aac agc tct ggc acc atc gag ctc gtg aag aag ggc tgc tgg cta gat              240
Asn Ser Ser Gly Thr Ile Glu Leu Val Lys Lys Gly Cys Trp Leu Asp
 65                  70                  75                  80 gac ttc aac tgc tac gat agg cag gag tgt gtg gcc act gag gag aac              288
Asp Phe Asn Cys Tyr Asp Arg Gln Glu Cys Val Ala Thr Glu Glu Asn
                     85                  90                  95 ccc cag gtg tac ttc tgc tgt gaa ggc aac ttc tgc aac gag cgc                  336
Pro Gln Val Tyr Phe Cys Cys Glu Gly Asn Phe Cys Asn Glu Arg
                100                 105                 110 ttc act cat ttg cca gag gct ggg ggc ccg gaa gga ccc tgg gcc tcc              384
Phe Thr His Leu Pro Glu Ala Gly Gly Pro Glu Gly Pro Trp Ala Ser
                115                 120                 125 acc acc atc ccc tct ggt ggg cct gaa gcc act gca gct gct gga gat              432
Thr Thr Ile Pro Ser Gly Gly Pro Glu Ala Thr Ala Ala Ala Gly Asp
130                 135                 140 caa ggc tcg ggg gcg ctt tgg ctg tgt ctg gaa ggc cca gct cat gaa              480
Gln Gly Ser Gly Ala Leu Trp Leu Cys Leu Glu Gly Pro Ala His Glu
145                 150                 155                 160

<210> SEQ ID NO 12
<211> LENGTH: 160
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: Ala, Phe, Gln, Val, Ile, Leu, Met, Lys, His,
      Trp or Tyr

<400> SEQUENCE: 12

Met Thr Ala Pro Trp Val Ala Leu Ala Leu Leu Trp Gly Ser Leu Cys
 1               5                  10                  15

Ala Gly Ser Gly Arg Gly Glu Ala Glu Thr Arg Xaa Cys Ile Tyr Tyr
                20                  25                  30

Asn Ala Asn Trp Glu Leu Glu Arg Thr Asn Gln Ser Gly Leu Glu Arg
                35                  40                  45

Cys Glu Gly Glu Gln Asp Lys Arg Leu His Cys Tyr Ala Ser Trp Arg
 50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Glu Gly Asn Phe Cys Asn Glu Arg
                100                 105                 110

Phe Thr His Leu Pro Glu Ala Gly Gly Pro Glu Gly Pro Trp Ala Ser
                115                 120                 125

Thr Thr Ile Pro Ser Gly Gly Pro Glu Ala Thr Ala Ala Ala Gly Asp
130                 135                 140

Gln Gly Ser Gly Ala Leu Trp Leu Cys Leu Glu Gly Pro Ala His Glu
145                 150                 155                 160

<210> SEQ ID NO 13
<211> LENGTH: 480
<212> TYPE: DNA
<213> ORGANISM: Homo sapiens
```

```
<220> FEATURE:
<221> NAME/KEY: CDS
<222> LOCATION: (1)..(480)
<220> FEATURE:
<221> NAME/KEY: modified_base
<222> LOCATION: (82)..(84)
<223> OTHER INFORMATION: a, c, t, g, unknown or other
<220> FEATURE:
<221> NAME/KEY: modified_base
<222> LOCATION: (118)..(120)
<223> OTHER INFORMATION: a, c, t, g, unknown or other

<400> SEQUENCE: 13 atg acg gcg ccc tgg gtg gcc ctc gcc ctc ctc tgg gga tcg ctg tgc      48
Met Thr Ala Pro Trp Val Ala Leu Ala Leu Leu Trp Gly Ser Leu Cys
1               5                   10                  15 gcc ggc tct ggg cgt ggg gag gct gag aca cgg nnn tgc atc tac tac      96
Ala Gly Ser Gly Arg Gly Glu Ala Glu Thr Arg Xaa Cys Ile Tyr Tyr
            20                  25                  30 aac gcc aac tgg gag ctg gag nnn acc aac cag agc ggc ctg gag cgc     144
Asn Ala Asn Trp Glu Leu Glu Xaa Thr Asn Gln Ser Gly Leu Glu Arg
        35                  40                  45 tgc gaa ggc gag cag gac aag cgg ctg cac tgc tac gcc tcc tgg cgc     192
Cys Glu Gly Glu Gln Asp Lys Arg Leu His Cys Tyr Ala Ser Trp Arg
    50                  55                  60 aac agc tct ggc acc atc gag ctc gtg aag aag ggc tgc tgg cta gat     240
Asn Ser Ser Gly Thr Ile Glu Leu Val Lys Lys Gly Cys Trp Leu Asp
65                  70                  75                  80 gac ttc aac tgc tac gat agg cag gag tgt gtg gcc act gag gag aac     288
Asp Phe Asn Cys Tyr Asp Arg Gln Glu Cys Val Ala Thr Glu Glu Asn
                85                  90                  95 ccc cag gtg tac ttc tgc tgt gaa ggc aac ttc tgc aac gag cgc         336
Pro Gln Val Tyr Phe Cys Cys Glu Gly Asn Phe Cys Asn Glu Arg
            100                 105                 110 ttc act cat ttg cca gag gct ggg ggc ccg gaa gga ccc tgg gcc tcc     384
Phe Thr His Leu Pro Glu Ala Gly Gly Pro Glu Gly Pro Trp Ala Ser
        115                 120                 125 acc acc atc ccc tct ggt ggg cct gaa gcc act gca gct gct gga gat     432
Thr Thr Ile Pro Ser Gly Gly Pro Glu Ala Thr Ala Ala Ala Gly Asp
    130                 135                 140 caa ggc tcg ggg gcg ctt tgg ctg tgt ctg gaa ggc cca gct cat gaa     480
Gln Gly Ser Gly Ala Leu Trp Leu Cys Leu Glu Gly Pro Ala His Glu
145                 150                 155                 160

<210> SEQ ID NO 14
<211> LENGTH: 160
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: Ala, Phe, Gln, Val, Ile, Leu, Met, Lys, His,
      Trp or Tyr
<220> FEATURE:
<221> NAME/KEY: MOD_RES
<222> LOCATION: (40)..(40)
<223> OTHER INFORMATION: Ala, Gly, Gln, Met, His, Lys or Asn

<400> SEQUENCE: 14

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Xaa Cys Ile Tyr Tyr
            20                  25                  30

Asn Ala Asn Trp Glu Leu Glu Xaa Thr Asn Gln Ser Gly Leu Glu Arg
        35                  40                  45
```

```
Cys Glu Gly Glu Gln Asp Lys Arg Leu His Cys Tyr Ala Ser Trp Arg
     50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                 85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Gly Pro Trp Ala Ser
        115                 120                 125

Thr Thr Ile Pro Ser Gly Gly Pro Glu Ala Thr Ala Ala Gly Asp
    130                 135                 140

Gln Gly Ser Gly Ala Leu Trp Leu Cys Leu Glu Gly Pro Ala His Glu
145                 150                 155                 160

<210> SEQ ID NO 15
<211> LENGTH: 480
<212> TYPE: DNA
<213> ORGANISM: Homo sapiens
<220> FEATURE:
<221> NAME/KEY: CDS
<222> LOCATION: (1)..(480)
<220> FEATURE:
<221> NAME/KEY: modified_base
<222> LOCATION: (118)..(120)
<223> OTHER INFORMATION: a, c, t, g, unknown or other

<400> SEQUENCE: 15 atg acg gcg ccc tgg gtg gcc ctc gcc ctc ctc tgg gga tcg ctg tgc      48
Met Thr Ala Pro Trp Val Ala Leu Ala Leu Leu Trp Gly Ser Leu Cys
 1               5                  10                  15 gcc ggc tct ggg cgt ggg gag gct gag aca cgg gag tgc atc tac tac      96
Ala Gly Ser Gly Arg Gly Glu Ala Glu Thr Arg Glu Cys Ile Tyr Tyr
            20                  25                  30 aac gcc aac tgg gag ctg gag nnn acc aac cag agc ggc ctg gag cgc     144
Asn Ala Asn Trp Glu Leu Glu Xaa Thr Asn Gln Ser Gly Leu Glu Arg
        35                  40                  45 tgc gaa ggc gag cag gac aag cgg ctg cac tgc tac gcc tcc tgg cgc     192
Cys Glu Gly Glu Gln Asp Lys Arg Leu His Cys Tyr Ala Ser Trp Arg
    50                  55                  60 aac agc tct ggc acc atc gag ctc gtg aag aag ggc tgc tgg cta gat     240
Asn Ser Ser Gly Thr Ile Glu Leu Val Lys Lys Gly Cys Trp Leu Asp
 65                  70                  75                  80 gac ttc aac tgc tac gat agg cag gag tgt gtg gcc act gag gag aac     288
Asp Phe Asn Cys Tyr Asp Arg Gln Glu Cys Val Ala Thr Glu Glu Asn
                 85                  90                  95 ccc cag gtg tac ttc tgc tgt gaa ggc aac ttc tgc aac gag cgc         336
Pro Gln Val Tyr Phe Cys Cys Cys Glu Gly Asn Phe Cys Asn Glu Arg
            100                 105                 110 ttc act cat ttg cca gag gct ggg ggc ccg gaa gga ccc tgg gcc tcc     384
Phe Thr His Leu Pro Glu Ala Gly Gly Pro Glu Gly Pro Trp Ala Ser
        115                 120                 125 acc acc atc ccc tct ggt ggg cct gaa gcc act gca gct gct gga gat     432
Thr Thr Ile Pro Ser Gly Gly Pro Glu Ala Thr Ala Ala Gly Asp
    130                 135                 140 caa ggc tcg ggg gcg ctt tgg ctg tgt ctg gaa ggc cca gct cat gaa     480
Gln Gly Ser Gly Ala Leu Trp Leu Cys Leu Glu Gly Pro Ala His Glu
145                 150                 155                 160

<210> SEQ ID NO 16
```

<211> LENGTH: 160
<212> TYPE: PRT
<213> ORGANISM: Homo sapiens
<220> FEATURE:
<221> NAME/KEY: MOD_RES
<222> LOCATION: (40)..(40)
<223> OTHER INFORMATION: Gly, Gln, Met, His, Lys or Asn

<400> SEQUENCE: 16

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Xaa Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Gly Pro Trp Ala Ser
        115                 120                 125

Thr Thr Ile Pro Ser Gly Gly Pro Glu Ala Thr Ala Ala Ala Gly Asp
    130                 135                 140

Gln Gly Ser Gly Ala Leu Trp Leu Cys Leu Glu Gly Pro Ala His Glu
145                 150                 155                 160
```

<210> SEQ ID NO 17
<211> LENGTH: 402
<212> TYPE: DNA
<213> ORGANISM: Homo sapiens
<220> FEATURE:
<221> NAME/KEY: CDS
<222> LOCATION: (1)..(402)

<400> SEQUENCE: 17

```
atg acg gcg ccc tgg gtg gcc ctc gcc ctc ctc tgg gga tcg ctg tgc      48
Met Thr Ala Pro Trp Val Ala Leu Ala Leu Leu Trp Gly Ser Leu Cys
1               5                   10                  15 gcc ggc tct ggg cgt ggg gag gct gag aca cgg gag tgc atc tac tac      96
Ala Gly Ser Gly Arg Gly Glu Ala Glu Thr Arg Glu Cys Ile Tyr Tyr
            20                  25                  30 aac gcc aac tgg gag ctg gag cgc acc aac cag agc ggc ctg gag cgc     144
Asn Ala Asn Trp Glu Leu Glu Arg Thr Asn Gln Ser Gly Leu Glu Arg
        35                  40                  45 tgc gaa ggc gag cag gac aag cgg ctg cac tgc tac gcc tcc tgg cgc     192
Cys Glu Gly Glu Gln Asp Lys Arg Leu His Cys Tyr Ala Ser Trp Arg
    50                  55                  60 aac agc tct ggc acc atc gag ctc gtg aag aag ggc tgc tgg cta gat     240
Asn Ser Ser Gly Thr Ile Glu Leu Val Lys Lys Gly Cys Trp Leu Asp
65                  70                  75                  80 gac ttc aac tgc tac gat agg cag gag tgt gtg gcc act gag gag aac     288
Asp Phe Asn Cys Tyr Asp Arg Gln Glu Cys Val Ala Thr Glu Glu Asn
                85                  90                  95 ccc cag gtg tac ttc tgc tgc tgt gaa ggc aac ttc tgc aac gag cgc     336
Pro Gln Val Tyr Phe Cys Cys Cys Glu Gly Asn Phe Cys Asn Glu Arg
            100                 105                 110
```

```
ttc act cat ttg cca gag gct ggg ggc ccg gaa gtc acg tac gag cca      384
Phe Thr His Leu Pro Glu Ala Gly Gly Pro Glu Val Thr Tyr Glu Pro
            115                 120                 125 ccc ccg aca gcc ccc acc                                              402
Pro Pro Thr Ala Pro Thr
        130
```

<210> SEQ ID NO 18
<211> LENGTH: 134
<212> TYPE: PRT
<213> ORGANISM: Homo sapiens

<400> SEQUENCE: 18

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Glu Gly Asn Phe Cys Asn Glu Arg
            100                 105                 110

Phe Thr His Leu Pro Glu Ala Gly Gly Pro Glu Val Thr Tyr Glu Pro
            115                 120                 125

Pro Pro Thr Ala Pro Thr
        130
```

<210> SEQ ID NO 19
<211> LENGTH: 402
<212> TYPE: DNA
<213> ORGANISM: Homo sapiens
<220> FEATURE:
<221> NAME/KEY: CDS
<222> LOCATION: (1)..(402)
<220> FEATURE:
<221> NAME/KEY: modified_base
<222> LOCATION: (84)..(84)
<223> OTHER INFORMATION: a, c, t, g, unknown or other

<400> SEQUENCE: 19

```
atg acg gcg ccc tgg gtg gcc ctc gcc ctc ctc tgg gga tcg ctg tgc      48
Met Thr Ala Pro Trp Val Ala Leu Ala Leu Leu Trp Gly Ser Leu Cys
1               5                   10                  15 gcc ggc tct ggg cgt ggg gag gct gag aca cgg gcn tgc atc tac tac      96
Ala Gly Ser Gly Arg Gly Glu Ala Glu Thr Arg Ala Cys Ile Tyr Tyr
            20                  25                  30 aac gcc aac tgg gag ctg gag cgc acc aac cag agc ggc ctg gag cgc      144
Asn Ala Asn Trp Glu Leu Glu Arg Thr Asn Gln Ser Gly Leu Glu Arg
        35                  40                  45 tgc gaa ggc gag cag gac aag cgg ctg cac tgc tac gcc tcc tgg cgc      192
Cys Glu Gly Glu Gln Asp Lys Arg Leu His Cys Tyr Ala Ser Trp Arg
50                  55                  60 aac agc tct ggc acc atc gag ctc gtg aag aag ggc tgc tgg cta gat      240
Asn Ser Ser Gly Thr Ile Glu Leu Val Lys Lys Gly Cys Trp Leu Asp
65                  70                  75                  80 gac ttc aac tgc tac gat agg cag gag tgt gtg gcc act gag gag aac      288
```

```
                                                                             -continued Asp Phe Asn Cys Tyr Asp Arg Gln Glu Cys Val Ala Thr Glu Glu Asn
                85                  90                  95 ccc cag gtg tac ttc tgc tgt gaa ggc aac ttc tgc aac gag cgc         336
Pro Gln Val Tyr Phe Cys Cys Glu Gly Asn Phe Cys Asn Glu Arg
            100                 105                 110 ttc act cat ttg cca gag gct ggg ggc ccg gaa gtc acg tac gag cca     384
Phe Thr His Leu Pro Glu Ala Gly Gly Pro Glu Val Thr Tyr Glu Pro
        115                 120                 125 ccc ccg aca gcc ccc acc                                             402
Pro Pro Thr Ala Pro Thr
        130

<210> SEQ ID NO 20
<211> LENGTH: 134
<212> TYPE: PRT
<213> ORGANISM: Homo sapiens

<400> SEQUENCE: 20

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Ala Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr
        130

<210> SEQ ID NO 21
<211> LENGTH: 402
<212> TYPE: DNA
<213> ORGANISM: Homo sapiens
<220> FEATURE:
<221> NAME/KEY: CDS
<222> LOCATION: (1)..(402)
<220> FEATURE:
<221> NAME/KEY: modified_base
<222> LOCATION: (84)..(84)
<223> OTHER INFORMATION: a, c, t, g, unknown or other
<220> FEATURE:
<221> NAME/KEY: modified_base
<222> LOCATION: (120)..(120)
<223> OTHER INFORMATION: a, c, t, g, unknown or other

<400> SEQUENCE: 21 atg acg gcg ccc tgg gtg gcc ctc gcc ctc ctc tgg gga tcg ctg tgc     48
Met Thr Ala Pro Trp Val Ala Leu Ala Leu Leu Trp Gly Ser Leu Cys
1               5                   10                  15 gcc ggc tct ggg cgt ggg gag gct gag aca cgg gcn tgc atc tac tac     96
Ala Gly Ser Gly Arg Gly Glu Ala Glu Thr Arg Ala Cys Ile Tyr Tyr
            20                  25                  30 aac gcc aac tgg gag ctg gag gcn acc aac cag agc ggc ctg gag cgc    144
Asn Ala Asn Trp Glu Leu Glu Ala Thr Asn Gln Ser Gly Leu Glu Arg
```

| | | | | | | | | | | | | | | | | |
|---|---|---|---|---|---|---|---|---|---|---|---|---|---|---|---|---|
| | | | 35 | | | | 40 | | | | 45 | | | | | |
| tgc | gaa | ggc | gag | cag | gac | aag | cgg | ctg | cac | tgc | tac | gcc | tcc | tgg | cgc | 192 |
| Cys | Glu | Gly | Glu | Gln | Asp | Lys | Arg | Leu | His | Cys | Tyr | Ala | Ser | Trp | Arg | |
| | 50 | | | | | 55 | | | | | 60 | | | | | |
| aac | agc | tct | ggc | acc | atc | gag | ctc | gtg | aag | aag | ggc | tgc | tgg | cta | gat | 240 |
| Asn | Ser | Ser | Gly | Thr | Ile | Glu | Leu | Val | Lys | Lys | Gly | Cys | Trp | Leu | Asp | |
| 65 | | | | | 70 | | | | | 75 | | | | | 80 | |
| gac | ttc | aac | tgc | tac | gat | agg | cag | gag | tgt | gtg | gcc | act | gag | gag | aac | 288 |
| Asp | Phe | Asn | Cys | Tyr | Asp | Arg | Gln | Glu | Cys | Val | Ala | Thr | Glu | Glu | Asn | |
| | | | | 85 | | | | | 90 | | | | | 95 | | |
| ccc | cag | gtg | tac | ttc | tgc | tgt | gaa | ggc | aac | ttc | tgc | aac | gag | cgc | | 336 |
| Pro | Gln | Val | Tyr | Phe | Cys | Cys | Glu | Gly | Asn | Phe | Cys | Asn | Glu | Arg | | |
| | | 100 | | | | | 105 | | | | | 110 | | | | |
| ttc | act | cat | ttg | cca | gag | gct | ggg | ggc | ccg | gaa | gtc | acg | tac | gag | cca | 384 |
| Phe | Thr | His | Leu | Pro | Glu | Ala | Gly | Gly | Pro | Glu | Val | Thr | Tyr | Glu | Pro | |
| | | | 115 | | | | | 120 | | | | | 125 | | | |
| ccc | ccg | aca | gcc | ccc | acc | | | | | | | | | | | 402 |
| Pro | Pro | Thr | Ala | Pro | Thr | | | | | | | | | | | |
| | | 130 | | | | | | | | | | | | | | |

<210> SEQ ID NO 22
<211> LENGTH: 134
<212> TYPE: PRT
<213> ORGANISM: Homo sapiens

<400> SEQUENCE: 22

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Ala Cys Ile Tyr Tyr
                20                  25                  30

Asn Ala Asn Trp Glu Leu Glu Ala Thr Asn Gln Ser Gly Leu Glu Arg
            35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Glu Gly Asn Phe Cys Asn Glu Arg
                100                 105                 110

Phe Thr His Leu Pro Glu Ala Gly Gly Pro Glu Val Thr Tyr Glu Pro
            115                 120                 125

Pro Pro Thr Ala Pro Thr
        130

<210> SEQ ID NO 23
<211> LENGTH: 402
<212> TYPE: DNA
<213> ORGANISM: Homo sapiens
<220> FEATURE:
<221> NAME/KEY: CDS
<222> LOCATION: (1)..(402)

<400> SEQUENCE: 23

| | | | | | | | | | | | | | | | | |
|---|---|---|---|---|---|---|---|---|---|---|---|---|---|---|---|---|
| atg | acg | gcg | ccc | tgg | gtg | gcc | ctc | gcc | ctc | ctc | tgg | gga | tcg | ctg | tgc | 48 |
| Met | Thr | Ala | Pro | Trp | Val | Ala | Leu | Ala | Leu | Leu | Trp | Gly | Ser | Leu | Cys | |
| 1 | | | | 5 | | | | | 10 | | | | | 15 | | |
| gcc | ggc | tct | ggg | cgt | ggg | gag | gct | gag | aca | cgg | tgg | tgc | atc | tac | tac | 96 |
| Ala | Gly | Ser | Gly | Arg | Gly | Glu | Ala | Glu | Thr | Arg | Trp | Cys | Ile | Tyr | Tyr | |
| | | | 20 | | | | | 25 | | | | | 30 | | | |

```
aac gcc aac tgg gag ctg gag cgc acc aac cag agc ggc ctg gag cgc      144
Asn Ala Asn Trp Glu Leu Glu Arg Thr Asn Gln Ser Gly Leu Glu Arg
         35                  40                  45 tgc gaa ggc gag cag gac aag cgg ctg cac tgc tac gcc tcc tgg cgc      192
Cys Glu Gly Glu Gln Asp Lys Arg Leu His Cys Tyr Ala Ser Trp Arg
 50                  55                  60 aac agc tct ggc acc atc gag ctc gtg aag aag ggc tgc tgg cta gat      240
Asn Ser Ser Gly Thr Ile Glu Leu Val Lys Lys Gly Cys Trp Leu Asp
65                  70                  75                  80 gac ttc aac tgc tac gat agg cag gag tgt gtg gcc act gag gag aac      288
Asp Phe Asn Cys Tyr Asp Arg Gln Glu Cys Val Ala Thr Glu Glu Asn
                 85                  90                  95 ccc cag gtg tac ttc tgc tgt gaa ggc aac ttc tgc aac gag cgc          336
Pro Gln Val Tyr Phe Cys Cys Glu Gly Asn Phe Cys Asn Glu Arg
            100                 105                 110 ttc act cat ttg cca gag gct ggg ggc ccg gaa gtc acg tac gag cca      384
Phe Thr His Leu Pro Glu Ala Gly Gly Pro Glu Val Thr Tyr Glu Pro
        115                 120                 125 ccc ccg aca gcc ccc acc                                              402
Pro Pro Thr Ala Pro Thr
        130

<210> SEQ ID NO 24
<211> LENGTH: 134
<212> TYPE: PRT
<213> ORGANISM: Homo sapiens

<400> SEQUENCE: 24

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Trp Cys Ile Tyr Tyr
            20                  25                  30

Asn Ala Asn Trp Glu Leu Glu Arg Thr Asn Gln Ser Gly Leu Glu Arg
         35                  40                  45

Cys Glu Gly Glu Gln Asp Lys Arg Leu His Cys Tyr Ala Ser Trp Arg
 50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                 85                  90                  95

Pro Gln Val Tyr Phe Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr
        130

<210> SEQ ID NO 25
<211> LENGTH: 402
<212> TYPE: DNA
<213> ORGANISM: Homo sapiens
<220> FEATURE:
<221> NAME/KEY: CDS
<222> LOCATION: (1)..(402)

<400> SEQUENCE: 25 atg acg gcg ccc tgg gtg gcc ctc gcc ctc ctc tgg gga tcg ctg tgc      48
Met Thr Ala Pro Trp Val Ala Leu Ala Leu Leu Trp Gly Ser Leu Cys
1               5                   10                  15
```

```
gcc ggc tct ggg cgt ggg gag gct gag aca cgg tac tgc atc tac tac      96
Ala Gly Ser Gly Arg Gly Glu Ala Glu Thr Arg Tyr Cys Ile Tyr Tyr
         20                  25                  30 aac gcc aac tgg gag ctg gag cgc acc aac cag agc ggc ctg gag cgc     144
Asn Ala Asn Trp Glu Leu Glu Arg Thr Asn Gln Ser Gly Leu Glu Arg
         35                  40                  45 tgc gaa ggc gag cag gac aag cgg ctg cac tgc tac gcc tcc tgg cgc     192
Cys Glu Gly Glu Gln Asp Lys Arg Leu His Cys Tyr Ala Ser Trp Arg
 50                  55                  60 aac agc tct ggc acc atc gag ctc gtg aag aag ggc tgc tgg cta gat     240
Asn Ser Ser Gly Thr Ile Glu Leu Val Lys Lys Gly Cys Trp Leu Asp
 65                  70                  75                  80 gac ttc aac tgc tac gat agg cag gag tgt gtg gcc act gag gag aac     288
Asp Phe Asn Cys Tyr Asp Arg Gln Glu Cys Val Ala Thr Glu Glu Asn
                 85                  90                  95 ccc cag gtg tac ttc tgc tgc tgt gaa ggc aac ttc tgc aac gag cgc     336
Pro Gln Val Tyr Phe Cys Cys Cys Glu Gly Asn Phe Cys Asn Glu Arg
                100                 105                 110 ttc act cat ttg cca gag gct ggg ggc ccg gaa gtc acg tac gag cca     384
Phe Thr His Leu Pro Glu Ala Gly Gly Pro Glu Val Thr Tyr Glu Pro
                115                 120                 125 ccc ccg aca gcc ccc acc                                              402
Pro Pro Thr Ala Pro Thr
    130
```

```
<210> SEQ ID NO 26
<211> LENGTH: 134
<212> TYPE: PRT
<213> ORGANISM: Homo sapiens

<400> SEQUENCE: 26

Met Thr Ala Pro Trp Val Ala Leu Ala Leu Leu Trp Gly Ser Leu Cys
 1               5                  10                  15

Ala Gly Ser Gly Arg Gly Glu Ala Glu Thr Arg Tyr Cys Ile Tyr Tyr
                 20                  25                  30

Asn Ala Asn Trp Glu Leu Glu Arg Thr Asn Gln Ser Gly Leu Glu Arg
             35                  40                  45

Cys Glu Gly Glu Gln Asp Lys Arg Leu His Cys Tyr Ala Ser Trp Arg
 50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                 85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
            115                 120                 125

Pro Pro Thr Ala Pro Thr
    130

<210> SEQ ID NO 27
<211> LENGTH: 402
<212> TYPE: DNA
<213> ORGANISM: Homo sapiens
<220> FEATURE:
<221> NAME/KEY: CDS
<222> LOCATION: (1)..(402)
<220> FEATURE:
<221> NAME/KEY: modified_base
<222> LOCATION: (82)..(84)
<223> OTHER INFORMATION: a, c, t, g, unknown or other
```

<400> SEQUENCE: 27

```
atg acg gcg ccc tgg gtg gcc ctc gcc ctc ctc tgg gga tcg ctg tgc        48
Met Thr Ala Pro Trp Val Ala Leu Ala Leu Leu Trp Gly Ser Leu Cys
1               5                   10                  15 gcc ggc tct ggg cgt ggg gag gct gag aca cgg nnn tgc atc tac tac        96
Ala Gly Ser Gly Arg Gly Glu Ala Glu Thr Arg Xaa Cys Ile Tyr Tyr
            20                  25                  30 aac gcc aac tgg gag ctg gag cgc acc aac cag agc ggc ctg gag cgc       144
Asn Ala Asn Trp Glu Leu Glu Arg Thr Asn Gln Ser Gly Leu Glu Arg
        35                  40                  45 tgc gaa ggc gag cag gac aag cgg ctg cac tgc tac gcc tcc tgg cgc       192
Cys Glu Gly Glu Gln Asp Lys Arg Leu His Cys Tyr Ala Ser Trp Arg
50                  55                  60 aac agc tct ggc acc atc gag ctc gtg aag aag ggc tgc tgg cta gat       240
Asn Ser Ser Gly Thr Ile Glu Leu Val Lys Lys Gly Cys Trp Leu Asp
65                  70                  75                  80 gac ttc aac tgc tac gat agg cag gag tgt gtg gcc act gag gag aac       288
Asp Phe Asn Cys Tyr Asp Arg Gln Glu Cys Val Ala Thr Glu Glu Asn
                85                  90                  95 ccc cag gtg tac ttc tgc tgt gaa ggc aac ttc tgc aac gag cgc           336
Pro Gln Val Tyr Phe Cys Cys Glu Gly Asn Phe Cys Asn Glu Arg
            100                 105                 110 ttc act cat ttg cca gag gct ggg ggc ccg gaa gtc acg tac gag cca       384
Phe Thr His Leu Pro Glu Ala Gly Gly Pro Glu Val Thr Tyr Glu Pro
        115                 120                 125 ccc ccg aca gcc ccc acc                                               402
Pro Pro Thr Ala Pro Thr
        130
```

<210> SEQ ID NO 28
<211> LENGTH: 134
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: Ala, Phe, Gln, Val, Ile, Leu, Met, Lys, His, Trp or Tyr

<400> SEQUENCE: 28

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Xaa Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr
        130
```

<210> SEQ ID NO 29
<211> LENGTH: 402
<212> TYPE: DNA
<213> ORGANISM: Homo sapiens
<220> FEATURE:
<221> NAME/KEY: CDS
<222> LOCATION: (1)..(402)
<220> FEATURE:
<221> NAME/KEY: modified_base
<222> LOCATION: (82)..(84)
<223> OTHER INFORMATION: a, c, t, g, unknown or other
<220> FEATURE:
<221> NAME/KEY: modified_base
<222> LOCATION: (118)..(120)
<223> OTHER INFORMATION: a, c, t, g, unknown or other

<400> SEQUENCE: 29

```
atg acg gcg ccc tgg gtg gcc ctc gcc ctc ctc tgg gga tcg ctg tgc        48
Met Thr Ala Pro Trp Val Ala Leu Ala Leu Leu Trp Gly Ser Leu Cys
1               5                   10                  15 gcc ggc tct ggg cgt ggg gag gct gag aca cgg nnn tgc atc tac tac        96
Ala Gly Ser Gly Arg Gly Glu Ala Glu Thr Arg Xaa Cys Ile Tyr Tyr
                20                  25                  30 aac gcc aac tgg gag ctg gag nnn acc aac cag agc ggc ctg gag cgc       144
Asn Ala Asn Trp Glu Leu Glu Xaa Thr Asn Gln Ser Gly Leu Glu Arg
            35                  40                  45 tgc gaa ggc gag cag gac aag cgg ctg cac tgc tac gcc tcc tgg cgc       192
Cys Glu Gly Glu Gln Asp Lys Arg Leu His Cys Tyr Ala Ser Trp Arg
    50                  55                  60 aac agc tct ggc acc atc gag ctc gtg aag aag ggc tgc tgg cta gat       240
Asn Ser Ser Gly Thr Ile Glu Leu Val Lys Lys Gly Cys Trp Leu Asp
65                  70                  75                  80 gac ttc aac tgc tac gat agg cag gag tgt gtg gcc act gag gag aac       288
Asp Phe Asn Cys Tyr Asp Arg Gln Glu Cys Val Ala Thr Glu Glu Asn
                85                  90                  95 ccc cag gtg tac ttc tgc tgt gaa ggc aac ttc tgc aac gag cgc           336
Pro Gln Val Tyr Phe Cys Cys Glu Gly Asn Phe Cys Asn Glu Arg
                100                 105                 110 ttc act cat ttg cca gag gct ggg ggc ccg gaa gtc acg tac gag cca       384
Phe Thr His Leu Pro Glu Ala Gly Gly Pro Glu Val Thr Tyr Glu Pro
            115                 120                 125 ccc ccg aca gcc ccc acc                                                402
Pro Pro Thr Ala Pro Thr
        130
```

<210> SEQ ID NO 30
<211> LENGTH: 134
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: Ala, Phe, Gln, Val, Ile, Leu, Met, Lys, His, Tyr or Trp
<220> FEATURE:
<221> NAME/KEY: MOD_RES
<222> LOCATION: (40)..(40)
<223> OTHER INFORMATION: Ala, Gly, Gln, Met, His, Lys or Asn

<400> SEQUENCE: 30

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Xaa Cys Ile Tyr Tyr
                20                  25                  30

Asn Ala Asn Trp Glu Leu Glu Xaa Thr Asn Gln Ser Gly Leu Glu Arg
```

```
                35                  40                  45
Cys Glu Gly Glu Gln Asp Lys Arg Leu His Cys Tyr Ala Ser Trp Arg
     50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                 85                  90                  95

Pro Gln Val Tyr Phe Cys Cys Glu Gly Asn Phe Cys Asn Glu Arg
             100                 105                 110

Phe Thr His Leu Pro Glu Ala Gly Gly Pro Glu Val Thr Tyr Glu Pro
             115                 120                 125

Pro Pro Thr Ala Pro Thr
         130
```

<210> SEQ ID NO 31
<211> LENGTH: 402
<212> TYPE: DNA
<213> ORGANISM: Homo sapiens
<220> FEATURE:
<221> NAME/KEY: CDS
<222> LOCATION: (1)..(402)
<220> FEATURE:
<221> NAME/KEY: modified_base
<222> LOCATION: (118)..(120)
<223> OTHER INFORMATION: a, c, t, g, unknown or other

<400> SEQUENCE: 31

```
atg acg gcg ccc tgg gtg gcc ctc gcc ctc ctc tgg gga tcg ctg tgc        48
Met Thr Ala Pro Trp Val Ala Leu Ala Leu Leu Trp Gly Ser Leu Cys
 1               5                  10                  15 gcc ggc tct ggg cgt ggg gag gct gag aca cgg gag tgc atc tac tac        96
Ala Gly Ser Gly Arg Gly Glu Ala Glu Thr Arg Glu Cys Ile Tyr Tyr
             20                  25                  30 aac gcc aac tgg gag ctg gag nnn acc aac cag agc ggc ctg gag cgc       144
Asn Ala Asn Trp Glu Leu Glu Xaa Thr Asn Gln Ser Gly Leu Glu Arg
         35                  40                  45 tgc gaa ggc gag cag gac aag cgg ctg cac tgc tac gcc tcc tgg cgc       192
Cys Glu Gly Glu Gln Asp Lys Arg Leu His Cys Tyr Ala Ser Trp Arg
     50                  55                  60 aac agc tct ggc acc atc gag ctc gtg aag aag ggc tgc tgg cta gat       240
Asn Ser Ser Gly Thr Ile Glu Leu Val Lys Lys Gly Cys Trp Leu Asp
 65                  70                  75                  80 gac ttc aac tgc tac gat agg cag gag tgt gtg gcc act gag gag aac       288
Asp Phe Asn Cys Tyr Asp Arg Gln Glu Cys Val Ala Thr Glu Glu Asn
                 85                  90                  95 ccc cag gtg tac ttc tgc tgt tgt gaa ggc aac ttc tgc aac gag cgc       336
Pro Gln Val Tyr Phe Cys Cys Cys Glu Gly Asn Phe Cys Asn Glu Arg
            100                 105                 110 ttc act cat ttg cca gag gct ggg ggc ccg gaa gtc acg tac gag cca       384
Phe Thr His Leu Pro Glu Ala Gly Gly Pro Glu Val Thr Tyr Glu Pro
            115                 120                 125 ccc ccg aca gcc ccc acc                                                402
Pro Pro Thr Ala Pro Thr
        130
```

<210> SEQ ID NO 32
<211> LENGTH: 134
<212> TYPE: PRT
<213> ORGANISM: Homo sapiens
<220> FEATURE:
<221> NAME/KEY: MOD_RES
<222> LOCATION: (40)..(40)

<223> OTHER INFORMATION: Gly, Gln, Met, His, Lys, Asn

<400> SEQUENCE: 32

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Xaa Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr
        130
```

<210> SEQ ID NO 33
<211> LENGTH: 402
<212> TYPE: DNA
<213> ORGANISM: Homo sapiens
<220> FEATURE:
<221> NAME/KEY: CDS
<222> LOCATION: (1)..(402)
<220> FEATURE:
<221> NAME/KEY: modified_base
<222> LOCATION: (84)..(84)
<223> OTHER INFORMATION: a, c, t, g, unknown or other
<220> FEATURE:
<221> NAME/KEY: modified_base
<222> LOCATION: (192)..(192)
<223> OTHER INFORMATION: a, c, t, g, unknown or other

<400> SEQUENCE: 33

```
atg acg gcg ccc tgg gtg gcc ctc gcc ctc ctc tgg gga tcg ctg tgc      48
Met Thr Ala Pro Trp Val Ala Leu Ala Leu Leu Trp Gly Ser Leu Cys
1               5                   10                  15 gcc ggc tct ggg cgt ggg gag gct gag aca cgg gcn tgc atc tac tac      96
Ala Gly Ser Gly Arg Gly Glu Ala Glu Thr Arg Ala Cys Ile Tyr Tyr
            20                  25                  30 aac gcc aac tgg gag ctg gag cgc acc aac cag agc ggc ctg gag cgc     144
Asn Ala Asn Trp Glu Leu Glu Arg Thr Asn Gln Ser Gly Leu Glu Arg
        35                  40                  45 tgc gaa ggc gag cag gac aag cgg ctg cac tgc tac gcc tcc tgg gcn     192
Cys Glu Gly Glu Gln Asp Lys Arg Leu His Cys Tyr Ala Ser Trp Ala
    50                  55                  60 aac agc tct ggc acc atc gag ctc gtg aag aag ggc tgc tgg cta gat     240
Asn Ser Ser Gly Thr Ile Glu Leu Val Lys Lys Gly Cys Trp Leu Asp
65                  70                  75                  80 gac ttc aac tgc tac gat agg cag gag tgt gtg gcc act gag gag aac     288
Asp Phe Asn Cys Tyr Asp Arg Gln Glu Cys Val Ala Thr Glu Glu Asn
                85                  90                  95 ccc cag gtg tac ttc tgc tgc tgt gaa ggc aac ttc tgc aac gag cgc     336
Pro Gln Val Tyr Phe Cys Cys Cys Glu Gly Asn Phe Cys Asn Glu Arg
            100                 105                 110 ttc act cat ttg cca gag gct ggg ggc ccg gaa gtc acg tac gag cca     384
```

```
                                                                                                402
ccc ccg aca gcc ccc acc
Pro Pro Thr Ala Pro Thr
        130
```

<210> SEQ ID NO 34
<211> LENGTH: 134
<212> TYPE: PRT
<213> ORGANISM: Homo sapiens

<400> SEQUENCE: 34

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Ala Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Ala
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr
    130
```

<210> SEQ ID NO 35
<211> LENGTH: 402
<212> TYPE: DNA
<213> ORGANISM: Homo sapiens
<220> FEATURE:
<221> NAME/KEY: CDS
<222> LOCATION: (1)..(402)
<220> FEATURE:
<221> NAME/KEY: modified_base
<222> LOCATION: (84)..(84)
<223> OTHER INFORMATION: a, c, t, g, unknown or other
<220> FEATURE:
<221> NAME/KEY: modified_base
<222> LOCATION: (120)..(120)
<223> OTHER INFORMATION: a, c, t, g, unknown or other
<220> FEATURE:
<221> NAME/KEY: modified_base
<222> LOCATION: (192)..(192)
<223> OTHER INFORMATION: a, c, t, g, unknown or other

<400> SEQUENCE: 35

```
atg acg gcg ccc tgg gtg gcc ctc gcc ctc ctc tgg gga tcg ctg tgc       48
Met Thr Ala Pro Trp Val Ala Leu Ala Leu Leu Trp Gly Ser Leu Cys
1               5                   10                  15 gcc ggc tct ggg cgt ggn gag gct gag aca cgg gcn tgc atc tac tac       96
Ala Gly Ser Gly Arg Gly Glu Ala Glu Thr Arg Ala Cys Ile Tyr Tyr
            20                  25                  30 aac gcc aac tgg gag ctg gag gcn acc aac cag agc ggc ctg gag cgc      144
Asn Ala Asn Trp Glu Leu Glu Ala Thr Asn Gln Ser Gly Leu Glu Arg
        35                  40                  45 tgc gaa ggc gag cag gac aag cgg ctg cac tgc tac gcc tcc tgg gcn      192
Cys Glu Gly Glu Gln Asp Lys Arg Leu His Cys Tyr Ala Ser Trp Ala
```

```
aac agc tct ggc acc atc gag ctc gtg aag aag ggc tgc tgg cta gat      240
Asn Ser Ser Gly Thr Ile Glu Leu Val Lys Lys Gly Cys Trp Leu Asp
 65                  70                  75                  80 gac ttc aac tgc tac gat agg cag gag tgt gtg gcc act gag gag aac      288
Asp Phe Asn Cys Tyr Asp Arg Gln Glu Cys Val Ala Thr Glu Glu Asn
                 85                  90                  95 ccc cag gtg tac ttc tgc tgt gaa ggc aac ttc tgc aac gag cgc          336
Pro Gln Val Tyr Phe Cys Cys Glu Gly Asn Phe Cys Asn Glu Arg
            100                 105                 110 ttc act cat ttg cca gag gct ggg ggc ccg gaa gtc acg tac gag cca      384
Phe Thr His Leu Pro Glu Ala Gly Gly Pro Glu Val Thr Tyr Glu Pro
        115                 120                 125 ccc ccg aca gcc ccc acc                                              402
Pro Pro Thr Ala Pro Thr
    130
```

<210> SEQ ID NO 36
<211> LENGTH: 134
<212> TYPE: PRT
<213> ORGANISM: Homo sapiens

<400> SEQUENCE: 36

```
Met Thr Ala Pro Trp Val Ala Leu Ala Leu Leu Trp Gly Ser Leu Cys
 1               5                  10                  15

Ala Gly Ser Gly Arg Gly Glu Ala Glu Thr Arg Ala Cys Ile Tyr Tyr
                20                  25                  30

Asn Ala Asn Trp Glu Leu Glu Ala Thr Asn Gln Ser Gly Leu Glu Arg
            35                  40                  45

Cys Glu Gly Glu Gln Asp Lys Arg Leu His Cys Tyr Ala Ser Trp Ala
        50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                 85                  90                  95

Pro Gln Val Tyr Phe Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr
    130
```

<210> SEQ ID NO 37
<211> LENGTH: 402
<212> TYPE: DNA
<213> ORGANISM: Homo sapiens
<220> FEATURE:
<221> NAME/KEY: CDS
<222> LOCATION: (1)..(402)
<220> FEATURE:
<221> NAME/KEY: modified_base
<222> LOCATION: (192)..(192)
<223> OTHER INFORMATION: a, c, t, g, unknown or other

<400> SEQUENCE: 37

```
atg acg gcg ccc tgg gtg gcc ctc gcc ctc ctc tgg gga tcg ctg tgc      48
Met Thr Ala Pro Trp Val Ala Leu Ala Leu Leu Trp Gly Ser Leu Cys
 1               5                  10                  15 gcc ggc tct ggg cgt ggg gag gct gag aca cgg tgg tgc atc tac tac      96
Ala Gly Ser Gly Arg Gly Glu Ala Glu Thr Arg Trp Cys Ile Tyr Tyr
                20                  25                  30
```

```
aac gcc aac tgg gag ctg gag cgc acc aac cag agc ggc ctg gag cgc    144
Asn Ala Asn Trp Glu Leu Glu Arg Thr Asn Gln Ser Gly Leu Glu Arg
         35                  40                  45 tgc gaa ggc gag cag gac aag cgg ctg cac tgc tac gcc tcc tgg gcn    192
Cys Glu Gly Glu Gln Asp Lys Arg Leu His Cys Tyr Ala Ser Trp Ala
 50                  55                  60 aac agc tct ggc acc atc gag ctc gtg aag aag ggc tgc tgg cta gat    240
Asn Ser Ser Gly Thr Ile Glu Leu Val Lys Lys Gly Cys Trp Leu Asp
 65                  70                  75                  80 gac ttc aac tgc tac gat agg cag gag tgt gtg gcc act gag gag aac    288
Asp Phe Asn Cys Tyr Asp Arg Gln Glu Cys Val Ala Thr Glu Glu Asn
                 85                  90                  95 ccc cag gtg tac ttc tgc tgt gaa ggc aac ttc tgc aac gag cgc        336
Pro Gln Val Tyr Phe Cys Cys Glu Gly Asn Phe Cys Asn Glu Arg
            100                 105                 110 ttc act cat ttg cca gag gct ggg ggc ccg gaa gtc acg tac gag cca    384
Phe Thr His Leu Pro Glu Ala Gly Gly Pro Glu Val Thr Tyr Glu Pro
            115                 120                 125 ccc ccg aca gcc ccc acc                                            402
Pro Pro Thr Ala Pro Thr
    130
```

<210> SEQ ID NO 38
<211> LENGTH: 134
<212> TYPE: PRT
<213> ORGANISM: Homo sapiens

<400> SEQUENCE: 38

```
Met Thr Ala Pro Trp Val Ala Leu Ala Leu Leu Trp Gly Ser Leu Cys
 1               5                  10                  15

Ala Gly Ser Gly Arg Gly Glu Ala Glu Thr Arg Trp Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Ala
 50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                 85                  90                  95

Pro Gln Val Tyr Phe Cys Cys Glu Gly Asn Phe Cys Asn Glu Arg
            100                 105                 110

Phe Thr His Leu Pro Glu Ala Gly Gly Pro Glu Val Thr Tyr Glu Pro
            115                 120                 125

Pro Pro Thr Ala Pro Thr
    130
```

<210> SEQ ID NO 39
<211> LENGTH: 402
<212> TYPE: DNA
<213> ORGANISM: Homo sapiens
<220> FEATURE:
<221> NAME/KEY: CDS
<222> LOCATION: (1)..(402)
<220> FEATURE:
<221> NAME/KEY: modified_base
<222> LOCATION: (192)..(192)
<223> OTHER INFORMATION: a, c, t, g, unknown or other

<400> SEQUENCE: 39

-continued

```
atg acg gcg ccc tgg gtg gcc ctc gcc ctc ctc tgg gga tcg ctg tgc        48
Met Thr Ala Pro Trp Val Ala Leu Ala Leu Leu Trp Gly Ser Leu Cys
1               5                   10                  15 gcc ggc tct ggg cgt ggg gag gct gag aca cgg tac tgc atc tac tac        96
Ala Gly Ser Gly Arg Gly Glu Ala Glu Thr Arg Tyr Cys Ile Tyr Tyr
            20                  25                  30 aac gcc aac tgg gag ctg gag cgc acc aac cag agc ggc ctg gag cgc       144
Asn Ala Asn Trp Glu Leu Glu Arg Thr Asn Gln Ser Gly Leu Glu Arg
        35                  40                  45 tgc gaa ggc gag cag gac aag cgg ctg cac tgc tac gcc tcc tgg gcn       192
Cys Glu Gly Glu Gln Asp Lys Arg Leu His Cys Tyr Ala Ser Trp Ala
    50                  55                  60 aac agc tct ggc acc atc gag ctc gtg aag aag ggc tgc tgg cta gat       240
Asn Ser Ser Gly Thr Ile Glu Leu Val Lys Lys Gly Cys Trp Leu Asp
65                  70                  75                  80 gac ttc aac tgc tac gat agg cag gag tgt gtg gcc act gag gag aac       288
Asp Phe Asn Cys Tyr Asp Arg Gln Glu Cys Val Ala Thr Glu Glu Asn
                85                  90                  95 ccc cag gtg tac ttc tgc tgc tgt gaa ggc aac ttc tgc aac gag cgc       336
Pro Gln Val Tyr Phe Cys Cys Cys Glu Gly Asn Phe Cys Asn Glu Arg
            100                 105                 110 ttc act cat ttg cca gag gct ggg ggc ccg gaa gtc acg tac gag cca       384
Phe Thr His Leu Pro Glu Ala Gly Gly Pro Glu Val Thr Tyr Glu Pro
        115                 120                 125 ccc ccg aca gcc ccc acc                                                402
Pro Pro Thr Ala Pro Thr
            130
```

<210> SEQ ID NO 40
<211> LENGTH: 134
<212> TYPE: PRT
<213> ORGANISM: Homo sapiens

<400> SEQUENCE: 40

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Tyr Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Ala
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr
            130
```

<210> SEQ ID NO 41
<211> LENGTH: 402
<212> TYPE: DNA
<213> ORGANISM: Homo sapiens
<220> FEATURE:
<221> NAME/KEY: CDS
<222> LOCATION: (1)..(402)

<220> FEATURE:
<221> NAME/KEY: modified_base
<222> LOCATION: (82)..(84)
<223> OTHER INFORMATION: a, c, t, g, unknown or other
<220> FEATURE:
<221> NAME/KEY: modified_base
<222> LOCATION: (192)..(192)
<223> OTHER INFORMATION: a, c, t, g, unknown or other

<400> SEQUENCE: 41

| atg | acg | gcg | ccc | tgg | gtg | gcc | ctc | gcc | ctc | ctc | tgg | gga | tcg | ctg | tgc | 48 |
|---|---|---|---|---|---|---|---|---|---|---|---|---|---|---|---|---|
| Met | Thr | Ala | Pro | Trp | Val | Ala | Leu | Ala | Leu | Leu | Trp | Gly | Ser | Leu | Cys | |
| 1 | | | | 5 | | | | | 10 | | | | | 15 | | |

| gcc | ggc | tct | ggg | cgt | ggg | gag | gct | gag | aca | cgg | nnn | tgc | atc | tac | tac | 96 |
|---|---|---|---|---|---|---|---|---|---|---|---|---|---|---|---|---|
| Ala | Gly | Ser | Gly | Arg | Gly | Glu | Ala | Glu | Thr | Arg | Xaa | Cys | Ile | Tyr | Tyr | |
| | | 20 | | | | | 25 | | | | | | 30 | | | |

| aac | gcc | aac | tgg | gag | ctg | gag | cgc | acc | aac | cag | agc | ggc | ctg | gag | cgc | 144 |
|---|---|---|---|---|---|---|---|---|---|---|---|---|---|---|---|---|
| Asn | Ala | Asn | Trp | Glu | Leu | Glu | Arg | Thr | Asn | Gln | Ser | Gly | Leu | Glu | Arg | |
| | 35 | | | | | 40 | | | | | 45 | | | | | |

| tgc | gaa | ggc | gag | cag | gac | aag | cgg | ctg | cac | tgc | tac | gcc | tcc | tgg | gcn | 192 |
|---|---|---|---|---|---|---|---|---|---|---|---|---|---|---|---|---|
| Cys | Glu | Gly | Glu | Gln | Asp | Lys | Arg | Leu | His | Cys | Tyr | Ala | Ser | Trp | Ala | |
| 50 | | | | | 55 | | | | | 60 | | | | | | |

| aac | agc | tct | ggc | acc | atc | gag | ctc | gtg | aag | aag | ggc | tgc | tgg | cta | gat | 240 |
|---|---|---|---|---|---|---|---|---|---|---|---|---|---|---|---|---|
| Asn | Ser | Ser | Gly | Thr | Ile | Glu | Leu | Val | Lys | Lys | Gly | Cys | Trp | Leu | Asp | |
| 65 | | | | 70 | | | | | 75 | | | | | 80 | | |

| gac | ttc | aac | tgc | tac | gat | agg | cag | gag | tgt | gtg | gcc | act | gag | gag | aac | 288 |
|---|---|---|---|---|---|---|---|---|---|---|---|---|---|---|---|---|
| Asp | Phe | Asn | Cys | Tyr | Asp | Arg | Gln | Glu | Cys | Val | Ala | Thr | Glu | Glu | Asn | |
| | | | 85 | | | | | 90 | | | | | 95 | | | |

| ccc | cag | gtg | tac | ttc | tgc | tgc | tgt | gaa | ggc | aac | ttc | tgc | aac | gag | cgc | 336 |
|---|---|---|---|---|---|---|---|---|---|---|---|---|---|---|---|---|
| Pro | Gln | Val | Tyr | Phe | Cys | Cys | Cys | Glu | Gly | Asn | Phe | Cys | Asn | Glu | Arg | |
| | | 100 | | | | | 105 | | | | | 110 | | | | |

| ttc | act | cat | ttg | cca | gag | gct | ggg | ggc | ccg | gaa | gtc | acg | tac | gag | cca | 384 |
|---|---|---|---|---|---|---|---|---|---|---|---|---|---|---|---|---|
| Phe | Thr | His | Leu | Pro | Glu | Ala | Gly | Gly | Pro | Glu | Val | Thr | Tyr | Glu | Pro | |
| | | 115 | | | | | 120 | | | | | 125 | | | | |

| ccc | ccg | aca | gcc | ccc | acc | | | | | | | | | | | 402 |
|---|---|---|---|---|---|---|---|---|---|---|---|---|---|---|---|---|
| Pro | Pro | Thr | Ala | Pro | Thr | | | | | | | | | | | |
| | 130 | | | | | | | | | | | | | | | |

<210> SEQ ID NO 42
<211> LENGTH: 134
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: Ala, Phe, Gln, Val, Ile, Leu, Met, Lys, His, Tyr or Trp

<400> SEQUENCE: 42

| Met | Thr | Ala | Pro | Trp | Val | Ala | Leu | Ala | Leu | Leu | Trp | Gly | Ser | Leu | Cys |
|---|---|---|---|---|---|---|---|---|---|---|---|---|---|---|---|
| 1 | | | | 5 | | | | | 10 | | | | | 15 | |

| Ala | Gly | Ser | Gly | Arg | Gly | Glu | Ala | Glu | Thr | Arg | Xaa | Cys | Ile | Tyr | Tyr |
|---|---|---|---|---|---|---|---|---|---|---|---|---|---|---|---|
| | | 20 | | | | | 25 | | | | | | 30 | | |

| Asn | Ala | Asn | Trp | Glu | Leu | Glu | Arg | Thr | Asn | Gln | Ser | Gly | Leu | Glu | Arg |
|---|---|---|---|---|---|---|---|---|---|---|---|---|---|---|---|
| | 35 | | | | | 40 | | | | | 45 | | | | |

| Cys | Glu | Gly | Glu | Gln | Asp | Lys | Arg | Leu | His | Cys | Tyr | Ala | Ser | Trp | Ala |
|---|---|---|---|---|---|---|---|---|---|---|---|---|---|---|---|
| 50 | | | | | 55 | | | | | 60 | | | | | |

| Asn | Ser | Ser | Gly | Thr | Ile | Glu | Leu | Val | Lys | Lys | Gly | Cys | Trp | Leu | Asp |
|---|---|---|---|---|---|---|---|---|---|---|---|---|---|---|---|
| 65 | | | | 70 | | | | | 75 | | | | | 80 | |

| Asp | Phe | Asn | Cys | Tyr | Asp | Arg | Gln | Glu | Cys | Val | Ala | Thr | Glu | Glu | Asn |
|---|---|---|---|---|---|---|---|---|---|---|---|---|---|---|---|
| | | | 85 | | | | | 90 | | | | | 95 | | |

Pro Gln Val Tyr Phe Cys Cys Cys Glu Gly Asn Phe Cys Asn Glu Arg

```
                    100                 105                 110
Phe Thr His Leu Pro Glu Ala Gly Gly Pro Glu Val Thr Tyr Glu Pro
        115                 120                 125

Pro Pro Thr Ala Pro Thr
    130

<210> SEQ ID NO 43
<211> LENGTH: 402
<212> TYPE: DNA
<213> ORGANISM: Homo sapiens
<220> FEATURE:
<221> NAME/KEY: CDS
<222> LOCATION: (1)..(402)
<220> FEATURE:
<221> NAME/KEY: modified_base
<222> LOCATION: (82)..(84)
<223> OTHER INFORMATION: a, c, t, g, unknown or other
<220> FEATURE:
<221> NAME/KEY: modified_base
<222> LOCATION: (118)..(120)
<223> OTHER INFORMATION: a, c, t, g, unknown or other
<220> FEATURE:
<221> NAME/KEY: modified_base
<222> LOCATION: (192)..(192)
<223> OTHER INFORMATION: a, c, t, g, unknown or other

<400> SEQUENCE: 43 atg acg gcg ccc tgg gtg gcc ctc gcc ctc ctc tgg gga tcg ctg tgc      48
Met Thr Ala Pro Trp Val Ala Leu Ala Leu Leu Trp Gly Ser Leu Cys
1               5                   10                  15 gcc ggc tct ggg cgt ggg gag gct gag aca cgg nnn tgc atc tac tac      96
Ala Gly Ser Gly Arg Gly Glu Ala Glu Thr Arg Xaa Cys Ile Tyr Tyr
            20                  25                  30 aac gcc aac tgg gag ctg gag nnn acc aac cag agc ggc ctg gag cgc     144
Asn Ala Asn Trp Glu Leu Glu Xaa Thr Asn Gln Ser Gly Leu Glu Arg
        35                  40                  45 tgc gaa ggc gag cag gac aag cgg ctg cac tgc tac gcc tcc tgg gcn     192
Cys Glu Gly Glu Gln Asp Lys Arg Leu His Cys Tyr Ala Ser Trp Ala
    50                  55                  60 aac agc tct ggc acc atc gag ctc gtg aag aag ggc tgc tgg cta gat     240
Asn Ser Ser Gly Thr Ile Glu Leu Val Lys Lys Gly Cys Trp Leu Asp
65                  70                  75                  80 gac ttc aac tgc tac gat agg cag gag tgt gtg gcc act gag gag aac     288
Asp Phe Asn Cys Tyr Asp Arg Gln Glu Cys Val Ala Thr Glu Glu Asn
                85                  90                  95 ccc cag gtg tac ttc tgc tgt gaa ggc aac ttc tgc aac gag cgc         336
Pro Gln Val Tyr Phe Cys Cys Glu Gly Asn Phe Cys Asn Glu Arg
                100                 105                 110 ttc act cat ttg cca gag gct ggg ggc ccg gaa gtc acg tac gag cca     384
Phe Thr His Leu Pro Glu Ala Gly Gly Pro Glu Val Thr Tyr Glu Pro
        115                 120                 125 ccc ccg aca gcc ccc acc                                             402
Pro Pro Thr Ala Pro Thr
    130

<210> SEQ ID NO 44
<211> LENGTH: 134
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: Ala, Phe, Gln, Val, Ile, Leu, Met, Lys, His,
      Trp or Tyr
<220> FEATURE:
<221> NAME/KEY: MOD_RES
```

```
<222> LOCATION: (40)..(40)
<223> OTHER INFORMATION: Ala, Gly, Gln, Met, His, Lys or Asn

<400> SEQUENCE: 44

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Xaa Cys Ile Tyr Tyr
            20                  25                  30

Asn Ala Asn Trp Glu Leu Glu Xaa Thr Asn Gln Ser Gly Leu Glu Arg
        35                  40                  45

Cys Glu Gly Glu Gln Asp Lys Arg Leu His Cys Tyr Ala Ser Trp Ala
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr
        130

<210> SEQ ID NO 45
<211> LENGTH: 402
<212> TYPE: DNA
<213> ORGANISM: Homo sapiens
<220> FEATURE:
<221> NAME/KEY: CDS
<222> LOCATION: (1)..(402)
<220> FEATURE:
<221> NAME/KEY: modified_base
<222> LOCATION: (118)..(120)
<223> OTHER INFORMATION: a, c, t, g, unknown or other
<220> FEATURE:
<221> NAME/KEY: modified_base
<222> LOCATION: (192)..(192)
<223> OTHER INFORMATION: a, c, t, g, unknown or other

<400> SEQUENCE: 45 atg acg gcg ccc tgg gtg gcc ctc gcc ctc ctc tgg gga tcg ctg tgc      48
Met Thr Ala Pro Trp Val Ala Leu Ala Leu Leu Trp Gly Ser Leu Cys
1               5                   10                  15 gcc ggc tct ggg cgt ggg gag gct gag aca cgg gag tgc atc tac tac      96
Ala Gly Ser Gly Arg Gly Glu Ala Glu Thr Arg Glu Cys Ile Tyr Tyr
            20                  25                  30 aac gcc aac tgg gag ctg gag nnn acc aac cag agc ggc ctg gag cgc     144
Asn Ala Asn Trp Glu Leu Glu Xaa Thr Asn Gln Ser Gly Leu Glu Arg
        35                  40                  45 tgc gaa ggc gag cag gac aag cgg ctg cac tgc tac gcc tcc tgg gcn     192
Cys Glu Gly Glu Gln Asp Lys Arg Leu His Cys Tyr Ala Ser Trp Ala
    50                  55                  60 aac agc tct ggc acc atc gag ctc gtg aag aag ggc tgc tgg cta gat     240
Asn Ser Ser Gly Thr Ile Glu Leu Val Lys Lys Gly Cys Trp Leu Asp
65                  70                  75                  80 gac ttc aac tgc tac gat agg cag gag tgt gtg gcc act gag gag aac     288
Asp Phe Asn Cys Tyr Asp Arg Gln Glu Cys Val Ala Thr Glu Glu Asn
                85                  90                  95 ccc cag gtg tac ttc tgc tgc tgt gaa ggc aac ttc tgc aac gag cgc     336
Pro Gln Val Tyr Phe Cys Cys Cys Glu Gly Asn Phe Cys Asn Glu Arg
            100                 105                 110
```

```
ttc act cat ttg cca gag gct ggg ggc ccg gaa gtc acg tac gag cca      384
Phe Thr His Leu Pro Glu Ala Gly Gly Pro Glu Val Thr Tyr Glu Pro
        115                 120                 125 ccc ccg aca gcc ccc acc                                              402
Pro Pro Thr Ala Pro Thr
    130
```

<210> SEQ ID NO 46
<211> LENGTH: 134
<212> TYPE: PRT
<213> ORGANISM: Homo sapiens
<220> FEATURE:
<221> NAME/KEY: MOD_RES
<222> LOCATION: (40)..(40)
<223> OTHER INFORMATION: Gly, Glu, Met, His, Lys or Asn

<400> SEQUENCE: 46

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Xaa Thr Asn Gln Ser Gly Leu Glu Arg
        35                  40                  45

Cys Glu Gly Glu Gln Asp Lys Arg Leu His Cys Tyr Ala Ser Trp Ala
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr
    130
```

<210> SEQ ID NO 47
<211> LENGTH: 512
<212> TYPE: PRT
<213> ORGANISM: Homo sapiens

<400> SEQUENCE: 47

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125
```

Pro Pro Thr Ala Pro Thr Leu Leu Thr Val Leu Ala Tyr Ser Leu Leu
130                 135                 140

Pro Ile Gly Gly Leu Ser Leu Ile Val Leu Leu Ala Phe Trp Met Tyr
145                 150                 155                 160

Arg His Arg Lys Pro Tyr Gly His Val Asp Ile His Glu Asp Pro
        165                 170                 175

Gly Pro Pro Pro Ser Pro Leu Val Gly Leu Lys Pro Leu Gln Leu
        180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

Val Leu Glu Gly Ala Ile Asn Phe Gln Arg Asp Ala Phe Leu Arg Ile
370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
        435                 440                 445

Gly Leu Ala Gln Leu Cys Val Thr Ile Glu Glu Cys Trp Asp His Asp
450                 455                 460

Ala Glu Ala Arg Leu Ser Ala Gly Cys Val Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510

<210> SEQ ID NO 48
<211> LENGTH: 426
<212> TYPE: PRT
<213> ORGANISM: Homo sapiens

<400> SEQUENCE: 48

-continued

```
Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
        195                 200                 205

Lys Val Val Asp Ala Arg Lys Ser Thr Trp His Val Phe Pro Val Ser
    210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Gly Glu Glu Gly Glu Gly Lys Lys Lys Lys
            260                 265                 270

Gly Gly Gly Glu Gly Gly Ala Gly Ala Asp Glu Glu Lys Glu Gln Ser
        275                 280                 285

His Arg Pro Phe Leu Met Leu Gln Ala Arg Gln Ser Glu Asp His Pro
    290                 295                 300

His Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
                325                 330                 335

Asp Trp Ile Ile Ala Pro Ser Gly Tyr His Ala Asn Tyr Cys Glu Gly
            340                 345                 350

Glu Cys Pro Ser His Ile Ala Gly Thr Ser Gly Ser Ser Leu Ser Phe
        355                 360                 365

His Ser Thr Val Ile Asn His Tyr Arg Met Arg Gly His Ser Pro Phe
    370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
                405                 410                 415
```

-continued

```
Asn Met Ile Val Glu Glu Cys Gly Cys Ser
            420                 425
```

<210> SEQ ID NO 49
<211> LENGTH: 375
<212> TYPE: PRT
<213> ORGANISM: Homo sapiens

<400> SEQUENCE: 49

```
Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
        290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
        355                 360                 365
```

-continued

Val Asp Arg Cys Gly Cys Ser
    370                 375

<210> SEQ ID NO 50
<211> LENGTH: 217
<212> TYPE: PRT
<213> ORGANISM: Homo sapiens

<400> SEQUENCE: 50

Ala Pro Glu Leu Leu Gly Gly Pro Ser Val Phe Leu Phe Pro Pro Lys
1               5                   10                  15

Pro Lys Asp Ile Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Gly Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 51
<211> LENGTH: 480
<212> TYPE: DNA
<213> ORGANISM: Homo sapiens
<220> FEATURE:
<221> NAME/KEY: CDS
<222> LOCATION: (1)..(480)
<220> FEATURE:
<221> NAME/KEY: modified_base
<222> LOCATION: (82)..(84)
<223> OTHER INFORMATION: a, c, t, g, unknown or other
<220> FEATURE:
<221> NAME/KEY: modified_base
<222> LOCATION: (118)..(120)
<223> OTHER INFORMATION: a, c, t, g, unknown or other

<400> SEQUENCE: 51 atg acg gcg ccc tgg gtg gcc ctc gcc ctc ctc tgg gga tcg ctg tgc         48
Met Thr Ala Pro Trp Val Ala Leu Ala Leu Leu Trp Gly Ser Leu Cys
1               5                   10                  15 gcc ggc tct ggg cgt ggg gag gct gag aca cgg nnn tgc atc tac tac         96
Ala Gly Ser Gly Arg Gly Glu Ala Glu Thr Arg Xaa Cys Ile Tyr Tyr

```
aac gcc aac tgg gag ctg gag nnn acc aac cag agc ggc ctg gag cgc      144
Asn Ala Asn Trp Glu Leu Glu Xaa Thr Asn Gln Ser Gly Leu Glu Arg
         35                  40                  45 tgc gaa ggc gag cag gac aag cgg ctg cac tgc tac gcc tcc tgg cgc      192
Cys Glu Gly Glu Gln Asp Lys Arg Leu His Cys Tyr Ala Ser Trp Arg
 50                  55                  60 aac agc tct ggc acc atc gag ctc gtg aag aag ggc tgc tgg cta gat      240
Asn Ser Ser Gly Thr Ile Glu Leu Val Lys Lys Gly Cys Trp Leu Asp
 65                  70                  75                  80 gac ttc aac tgc tac gat agg cag gag tgt gtg gcc act gag gag aac      288
Asp Phe Asn Cys Tyr Asp Arg Gln Glu Cys Val Ala Thr Glu Glu Asn
                 85                  90                  95 ccc cag gtg tac ttc tgc tgt gaa ggc aac ttc tgc aac gag cgc          336
Pro Gln Val Tyr Phe Cys Cys Glu Gly Asn Phe Cys Asn Glu Arg
            100                 105                 110 ttc act cat ttg cca gag gct ggg ggc ccg gaa gga ccc tgg gcc tcc      384
Phe Thr His Leu Pro Glu Ala Gly Gly Pro Glu Gly Pro Trp Ala Ser
            115                 120                 125 acc acc atc ccc tct ggt ggg cct gaa gcc act gca gct gct gga gat      432
Thr Thr Ile Pro Ser Gly Gly Pro Glu Ala Thr Ala Ala Ala Gly Asp
130                 135                 140 caa ggc tcg ggg gcg ctt tgg ctg tgt ctg gaa ggc cca gct cat gaa      480
Gln Gly Ser Gly Ala Leu Trp Leu Cys Leu Glu Gly Pro Ala His Glu
145                 150                 155                 160
```

<210> SEQ ID NO 52
<211> LENGTH: 160
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (40)..(40)
<223> OTHER INFORMATION: Any amino acid

<400> SEQUENCE: 52

```
Met Thr Ala Pro Trp Val Ala Leu Ala Leu Leu Trp Gly Ser Leu Cys
 1               5                  10                  15

Ala Gly Ser Gly Arg Gly Glu Ala Glu Thr Arg Xaa Cys Ile Tyr Tyr
                 20                  25                  30

Asn Ala Asn Trp Glu Leu Glu Xaa Thr Asn Gln Ser Gly Leu Glu Arg
         35                  40                  45

Cys Glu Gly Glu Gln Asp Lys Arg Leu His Cys Tyr Ala Ser Trp Arg
 50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                 85                  90                  95

Pro Gln Val Tyr Phe Cys Cys Glu Gly Asn Phe Cys Asn Glu Arg
            100                 105                 110

Phe Thr His Leu Pro Glu Ala Gly Gly Pro Glu Gly Pro Trp Ala Ser
            115                 120                 125

Thr Thr Ile Pro Ser Gly Gly Pro Glu Ala Thr Ala Ala Ala Gly Asp
130                 135                 140

Gln Gly Ser Gly Ala Leu Trp Leu Cys Leu Glu Gly Pro Ala His Glu
145                 150                 155                 160
```

<210> SEQ ID NO 53
<211> LENGTH: 402
<212> TYPE: DNA
<213> ORGANISM: Homo sapiens
<220> FEATURE:
<221> NAME/KEY: CDS
<222> LOCATION: (1)..(402)
<220> FEATURE:
<221> NAME/KEY: modified_base
<222> LOCATION: (82)..(84)
<223> OTHER INFORMATION: a, c, t, g, unknown or other
<220> FEATURE:
<221> NAME/KEY: modified_base
<222> LOCATION: (118)..(120)
<223> OTHER INFORMATION: a, c, t, g, unknown or other

<400> SEQUENCE: 53

```
atg acg gcg ccc tgg gtg gcc ctc gcc ctc ctc tgg gga tcg ctg tgc      48
Met Thr Ala Pro Trp Val Ala Leu Ala Leu Leu Trp Gly Ser Leu Cys
1               5                   10                  15 gcc ggc tct ggg cgt ggg gag gct gag aca cgg nnn tgc atc tac tac      96
Ala Gly Ser Gly Arg Gly Glu Ala Glu Thr Arg Xaa Cys Ile Tyr Tyr
                20                  25                  30 aac gcc aac tgg gag ctg gag nnn acc aac cag agc ggc ctg gag cgc     144
Asn Ala Asn Trp Glu Leu Glu Xaa Thr Asn Gln Ser Gly Leu Glu Arg
            35                  40                  45 tgc gaa ggc gag cag gac aag cgg ctg cac tgc tac gcc tcc tgg cgc     192
Cys Glu Gly Glu Gln Asp Lys Arg Leu His Cys Tyr Ala Ser Trp Arg
50                  55                  60 aac agc tct ggc acc atc gag ctc gtg aag aag ggc tgc tgg cta gat     240
Asn Ser Ser Gly Thr Ile Glu Leu Val Lys Lys Gly Cys Trp Leu Asp
65                  70                  75                  80 gac ttc aac tgc tac gat agg cag gag tgt gtg gcc act gag gag aac     288
Asp Phe Asn Cys Tyr Asp Arg Gln Glu Cys Val Ala Thr Glu Glu Asn
                85                  90                  95 ccc cag gtg tac ttc tgc tgc tgt gaa ggc aac ttc tgc aac gag cgc     336
Pro Gln Val Tyr Phe Cys Cys Cys Glu Gly Asn Phe Cys Asn Glu Arg
            100                 105                 110 ttc act cat ttg cca gag gct ggg ggc ccg gaa gtc acg tac gag cca     384
Phe Thr His Leu Pro Glu Ala Gly Gly Pro Glu Val Thr Tyr Glu Pro
        115                 120                 125 ccc ccg aca gcc ccc acc                                              402
Pro Pro Thr Ala Pro Thr
        130
```

<210> SEQ ID NO 54
<211> LENGTH: 134
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (40)..(40)
<223> OTHER INFORMATION: Any amino acid

<400> SEQUENCE: 54

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Xaa Cys Ile Tyr Tyr
                20                  25                  30

Asn Ala Asn Trp Glu Leu Glu Xaa Thr Asn Gln Ser Gly Leu Glu Arg
```

```
                35                  40                  45
Cys Glu Gly Glu Gln Asp Lys Arg Leu His Cys Tyr Ala Ser Trp Arg
         50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                 85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr
    130

<210> SEQ ID NO 55
<211> LENGTH: 402
<212> TYPE: DNA
<213> ORGANISM: Homo sapiens
<220> FEATURE:
<221> NAME/KEY: CDS
<222> LOCATION: (1)..(402)
<220> FEATURE:
<221> NAME/KEY: modified_base
<222> LOCATION: (82)..(84)
<223> OTHER INFORMATION: a, c, t, g, unknown or other
<220> FEATURE:
<221> NAME/KEY: modified_base
<222> LOCATION: (118)..(120)
<223> OTHER INFORMATION: a, c, t, g, unknown or other
<220> FEATURE:
<221> NAME/KEY: modified_base
<222> LOCATION: (192)..(192)
<223> OTHER INFORMATION: a, c, t, g, unknown or other

<400> SEQUENCE: 55 atg acg gcg ccc tgg gtg gcc ctc gcc ctc ctc tgg gga tcg ctg tgc       48
Met Thr Ala Pro Trp Val Ala Leu Ala Leu Leu Trp Gly Ser Leu Cys
 1               5                  10                  15 gcc ggc tct ggg cgt ggg gag gct gag aca cgg nnn tgc atc tac tac       96
Ala Gly Ser Gly Arg Gly Glu Ala Glu Thr Arg Xaa Cys Ile Tyr Tyr
             20                  25                  30 aac gcc aac tgg gag ctg gag nnn acc aac cag agc ggc ctg gag cgc      144
Asn Ala Asn Trp Glu Leu Glu Xaa Thr Asn Gln Ser Gly Leu Glu Arg
         35                  40                  45 tgc gaa ggc gag cag gac aag cgg ctg cac tgc tac gcc tcc tgg gcn      192
Cys Glu Gly Glu Gln Asp Lys Arg Leu His Cys Tyr Ala Ser Trp Ala
     50                  55                  60 aac agc tct ggc acc atc gag ctc gtg aag aag ggc tgc tgg cta gat      240
Asn Ser Ser Gly Thr Ile Glu Leu Val Lys Lys Gly Cys Trp Leu Asp
 65                  70                  75                  80 gac ttc aac tgc tac gat agg cag gag tgt gtg gcc act gag gag aac      288
Asp Phe Asn Cys Tyr Asp Arg Gln Glu Cys Val Ala Thr Glu Glu Asn
                 85                  90                  95 ccc cag gtg tac ttc tgc tgc tgt gaa ggc aac ttc tgc aac gag cgc      336
Pro Gln Val Tyr Phe Cys Cys Cys Glu Gly Asn Phe Cys Asn Glu Arg
            100                 105                 110 ttc act cat ttg cca gag gct ggg ggc ccg gaa gtc acg tac gag cca      384
Phe Thr His Leu Pro Glu Ala Gly Gly Pro Glu Val Thr Tyr Glu Pro
        115                 120                 125 ccc ccg aca gcc ccc acc                                              402
Pro Pro Thr Ala Pro Thr
    130
```

<210> SEQ ID NO 56
<211> LENGTH: 134
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (40)..(40)
<223> OTHER INFORMATION: Any amino acid

<400> SEQUENCE: 56

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Xaa Cys Ile Tyr Tyr
            20                  25                  30

Asn Ala Asn Trp Glu Leu Glu Xaa Thr Asn Gln Ser Gly Leu Glu Arg
        35                  40                  45

Cys Glu Gly Glu Gln Asp Lys Arg Leu His Cys Tyr Ala Ser Trp Ala
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr
        130
```

<210> SEQ ID NO 57
<211> LENGTH: 1047
<212> TYPE: DNA
<213> ORGANISM: Homo sapiens
<220> FEATURE:
<221> NAME/KEY: CDS
<222> LOCATION: (1)..(1044)

<400> SEQUENCE: 57

```
tct ggg cgt ggg gag gct gag aca cgg gag tgc atc tac tac aac gcc    48
Ser Gly Arg Gly Glu Ala Glu Thr Arg Glu Cys Ile Tyr Tyr Asn Ala
1               5                   10                  15 aac tgg gag ctg gag cgc acc aac cag agc ggc ctg gag cgc tgc gaa    96
Asn Trp Glu Leu Glu Arg Thr Asn Gln Ser Gly Leu Glu Arg Cys Glu
            20                  25                  30 ggc gag cag gac aag cgg ctg cac tgc tac gcc tcc tgg cgc aac agc   144
Gly Glu Gln Asp Lys Arg Leu His Cys Tyr Ala Ser Trp Arg Asn Ser
        35                  40                  45 tct ggc acc atc gag ctc gtg aag aag ggc tgc tgg cta gat gac ttc   192
Ser Gly Thr Ile Glu Leu Val Lys Lys Gly Cys Trp Leu Asp Asp Phe
    50                  55                  60 aac tgc tac gat agg cag gag tgt gtg gcc act gag gag aac ccc cag   240
Asn Cys Tyr Asp Arg Gln Glu Cys Val Ala Thr Glu Glu Asn Pro Gln
65                  70                  75                  80 gtg tac ttc tgc tgc tgt gaa ggc aac ttc tgc aac gag cgc ttc act   288
Val Tyr Phe Cys Cys Cys Glu Gly Asn Phe Cys Asn Glu Arg Phe Thr
                85                  90                  95 cat ttg cca gag gct ggg ggc ccg gaa gtc acg tac gag cca ccc ccg   336
```

```
His Leu Pro Glu Ala Gly Gly Pro Glu Val Thr Tyr Glu Pro Pro
                100                 105                 110 aca gcc ccc act gga gga gga gga tct gac aaa act cac aca tgc cca      384
Thr Ala Pro Thr Gly Gly Gly Gly Ser Asp Lys Thr His Thr Cys Pro
            115                 120                 125 ccg tgc cca gca cct gaa ctc ctg ggg gga ccg tca gtc ttc ctc ttc      432
Pro Cys Pro Ala Pro Glu Leu Leu Gly Gly Pro Ser Val Phe Leu Phe
130                 135                 140 ccc cca aaa ccc aag gac atc ctc atg atc tcc cgg acc cct gag gtc      480
Pro Pro Lys Pro Lys Asp Ile Leu Met Ile Ser Arg Thr Pro Glu Val
145                 150                 155                 160 aca tgc gtg gtg gtg gac gtg agc cac gaa gac cct gag gtc aag ttc      528
Thr Cys Val Val Val Asp Val Ser His Glu Asp Pro Glu Val Lys Phe
                165                 170                 175 aac tgg tac gtg ggc ggc gtg gag gtg cat aat gcc aag aca aag ccg      576
Asn Trp Tyr Val Gly Gly Val Glu Val His Asn Ala Lys Thr Lys Pro
                180                 185                 190 cgg gag gag cag tac aac agc acg tac cgt gtg gtc agc gtc ctc acc      624
Arg Glu Glu Gln Tyr Asn Ser Thr Tyr Arg Val Val Ser Val Leu Thr
            195                 200                 205 gtc ctg cac cag gac tgg ctg aat ggc aag gag tac aag tgc aag gtc      672
Val Leu His Gln Asp Trp Leu Asn Gly Lys Glu Tyr Lys Cys Lys Val
210                 215                 220 tcc aac aaa gcc ctc cca gcc ccc atc gag aaa acc atc tcc aaa gcc      720
Ser Asn Lys Ala Leu Pro Ala Pro Ile Glu Lys Thr Ile Ser Lys Ala
225                 230                 235                 240 aaa ggg cag ccc cga gaa cca cag gtg tac acc ctg ccc cca tcc cgg      768
Lys Gly Gln Pro Arg Glu Pro Gln Val Tyr Thr Leu Pro Pro Ser Arg
                245                 250                 255 gat gag ctg acc aag aac cag gtc agc ctg acc tgc ctg gtc aaa ggc      816
Asp Glu Leu Thr Lys Asn Gln Val Ser Leu Thr Cys Leu Val Lys Gly
                260                 265                 270 ttc tat ccc agc gac atc gcc gtg gag tgg gag agc aat ggg cag ccg      864
Phe Tyr Pro Ser Asp Ile Ala Val Glu Trp Glu Ser Asn Gly Gln Pro
            275                 280                 285 gag aac aac tac aag acc acg cct ccc gtg ctg gac tcc gac ggc tcc      912
Glu Asn Asn Tyr Lys Thr Thr Pro Pro Val Leu Asp Ser Asp Gly Ser
290                 295                 300 ttc ttc ctc tac agc aag ctc acc gtg gac aag agc agg tgg cag cag      960
Phe Phe Leu Tyr Ser Lys Leu Thr Val Asp Lys Ser Arg Trp Gln Gln
305                 310                 315                 320 ggg aac gtc ttc tca tgc tcc gtg atg cat gag gct ctg cac aac cac     1008
Gly Asn Val Phe Ser Cys Ser Val Met His Glu Ala Leu His Asn His
                325                 330                 335 tac acg cag aag agc ctc tcc ctg tct ccg ggt aaa tga                 1047
Tyr Thr Gln Lys Ser Leu Ser Leu Ser Pro Gly Lys
            340                 345

<210> SEQ ID NO 58
<211> LENGTH: 348
<212> TYPE: PRT
<213> ORGANISM: Homo sapiens

<400> SEQUENCE: 58

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45
```

```
Ser Gly Thr Ile Glu Leu Val Lys Lys Gly Cys Trp Leu Asp Asp Phe
 50                  55                  60

Asn Cys Tyr Asp Arg Gln Glu Cys Val Ala Thr Glu Glu Asn Pro Gln
 65                  70                  75                  80

Val Tyr Phe Cys Cys Cys Glu Gly Asn Phe Cys Asn Glu Arg Phe Thr
                 85                  90                  95

His Leu Pro Glu Ala Gly Gly Pro Glu Val Thr Tyr Glu Pro Pro Pro
            100                 105                 110

Thr Ala Pro Thr Gly Gly Gly Ser Asp Lys Thr His Thr Cys Pro
        115                 120                 125

Pro Cys Pro Ala Pro Glu Leu Leu Gly Gly Pro Ser Val Phe Leu Phe
    130                 135                 140

Pro Pro Lys Pro Lys Asp Ile Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Gly Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Asp Glu Leu Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345
```

```
<210> SEQ ID NO 59
<211> LENGTH: 1047
<212> TYPE: DNA
<213> ORGANISM: Homo sapiens
<220> FEATURE:
<221> NAME/KEY: CDS
<222> LOCATION: (1)..(1044)

<400> SEQUENCE: 59 tct ggg cgt ggg gag gct gag aca cgg gcg tgc atc tac tac aac gcc    48
Ser Gly Arg Gly Glu Ala Glu Thr Arg Ala Cys Ile Tyr Tyr Asn Ala
1               5                   10                  15 aac tgg gag ctg gag cgc acc aac cag agc ggc ctg gag cgc tgc gaa    96
Asn Trp Glu Leu Glu Arg Thr Asn Gln Ser Gly Leu Glu Arg Cys Glu
            20                  25                  30 ggc gag cag gac aag cgg ctg cac tgc tac gcc tcc tgg cgc aac agc   144
Gly Glu Gln Asp Lys Arg Leu His Cys Tyr Ala Ser Trp Arg Asn Ser
```

```
             35                  40                  45
tct ggc acc atc gag ctc gtg aag aag ggc tgc tgg cta gat gac ttc      192
Ser Gly Thr Ile Glu Leu Val Lys Lys Gly Cys Trp Leu Asp Asp Phe
 50                  55                  60 aac tgc tac gat agg cag gag tgt gtg gcc act gag gag aac ccc cag      240
Asn Cys Tyr Asp Arg Gln Glu Cys Val Ala Thr Glu Glu Asn Pro Gln
 65                  70                  75                  80 gtg tac ttc tgc tgc tgt gaa ggc aac ttc tgc aac gag cgc ttc act      288
Val Tyr Phe Cys Cys Cys Glu Gly Asn Phe Cys Asn Glu Arg Phe Thr
                 85                  90                  95 cat ttg cca gag gct ggg ggc ccg gaa gtc acg tac gag cca ccc ccg      336
His Leu Pro Glu Ala Gly Gly Pro Glu Val Thr Tyr Glu Pro Pro Pro
            100                 105                 110 aca gcc ccc act gga gga gga gga tct gac aaa act cac aca tgc cca      384
Thr Ala Pro Thr Gly Gly Gly Gly Ser Asp Lys Thr His Thr Cys Pro
        115                 120                 125 ccg tgc cca gca cct gaa ctc ctg ggg gga ccg tca gtc ttc ctc ttc      432
Pro Cys Pro Ala Pro Glu Leu Leu Gly Gly Pro Ser Val Phe Leu Phe
    130                 135                 140 ccc cca aaa ccc aag gac atc ctc atg atc tcc cgg acc cct gag gtc      480
Pro Pro Lys Pro Lys Asp Ile Leu Met Ile Ser Arg Thr Pro Glu Val
145                 150                 155                 160 aca tgc gtg gtg gtg gac gtg agc cac gaa gac cct gag gtc aag ttc      528
Thr Cys Val Val Val Asp Val Ser His Glu Asp Pro Glu Val Lys Phe
                165                 170                 175 aac tgg tac gtg ggc ggc gtg gag gtg cat aat gcc aag aca aag ccg      576
Asn Trp Tyr Val Gly Gly Val Glu Val His Asn Ala Lys Thr Lys Pro
            180                 185                 190 cgg gag gag cag tac aac agc acg tac cgt gtg gtc agc gtc ctc acc      624
Arg Glu Glu Gln Tyr Asn Ser Thr Tyr Arg Val Val Ser Val Leu Thr
        195                 200                 205 gtc ctg cac cag gac tgg ctg aat ggc aag gag tac aag tgc aag gtc      672
Val Leu His Gln Asp Trp Leu Asn Gly Lys Glu Tyr Lys Cys Lys Val
    210                 215                 220 tcc aac aaa gcc ctc cca gcc ccc atc gag aaa acc atc tcc aaa gcc      720
Ser Asn Lys Ala Leu Pro Ala Pro Ile Glu Lys Thr Ile Ser Lys Ala
225                 230                 235                 240 aaa ggg cag ccc cga gaa cca cag gtg tac acc ctg ccc cca tcc cgg      768
Lys Gly Gln Pro Arg Glu Pro Gln Val Tyr Thr Leu Pro Pro Ser Arg
                245                 250                 255 gat gag ctg acc aag aac cag gtc agc ctg acc tgc ctg gtc aaa ggc      816
Asp Glu Leu Thr Lys Asn Gln Val Ser Leu Thr Cys Leu Val Lys Gly
            260                 265                 270 ttc tat ccc agc gac atc gcc gtg gag tgg gag agc aat ggg cag ccg      864
Phe Tyr Pro Ser Asp Ile Ala Val Glu Trp Glu Ser Asn Gly Gln Pro
        275                 280                 285 gag aac aac tac aag acc acg cct ccc gtg ctg gac tcc gac ggc tcc      912
Glu Asn Asn Tyr Lys Thr Thr Pro Pro Val Leu Asp Ser Asp Gly Ser
    290                 295                 300 ttc ttc ctc tac agc aag ctc acc gtg gac aag agc agg tgg cag cag      960
Phe Phe Leu Tyr Ser Lys Leu Thr Val Asp Lys Ser Arg Trp Gln Gln
305                 310                 315                 320 ggg aac gtc ttc tca tgc tcc gtg atg cat gag gct ctg cac aac cac     1008
Gly Asn Val Phe Ser Cys Ser Val Met His Glu Ala Leu His Asn His
                325                 330                 335 tac acg cag aag agc ctc tcc ctg tct ccg ggt aaa tga                 1047
Tyr Thr Gln Lys Ser Leu Ser Leu Ser Pro Gly Lys
            340                 345
```

<210> SEQ ID NO 60
<211> LENGTH: 348
<212> TYPE: PRT
<213> ORGANISM: Homo sapiens

<400> SEQUENCE: 60

```
Ser Gly Arg Gly Glu Ala Glu Thr Arg Ala Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr Gly Gly Gly Ser Asp Lys Thr His Thr Cys Pro
        115                 120                 125

Pro Cys Pro Ala Pro Glu Leu Leu Gly Gly Pro Ser Val Phe Leu Phe
    130                 135                 140

Pro Pro Lys Pro Lys Asp Ile Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Gly Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Asp Glu Leu Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345
```

<210> SEQ ID NO 61
<211> LENGTH: 1047
<212> TYPE: DNA
<213> ORGANISM: Homo sapiens
<220> FEATURE:

<221> NAME/KEY: CDS
<222> LOCATION: (1)..(1044)

<400> SEQUENCE: 61

| | | | | | | | | | | | | | | | | |
|---|---|---|---|---|---|---|---|---|---|---|---|---|---|---|---|---|
| tct | ggg | cgt | ggg | gag | gct | gag | aca | cgg | tgg | tgc | ctc | tac | tac | aac | gcc | 48 |
| Ser | Gly | Arg | Gly | Glu | Ala | Glu | Thr | Arg | Trp | Cys | Leu | Tyr | Tyr | Asn | Ala | |
| 1 | | | | 5 | | | | | 10 | | | | | 15 | | |
| aac | tgg | gag | ctg | gag | cgc | acc | aac | cag | agc | ggc | ctg | gag | cgc | tgc | gaa | 96 |
| Asn | Trp | Glu | Leu | Glu | Arg | Thr | Asn | Gln | Ser | Gly | Leu | Glu | Arg | Cys | Glu | |
| | | | 20 | | | | | 25 | | | | | 30 | | | |
| ggc | gag | cag | gac | aag | cgg | ctg | cac | tgc | tac | gcc | tcc | tgg | cgc | aac | agc | 144 |
| Gly | Glu | Gln | Asp | Lys | Arg | Leu | His | Cys | Tyr | Ala | Ser | Trp | Arg | Asn | Ser | |
| | | 35 | | | | | 40 | | | | | 45 | | | | |
| tct | ggc | acc | atc | gag | ctc | gtg | aag | aag | ggc | tgc | tgg | cta | gat | gac | ttc | 192 |
| Ser | Gly | Thr | Ile | Glu | Leu | Val | Lys | Lys | Gly | Cys | Trp | Leu | Asp | Asp | Phe | |
| 50 | | | | | 55 | | | | | 60 | | | | | | |
| aac | tgc | tac | gat | agg | cag | gag | tgt | gtg | gcc | act | gag | gag | aac | ccc | cag | 240 |
| Asn | Cys | Tyr | Asp | Arg | Gln | Glu | Cys | Val | Ala | Thr | Glu | Glu | Asn | Pro | Gln | |
| 65 | | | | | 70 | | | | | 75 | | | | | 80 | |
| gtg | tac | ttc | tgc | tgc | tgt | gaa | ggc | aac | ttc | tgc | aac | gag | cgc | ttc | act | 288 |
| Val | Tyr | Phe | Cys | Cys | Cys | Glu | Gly | Asn | Phe | Cys | Asn | Glu | Arg | Phe | Thr | |
| | | | | 85 | | | | | 90 | | | | | 95 | | |
| cat | ttg | cca | gag | gct | ggg | ggc | ccg | gaa | gtc | acg | tac | gag | cca | ccc | ccg | 336 |
| His | Leu | Pro | Glu | Ala | Gly | Gly | Pro | Glu | Val | Thr | Tyr | Glu | Pro | Pro | Pro | |
| | | | 100 | | | | | 105 | | | | | 110 | | | |
| aca | gcc | ccc | act | gga | gga | gga | gga | tct | gac | aaa | act | cac | aca | tgc | cca | 384 |
| Thr | Ala | Pro | Thr | Gly | Gly | Gly | Gly | Ser | Asp | Lys | Thr | His | Thr | Cys | Pro | |
| | | | 115 | | | | | 120 | | | | | 125 | | | |
| ccg | tgc | cca | gca | cct | gaa | ctc | ctg | ggg | gga | ccg | tca | gtc | ttc | ctc | ttc | 432 |
| Pro | Cys | Pro | Ala | Pro | Glu | Leu | Leu | Gly | Gly | Pro | Ser | Val | Phe | Leu | Phe | |
| | | 130 | | | | | 135 | | | | | 140 | | | | |
| ccc | cca | aaa | ccc | aag | gac | atc | ctc | atg | atc | tcc | cgg | acc | cct | gag | gtc | 480 |
| Pro | Pro | Lys | Pro | Lys | Asp | Ile | Leu | Met | Ile | Ser | Arg | Thr | Pro | Glu | Val | |
| 145 | | | | | 150 | | | | | 155 | | | | | 160 | |
| aca | tgc | gtg | gtg | gtg | gac | gtg | agc | cac | gaa | gac | cct | gag | gtc | aag | ttc | 528 |
| Thr | Cys | Val | Val | Val | Asp | Val | Ser | His | Glu | Asp | Pro | Glu | Val | Lys | Phe | |
| | | | | 165 | | | | | 170 | | | | | 175 | | |
| aac | tgg | tac | gtg | ggc | ggc | gtg | gag | gtg | cat | aat | gcc | aag | aca | aag | ccg | 576 |
| Asn | Trp | Tyr | Val | Gly | Gly | Val | Glu | Val | His | Asn | Ala | Lys | Thr | Lys | Pro | |
| | | | 180 | | | | | 185 | | | | | 190 | | | |
| cgg | gag | gag | cag | tac | aac | agc | acg | tac | cgt | gtg | gtc | agc | gtc | ctc | acc | 624 |
| Arg | Glu | Glu | Gln | Tyr | Asn | Ser | Thr | Tyr | Arg | Val | Val | Ser | Val | Leu | Thr | |
| | | | 195 | | | | | 200 | | | | | 205 | | | |
| gtc | ctg | cac | cag | gac | tgg | ctg | aat | ggc | aag | gag | tac | aag | tgc | aag | gtc | 672 |
| Val | Leu | His | Gln | Asp | Trp | Leu | Asn | Gly | Lys | Glu | Tyr | Lys | Cys | Lys | Val | |
| | | 210 | | | | | 215 | | | | | 220 | | | | |
| tcc | aac | aaa | gcc | ctc | cca | gcc | ccc | att | gag | aaa | acc | atc | tcc | aaa | gcc | 720 |
| Ser | Asn | Lys | Ala | Leu | Pro | Ala | Pro | Ile | Glu | Lys | Thr | Ile | Ser | Lys | Ala | |
| 225 | | | | | 230 | | | | | 235 | | | | | 240 | |
| aaa | ggg | cag | ccc | cga | gaa | cca | cag | gtg | tac | acc | ctg | ccc | cca | tcc | cgg | 768 |
| Lys | Gly | Gln | Pro | Arg | Glu | Pro | Gln | Val | Tyr | Thr | Leu | Pro | Pro | Ser | Arg | |
| | | | | 245 | | | | | 250 | | | | | 255 | | |
| gat | gag | ctg | acc | aag | aac | cag | gtc | agc | ctg | acc | tgc | ctg | gtc | aaa | ggc | 816 |
| Asp | Glu | Leu | Thr | Lys | Asn | Gln | Val | Ser | Leu | Thr | Cys | Leu | Val | Lys | Gly | |
| | | | 260 | | | | | 265 | | | | | 270 | | | |
| ttc | tat | ccc | agc | gac | atc | gcc | gtg | gag | tgg | gag | agc | aat | ggg | cag | ccg | 864 |
| Phe | Tyr | Pro | Ser | Asp | Ile | Ala | Val | Glu | Trp | Glu | Ser | Asn | Gly | Gln | Pro | |
| | | 275 | | | | | 280 | | | | | 285 | | | | |
| gag | aac | aac | tac | aag | acc | acg | cct | ccc | gtg | ctg | gac | tcc | gac | ggc | tcc | 912 |
| Glu | Asn | Asn | Tyr | Lys | Thr | Thr | Pro | Pro | Val | Leu | Asp | Ser | Asp | Gly | Ser | |

|  |  |  |  |  |  |  |  |  |  |  |  |  |  |  |  |
|--|--|--|--|--|--|--|--|--|--|--|--|--|--|--|--|
| ttc | ttc | ctc | tac | agc | aag | ctc | acc | gtg | gac | aag | agc | agg | tgg | cag | cag |
| Phe | Phe | Leu | Tyr | Ser | Lys | Leu | Thr | Val | Asp | Lys | Ser | Arg | Trp | Gln | Gln |
| 305 |  |  |  |  | 310 |  |  |  |  | 315 |  |  |  |  | 320 |

960

|  |  |  |  |  |  |  |  |  |  |  |  |  |
|--|--|--|--|--|--|--|--|--|--|--|--|--|
| ggg | aac | gtc | ttc | tca | tgc | tcc | gtg | atg | cat | gag | gct | ctg | cac | aac | cac |
| Gly | Asn | Val | Phe | Ser | Cys | Ser | Val | Met | His | Glu | Ala | Leu | His | Asn | His |
|  |  |  |  | 325 |  |  |  |  | 330 |  |  |  |  | 335 |  |

1008

| tac | acg | cag | aag | agc | ctc | tcc | ctg | tct | ccg | ggt | aaa | tga |
|--|--|--|--|--|--|--|--|--|--|--|--|--|
| Tyr | Thr | Gln | Lys | Ser | Leu | Ser | Leu | Ser | Pro | Gly | Lys |  |
|  |  |  | 340 |  |  |  |  | 345 |  |  |  |  |

1047

<210> SEQ ID NO 62
<211> LENGTH: 348
<212> TYPE: PRT
<213> ORGANISM: Homo sapiens

<400> SEQUENCE: 62

Ser Gly Arg Gly Glu Ala Glu Thr Arg Trp Cys Leu Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr Gly Gly Gly Ser Asp Lys Thr His Thr Cys Pro
        115                 120                 125

Pro Cys Pro Ala Pro Glu Leu Leu Gly Gly Pro Ser Val Phe Leu Phe
    130                 135                 140

Pro Pro Lys Pro Lys Asp Ile Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Gly Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Asp Glu Leu Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

```
Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345

<210> SEQ ID NO 63
<211> LENGTH: 1047
<212> TYPE: DNA
<213> ORGANISM: Homo sapiens
<220> FEATURE:
<221> NAME/KEY: CDS
<222> LOCATION: (1)..(1044)

<400> SEQUENCE: 63 tct ggg cgt ggg gag gct gag aca cgg tac tgc atc tac tac aac gcc     48
Ser Gly Arg Gly Glu Ala Glu Thr Arg Tyr Cys Ile Tyr Tyr Asn Ala
1               5                   10                  15 aac tgg gag ctg gag cgc acc aac cag agc ggc ctg gag cgc tgc gaa    96
Asn Trp Glu Leu Glu Arg Thr Asn Gln Ser Gly Leu Glu Arg Cys Glu
                20                  25                  30 ggc gag cag gac aag cgg ctg cac tgc tac gcc tcc tgg cgc aac agc    144
Gly Glu Gln Asp Lys Arg Leu His Cys Tyr Ala Ser Trp Arg Asn Ser
            35                  40                  45 tct ggc acc atc gag ctc gtg aag aag ggc tgc tgg cta gat gac ttc    192
Ser Gly Thr Ile Glu Leu Val Lys Lys Gly Cys Trp Leu Asp Asp Phe
        50                  55                  60 aac tgc tac gat agg cag gag tgt gtg gcc act gag gag aac ccc cag    240
Asn Cys Tyr Asp Arg Gln Glu Cys Val Ala Thr Glu Glu Asn Pro Gln
65                  70                  75                  80 gtg tac ttc tgc tgc tgt gaa ggc aac ttc tgc aac gag cgc ttc act    288
Val Tyr Phe Cys Cys Cys Glu Gly Asn Phe Cys Asn Glu Arg Phe Thr
                85                  90                  95 cat ttg cca gag gct ggg ggc ccg gaa gtc acg tac gag cca ccc ccg    336
His Leu Pro Glu Ala Gly Gly Pro Glu Val Thr Tyr Glu Pro Pro Pro
                100                 105                 110 aca gcc ccc act gga gga gga gga tct gac aaa act cac aca tgc cca    384
Thr Ala Pro Thr Gly Gly Gly Gly Ser Asp Lys Thr His Thr Cys Pro
            115                 120                 125 ccg tgc cca gca cct gaa ctc ctg ggg gga ccg tca gtc ttc ctc ttc    432
Pro Cys Pro Ala Pro Glu Leu Leu Gly Gly Pro Ser Val Phe Leu Phe
        130                 135                 140 ccc cca aaa ccc aag gac atc ctc atg atc tcc cgg acc cct gag gtc    480
Pro Pro Lys Pro Lys Asp Ile Leu Met Ile Ser Arg Thr Pro Glu Val
145                 150                 155                 160 aca tgc gtg gtg gtg gac gtg agc cac gaa gac cct gag gtc aag ttc    528
Thr Cys Val Val Val Asp Val Ser His Glu Asp Pro Glu Val Lys Phe
                165                 170                 175 aac tgg tac gtg ggc ggc gtg gag gtg cat aat gcc aag aca aag ccg    576
Asn Trp Tyr Val Gly Gly Val Glu Val His Asn Ala Lys Thr Lys Pro
                180                 185                 190 cgg gag gag cag tac aac agc acg tac cgt gtg gtc agc gtc ctc acc    624
Arg Glu Glu Gln Tyr Asn Ser Thr Tyr Arg Val Val Ser Val Leu Thr
            195                 200                 205 gtc ctg cac cag gac tgg ctg aat ggc aag gag tac aag tgc aag gtc    672
Val Leu His Gln Asp Trp Leu Asn Gly Lys Glu Tyr Lys Cys Lys Val
        210                 215                 220 tcc aac aaa gcc ctc cca gcc ccc atc gag aaa acc atc tcc aaa gcc    720
Ser Asn Lys Ala Leu Pro Ala Pro Ile Glu Lys Thr Ile Ser Lys Ala
225                 230                 235                 240
```

```
aaa ggg cag ccc cga gaa cca cag gtg tac acc ctg ccc cca tcc cgg      768
Lys Gly Gln Pro Arg Glu Pro Gln Val Tyr Thr Leu Pro Pro Ser Arg
            245                 250                 255 gat gag ctg acc aag aac cag gtc agc ctg acc tgc ctg gtc aaa ggc      816
Asp Glu Leu Thr Lys Asn Gln Val Ser Leu Thr Cys Leu Val Lys Gly
                260                 265                 270 ttc tat ccc agc gac atc gcc gtg gag tgg gag agc aat ggg cag ccg      864
Phe Tyr Pro Ser Asp Ile Ala Val Glu Trp Glu Ser Asn Gly Gln Pro
            275                 280                 285 gag aac aac tac aag acc acg cct ccc gtg ctg gac tcc gac ggc tcc      912
Glu Asn Asn Tyr Lys Thr Thr Pro Pro Val Leu Asp Ser Asp Gly Ser
        290                 295                 300 ttc ttc ctc tac agc aag ctc acc gtg gac aag agc agg tgg cag cag      960
Phe Phe Leu Tyr Ser Lys Leu Thr Val Asp Lys Ser Arg Trp Gln Gln
305                 310                 315                 320 ggg aac gtc ttc tca tgc tcc gtg atg cat gag gct ctg cac aac cac     1008
Gly Asn Val Phe Ser Cys Ser Val Met His Glu Ala Leu His Asn His
                325                 330                 335 tac acg cag aag agc ctc tcc ctg tct ccg ggt aaa tga                 1047
Tyr Thr Gln Lys Ser Leu Ser Leu Ser Pro Gly Lys
            340                 345
```

<210> SEQ ID NO 64
<211> LENGTH: 348
<212> TYPE: PRT
<213> ORGANISM: Homo sapiens

<400> SEQUENCE: 64

```
Ser Gly Arg Gly Glu Ala Glu Thr Arg Tyr Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr Gly Gly Gly Ser Asp Lys Thr His Thr Cys Pro
        115                 120                 125

Pro Cys Pro Ala Pro Glu Leu Leu Gly Gly Pro Ser Val Phe Leu Phe
    130                 135                 140

Pro Pro Lys Pro Lys Asp Ile Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Gly Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220
```

```
Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
            245                 250                 255

Asp Glu Leu Thr Lys Asn Gln Val Ser Leu Thr Cys Leu Val Lys Gly
        260                 265                 270

Phe Tyr Pro Ser Asp Ile Ala Val Glu Trp Glu Ser Asn Gly Gln Pro
    275                 280                 285

Glu Asn Asn Tyr Lys Thr Thr Pro Pro Val Leu Asp Ser Asp Gly Ser
290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345

<210> SEQ ID NO 65
<211> LENGTH: 1047
<212> TYPE: DNA
<213> ORGANISM: Homo sapiens
<220> FEATURE:
<221> NAME/KEY: CDS
<222> LOCATION: (1)..(1044)

<400> SEQUENCE: 65 tct ggg cgt ggg gag gct gag aca cgg gag tgc atc tac tac aac gcc    48
Ser Gly Arg Gly Glu Ala Glu Thr Arg Glu Cys Ile Tyr Tyr Asn Ala
1               5                   10                  15 aac tgg gag ctg gag ggc acc aac cag agc ggc ctg gag cgc tgc gaa    96
Asn Trp Glu Leu Glu Gly Thr Asn Gln Ser Gly Leu Glu Arg Cys Glu
            20                  25                  30 ggc gag cag gac aag cgg ctg ccc tgc tac gcc tcc tgg cgc aac agc    144
Gly Glu Gln Asp Lys Arg Leu Pro Cys Tyr Ala Ser Trp Arg Asn Ser
        35                  40                  45 tct ggc ccc atc gag ctc gtg aag aag ggc tgc tgg cta gat gac ttc    192
Ser Gly Pro Ile Glu Leu Val Lys Lys Gly Cys Trp Leu Asp Asp Phe
    50                  55                  60 aac tgc tac gat agg cag gag tgt gtg gcc act gag gag aac ccc cag    240
Asn Cys Tyr Asp Arg Gln Glu Cys Val Ala Thr Glu Glu Asn Pro Gln
65                  70                  75                  80 gtg tac ttc tgc tgc tgt gaa ggc aac ttc tgc aac gag cgc ttc act    288
Val Tyr Phe Cys Cys Cys Glu Gly Asn Phe Cys Asn Glu Arg Phe Thr
                85                  90                  95 cat ttg cca gag gct ggg ggc ccg gaa gtc acg tac gag cca ccc ccg    336
His Leu Pro Glu Ala Gly Gly Pro Glu Val Thr Tyr Glu Pro Pro Pro
            100                 105                 110 aca gcc ccc act gga gga gga gga tct gac aaa act cac aca tgc cca    384
Thr Ala Pro Thr Gly Gly Gly Gly Ser Asp Lys Thr His Thr Cys Pro
        115                 120                 125 ccg tgc cca gca cct gaa ctc ctg ggg gga ccg tca gtc ttc ctc ttc    432
Pro Cys Pro Ala Pro Glu Leu Leu Gly Gly Pro Ser Val Phe Leu Phe
    130                 135                 140 ccc cca aaa ccc aag gac atc ctc atg atc tcc cgg acc cct gag gtc    480
Pro Pro Lys Pro Lys Asp Ile Leu Met Ile Ser Arg Thr Pro Glu Val
145                 150                 155                 160 aca tgc gtg gtg gtg gac gtg agc cac gaa gac cct gag gtc aag ttc    528
Thr Cys Val Val Val Asp Val Ser His Glu Asp Pro Glu Val Lys Phe
                165                 170                 175
```

| | | | | | | | | | | | | | | | |
|---|---|---|---|---|---|---|---|---|---|---|---|---|---|---|---|
| aac | tgg | tac | gtg | ggc | ggc | gtg | gag | gtg | cat | aat | gcc | aag | aca | aag | ccg | 576 |
| Asn | Trp | Tyr | Val | Gly | Gly | Val | Glu | Val | His | Asn | Ala | Lys | Thr | Lys | Pro |
| | | | 180 | | | | | 185 | | | | | 190 | | |

| cgg | gag | gag | cag | tac | aac | agc | acg | tac | cgt | gtg | gtc | agc | gtc | ctc | acc | 624 |
| Arg | Glu | Glu | Gln | Tyr | Asn | Ser | Thr | Tyr | Arg | Val | Val | Ser | Val | Leu | Thr |
| | | 195 | | | | | 200 | | | | | 205 | | | |

| gtc | ctg | cac | cag | gac | tgg | ctg | aat | ggc | aag | gag | tac | aag | tgc | aag | gtc | 672 |
| Val | Leu | His | Gln | Asp | Trp | Leu | Asn | Gly | Lys | Glu | Tyr | Lys | Cys | Lys | Val |
| 210 | | | | | | 215 | | | | | 220 | | | | |

| tcc | aac | aaa | gcc | ctc | cca | gcc | ccc | atc | gag | aaa | acc | atc | tcc | aaa | gcc | 720 |
| Ser | Asn | Lys | Ala | Leu | Pro | Ala | Pro | Ile | Glu | Lys | Thr | Ile | Ser | Lys | Ala |
| 225 | | | | 230 | | | | | 235 | | | | | 240 | |

| aaa | ggg | cag | ccc | cga | gaa | cca | cag | gtg | tac | acc | ctg | ccc | cca | tcc | cgg | 768 |
| Lys | Gly | Gln | Pro | Arg | Glu | Pro | Gln | Val | Tyr | Thr | Leu | Pro | Pro | Ser | Arg |
| | | | | 245 | | | | | 250 | | | | | 255 | |

| gat | gag | ctg | acc | aag | aac | cag | gtc | agc | ctg | acc | tgc | ctg | gtc | aaa | ggc | 816 |
| Asp | Glu | Leu | Thr | Lys | Asn | Gln | Val | Ser | Leu | Thr | Cys | Leu | Val | Lys | Gly |
| | | | 260 | | | | | 265 | | | | | 270 | | |

| ttc | tat | ccc | agc | gac | atc | gcc | gtg | gag | tgg | gag | agc | aat | ggg | cag | ccg | 864 |
| Phe | Tyr | Pro | Ser | Asp | Ile | Ala | Val | Glu | Trp | Glu | Ser | Asn | Gly | Gln | Pro |
| | | 275 | | | | | 280 | | | | | 285 | | | |

| gag | aac | aac | tac | aag | acc | acg | cct | ccc | gtg | ctg | gac | tcc | gac | ggc | tcc | 912 |
| Glu | Asn | Asn | Tyr | Lys | Thr | Thr | Pro | Pro | Val | Leu | Asp | Ser | Asp | Gly | Ser |
| 290 | | | | | 295 | | | | | 300 | | | | | |

| ttc | ttc | ctc | tac | agc | aag | ctc | acc | gtg | gac | aag | agc | agg | tgg | cag | cag | 960 |
| Phe | Phe | Leu | Tyr | Ser | Lys | Leu | Thr | Val | Asp | Lys | Ser | Arg | Trp | Gln | Gln |
| 305 | | | | | 310 | | | | | 315 | | | | | 320 |

| ggg | aac | gtc | ttc | tca | tgc | tcc | gtg | atg | cat | gag | gct | ctg | cac | aac | cac | 1008 |
| Gly | Asn | Val | Phe | Ser | Cys | Ser | Val | Met | His | Glu | Ala | Leu | His | Asn | His |
| | | | | 325 | | | | | 330 | | | | | 335 | |

| tac | acg | cag | aag | agc | ctc | tcc | ctg | tct | ccg | ggt | aaa | tga | | | | 1047 |
| Tyr | Thr | Gln | Lys | Ser | Leu | Ser | Leu | Ser | Pro | Gly | Lys | | | | |
| | | | 340 | | | | | 345 | | | | | | | |

<210> SEQ ID NO 66
<211> LENGTH: 348
<212> TYPE: PRT
<213> ORGANISM: Homo sapiens

<400> SEQUENCE: 66

Ser Gly Arg Gly Glu Ala Glu Thr Arg Glu Cys Ile Tyr Tyr Asn Ala
1               5                   10                  15

Asn Trp Glu Leu Glu Gly Thr Asn Gln Ser Gly Leu Glu Arg Cys Glu
            20                  25                  30

Gly Glu Gln Asp Lys Arg Leu Pro Cys Tyr Ala Ser Trp Arg Asn Ser
        35                  40                  45

Ser Gly Pro Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr Gly Gly Gly Ser Asp Lys Thr His Thr Cys Pro
        115                 120                 125

Pro Cys Pro Ala Pro Glu Leu Leu Gly Gly Pro Ser Val Phe Leu Phe
    130                 135                 140

```
Pro Pro Lys Pro Lys Asp Ile Leu Met Ile Ser Arg Thr Pro Glu Val
145                 150                 155                 160

Thr Cys Val Val Val Asp Val Ser His Glu Asp Pro Glu Val Lys Phe
            165                 170                 175

Asn Trp Tyr Val Gly Val Glu Val His Asn Ala Lys Thr Lys Pro
        180                 185                 190

Arg Glu Glu Gln Tyr Asn Ser Thr Tyr Arg Val Val Ser Val Leu Thr
            195                 200                 205

Val Leu His Gln Asp Trp Leu Asn Gly Lys Glu Tyr Lys Cys Lys Val
        210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
            245                 250                 255

Asp Glu Leu Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
            325                 330                 335

Tyr Thr Gln Lys Ser Leu Ser Leu Ser Pro Gly Lys
            340                 345

<210> SEQ ID NO 67
<211> LENGTH: 1125
<212> TYPE: DNA
<213> ORGANISM: Homo sapiens
<220> FEATURE:
<221> NAME/KEY: CDS
<222> LOCATION: (1)..(1122)

<400> SEQUENCE: 67 tct ggg cgt ggg gag gct gag aca cgg gag tgc atc tac tac aac gcc    48
Ser Gly Arg Gly Glu Ala Glu Thr Arg Glu Cys Ile Tyr Tyr Asn Ala
1               5                   10                  15 aac tgg gag ctg gag cgc acc aac cag agc ggc ctg gag cgc tgc gaa    96
Asn Trp Glu Leu Glu Arg Thr Asn Gln Ser Gly Leu Glu Arg Cys Glu
            20                  25                  30 ggc gag cag gac aag cgg ctg cac tgc tac gcc tcc tgg cgc aac agc   144
Gly Glu Gln Asp Lys Arg Leu His Cys Tyr Ala Ser Trp Arg Asn Ser
        35                  40                  45 tct ggc acc atc gag ctc gtg aag aag ggc tgt tgg cta gat gac ttc   192
Ser Gly Thr Ile Glu Leu Val Lys Lys Gly Cys Trp Leu Asp Asp Phe
50                  55                  60 aac tgc tac gat agg cag gag tgt gtg gcc act gag gag aac ccc cag   240
Asn Cys Tyr Asp Arg Gln Glu Cys Val Ala Thr Glu Glu Asn Pro Gln
65                  70                  75                  80 gtg tac ttc tgc tgc tgt gaa ggc aac ttc tgc aac gag cgc ttc act   288
Val Tyr Phe Cys Cys Cys Glu Gly Asn Phe Cys Asn Glu Arg Phe Thr
                85                  90                  95 cat ttg cca gag gct ggg ggc ccg gaa gga ccc tgg gcc tcc acc acc   336
His Leu Pro Glu Ala Gly Gly Pro Glu Gly Pro Trp Ala Ser Thr Thr
            100                 105                 110 atc ccc tct ggt ggg cct gaa gcc act gca gct gct gga gat caa ggc   384
```

```
Ile Pro Ser Gly Gly Pro Glu Ala Thr Ala Ala Ala Gly Asp Gln Gly
            115                 120                 125 tcg ggg gcg ctt tgg ctg tgt ctg gaa ggc cca gct cat gaa gga gga        432
Ser Gly Ala Leu Trp Leu Cys Leu Glu Gly Pro Ala His Glu Gly Gly
        130                 135                 140 gga gga tct gac aaa act cac aca tgc cca ccg tgc cca gca cct gaa        480
Gly Gly Ser Asp Lys Thr His Thr Cys Pro Pro Cys Pro Ala Pro Glu
145                 150                 155                 160 ctc ctg ggg gga ccg tca gtc ttc ctc ttc ccc cca aaa ccc aag gac        528
Leu Leu Gly Gly Pro Ser Val Phe Leu Phe Pro Pro Lys Pro Lys Asp
                165                 170                 175 acc ctc atg atc tcc cgg acc cct gag gtc aca tgc gtg gtg gtg gac        576
Thr Leu Met Ile Ser Arg Thr Pro Glu Val Thr Cys Val Val Val Asp
            180                 185                 190 gtg agc cac gaa gac cct gag gtc aag ttc aac tgg tac gtg gac ggc        624
Val Ser His Glu Asp Pro Glu Val Lys Phe Asn Trp Tyr Val Asp Gly
        195                 200                 205 gtg gag gtg cat aat gcc aag aca aag ccg cgg gag gag cag tac aac        672
Val Glu Val His Asn Ala Lys Thr Lys Pro Arg Glu Glu Gln Tyr Asn
    210                 215                 220 agc acg tac cgt gtg gtc agc gtc ctc acc gtc ctg cac cag gac tgg        720
Ser Thr Tyr Arg Val Val Ser Val Leu Thr Val Leu His Gln Asp Trp
225                 230                 235                 240 ctg aat ggc aag gag tac aag tgc aag gtc tcc aac aaa gcc ctc cca        768
Leu Asn Gly Lys Glu Tyr Lys Cys Lys Val Ser Asn Lys Ala Leu Pro
                245                 250                 255 gcc ccc atc gag aaa acc atc tcc aaa gcc aaa ggg cag ccc cga gaa        816
Ala Pro Ile Glu Lys Thr Ile Ser Lys Ala Lys Gly Gln Pro Arg Glu
            260                 265                 270 cca cag gtg tac acc ctg ccc cca tcc cgg gat gag ctg acc aag aac        864
Pro Gln Val Tyr Thr Leu Pro Pro Ser Arg Asp Glu Leu Thr Lys Asn
        275                 280                 285 cag gtc agc ctg acc tgc ctg gtc aaa ggc ttc tat ccc agc gac atc        912
Gln Val Ser Leu Thr Cys Leu Val Lys Gly Phe Tyr Pro Ser Asp Ile
    290                 295                 300 gcc gtg gag tgg gag agc aat ggg cag ccg gag aac aac tac aag acc        960
Ala Val Glu Trp Glu Ser Asn Gly Gln Pro Glu Asn Asn Tyr Lys Thr
305                 310                 315                 320 acg cct ccc gtg ctg gac tcc gac ggc tcc ttc ttc ctc tac agc aag       1008
Thr Pro Pro Val Leu Asp Ser Asp Gly Ser Phe Phe Leu Tyr Ser Lys
                325                 330                 335 ctc acc gtg gac aag agc agg tgg cag cag ggg aac gtc ttc tca tgc       1056
Leu Thr Val Asp Lys Ser Arg Trp Gln Gln Gly Asn Val Phe Ser Cys
            340                 345                 350 tcc gtg atg cat gag gct ctg cac aac cac tac acg cag aag agc ctc       1104
Ser Val Met His Glu Ala Leu His Asn His Tyr Thr Gln Lys Ser Leu
        355                 360                 365 tcc ctg tct ccg ggt aaa tga                                           1125
Ser Leu Ser Pro Gly Lys
    370

<210> SEQ ID NO 68
<211> LENGTH: 374
<212> TYPE: PRT
<213> ORGANISM: Homo sapiens

<400> SEQUENCE: 68

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
```

```
                   20                  25                  30
Gly Glu Gln Asp Lys Arg Leu His Cys Tyr Ala Ser Trp Arg Asn Ser
            35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Gly Pro Trp Ala Ser Thr Thr
            100                 105                 110

Ile Pro Ser Gly Gly Pro Glu Ala Thr Ala Ala Gly Asp Gln Gly
            115                 120                 125

Ser Gly Ala Leu Trp Leu Cys Leu Glu Gly Pro Ala His Glu Gly Gly
    130                 135                 140

Gly Gly Ser Asp Lys Thr His Thr Cys Pro Pro Cys Pro Ala Pro Glu
145                 150                 155                 160

Leu Leu Gly Gly Pro Ser Val Phe Leu Phe Pro Pro Lys Pro Lys Asp
                165                 170                 175

Thr Leu Met Ile Ser Arg Thr Pro Glu Val Thr Cys Val Val Val Asp
            180                 185                 190

Val Ser His Glu Asp Pro Glu Val Lys Phe Asn Trp Tyr Val Asp Gly
        195                 200                 205

Val Glu Val His Asn Ala Lys Thr Lys Pro Arg Glu Glu Gln Tyr Asn
    210                 215                 220

Ser Thr Tyr Arg Val Val Ser Val Leu Thr Val Leu His Gln Asp Trp
225                 230                 235                 240

Leu Asn Gly Lys Glu Tyr Lys Cys Lys Val Ser Asn Lys Ala Leu Pro
                245                 250                 255

Ala Pro Ile Glu Lys Thr Ile Ser Lys Ala Lys Gly Gln Pro Arg Glu
            260                 265                 270

Pro Gln Val Tyr Thr Leu Pro Pro Ser Arg Asp Glu Leu Thr Lys Asn
        275                 280                 285

Gln Val Ser Leu Thr Cys Leu Val Lys Gly Phe Tyr Pro Ser Asp Ile
    290                 295                 300

Ala Val Glu Trp Glu Ser Asn Gly Gln Pro Glu Asn Asn Tyr Lys Thr
305                 310                 315                 320

Thr Pro Pro Val Leu Asp Ser Asp Gly Ser Phe Phe Leu Tyr Ser Lys
                325                 330                 335

Leu Thr Val Asp Lys Ser Arg Trp Gln Gln Gly Asn Val Phe Ser Cys
            340                 345                 350

Ser Val Met His Glu Ala Leu His Asn His Tyr Thr Gln Lys Ser Leu
        355                 360                 365

Ser Leu Ser Pro Gly Lys
        370

<210> SEQ ID NO 69
<211> LENGTH: 1125
<212> TYPE: DNA
<213> ORGANISM: Homo sapiens
<220> FEATURE:
<221> NAME/KEY: CDS
<222> LOCATION: (1)..(1122)
<220> FEATURE:
<221> NAME/KEY: modified_base
<222> LOCATION: (30)..(30)
```

<223> OTHER INFORMATION: a, c, t, g, unknown or other

<400> SEQUENCE: 69

```
tct ggg cgt ggg gag gct gag aca cgg gcn tgc atc tac tac aac gcc     48
Ser Gly Arg Gly Glu Ala Glu Thr Arg Ala Cys Ile Tyr Tyr Asn Ala
 1               5                  10                  15 aac tgg gag ctg gag cgc acc aac cag agc ggc ctg gag cgc tgc gaa     96
Asn Trp Glu Leu Glu Arg Thr Asn Gln Ser Gly Leu Glu Arg Cys Glu
             20                  25                  30 ggc gag cag gac aag cgg ctg cac tgc tac gcc tcc tgg cgc aac agc    144
Gly Glu Gln Asp Lys Arg Leu His Cys Tyr Ala Ser Trp Arg Asn Ser
         35                  40                  45 tct ggc acc atc gag ctc gtg aag aag ggc tgc tgg cta gat gac ttc    192
Ser Gly Thr Ile Glu Leu Val Lys Lys Gly Cys Trp Leu Asp Asp Phe
     50                  55                  60 aac tgc tac gat agg cag gag tgt gtg gcc act gag gag aac ccc cag    240
Asn Cys Tyr Asp Arg Gln Glu Cys Val Ala Thr Glu Glu Asn Pro Gln
 65                  70                  75                  80 gtg tac ttc tgc tgc tgt gaa ggc aac ttc tgc aac gag cgc ttc act    288
Val Tyr Phe Cys Cys Cys Glu Gly Asn Phe Cys Asn Glu Arg Phe Thr
                 85                  90                  95 cat ttg cca gag gct ggg ggc ccg gaa gga ccc tgg gcc tcc acc acc    336
His Leu Pro Glu Ala Gly Gly Pro Glu Gly Pro Trp Ala Ser Thr Thr
            100                 105                 110 atc ccc tct ggt ggg cct gaa gcc act gca gct gct gga gat caa ggc    384
Ile Pro Ser Gly Gly Pro Glu Ala Thr Ala Ala Ala Gly Asp Gln Gly
        115                 120                 125 tcg ggg gcg ctt tgg ctg tgt ctg gaa ggc cca gct cat gaa gga gga    432
Ser Gly Ala Leu Trp Leu Cys Leu Glu Gly Pro Ala His Glu Gly Gly
    130                 135                 140 gga gga tct gac aaa act cac aca tgc cca ccg tgc cca gca cct gaa    480
Gly Gly Ser Asp Lys Thr His Thr Cys Pro Pro Cys Pro Ala Pro Glu
145                 150                 155                 160 ctc ctg ggg gga ccg tca gtc ttc ctc ttc ccc cca aaa ccc aag gac    528
Leu Leu Gly Gly Pro Ser Val Phe Leu Phe Pro Pro Lys Pro Lys Asp
                165                 170                 175 acc ctc atg atc tcc cgg acc cct gag gtc aca tgc gtg gtg gtg gac    576
Thr Leu Met Ile Ser Arg Thr Pro Glu Val Thr Cys Val Val Val Asp
            180                 185                 190 gtg agc cac gaa gac cct gag gtc aag ttc aac tgg tac gtg gac ggc    624
Val Ser His Glu Asp Pro Glu Val Lys Phe Asn Trp Tyr Val Asp Gly
        195                 200                 205 gtg gag gtg cat aat gcc aag aca aag ccg cgg gag gag cag tac aac    672
Val Glu Val His Asn Ala Lys Thr Lys Pro Arg Glu Glu Gln Tyr Asn
    210                 215                 220 agc acg tac cgt gtg gtc agc gtc ctc acc gtc ctg cac cag gac tgg    720
Ser Thr Tyr Arg Val Val Ser Val Leu Thr Val Leu His Gln Asp Trp
225                 230                 235                 240 ctg aat ggc aag gag tac aag tgc aag gtc tcc aac aaa gcc ctc cca    768
Leu Asn Gly Lys Glu Tyr Lys Cys Lys Val Ser Asn Lys Ala Leu Pro
                245                 250                 255 gcc ccc atc gag aaa acc atc tcc aaa gcc aaa ggg cag ccc cga gaa    816
Ala Pro Ile Glu Lys Thr Ile Ser Lys Ala Lys Gly Gln Pro Arg Glu
            260                 265                 270 cca cag gtg tac acc ctg ccc cca tcc cgg gat gag ctg acc aag aac    864
Pro Gln Val Tyr Thr Leu Pro Pro Ser Arg Asp Glu Leu Thr Lys Asn
        275                 280                 285 cag gtc agc ctg acc tgc ctg gtc aaa ggc ttc tat ccc agc gac atc    912
Gln Val Ser Leu Thr Cys Leu Val Lys Gly Phe Tyr Pro Ser Asp Ile
    290                 295                 300
```

```
gcc gtg gag tgg gag agc aat ggg cag ccg gag aac aac tac aag acc    960
Ala Val Glu Trp Glu Ser Asn Gly Gln Pro Glu Asn Asn Tyr Lys Thr
305                 310                 315                 320 acg cct ccc gtg ctg gac tcc gac ggc tcc ttc ttc ctc tac agc aag   1008
Thr Pro Pro Val Leu Asp Ser Asp Gly Ser Phe Phe Leu Tyr Ser Lys
                325                 330                 335 ctc acc gtg gac aag agc agg tgg cag cag ggg aac gtc ttc tca tgc   1056
Leu Thr Val Asp Lys Ser Arg Trp Gln Gln Gly Asn Val Phe Ser Cys
            340                 345                 350 tcc gtg atg cat gag gct ctg cac aac cac tac acg cag aag agc ctc   1104
Ser Val Met His Glu Ala Leu His Asn His Tyr Thr Gln Lys Ser Leu
        355                 360                 365 tcc ctg tct ccg ggt aaa tga                                       1125
Ser Leu Ser Pro Gly Lys
    370

<210> SEQ ID NO 70
<211> LENGTH: 374
<212> TYPE: PRT
<213> ORGANISM: Homo sapiens

<400> SEQUENCE: 70

Ser Gly Arg Gly Glu Ala Glu Thr Arg Ala Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Gly Pro Trp Ala Ser Thr Thr
            100                 105                 110

Ile Pro Ser Gly Gly Pro Glu Ala Thr Ala Ala Ala Gly Asp Gln Gly
        115                 120                 125

Ser Gly Ala Leu Trp Leu Cys Leu Glu Gly Pro Ala His Glu Gly Gly
    130                 135                 140

Gly Gly Ser Asp Lys Thr His Thr Cys Pro Pro Cys Pro Ala Pro Glu
145                 150                 155                 160

Leu Leu Gly Gly Pro Ser Val Phe Leu Phe Pro Pro Lys Pro Lys Asp
                165                 170                 175

Thr Leu Met Ile Ser Arg Thr Pro Glu Val Thr Cys Val Val Val Asp
            180                 185                 190

Val Ser His Glu Asp Pro Glu Val Lys Phe Asn Trp Tyr Val Asp Gly
        195                 200                 205

Val Glu Val His Asn Ala Lys Thr Lys Pro Arg Glu Glu Gln Tyr Asn
    210                 215                 220

Ser Thr Tyr Arg Val Val Ser Val Leu Thr Val Leu His Gln Asp Trp
225                 230                 235                 240

Leu Asn Gly Lys Glu Tyr Lys Cys Lys Val Ser Asn Lys Ala Leu Pro
                245                 250                 255

Ala Pro Ile Glu Lys Thr Ile Ser Lys Ala Lys Gly Gln Pro Arg Glu
            260                 265                 270
```

```
Pro Gln Val Tyr Thr Leu Pro Pro Ser Arg Asp Glu Leu Thr Lys Asn
        275                 280                 285

Gln Val Ser Leu Thr Cys Leu Val Lys Gly Phe Tyr Pro Ser Asp Ile
    290                 295                 300

Ala Val Glu Trp Glu Ser Asn Gly Gln Pro Glu Asn Asn Tyr Lys Thr
305                 310                 315                 320

Thr Pro Pro Val Leu Asp Ser Asp Gly Ser Phe Phe Leu Tyr Ser Lys
                325                 330                 335

Leu Thr Val Asp Lys Ser Arg Trp Gln Gln Gly Asn Val Phe Ser Cys
                340                 345                 350

Ser Val Met His Glu Ala Leu His Asn His Tyr Thr Gln Lys Ser Leu
        355                 360                 365

Ser Leu Ser Pro Gly Lys
    370

<210> SEQ ID NO 71
<211> LENGTH: 1125
<212> TYPE: DNA
<213> ORGANISM: Homo sapiens
<220> FEATURE:
<221> NAME/KEY: CDS
<222> LOCATION: (1)..(1122)

<400> SEQUENCE: 71 tct ggg cgt ggg gag gct gag aca cgg tgg tgc atc tac tac aac gcc      48
Ser Gly Arg Gly Glu Ala Glu Thr Arg Trp Cys Ile Tyr Tyr Asn Ala
1               5                   10                  15 aac tgg gag ctg gag cgc acc aac cag agc ggc ctg gag cgc tgc gaa      96
Asn Trp Glu Leu Glu Arg Thr Asn Gln Ser Gly Leu Glu Arg Cys Glu
            20                  25                  30 ggc gag cag gac aag cgg ctg cac tgc tac gcc tcc tgg cgc aac agc     144
Gly Glu Gln Asp Lys Arg Leu His Cys Tyr Ala Ser Trp Arg Asn Ser
        35                  40                  45 tct ggc acc atc gag ctc gtg aag aag ggc tgc tgg cta gat gac ttc     192
Ser Gly Thr Ile Glu Leu Val Lys Lys Gly Cys Trp Leu Asp Asp Phe
    50                  55                  60 aac tgc tac gat agg cag gag tgt gtg gcc act gag gag aac ccc cag     240
Asn Cys Tyr Asp Arg Gln Glu Cys Val Ala Thr Glu Glu Asn Pro Gln
65                  70                  75                  80 gtg tac ttc tgc tgc tgt gaa ggc aac ttc tgc aac gag cgc ttc act     288
Val Tyr Phe Cys Cys Cys Glu Gly Asn Phe Cys Asn Glu Arg Phe Thr
                85                  90                  95 cat ttg cca gag gct ggg ggc ccg gaa gga ccc tgg gcc tcc acc acc     336
His Leu Pro Glu Ala Gly Gly Pro Glu Gly Pro Trp Ala Ser Thr Thr
            100                 105                 110 atc ccc tct ggt ggg cct gaa gcc act gca gct gct gga gat caa ggc     384
Ile Pro Ser Gly Gly Pro Glu Ala Thr Ala Ala Ala Gly Asp Gln Gly
        115                 120                 125 tcg ggg gcg ctt tgg ctg tgt ctg gaa ggc cca gct cat gaa gga gga     432
Ser Gly Ala Leu Trp Leu Cys Leu Glu Gly Pro Ala His Glu Gly Gly
    130                 135                 140 gga gga tct gac aaa act cac aca tgc cca ccg tgc cca gca cct gaa     480
Gly Gly Ser Asp Lys Thr His Thr Cys Pro Pro Cys Pro Ala Pro Glu
145                 150                 155                 160 ctc ctg ggg gga ccg tca gtc ttc ctc ttc ccc cca aaa ccc aag gac     528
Leu Leu Gly Gly Pro Ser Val Phe Leu Phe Pro Pro Lys Pro Lys Asp
                165                 170                 175 acc ctc atg atc tcc cgg acc cct gag gtc aca tgc gtg gtg gtg gac     576
Thr Leu Met Ile Ser Arg Thr Pro Glu Val Thr Cys Val Val Val Asp
```

```
gtg agc cac gaa gac cct gag gtc aag ttc aac tgg tac gtg gac ggc    624
Val Ser His Glu Asp Pro Glu Val Lys Phe Asn Trp Tyr Val Asp Gly
        195                 200                 205 gtg gag gtg cat aat gcc aag aca aag ccg cgg gag gag cag tac aac    672
Val Glu Val His Asn Ala Lys Thr Lys Pro Arg Glu Glu Gln Tyr Asn
    210                 215                 220 agc acg tac cgt gtg gtc agc gtc ctc acc gtc ctg cac cag gac tgg    720
Ser Thr Tyr Arg Val Val Ser Val Leu Thr Val Leu His Gln Asp Trp
225                 230                 235                 240 ctg aat ggc aag gag tac aag tgc aag gtc tcc aac aaa gcc ctc cca    768
Leu Asn Gly Lys Glu Tyr Lys Cys Lys Val Ser Asn Lys Ala Leu Pro
                245                 250                 255 gcc ccc atc gag aaa acc atc tcc aaa gcc aaa ggg cag ccc cga gaa    816
Ala Pro Ile Glu Lys Thr Ile Ser Lys Ala Lys Gly Gln Pro Arg Glu
            260                 265                 270 cca cag gtg tac acc ctg ccc cca tcc cgg gat gag ctg acc aag aac    864
Pro Gln Val Tyr Thr Leu Pro Pro Ser Arg Asp Glu Leu Thr Lys Asn
        275                 280                 285 cag gtc agc ctg acc tgc ctg gtc aaa ggc ttc tat ccc agc gac atc    912
Gln Val Ser Leu Thr Cys Leu Val Lys Gly Phe Tyr Pro Ser Asp Ile
    290                 295                 300 gcc gtg gag tgg gag agc aat ggg cag ccg gag aac aac tac aag acc    960
Ala Val Glu Trp Glu Ser Asn Gly Gln Pro Glu Asn Asn Tyr Lys Thr
305                 310                 315                 320 acg cct ccc gtg ctg gac tcc gac ggc tcc ttc ttc ctc tac agc aag   1008
Thr Pro Pro Val Leu Asp Ser Asp Gly Ser Phe Phe Leu Tyr Ser Lys
                325                 330                 335 ctc acc gtg gac aag agc agg tgg cag cag ggg aac gtc ttc tca tgc   1056
Leu Thr Val Asp Lys Ser Arg Trp Gln Gln Gly Asn Val Phe Ser Cys
            340                 345                 350 tcc gtg atg cat gag gct ctg cac aac cac tac acg cag aag agc ctc   1104
Ser Val Met His Glu Ala Leu His Asn His Tyr Thr Gln Lys Ser Leu
        355                 360                 365 tcc ctg tct ccg ggt aaa tga                                        1125
Ser Leu Ser Pro Gly Lys
    370

<210> SEQ ID NO 72
<211> LENGTH: 374
<212> TYPE: PRT
<213> ORGANISM: Homo sapiens

<400> SEQUENCE: 72

Ser Gly Arg Gly Glu Ala Glu Thr Arg Trp Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Gly Pro Trp Ala Ser Thr Thr
            100                 105                 110
```

Ile Pro Ser Gly Gly Pro Glu Ala Thr Ala Ala Gly Asp Gln Gly
            115                 120                 125

Ser Gly Ala Leu Trp Leu Cys Leu Glu Gly Pro Ala His Glu Gly Gly
    130                 135                 140

Gly Gly Ser Asp Lys Thr His Thr Cys Pro Pro Cys Pro Ala Pro Glu
145                 150                 155                 160

Leu Leu Gly Gly Pro Ser Val Phe Leu Phe Pro Pro Lys Pro Lys Asp
                165                 170                 175

Thr Leu Met Ile Ser Arg Thr Pro Glu Val Thr Cys Val Val Val Asp
            180                 185                 190

Val Ser His Glu Asp Pro Glu Val Lys Phe Asn Trp Tyr Val Asp Gly
        195                 200                 205

Val Glu Val His Asn Ala Lys Thr Lys Pro Arg Glu Glu Gln Tyr Asn
    210                 215                 220

Ser Thr Tyr Arg Val Val Ser Val Leu Thr Val Leu His Gln Asp Trp
225                 230                 235                 240

Leu Asn Gly Lys Glu Tyr Lys Cys Lys Val Ser Asn Lys Ala Leu Pro
                245                 250                 255

Ala Pro Ile Glu Lys Thr Ile Ser Lys Ala Lys Gly Gln Pro Arg Glu
            260                 265                 270

Pro Gln Val Tyr Thr Leu Pro Pro Ser Arg Asp Glu Leu Thr Lys Asn
        275                 280                 285

Gln Val Ser Leu Thr Cys Leu Val Lys Gly Phe Tyr Pro Ser Asp Ile
    290                 295                 300

Ala Val Glu Trp Glu Ser Asn Gly Gln Pro Glu Asn Asn Tyr Lys Thr
305                 310                 315                 320

Thr Pro Pro Val Leu Asp Ser Asp Gly Ser Phe Phe Leu Tyr Ser Lys
                325                 330                 335

Leu Thr Val Asp Lys Ser Arg Trp Gln Gln Gly Asn Val Phe Ser Cys
            340                 345                 350

Ser Val Met His Glu Ala Leu His Asn His Tyr Thr Gln Lys Ser Leu
        355                 360                 365

Ser Leu Ser Pro Gly Lys
    370

<210> SEQ ID NO 73
<211> LENGTH: 18
<212> TYPE: PRT
<213> ORGANISM: Homo sapiens

<400> SEQUENCE: 73

Met Thr Ala Pro Trp Val Ala Leu Ala Leu Leu Trp Gly Ser Leu Trp
1               5                   10                  15

Pro Gly

<210> SEQ ID NO 74
<211> LENGTH: 18
<212> TYPE: PRT
<213> ORGANISM: Homo sapiens

<400> SEQUENCE: 74

Met Thr Ala Pro Trp Val Ala Leu Ala Leu Leu Trp Gly Ser Leu Cys
1               5                   10                  15

Ala Gly

<210> SEQ ID NO 75

```
<211> LENGTH: 5
<212> TYPE: PRT
<213> ORGANISM: Homo sapiens

<400> SEQUENCE: 75

Gly Gly Gly Gly Ser
1               5

<210> SEQ ID NO 76
<211> LENGTH: 15
<212> TYPE: PRT
<213> ORGANISM: Homo sapiens

<400> SEQUENCE: 76

Glu Pro Lys Ser Cys Asp Lys Thr His Thr Cys Pro Pro Cys Pro
1               5                   10                  15

<210> SEQ ID NO 77
<211> LENGTH: 12
<212> TYPE: PRT
<213> ORGANISM: Homo sapiens

<400> SEQUENCE: 77

Glu Arg Lys Cys Cys Val Glu Cys Pro Pro Cys Pro
1               5                   10

<210> SEQ ID NO 78
<211> LENGTH: 12
<212> TYPE: PRT
<213> ORGANISM: Homo sapiens

<400> SEQUENCE: 78

Glu Ser Lys Thr Gly Pro Pro Cys Pro Ser Cys Pro
1               5                   10

<210> SEQ ID NO 79
<211> LENGTH: 12
<212> TYPE: PRT
<213> ORGANISM: Homo sapiens

<400> SEQUENCE: 79

Gly Gly Gly Gly Ser Val Glu Cys Pro Pro Cys Pro
1               5                   10

<210> SEQ ID NO 80
<211> LENGTH: 216
<212> TYPE: PRT
<213> ORGANISM: Homo sapiens

<400> SEQUENCE: 80

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
                20                  25                  30

Val Asp Val Ser His Glu Asp Pro Glu Val Gln Phe Asn Trp Tyr Val
            35                  40                  45

Asp Gly Val Glu Val His Asn Ala Lys Thr Lys Pro Arg Glu Glu Gln
        50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95
```

```
Leu Pro Ala Pro Ile Glu Lys Thr Ile Ser Lys Thr Lys Gly Gln Pro
                100                 105                 110

Arg Glu Pro Gln Val Tyr Thr Leu Pro Pro Ser Arg Glu Glu Met Thr
            115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215
```

```
<210> SEQ ID NO 81
<211> LENGTH: 648
<212> TYPE: DNA
<213> ORGANISM: Homo sapiens
<220> FEATURE:
<221> NAME/KEY: CDS
<222> LOCATION: (1)..(648)
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other
<220> FEATURE:
<221> NAME/KEY: modified_base
<222> LOCATION: (21)..(24)
<223> OTHER INFORMATION: a, c, t, g, unknown or other
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: modified_base
<222> LOCATION: (42)..(42)
<223> OTHER INFORMATION: a, c, t, g, unknown or other
<220> FEATURE:
<221> NAME/KEY: modified_base
<222> LOCATION: (48)..(48)
```

```
<223> OTHER INFORMATION: a, c, t, g, unknown or other
<220> FEATURE:
<221> NAME/KEY: modified_base
<222> LOCATION: (57)..(57)
<223> OTHER INFORMATION: a, c, t, g, unknown or other
<220> FEATURE:
<221> NAME/KEY: modified_base
<222> LOCATION: (60)..(60)
<223> OTHER INFORMATION: a, c, t, g, unknown or other
<220> FEATURE:
<221> NAME/KEY: modified_base
<222> LOCATION: (67)..(72)
<223> OTHER INFORMATION: a, c, t, g, unknown or other
<220> FEATURE:
<221> NAME/KEY: modified_base
<222> LOCATION: (75)..(75)
<223> OTHER INFORMATION: a, c, t, g, unknown or other
<220> FEATURE:
<221> NAME/KEY: modified_base
<222> LOCATION: (78)..(78)
<223> OTHER INFORMATION: a, c, t, g, unknown or other
<220> FEATURE:
<221> NAME/KEY: modified_base
<222> LOCATION: (84)..(84)
<223> OTHER INFORMATION: a, c, t, g, unknown or other
<220> FEATURE:
<221> NAME/KEY: modified_base
<222> LOCATION: (87)..(87)
<223> OTHER INFORMATION: a, c, t, g, unknown or other
<220> FEATURE:
<221> NAME/KEY: modified_base
<222> LOCATION: (93)..(93)
<223> OTHER INFORMATION: a, c, t, g, unknown or other
<220> FEATURE:
<221> NAME/KEY: modified_base
<222> LOCATION: (96)..(96)
<223> OTHER INFORMATION: a, c, t, g, unknown or other
<220> FEATURE:
<221> NAME/KEY: modified_base
<222> LOCATION: (99)..(99)
<223> OTHER INFORMATION: a, c, t, g, unknown or other
<220> FEATURE:
<221> NAME/KEY: modified_base
<222> LOCATION: (105)..(108)
<223> OTHER INFORMATION: a, c, t, g, unknown or other
<220> FEATURE:
<221> NAME/KEY: modified_base
<222> LOCATION: (120)..(120)
<223> OTHER INFORMATION: a, c, t, g, unknown or other
<220> FEATURE:
<221> NAME/KEY: modified_base
<222> LOCATION: (126)..(126)
<223> OTHER INFORMATION: a, c, t, g, unknown or other
<220> FEATURE:
<221> NAME/KEY: modified_base
<222> LOCATION: (144)..(144)
<223> OTHER INFORMATION: a, c, t, g, unknown or other
<220> FEATURE:
<221> NAME/KEY: modified_base
<222> LOCATION: (150)..(150)
<223> OTHER INFORMATION: a, c, t, g, unknown or other
<220> FEATURE:
<221> NAME/KEY: modified_base
<222> LOCATION: (153)..(153)
<223> OTHER INFORMATION: a, c, t, g, unknown or other
<220> FEATURE:
<221> NAME/KEY: modified_base
<222> LOCATION: (159)..(159)
<223> OTHER INFORMATION: a, c, t, g, unknown or other
<220> FEATURE:
<221> NAME/KEY: modified_base
<222> LOCATION: (168)..(168)
<223> OTHER INFORMATION: a, c, t, g, unknown or other
<220> FEATURE:
<221> NAME/KEY: modified_base
<222> LOCATION: (174)..(174)
<223> OTHER INFORMATION: a, c, t, g, unknown or other
<220> FEATURE:
<221> NAME/KEY: modified_base
```

```
<222> LOCATION: (180)..(183)
<223> OTHER INFORMATION: a, c, t, g, unknown or other
<220> FEATURE:
<221> NAME/KEY: modified_base
<222> LOCATION: (199)..(201)
<223> OTHER INFORMATION: a, c, t, g, unknown or other
<220> FEATURE:
<221> NAME/KEY: modified_base
<222> LOCATION: (204)..(204)
<223> OTHER INFORMATION: a, c, t, g, unknown or other
<220> FEATURE:
<221> NAME/KEY: modified_base
<222> LOCATION: (208)..(210)
<223> OTHER INFORMATION: a, c, t, g, unknown or other
<220> FEATURE:
<221> NAME/KEY: modified_base
<222> LOCATION: (213)..(213)
<223> OTHER INFORMATION: a, c, t, g, unknown or other
<220> FEATURE:
<221> NAME/KEY: modified_base
<222> LOCATION: (216)..(219)
<223> OTHER INFORMATION: a, c, t, g, unknown or other
<220> FEATURE:
<221> NAME/KEY: modified_base
<222> LOCATION: (222)..(222)
<223> OTHER INFORMATION: a, c, t, g, unknown or other
<220> FEATURE:
<221> NAME/KEY: modified_base
<222> LOCATION: (225)..(225)
<223> OTHER INFORMATION: a, c, t, g, unknown or other
<220> FEATURE:
<221> NAME/KEY: modified_base
<222> LOCATION: (228)..(228)
<223> OTHER INFORMATION: a, c, t, g, unknown or other
<220> FEATURE:
<221> NAME/KEY: modified_base
<222> LOCATION: (231)..(231)
<223> OTHER INFORMATION: a, c, t, g, unknown or other
<220> FEATURE:
<221> NAME/KEY: modified_base
<222> LOCATION: (234)..(234)
<223> OTHER INFORMATION: a, c, t, g, unknown or other
<220> FEATURE:
<221> NAME/KEY: modified_base
<222> LOCATION: (249)..(249)
<223> OTHER INFORMATION: a, c, t, g, unknown or other
<220> FEATURE:
<221> NAME/KEY: modified_base
<222> LOCATION: (255)..(255)
<223> OTHER INFORMATION: a, c, t, g, unknown or other
<220> FEATURE:
<221> NAME/KEY: modified_base
<222> LOCATION: (276)..(279)
<223> OTHER INFORMATION: a, c, t, g, unknown or other
<220> FEATURE:
<221> NAME/KEY: modified_base
<222> LOCATION: (288)..(288)
<223> OTHER INFORMATION: a, c, t, g, unknown or other
<220> FEATURE:
<221> NAME/KEY: modified_base
<222> LOCATION: (291)..(291)
<223> OTHER INFORMATION: a, c, t, g, unknown or other
<220> FEATURE:
<221> NAME/KEY: modified_base
<222> LOCATION: (294)..(294)
<223> OTHER INFORMATION: a, c, t, g, unknown or other
<220> FEATURE:
<221> NAME/KEY: modified_base
<222> LOCATION: (297)..(297)
<223> OTHER INFORMATION: a, c, t, g, unknown or other
<220> FEATURE:
<221> NAME/KEY: modified_base
<222> LOCATION: (300)..(300)
<223> OTHER INFORMATION: a, c, t, g, unknown or other
<220> FEATURE:
<221> NAME/KEY: modified_base
<222> LOCATION: (312)..(312)
<223> OTHER INFORMATION: a, c, t, g, unknown or other
<220> FEATURE:
```

```
<221> NAME/KEY: modified_base
<222> LOCATION: (316)..(318)
<223> OTHER INFORMATION: a, c, t, g, unknown or other
<220> FEATURE:
<221> NAME/KEY: modified_base
<222> LOCATION: (324)..(324)
<223> OTHER INFORMATION: a, c, t, g, unknown or other
<220> FEATURE:
<221> NAME/KEY: modified_base
<222> LOCATION: (330)..(330)
<223> OTHER INFORMATION: a, c, t, g, unknown or other
<220> FEATURE:
<221> NAME/KEY: modified_base
<222> LOCATION: (336)..(339)
<223> OTHER INFORMATION: a, c, t, g, unknown or other
<220> FEATURE:
<221> NAME/KEY: modified_base
<222> LOCATION: (345)..(345)
<223> OTHER INFORMATION: a, c, t, g, unknown or other
<220> FEATURE:
<221> NAME/KEY: modified_base
<222> LOCATION: (351)..(351)
<223> OTHER INFORMATION: a, c, t, g, unknown or other
<220> FEATURE:
<221> NAME/KEY: modified_base
<222> LOCATION: (357)..(357)
<223> OTHER INFORMATION: a, c, t, g, unknown or other
<220> FEATURE:
<221> NAME/KEY: modified_base
<222> LOCATION: (360)..(360)
<223> OTHER INFORMATION: a, c, t, g, unknown or other
<220> FEATURE:
<221> NAME/KEY: modified_base
<222> LOCATION: (363)..(363)
<223> OTHER INFORMATION: a, c, t, g, unknown or other
<220> FEATURE:
<221> NAME/KEY: modified_base
<222> LOCATION: (366)..(372)
<223> OTHER INFORMATION: a, c, t, g, unknown or other
<220> FEATURE:
<221> NAME/KEY: modified_base
<222> LOCATION: (384)..(384)
<223> OTHER INFORMATION: a, c, t, g, unknown or other
<220> FEATURE:
<221> NAME/KEY: modified_base
<222> LOCATION: (396)..(399)
<223> OTHER INFORMATION: a, c, t, g, unknown or other
<220> FEATURE:
<221> NAME/KEY: modified_base
<222> LOCATION: (402)..(402)
<223> OTHER INFORMATION: a, c, t, g, unknown or other
<220> FEATURE:
<221> NAME/KEY: modified_base
<222> LOCATION: (405)..(405)
<223> OTHER INFORMATION: a, c, t, g, unknown or other
<220> FEATURE:
<221> NAME/KEY: modified_base
<222> LOCATION: (411)..(411)
<223> OTHER INFORMATION: a, c, t, g, unknown or other
<220> FEATURE:
<221> NAME/KEY: modified_base
<222> LOCATION: (414)..(414)
<223> OTHER INFORMATION: a, c, t, g, unknown or other
<220> FEATURE:
<221> NAME/KEY: modified_base
<222> LOCATION: (420)..(420)
<223> OTHER INFORMATION: a, c, t, g, unknown or other
<220> FEATURE:
<221> NAME/KEY: modified_base
<222> LOCATION: (429)..(432)
<223> OTHER INFORMATION: a, c, t, g, unknown or other
<220> FEATURE:
<221> NAME/KEY: modified_base
<222> LOCATION: (441)..(441)
<223> OTHER INFORMATION: a, c, t, g, unknown or other
<220> FEATURE:
<221> NAME/KEY: modified_base
<222> LOCATION: (444)..(444)
<223> OTHER INFORMATION: a, c, t, g, unknown or other
```

-continued

```
<220> FEATURE:
<221> NAME/KEY: modified_base
<222> LOCATION: (454)..(456)
<223> OTHER INFORMATION: a, c, t, g, unknown or other
<220> FEATURE:
<221> NAME/KEY: modified_base
<222> LOCATION: (462)..(462)
<223> OTHER INFORMATION: a, c, t, g, unknown or other
<220> FEATURE:
<221> NAME/KEY: modified_base
<222> LOCATION: (468)..(468)
<223> OTHER INFORMATION: a, c, t, g, unknown or other
<220> FEATURE:
<221> NAME/KEY: modified_base
<222> LOCATION: (486)..(486)
<223> OTHER INFORMATION: a, c, t, g, unknown or other
<220> FEATURE:
<221> NAME/KEY: modified_base
<222> LOCATION: (489)..(489)
<223> OTHER INFORMATION: a, c, t, g, unknown or other
<220> FEATURE:
<221> NAME/KEY: modified_base
<222> LOCATION: (492)..(492)
<223> OTHER INFORMATION: a, c, t, g, unknown or other
<220> FEATURE:
<221> NAME/KEY: modified_base
<222> LOCATION: (495)..(495)
<223> OTHER INFORMATION: a, c, t, g, unknown or other
<220> FEATURE:
<221> NAME/KEY: modified_base
<222> LOCATION: (501)..(501)
<223> OTHER INFORMATION: a, c, t, g, unknown or other
<220> FEATURE:
<221> NAME/KEY: modified_base
<222> LOCATION: (505)..(507)
<223> OTHER INFORMATION: a, c, t, g, unknown or other
<220> FEATURE:
<221> NAME/KEY: modified_base
<222> LOCATION: (513)..(516)
<223> OTHER INFORMATION: a, c, t, g, unknown or other
<220> FEATURE:
<221> NAME/KEY: modified_base
<222> LOCATION: (525)..(525)
<223> OTHER INFORMATION: a, c, t, g, unknown or other
<220> FEATURE:
<221> NAME/KEY: modified_base
<222> LOCATION: (529)..(531)
<223> OTHER INFORMATION: a, c, t, g, unknown or other
<220> FEATURE:
<221> NAME/KEY: modified_base
<222> LOCATION: (537)..(537)
<223> OTHER INFORMATION: a, c, t, g, unknown or other
<220> FEATURE:
<221> NAME/KEY: modified_base
<222> LOCATION: (540)..(540)
<223> OTHER INFORMATION: a, c, t, g, unknown or other
<220> FEATURE:
<221> NAME/KEY: modified_base
<222> LOCATION: (543)..(543)
<223> OTHER INFORMATION: a, c, t, g, unknown or other
<220> FEATURE:
<221> NAME/KEY: modified_base
<222> LOCATION: (550)..(555)
<223> OTHER INFORMATION: a, c, t, g, unknown or other
<220> FEATURE:
<221> NAME/KEY: modified_base
<222> LOCATION: (567)..(567)
<223> OTHER INFORMATION: a, c, t, g, unknown or other
<220> FEATURE:
<221> NAME/KEY: modified_base
<222> LOCATION: (573)..(573)
<223> OTHER INFORMATION: a, c, t, g, unknown or other
<220> FEATURE:
<221> NAME/KEY: modified_base
<222> LOCATION: (577)..(579)
<223> OTHER INFORMATION: a, c, t, g, unknown or other
<220> FEATURE:
<221> NAME/KEY: modified_base
<222> LOCATION: (583)..(585)
```

```
<223> OTHER INFORMATION: a, c, t, g, unknown or other
<220> FEATURE:
<221> NAME/KEY: modified_base
<222> LOCATION: (588)..(588)
<223> OTHER INFORMATION: a, c, t, g, unknown or other
<220> FEATURE:
<221> NAME/KEY: modified_base
<222> LOCATION: (600)..(600)
<223> OTHER INFORMATION: a, c, t, g, unknown or other
<220> FEATURE:
<221> NAME/KEY: modified_base
<222> LOCATION: (603)..(603)
<223> OTHER INFORMATION: a, c, t, g, unknown or other
<220> FEATURE:
<221> NAME/KEY: modified_base
<222> LOCATION: (618)..(618)
<223> OTHER INFORMATION: a, c, t, g, unknown or other
<220> FEATURE:
<221> NAME/KEY: modified_base
<222> LOCATION: (625)..(627)
<223> OTHER INFORMATION: a, c, t, g, unknown or other
<220> FEATURE:
<221> NAME/KEY: modified_base
<222> LOCATION: (630)..(633)
<223> OTHER INFORMATION: a, c, t, g, unknown or other
<220> FEATURE:
<221> NAME/KEY: modified_base
<222> LOCATION: (636)..(639)
<223> OTHER INFORMATION: a, c, t, g, unknown or other
<220> FEATURE:
<221> NAME/KEY: modified_base
<222> LOCATION: (642)..(642)
<223> OTHER INFORMATION: a, c, t, g, unknown or other
<220> FEATURE:
<221> NAME/KEY: modified_base
<222> LOCATION: (645)..(645)
<223> OTHER INFORMATION: a, c, t, g, unknown or other

<400> SEQUENCE: 81 gcn ccn ccn gtn gcn ggn ccn nnn gtn tty ytn tty ccn ccn aar ccn      48
Ala Pro Pro Val Ala Gly Pro Ser Val Phe Leu Phe Pro Pro Lys Pro
1               5                   10                  15 aar gay acn ytn atg ath nnn nnn acn ccn gar gtn acn tgy gtn gtn      96
Lys Asp Thr Leu Met Ile Ser Arg Thr Pro Glu Val Thr Cys Val Val
            20                  25                  30 gtn gay gtn nnn cay gar gay ccn gar gtn car tty aay tgg tay gtn     144
Val Asp Val Ser His Glu Asp Pro Glu Val Gln Phe Asn Trp Tyr Val
        35                  40                  45 gay ggn gtn gar gtn cay aay gcn aar acn aar ccn nnn gar gar car     192
Asp Gly Val Glu Val His Asn Ala Lys Thr Lys Pro Arg Glu Glu Gln
50                  55                  60 tty aay nnn acn tty nnn gtn gtn nnn gtn ytn acn gtn gtn cay car     240
Phe Asn Ser Thr Phe Arg Val Val Ser Val Leu Thr Val Val His Gln
65                  70                  75                  80 gay tgg ytn aay ggn aar gar tay aar tgy aar gtn nnn aay aar ggn     288
Asp Trp Leu Asn Gly Lys Glu Tyr Lys Cys Lys Val Ser Asn Lys Gly
                85                  90                  95 ytn ccn gcn ccn ath gar aar acn ath nnn aar acn aar ggn car ccn     336
Leu Pro Ala Pro Ile Glu Lys Thr Ile Ser Lys Thr Lys Gly Gln Pro
            100                 105                 110 nnn gar ccn car gtn tay acn ytn ccn ccn nnn nnn gar gar atg acn     384
Arg Glu Pro Gln Val Tyr Thr Leu Pro Pro Ser Arg Glu Glu Met Thr
        115                 120                 125 aar aay car gtn nnn ytn acn tgy ytn gtn aar ggn tty tay ccn nnn     432
Lys Asn Gln Val Ser Leu Thr Cys Leu Val Lys Gly Phe Tyr Pro Ser
130                 135                 140 gay ath gcn gtn gar tgg gar nnn aay ggn car ccn gar aay aay tay     480
Asp Ile Ala Val Glu Trp Glu Ser Asn Gly Gln Pro Glu Asn Asn Tyr
145                 150                 155

| | | | | | | | | | | | | |
|---|---|---|---|---|---|---|---|---|---|---|---|---|
| aar | acn | acn | ccn | ccn | atg | ytn | gay | nnn | gay | ggn | nnn | tty | tty | ytn | tay | 528
| Lys | Thr | Thr | Pro | Pro | Met | Leu | Asp | Ser | Asp | Gly | Ser | Phe | Phe | Leu | Tyr |
| | | | 165 | | | | 170 | | | | | 175 | | |

```
aar acn acn ccn ccn atg ytn gay nnn gay ggn nnn tty tty ytn tay      528
Lys Thr Thr Pro Pro Met Leu Asp Ser Asp Gly Ser Phe Phe Leu Tyr
            165                 170                 175 nnn aar ytn acn gtn gay aar nnn nnn tgg car car ggn aay gtn tty      576
Ser Lys Leu Thr Val Asp Lys Ser Arg Trp Gln Gln Gly Asn Val Phe
        180                 185                 190 nnn tgy nnn gtn atg cay gar gcn ytn cay aay cay tay acn car aar      624
Ser Cys Ser Val Met His Glu Ala Leu His Asn His Tyr Thr Gln Lys
            195                 200                 205 nnn ytn nnn ytn nnn ccn ggn aar                                      648
Ser Leu Ser Leu Ser Pro Gly Lys
            210                 215

<210> SEQ ID NO 82
<211> LENGTH: 217
<212> TYPE: PRT
<213> ORGANISM: Homo sapiens

<400> SEQUENCE: 82

Ala Pro Glu Leu Leu Gly Gly Pro Ser Val Phe Leu Phe Pro Pro Lys
1               5                   10                  15

Pro Lys Asp Ile Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Gly Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 83
<211> LENGTH: 651
<212> TYPE: DNA
<213> ORGANISM: Homo sapiens

<400> SEQUENCE: 83
cctgaactcc tggggggacc gtcagtcttc ctcttccccc caaaacccaa ggacatcctc      60
atgatctccc ggacccctga ggtcacatgc gtggtggtgg acgtgagcca cgaagaccct     120
```

```
gaggtcaagt tcaactggta cgtgggcggc gtggaggtgc ataatgccaa gacaaagccg    180
cgggaggagc agtacaacag cacgtaccgt gtggtcagcg tcctcaccgt cctgcaccag    240
gactggctga atggcaagga gtacaagtgc aaggtctcca acaaagccct cccagccccc    300
atcgagaaaa ccatctccaa agccaaaggg cagccccgag aaccacaggt gtacaccctg    360
cccccatccc gggatgagct gaccaagaac caggtcagcc tgacctgcct ggtcaaaggc    420
ttctatccca gcgacatcgc cgtggagtgg gagagcaatg ggcagccgga gaacaactac    480
aagaccacgc ctcccgtgct ggactccgac ggctccttct tcctctacag caagctcacc    540
gtggacaaga gcaggtggca gcaggggaac gtcttctcat gctccgtgat gcatgaggct    600
ctgcacaacc actacacgca gaagagcctc tccctgtctc cgggtaaatg a             651
```

<210> SEQ ID NO 84
<211> LENGTH: 217
<212> TYPE: PRT
<213> ORGANISM: Homo sapiens
<400> SEQUENCE: 84

```
Ala Pro Glu Phe Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
             20                  25                  30

Val Val Asp Val Ser Gln Glu Asp Pro Glu Val Gln Phe Asn Trp Tyr
         35                  40                  45

Val Asp Gly Val Glu Val His Asn Ala Lys Thr Lys Pro Arg Glu Glu
     50                  55                  60

Gln Phe Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215
```

<210> SEQ ID NO 85
<211> LENGTH: 651
<212> TYPE: DNA
<213> ORGANISM: Homo sapiens
<220> FEATURE:
<221> NAME/KEY: CDS
<222> LOCATION: (1)..(651)
<220> FEATURE:
<221> NAME/KEY: modified_base
<222> LOCATION: (3)..(3)

```
<223> OTHER INFORMATION: a, c, t, g, unknown or other
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(27)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: modified_base
<222> LOCATION: (42)..(42)
<223> OTHER INFORMATION: a, c, t, g, unknown or other
<220> FEATURE:
<221> NAME/KEY: modified_base
<222> LOCATION: (45)..(45)
<223> OTHER INFORMATION: a, c, t, g, unknown or other
<220> FEATURE:
<221> NAME/KEY: modified_base
<222> LOCATION: (51)..(51)
<223> OTHER INFORMATION: a, c, t, g, unknown or other
<220> FEATURE:
<221> NAME/KEY: modified_base
<222> LOCATION: (60)..(60)
<223> OTHER INFORMATION: a, c, t, g, unknown or other
<220> FEATURE:
<221> NAME/KEY: modified_base
<222> LOCATION: (63)..(63)
<223> OTHER INFORMATION: a, c, t, g, unknown or other
<220> FEATURE:
<221> NAME/KEY: modified_base
<222> LOCATION: (70)..(75)
<223> OTHER INFORMATION: a, c, t, g, unknown or other
<220> FEATURE:
<221> NAME/KEY: modified_base
<222> LOCATION: (78)..(78)
<223> OTHER INFORMATION: a, c, t, g, unknown or other
<220> FEATURE:
<221> NAME/KEY: modified_base
<222> LOCATION: (81)..(81)
<223> OTHER INFORMATION: a, c, t, g, unknown or other
<220> FEATURE:
<221> NAME/KEY: modified_base
<222> LOCATION: (87)..(87)
<223> OTHER INFORMATION: a, c, t, g, unknown or other
<220> FEATURE:
<221> NAME/KEY: modified_base
<222> LOCATION: (90)..(90)
<223> OTHER INFORMATION: a, c, t, g, unknown or other
<220> FEATURE:
<221> NAME/KEY: modified_base
<222> LOCATION: (96)..(96)
<223> OTHER INFORMATION: a, c, t, g, unknown or other
<220> FEATURE:
<221> NAME/KEY: modified_base
<222> LOCATION: (99)..(99)
<223> OTHER INFORMATION: a, c, t, g, unknown or other
<220> FEATURE:
<221> NAME/KEY: modified_base
```

```
<222> LOCATION: (102)..(102)
<223> OTHER INFORMATION: a, c, t, g, unknown or other
<220> FEATURE:
<221> NAME/KEY: modified_base
<222> LOCATION: (108)..(111)
<223> OTHER INFORMATION: a, c, t, g, unknown or other
<220> FEATURE:
<221> NAME/KEY: modified_base
<222> LOCATION: (123)..(123)
<223> OTHER INFORMATION: a, c, t, g, unknown or other
<220> FEATURE:
<221> NAME/KEY: modified_base
<222> LOCATION: (129)..(129)
<223> OTHER INFORMATION: a, c, t, g, unknown or other
<220> FEATURE:
<221> NAME/KEY: modified_base
<222> LOCATION: (147)..(147)
<223> OTHER INFORMATION: a, c, t, g, unknown or other
<220> FEATURE:
<221> NAME/KEY: modified_base
<222> LOCATION: (153)..(153)
<223> OTHER INFORMATION: a, c, t, g, unknown or other
<220> FEATURE:
<221> NAME/KEY: modified_base
<222> LOCATION: (156)..(156)
<223> OTHER INFORMATION: a, c, t, g, unknown or other
<220> FEATURE:
<221> NAME/KEY: modified_base
<222> LOCATION: (162)..(162)
<223> OTHER INFORMATION: a, c, t, g, unknown or other
<220> FEATURE:
<221> NAME/KEY: modified_base
<222> LOCATION: (171)..(171)
<223> OTHER INFORMATION: a, c, t, g, unknown or other
<220> FEATURE:
<221> NAME/KEY: modified_base
<222> LOCATION: (177)..(177)
<223> OTHER INFORMATION: a, c, t, g, unknown or other
<220> FEATURE:
<221> NAME/KEY: modified_base
<222> LOCATION: (183)..(186)
<223> OTHER INFORMATION: a, c, t, g, unknown or other
<220> FEATURE:
<221> NAME/KEY: modified_base
<222> LOCATION: (202)..(204)
<223> OTHER INFORMATION: a, c, t, g, unknown or other
<220> FEATURE:
<221> NAME/KEY: modified_base
<222> LOCATION: (207)..(207)
<223> OTHER INFORMATION: a, c, t, g, unknown or other
<220> FEATURE:
<221> NAME/KEY: modified_base
<222> LOCATION: (211)..(213)
<223> OTHER INFORMATION: a, c, t, g, unknown or other
<220> FEATURE:
<221> NAME/KEY: modified_base
<222> LOCATION: (216)..(216)
<223> OTHER INFORMATION: a, c, t, g, unknown or other
<220> FEATURE:
<221> NAME/KEY: modified_base
<222> LOCATION: (219)..(222)
<223> OTHER INFORMATION: a, c, t, g, unknown or other
<220> FEATURE:
<221> NAME/KEY: modified_base
<222> LOCATION: (225)..(225)
<223> OTHER INFORMATION: a, c, t, g, unknown or other
<220> FEATURE:
<221> NAME/KEY: modified_base
<222> LOCATION: (228)..(228)
<223> OTHER INFORMATION: a, c, t, g, unknown or other
<220> FEATURE:
<221> NAME/KEY: modified_base
<222> LOCATION: (231)..(231)
<223> OTHER INFORMATION: a, c, t, g, unknown or other
<220> FEATURE:
<221> NAME/KEY: modified_base
<222> LOCATION: (234)..(234)
<223> OTHER INFORMATION: a, c, t, g, unknown or other
<220> FEATURE:
```

```
<221> NAME/KEY: modified_base
<222> LOCATION: (237)..(237)
<223> OTHER INFORMATION: a, c, t, g, unknown or other
<220> FEATURE:
<221> NAME/KEY: modified_base
<222> LOCATION: (252)..(252)
<223> OTHER INFORMATION: a, c, t, g, unknown or other
<220> FEATURE:
<221> NAME/KEY: modified_base
<222> LOCATION: (258)..(258)
<223> OTHER INFORMATION: a, c, t, g, unknown or other
<220> FEATURE:
<221> NAME/KEY: modified_base
<222> LOCATION: (279)..(282)
<223> OTHER INFORMATION: a, c, t, g, unknown or other
<220> FEATURE:
<221> NAME/KEY: modified_base
<222> LOCATION: (291)..(291)
<223> OTHER INFORMATION: a, c, t, g, unknown or other
<220> FEATURE:
<221> NAME/KEY: modified_base
<222> LOCATION: (294)..(294)
<223> OTHER INFORMATION: a, c, t, g, unknown or other
<220> FEATURE:
<221> NAME/KEY: modified_base
<222> LOCATION: (297)..(303)
<223> OTHER INFORMATION: a, c, t, g, unknown or other
<220> FEATURE:
<221> NAME/KEY: modified_base
<222> LOCATION: (315)..(315)
<223> OTHER INFORMATION: a, c, t, g, unknown or other
<220> FEATURE:
<221> NAME/KEY: modified_base
<222> LOCATION: (319)..(321)
<223> OTHER INFORMATION: a, c, t, g, unknown or other
<220> FEATURE:
<221> NAME/KEY: modified_base
<222> LOCATION: (327)..(327)
<223> OTHER INFORMATION: a, c, t, g, unknown or other
<220> FEATURE:
<221> NAME/KEY: modified_base
<222> LOCATION: (333)..(333)
<223> OTHER INFORMATION: a, c, t, g, unknown or other
<220> FEATURE:
<221> NAME/KEY: modified_base
<222> LOCATION: (339)..(342)
<223> OTHER INFORMATION: a, c, t, g, unknown or other
<220> FEATURE:
<221> NAME/KEY: modified_base
<222> LOCATION: (348)..(348)
<223> OTHER INFORMATION: a, c, t, g, unknown or other
<220> FEATURE:
<221> NAME/KEY: modified_base
<222> LOCATION: (354)..(354)
<223> OTHER INFORMATION: a, c, t, g, unknown or other
<220> FEATURE:
<221> NAME/KEY: modified_base
<222> LOCATION: (360)..(360)
<223> OTHER INFORMATION: a, c, t, g, unknown or other
<220> FEATURE:
<221> NAME/KEY: modified_base
<222> LOCATION: (363)..(363)
<223> OTHER INFORMATION: a, c, t, g, unknown or other
<220> FEATURE:
<221> NAME/KEY: modified_base
<222> LOCATION: (366)..(366)
<223> OTHER INFORMATION: a, c, t, g, unknown or other
<220> FEATURE:
<221> NAME/KEY: modified_base
<222> LOCATION: (369)..(372)
<223> OTHER INFORMATION: a, c, t, g, unknown or other
<220> FEATURE:
<221> NAME/KEY: modified_base
<222> LOCATION: (387)..(387)
<223> OTHER INFORMATION: a, c, t, g, unknown or other
<220> FEATURE:
<221> NAME/KEY: modified_base
<222> LOCATION: (399)..(402)
<223> OTHER INFORMATION: a, c, t, g, unknown or other
```

-continued

```
<220> FEATURE:
<221> NAME/KEY: modified_base
<222> LOCATION: (405)..(405)
<223> OTHER INFORMATION: a, c, t, g, unknown or other
<220> FEATURE:
<221> NAME/KEY: modified_base
<222> LOCATION: (408)..(408)
<223> OTHER INFORMATION: a, c, t, g, unknown or other
<220> FEATURE:
<221> NAME/KEY: modified_base
<222> LOCATION: (414)..(414)
<223> OTHER INFORMATION: a, c, t, g, unknown or other
<220> FEATURE:
<221> NAME/KEY: modified_base
<222> LOCATION: (417)..(417)
<223> OTHER INFORMATION: a, c, t, g, unknown or other
<220> FEATURE:
<221> NAME/KEY: modified_base
<222> LOCATION: (423)..(423)
<223> OTHER INFORMATION: a, c, t, g, unknown or other
<220> FEATURE:
<221> NAME/KEY: modified_base
<222> LOCATION: (432)..(435)
<223> OTHER INFORMATION: a, c, t, g, unknown or other
<220> FEATURE:
<221> NAME/KEY: modified_base
<222> LOCATION: (444)..(444)
<223> OTHER INFORMATION: a, c, t, g, unknown or other
<220> FEATURE:
<221> NAME/KEY: modified_base
<222> LOCATION: (447)..(447)
<223> OTHER INFORMATION: a, c, t, g, unknown or other
<220> FEATURE:
<221> NAME/KEY: modified_base
<222> LOCATION: (457)..(459)
<223> OTHER INFORMATION: a, c, t, g, unknown or other
<220> FEATURE:
<221> NAME/KEY: modified_base
<222> LOCATION: (465)..(465)
<223> OTHER INFORMATION: a, c, t, g, unknown or other
<220> FEATURE:
<221> NAME/KEY: modified_base
<222> LOCATION: (471)..(471)
<223> OTHER INFORMATION: a, c, t, g, unknown or other
<220> FEATURE:
<221> NAME/KEY: modified_base
<222> LOCATION: (489)..(489)
<223> OTHER INFORMATION: a, c, t, g, unknown or other
<220> FEATURE:
<221> NAME/KEY: modified_base
<222> LOCATION: (492)..(492)
<223> OTHER INFORMATION: a, c, t, g, unknown or other
<220> FEATURE:
<221> NAME/KEY: modified_base
<222> LOCATION: (495)..(495)
<223> OTHER INFORMATION: a, c, t, g, unknown or other
<220> FEATURE:
<221> NAME/KEY: modified_base
<222> LOCATION: (498)..(498)
<223> OTHER INFORMATION: a, c, t, g, unknown or other
<220> FEATURE:
<221> NAME/KEY: modified_base
<222> LOCATION: (501)..(501)
<223> OTHER INFORMATION: a, c, t, g, unknown or other
<220> FEATURE:
<221> NAME/KEY: modified_base
<222> LOCATION: (504)..(504)
<223> OTHER INFORMATION: a, c, t, g, unknown or other
<220> FEATURE:
<221> NAME/KEY: modified_base
<222> LOCATION: (508)..(510)
<223> OTHER INFORMATION: a, c, t, g, unknown or other
<220> FEATURE:
<221> NAME/KEY: modified_base
<222> LOCATION: (516)..(519)
<223> OTHER INFORMATION: a, c, t, g, unknown or other
<220> FEATURE:
<221> NAME/KEY: modified_base
<222> LOCATION: (528)..(528)
```

-continued

```
<223> OTHER INFORMATION: a, c, t, g, unknown or other
<220> FEATURE:
<221> NAME/KEY: modified_base
<222> LOCATION: (532)..(537)
<223> OTHER INFORMATION: a, c, t, g, unknown or other
<220> FEATURE:
<221> NAME/KEY: modified_base
<222> LOCATION: (540)..(540)
<223> OTHER INFORMATION: a, c, t, g, unknown or other
<220> FEATURE:
<221> NAME/KEY: modified_base
<222> LOCATION: (543)..(543)
<223> OTHER INFORMATION: a, c, t, g, unknown or other
<220> FEATURE:
<221> NAME/KEY: modified_base
<222> LOCATION: (546)..(546)
<223> OTHER INFORMATION: a, c, t, g, unknown or other
<220> FEATURE:
<221> NAME/KEY: modified_base
<222> LOCATION: (553)..(558)
<223> OTHER INFORMATION: a, c, t, g, unknown or other
<220> FEATURE:
<221> NAME/KEY: modified_base
<222> LOCATION: (570)..(570)
<223> OTHER INFORMATION: a, c, t, g, unknown or other
<220> FEATURE:
<221> NAME/KEY: modified_base
<222> LOCATION: (576)..(576)
<223> OTHER INFORMATION: a, c, t, g, unknown or other
<220> FEATURE:
<221> NAME/KEY: modified_base
<222> LOCATION: (580)..(582)
<223> OTHER INFORMATION: a, c, t, g, unknown or other
<220> FEATURE:
<221> NAME/KEY: modified_base
<222> LOCATION: (586)..(588)
<223> OTHER INFORMATION: a, c, t, g, unknown or other
<220> FEATURE:
<221> NAME/KEY: modified_base
<222> LOCATION: (591)..(591)
<223> OTHER INFORMATION: a, c, t, g, unknown or other
<220> FEATURE:
<221> NAME/KEY: modified_base
<222> LOCATION: (603)..(603)
<223> OTHER INFORMATION: a, c, t, g, unknown or other
<220> FEATURE:
<221> NAME/KEY: modified_base
<222> LOCATION: (606)..(606)
<223> OTHER INFORMATION: a, c, t, g, unknown or other
<220> FEATURE:
<221> NAME/KEY: modified_base
<222> LOCATION: (621)..(621)
<223> OTHER INFORMATION: a, c, t, g, unknown or other
<220> FEATURE:
<221> NAME/KEY: modified_base
<222> LOCATION: (628)..(630)
<223> OTHER INFORMATION: a, c, t, g, unknown or other
<220> FEATURE:
<221> NAME/KEY: modified_base
<222> LOCATION: (633)..(636)
<223> OTHER INFORMATION: a, c, t, g, unknown or other
<220> FEATURE:
<221> NAME/KEY: modified_base
<222> LOCATION: (639)..(642)
<223> OTHER INFORMATION: a, c, t, g, unknown or other
<220> FEATURE:
<221> NAME/KEY: modified_base
<222> LOCATION: (645)..(645)
<223> OTHER INFORMATION: a, c, t, g, unknown or other
<220> FEATURE:
<221> NAME/KEY: modified_base
<222> LOCATION: (648)..(648)
<223> OTHER INFORMATION: a, c, t, g, unknown or other

<400> SEQUENCE: 85 gcn ccn gar tty ytn ggn ggn ccn nnn gtn tty ytn tty ccn ccn aar      48
Ala Pro Glu Phe Leu Gly Gly Pro Ser Val Phe Leu Phe Pro Pro Lys
1               5                   10                  15
```

| | | |
|---|---|---|
| ccn aar gay acn ytn atg ath nnn nnn acn ccn gar gtn acn tgy gtn<br>Pro Lys Asp Thr Leu Met Ile Ser Arg Thr Pro Glu Val Thr Cys Val<br>20 25 30 | | 96 |
| gtn gtn gay gtn nnn car gar gay ccn gar gtn car tty aay tgg tay<br>Val Val Asp Val Ser Gln Glu Asp Pro Glu Val Gln Phe Asn Trp Tyr<br>35 40 45 | | 144 |
| gtn gay ggn gtn gar gtn cay aay gcn aar acn aar ccn nnn gar gar<br>Val Asp Gly Val Glu Val His Asn Ala Lys Thr Lys Pro Arg Glu Glu<br>50 55 60 | | 192 |
| car tty aay nnn acn tay nnn gtn gtn nnn gtn ytn acn gtn ytn cay<br>Gln Phe Asn Ser Thr Tyr Arg Val Val Ser Val Leu Thr Val Leu His<br>65 70 75 80 | | 240 |
| car gay tgg ytn aay ggn aar gar tay aar tgy aar gtn nnn aay aar<br>Gln Asp Trp Leu Asn Gly Lys Glu Tyr Lys Cys Lys Val Ser Asn Lys<br>85 90 95 | | 288 |
| ggn ytn ccn nnn nnn ath gar aar acn ath nnn aar gcn aar ggn car<br>Gly Leu Pro Ser Ser Ile Glu Lys Thr Ile Ser Lys Ala Lys Gly Gln<br>100 105 110 | | 336 |
| ccn nnn gar ccn car gtn tay acn ytn ccn ccn nnn car gar gar atg<br>Pro Arg Glu Pro Gln Val Tyr Thr Leu Pro Pro Ser Gln Glu Glu Met<br>115 120 125 | | 384 |
| acn aar aay car gtn nnn ytn acn tgy ytn gtn aar ggn tty tay ccn<br>Thr Lys Asn Gln Val Ser Leu Thr Cys Leu Val Lys Gly Phe Tyr Pro<br>130 135 140 | | 432 |
| nnn gay ath gcn gtn gar tgg gar nnn aay ggn car ccn gar aay aay<br>Ser Asp Ile Ala Val Glu Trp Glu Ser Asn Gly Gln Pro Glu Asn Asn<br>145 150 155 160 | | 480 |
| tay aar acn acn ccn ccn gtn ytn gay nnn gay ggn nnn tty tty ytn<br>Tyr Lys Thr Thr Pro Pro Val Leu Asp Ser Asp Gly Ser Phe Phe Leu<br>165 170 175 | | 528 |
| tay nnn nnn ytn acn gtn gay aar nnn nnn tgg car gar ggn aay gtn<br>Tyr Ser Arg Leu Thr Val Asp Lys Ser Arg Trp Gln Glu Gly Asn Val<br>180 185 190 | | 576 |
| tty nnn tgy nnn gtn atg cay gar gcn ytn cay aay cay tay acn car<br>Phe Ser Cys Ser Val Met His Glu Ala Leu His Asn His Tyr Thr Gln<br>195 200 205 | | 624 |
| aar nnn ytn nnn ytn nnn ytn ggn aar<br>Lys Ser Leu Ser Leu Ser Leu Gly Lys<br>210 215 | | 651 |

<210> SEQ ID NO 86
<211> LENGTH: 110
<212> TYPE: PRT
<213> ORGANISM: Homo sapiens

<400> SEQUENCE: 86

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 87
<211> LENGTH: 110
<212> TYPE: PRT
<213> ORGANISM: Homo sapiens

<400> SEQUENCE: 87

Glu Thr Arg Trp Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 88
<211> LENGTH: 110
<212> TYPE: PRT
<213> ORGANISM: Homo sapiens

<400> SEQUENCE: 88

Glu Thr Arg Tyr Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 89
<211> LENGTH: 338
<212> TYPE: PRT
<213> ORGANISM: Homo sapiens

<400> SEQUENCE: 89

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln

```
            50                  55                  60
Glu Cys Val Ala Thr Glu Asn Pro Gln Val Tyr Phe Cys Cys Cys
 65                  70                  75                  80

Glu Gly Asn Phe Cys Asn Glu Arg Phe Thr His Leu Pro Glu Ala Gly
                 85                  90                  95

Gly Pro Glu Val Thr Tyr Glu Pro Pro Thr Ala Pro Thr Gly Gly
                100                 105                 110

Gly Gly Ser Val Glu Cys Pro Pro Cys Pro Ala Pro Val Ala Gly
            115                 120                 125

Pro Ser Val Phe Leu Phe Pro Pro Lys Pro Lys Asp Thr Leu Met Ile
130                 135                 140

Ser Arg Thr Pro Glu Val Thr Cys Val Val Asp Val Ser His Glu
145                 150                 155                 160

Asp Pro Glu Val Gln Phe Asn Trp Tyr Val Asp Gly Val Glu Val His
                165                 170                 175

Asn Ala Lys Thr Lys Pro Arg Glu Glu Gln Phe Asn Ser Thr Phe Arg
            180                 185                 190

Val Val Ser Val Leu Thr Val Val His Gln Asp Trp Leu Asn Gly Lys
        195                 200                 205

Glu Tyr Lys Cys Lys Val Ser Asn Lys Gly Leu Pro Ala Pro Ile Glu
210                 215                 220

Lys Thr Ile Ser Lys Thr Lys Gly Gln Pro Arg Glu Pro Gln Val Tyr
225                 230                 235                 240

Thr Leu Pro Pro Ser Arg Glu Glu Met Thr Lys Asn Gln Val Ser Leu
                245                 250                 255

Thr Cys Leu Val Lys Gly Phe Tyr Pro Ser Asp Ile Ala Val Glu Trp
            260                 265                 270

Glu Ser Asn Gly Gln Pro Glu Asn Tyr Lys Thr Thr Pro Pro Met
        275                 280                 285

Leu Asp Ser Asp Gly Ser Phe Phe Leu Tyr Ser Lys Leu Thr Val Asp
290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335

Gly Lys

<210> SEQ ID NO 90
<211> LENGTH: 1014
<212> TYPE: DNA
<213> ORGANISM: Homo sapiens
<220> FEATURE:
<221> NAME/KEY: CDS
<222> LOCATION: (1)..(1014)

<400> SEQUENCE: 90 gag aca cgg gag tgc atc tac tac aac gcc aac tgg gag ctg gag cgc      48
Glu Thr Arg Glu Cys Ile Tyr Tyr Asn Ala Asn Trp Glu Leu Glu Arg
 1               5                  10                  15 acc aac cag agc ggc ctg gag cgc tgc gaa ggc gag cag gac aag cgg      96
Thr Asn Gln Ser Gly Leu Glu Arg Cys Glu Gly Glu Gln Asp Lys Arg
            20                  25                  30 ctg cac tgc tac gcc tcc tgg cgc aac agc tct ggc acc atc gag ctc     144
Leu His Cys Tyr Ala Ser Trp Arg Asn Ser Ser Gly Thr Ile Glu Leu
        35                  40                  45 gtg aag aag ggc tgc tgg cta gat gac ttc aac tgc tac gat agg cag     192
```

```
Val Lys Lys Gly Cys Trp Leu Asp Asp Phe Asn Cys Tyr Asp Arg Gln
    50                  55                  60 gag tgt gtg gcc act gag gag aac ccc cag gtg tac ttc tgc tgc tgt      240
Glu Cys Val Ala Thr Glu Glu Asn Pro Gln Val Tyr Phe Cys Cys Cys
65                  70                  75                  80 gag ggc aac ttc tgc aac gag cgc ttc act cat ttg cca gag gct ggg      288
Glu Gly Asn Phe Cys Asn Glu Arg Phe Thr His Leu Pro Glu Ala Gly
                85                  90                  95 ggc ccg gaa gtc acg tac gag cca ccc ccg aca gcc ccc acc gga gga      336
Gly Pro Glu Val Thr Tyr Glu Pro Pro Pro Thr Ala Pro Thr Gly Gly
            100                 105                 110 gga gga tct gtc gag tgc cca ccg tgc cca gca cca cct gtg gca gga      384
Gly Gly Ser Val Glu Cys Pro Pro Cys Pro Ala Pro Pro Val Ala Gly
        115                 120                 125 ccg tca gtc ttc ctc ttc ccc cca aaa ccc aag gac acc ctc atg atc      432
Pro Ser Val Phe Leu Phe Pro Pro Lys Pro Lys Asp Thr Leu Met Ile
    130                 135                 140 tcc cgg acc cct gag gtc acg tgc gtg gtg gtg gac gtg agc cac gaa      480
Ser Arg Thr Pro Glu Val Thr Cys Val Val Val Asp Val Ser His Glu
145                 150                 155                 160 gac ccc gag gtc cag ttc aac tgg tac gtg gac ggc gtg gag gtg cat      528
Asp Pro Glu Val Gln Phe Asn Trp Tyr Val Asp Gly Val Glu Val His
                165                 170                 175 aat gcc aag aca aag cca cgg gag gag cag ttc aac agc acg ttc cgt      576
Asn Ala Lys Thr Lys Pro Arg Glu Glu Gln Phe Asn Ser Thr Phe Arg
            180                 185                 190 gtg gtc agc gtc ctc acc gtt gtg cac cag gac tgg ctg aac ggc aag      624
Val Val Ser Val Leu Thr Val Val His Gln Asp Trp Leu Asn Gly Lys
        195                 200                 205 gag tac aag tgc aag gtc tcc aac aaa ggc ctc cca gcc ccc atc gag      672
Glu Tyr Lys Cys Lys Val Ser Asn Lys Gly Leu Pro Ala Pro Ile Glu
    210                 215                 220 aaa acc atc tcc aaa acc aaa ggg cag ccc cga gaa cca cag gtg tac      720
Lys Thr Ile Ser Lys Thr Lys Gly Gln Pro Arg Glu Pro Gln Val Tyr
225                 230                 235                 240 acc ctg ccc cca tcc cgg gag gag atg acc aag aac cag gtc agc ctg      768
Thr Leu Pro Pro Ser Arg Glu Glu Met Thr Lys Asn Gln Val Ser Leu
                245                 250                 255 acc tgc ctg gtc aaa ggc ttc tat ccc agc gac atc gcc gtg gag tgg      816
Thr Cys Leu Val Lys Gly Phe Tyr Pro Ser Asp Ile Ala Val Glu Trp
            260                 265                 270 gag agc aat ggg cag ccg gag aac aac tac aag acc aca cct ccc atg      864
Glu Ser Asn Gly Gln Pro Glu Asn Asn Tyr Lys Thr Thr Pro Pro Met
        275                 280                 285 ctg gac tcc gac ggc tcc ttc ttc ctc tac agc aag ctc acc gtg gac      912
Leu Asp Ser Asp Gly Ser Phe Phe Leu Tyr Ser Lys Leu Thr Val Asp
    290                 295                 300 aag agc agg tgg cag cag ggg aac gtc ttc tca tgc tcc gtg atg cat      960
Lys Ser Arg Trp Gln Gln Gly Asn Val Phe Ser Cys Ser Val Met His
305                 310                 315                 320 gag gct ctg cac aac cac tac acg cag aag agc ctc tcc ctg tct ccg     1008
Glu Ala Leu His Asn His Tyr Thr Gln Lys Ser Leu Ser Leu Ser Pro
                325                 330                 335 ggt aaa                                                              1014
Gly Lys <210> SEQ ID NO 91
<211> LENGTH: 338
<212> TYPE: PRT
<213> ORGANISM: Homo sapiens
```

<400> SEQUENCE: 91

```
Glu Thr Arg Trp Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr Ala Pro Thr Gly Gly
            100                 105                 110

Gly Gly Ser Val Glu Cys Pro Pro Cys Pro Ala Pro Val Ala Gly
        115                 120                 125

Pro Ser Val Phe Leu Phe Pro Pro Lys Pro Lys Asp Thr Leu Met Ile
    130                 135                 140

Ser Arg Thr Pro Glu Val Thr Cys Val Val Val Asp Val Ser His Glu
145                 150                 155                 160

Asp Pro Glu Val Gln Phe Asn Trp Tyr Val Asp Gly Val Glu Val His
                165                 170                 175

Asn Ala Lys Thr Lys Pro Arg Glu Glu Gln Phe Asn Ser Thr Phe Arg
            180                 185                 190

Val Val Ser Val Leu Thr Val Val His Gln Asp Trp Leu Asn Gly Lys
        195                 200                 205

Glu Tyr Lys Cys Lys Val Ser Asn Lys Gly Leu Pro Ala Pro Ile Glu
    210                 215                 220

Lys Thr Ile Ser Lys Thr Lys Gly Gln Pro Arg Glu Pro Gln Val Tyr
225                 230                 235                 240

Thr Leu Pro Pro Ser Arg Glu Glu Met Thr Lys Asn Gln Val Ser Leu
                245                 250                 255

Thr Cys Leu Val Lys Gly Phe Tyr Pro Ser Asp Ile Ala Val Glu Trp
            260                 265                 270

Glu Ser Asn Gly Gln Pro Glu Asn Asn Tyr Lys Thr Thr Pro Pro Met
        275                 280                 285

Leu Asp Ser Asp Gly Ser Phe Phe Leu Tyr Ser Lys Leu Thr Val Asp
    290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335

Gly Lys
```

<210> SEQ ID NO 92
<211> LENGTH: 1014
<212> TYPE: DNA
<213> ORGANISM: Homo sapiens
<220> FEATURE:
<221> NAME/KEY: CDS
<222> LOCATION: (1)..(1014)

<400> SEQUENCE: 92

```
gag aca cgg tgg tgc atc tac tac aac gcc aac tgg gag ctg gag cgc     48
Glu Thr Arg Trp Cys Ile Tyr Tyr Asn Ala Asn Trp Glu Leu Glu Arg
1               5                   10                  15 acc aac cag agc ggc ctg gag cgc tgc gaa ggc gag cag gac aag cgg     96
Thr Asn Gln Ser Gly Leu Glu Arg Cys Glu Gly Glu Gln Asp Lys Arg
            20                  25                  30 ctg cac tgc tac gcc tcc tgg cgc aac agc tct ggc acc atc gag ctc    144
Leu His Cys Tyr Ala Ser Trp Arg Asn Ser Ser Gly Thr Ile Glu Leu
        35                  40                  45 gtg aag aag ggc tgc tgg cta gat gac ttc aac tgc tac gat agg cag    192
Val Lys Lys Gly Cys Trp Leu Asp Asp Phe Asn Cys Tyr Asp Arg Gln
50                  55                  60 gag tgt gtg gcc act gag gag aac ccc cag gtg tac ttc tgc tgc tgt    240
Glu Cys Val Ala Thr Glu Glu Asn Pro Gln Val Tyr Phe Cys Cys Cys
65                  70                  75                  80 gag ggc aac ttc tgc aac gag cgc ttc act cat ttg cca gag gct ggg    288
Glu Gly Asn Phe Cys Asn Glu Arg Phe Thr His Leu Pro Glu Ala Gly
            85                  90                  95 ggc ccg gaa gtc acg tac gag cca ccc ccg aca gcc ccc acc gga gga    336
Gly Pro Glu Val Thr Tyr Glu Pro Pro Pro Thr Ala Pro Thr Gly Gly
        100                 105                 110 gga gga tct gtc gag tgc cca ccg tgc cca gca cca cct gtg gca gga    384
Gly Gly Ser Val Glu Cys Pro Pro Cys Pro Ala Pro Pro Val Ala Gly
                115                 120                 125 ccg tca gtc ttc ctc ttc ccc cca aaa ccc aag gac acc ctc atg atc    432
Pro Ser Val Phe Leu Phe Pro Pro Lys Pro Lys Asp Thr Leu Met Ile
130                 135                 140 tcc cgg acc cct gag gtc acg tgc gtg gtg gtg gac gtg agc cac gaa    480
Ser Arg Thr Pro Glu Val Thr Cys Val Val Val Asp Val Ser His Glu
145                 150                 155                 160 gac ccc gag gtc cag ttc aac tgg tac gtg gac ggc gtg gag gtg cat    528
Asp Pro Glu Val Gln Phe Asn Trp Tyr Val Asp Gly Val Glu Val His
            165                 170                 175 aat gcc aag aca aag cca cgg gag gag cag ttc aac agc acg ttc cgt    576
Asn Ala Lys Thr Lys Pro Arg Glu Glu Gln Phe Asn Ser Thr Phe Arg
        180                 185                 190 gtg gtc agc gtc ctc acc gtt gtg cac cag gac tgg ctg aac ggc aag    624
Val Val Ser Val Leu Thr Val Val His Gln Asp Trp Leu Asn Gly Lys
                195                 200                 205 gag tac aag tgc aag gtc tcc aac aaa ggc ctc cca gcc ccc atc gag    672
Glu Tyr Lys Cys Lys Val Ser Asn Lys Gly Leu Pro Ala Pro Ile Glu
210                 215                 220 aaa acc atc tcc aaa acc aaa ggg cag ccc cga gaa cca cag gtg tac    720
Lys Thr Ile Ser Lys Thr Lys Gly Gln Pro Arg Glu Pro Gln Val Tyr
225                 230                 235                 240 acc ctg ccc cca tcc cgg gag gag atg acc aag aac cag gtc agc ctg    768
Thr Leu Pro Pro Ser Arg Glu Glu Met Thr Lys Asn Gln Val Ser Leu
            245                 250                 255 acc tgc ctg gtc aaa ggc ttc tat ccc agc gac atc gcc gtg gag tgg    816
Thr Cys Leu Val Lys Gly Phe Tyr Pro Ser Asp Ile Ala Val Glu Trp
        260                 265                 270 gag agc aat ggg cag ccg gag aac aac tac aag acc aca cct ccc atg    864
Glu Ser Asn Gly Gln Pro Glu Asn Asn Tyr Lys Thr Thr Pro Pro Met
                275                 280                 285 ctg gac tcc gac ggc tcc ttc ttc ctc tac agc aag ctc acc gtg gac    912
Leu Asp Ser Asp Gly Ser Phe Phe Leu Tyr Ser Lys Leu Thr Val Asp
290                 295                 300 aag agc agg tgg cag cag ggg aac gtc ttc tca tgc tcc gtg atg cat    960
Lys Ser Arg Trp Gln Gln Gly Asn Val Phe Ser Cys Ser Val Met His
305                 310                 315                 320
```

```
gag gct ctg cac aac cac tac acg cag aag agc ctc tcc ctg tct ccg      1008
Glu Ala Leu His Asn His Tyr Thr Gln Lys Ser Leu Ser Leu Ser Pro
            325                 330                 335 ggt aaa                                                               1014
Gly Lys
```

<210> SEQ ID NO 93
<211> LENGTH: 338
<212> TYPE: PRT
<213> ORGANISM: Homo sapiens

<400> SEQUENCE: 93

```
Glu Thr Arg Tyr Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr Ala Pro Thr Gly Gly
            100                 105                 110

Gly Gly Ser Val Glu Cys Pro Pro Cys Pro Ala Pro Pro Val Ala Gly
        115                 120                 125

Pro Ser Val Phe Leu Phe Pro Pro Lys Pro Lys Asp Thr Leu Met Ile
    130                 135                 140

Ser Arg Thr Pro Glu Val Thr Cys Val Val Val Asp Val Ser His Glu
145                 150                 155                 160

Asp Pro Glu Val Gln Phe Asn Trp Tyr Val Asp Gly Val Glu Val His
                165                 170                 175

Asn Ala Lys Thr Lys Pro Arg Glu Glu Gln Phe Asn Ser Thr Phe Arg
            180                 185                 190

Val Val Ser Val Leu Thr Val Val His Gln Asp Trp Leu Asn Gly Lys
        195                 200                 205

Glu Tyr Lys Cys Lys Val Ser Asn Lys Gly Leu Pro Ala Pro Ile Glu
    210                 215                 220

Lys Thr Ile Ser Lys Thr Lys Gly Gln Pro Arg Glu Pro Gln Val Tyr
225                 230                 235                 240

Thr Leu Pro Pro Ser Arg Glu Glu Met Thr Lys Asn Gln Val Ser Leu
                245                 250                 255

Thr Cys Leu Val Lys Gly Phe Tyr Pro Ser Asp Ile Ala Val Glu Trp
            260                 265                 270

Glu Ser Asn Gly Gln Pro Glu Asn Asn Tyr Lys Thr Thr Pro Pro Met
        275                 280                 285

Leu Asp Ser Asp Gly Ser Phe Phe Leu Tyr Ser Lys Leu Thr Val Asp
    290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335
```

Gly Lys

<210> SEQ ID NO 94
<211> LENGTH: 1014
<212> TYPE: DNA
<213> ORGANISM: Homo sapiens
<220> FEATURE:
<221> NAME/KEY: CDS
<222> LOCATION: (1)..(1014)

<400> SEQUENCE: 94

| | | | | | | | | | | | | | | | | |
|---|---|---|---|---|---|---|---|---|---|---|---|---|---|---|---|---|
| gag | aca | cgg | tac | tgc | atc | tac | tac | aac | gcc | aac | tgg | gag | ctg | gag | cgc | 48 |
| Glu | Thr | Arg | Tyr | Cys | Ile | Tyr | Tyr | Asn | Ala | Asn | Trp | Glu | Leu | Glu | Arg | |
| 1 | | | | 5 | | | | | 10 | | | | | 15 | | |
| acc | aac | cag | agc | ggc | ctg | gag | cgc | tgc | gaa | ggc | gag | cag | gac | aag | cgg | 96 |
| Thr | Asn | Gln | Ser | Gly | Leu | Glu | Arg | Cys | Glu | Gly | Glu | Gln | Asp | Lys | Arg | |
| | | | 20 | | | | | 25 | | | | | 30 | | | |
| ctg | cac | tgc | tac | gcc | tcc | tgg | cgc | aac | agc | tct | ggc | acc | atc | gag | ctc | 144 |
| Leu | His | Cys | Tyr | Ala | Ser | Trp | Arg | Asn | Ser | Ser | Gly | Thr | Ile | Glu | Leu | |
| | | 35 | | | | | 40 | | | | | 45 | | | | |
| gtg | aag | aag | ggc | tgc | tgg | cta | gat | gac | ttc | aac | tgc | tac | gat | agg | cag | 192 |
| Val | Lys | Lys | Gly | Cys | Trp | Leu | Asp | Asp | Phe | Asn | Cys | Tyr | Asp | Arg | Gln | |
| 50 | | | | | 55 | | | | | 60 | | | | | | |
| gag | tgt | gtg | gcc | act | gag | gag | aac | ccc | cag | gtg | tac | ttc | tgc | tgc | tgt | 240 |
| Glu | Cys | Val | Ala | Thr | Glu | Glu | Asn | Pro | Gln | Val | Tyr | Phe | Cys | Cys | Cys | |
| 65 | | | | | 70 | | | | | 75 | | | | | 80 | |
| gag | ggc | aac | ttc | tgc | aac | gag | cgc | ttc | act | cat | ttg | cca | gag | gct | ggg | 288 |
| Glu | Gly | Asn | Phe | Cys | Asn | Glu | Arg | Phe | Thr | His | Leu | Pro | Glu | Ala | Gly | |
| | | | | 85 | | | | | 90 | | | | | 95 | | |
| ggc | ccg | gaa | gtc | acg | tac | gag | cca | ccc | ccg | aca | gcc | ccc | acc | gga | gga | 336 |
| Gly | Pro | Glu | Val | Thr | Tyr | Glu | Pro | Pro | Pro | Thr | Ala | Pro | Thr | Gly | Gly | |
| | | | 100 | | | | | 105 | | | | | 110 | | | |
| gga | gga | tct | gtc | gag | tgc | cca | ccg | tgc | cca | gca | cca | cct | gtg | gca | gga | 384 |
| Gly | Gly | Ser | Val | Glu | Cys | Pro | Pro | Cys | Pro | Ala | Pro | Pro | Val | Ala | Gly | |
| | | | 115 | | | | | 120 | | | | | 125 | | | |
| ccg | tca | gtc | ttc | ctc | ttc | ccc | cca | aaa | ccc | aag | gac | acc | ctc | atg | atc | 432 |
| Pro | Ser | Val | Phe | Leu | Phe | Pro | Pro | Lys | Pro | Lys | Asp | Thr | Leu | Met | Ile | |
| | | 130 | | | | | 135 | | | | | 140 | | | | |
| tcc | cgg | acc | cct | gag | gtc | acg | tgc | gtg | gtg | gtg | gac | gtg | agc | cac | gaa | 480 |
| Ser | Arg | Thr | Pro | Glu | Val | Thr | Cys | Val | Val | Val | Asp | Val | Ser | His | Glu | |
| 145 | | | | | 150 | | | | | 155 | | | | | 160 | |
| gac | ccc | gag | gtc | cag | ttc | aac | tgg | tac | gtg | gac | ggc | gtg | gag | gtg | cat | 528 |
| Asp | Pro | Glu | Val | Gln | Phe | Asn | Trp | Tyr | Val | Asp | Gly | Val | Glu | Val | His | |
| | | | | 165 | | | | | 170 | | | | | 175 | | |
| aat | gcc | aag | aca | aag | cca | cgg | gag | gag | cag | ttc | aac | agc | acg | ttc | cgt | 576 |
| Asn | Ala | Lys | Thr | Lys | Pro | Arg | Glu | Glu | Gln | Phe | Asn | Ser | Thr | Phe | Arg | |
| | | | 180 | | | | | 185 | | | | | 190 | | | |
| gtg | gtc | agc | gtc | ctc | acc | gtt | gtg | cac | cag | gac | tgg | ctg | aac | ggc | aag | 624 |
| Val | Val | Ser | Val | Leu | Thr | Val | Val | His | Gln | Asp | Trp | Leu | Asn | Gly | Lys | |
| | | | | 195 | | | | | 200 | | | | | 205 | | |
| gag | tac | aag | tgc | aag | gtc | tcc | aac | aaa | ggc | ctc | cca | gcc | ccc | atc | gag | 672 |
| Glu | Tyr | Lys | Cys | Lys | Val | Ser | Asn | Lys | Gly | Leu | Pro | Ala | Pro | Ile | Glu | |
| | | 210 | | | | | 215 | | | | | 220 | | | | |
| aaa | acc | atc | tcc | aaa | acc | aaa | ggg | cag | ccc | cga | gaa | cca | cag | gtg | tac | 720 |
| Lys | Thr | Ile | Ser | Lys | Thr | Lys | Gly | Gln | Pro | Arg | Glu | Pro | Gln | Val | Tyr | |
| 225 | | | | | 230 | | | | | 235 | | | | | 240 | |
| acc | ctg | ccc | cca | tcc | cgg | gag | gag | atg | acc | aag | aac | cag | gtc | agc | ctg | 768 |
| Thr | Leu | Pro | Pro | Ser | Arg | Glu | Glu | Met | Thr | Lys | Asn | Gln | Val | Ser | Leu | |
| | | | | 245 | | | | | 250 | | | | | 255 | | |
| acc | tgc | ctg | gtc | aaa | ggc | ttc | tat | ccc | agc | gac | atc | gcc | gtg | gag | tgg | 816 |
| Thr | Cys | Leu | Val | Lys | Gly | Phe | Tyr | Pro | Ser | Asp | Ile | Ala | Val | Glu | Trp | |

```
                   260                 265                 270
gag agc aat ggg cag ccg gag aac aac tac aag acc aca cct ccc atg       864
Glu Ser Asn Gly Gln Pro Glu Asn Asn Tyr Lys Thr Thr Pro Pro Met
            275                 280                 285 ctg gac tcc gac ggc tcc ttc ttc ctc tac agc aag ctc acc gtg gac       912
Leu Asp Ser Asp Gly Ser Phe Phe Leu Tyr Ser Lys Leu Thr Val Asp
        290                 295                 300 aag agc agg tgg cag cag ggg aac gtc ttc tca tgc tcc gtg atg cat       960
Lys Ser Arg Trp Gln Gln Gly Asn Val Phe Ser Cys Ser Val Met His
305                 310                 315                 320 gag gct ctg cac aac cac tac acg cag aag agc ctc tcc ctg tct ccg      1008
Glu Ala Leu His Asn His Tyr Thr Gln Lys Ser Leu Ser Leu Ser Pro
                325                 330                 335 ggt aaa                                                               1014
Gly Lys
```

<210> SEQ ID NO 95
<211> LENGTH: 338
<212> TYPE: PRT
<213> ORGANISM: Homo sapiens

<400> SEQUENCE: 95

```
Glu Thr Arg Ala Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr Gly Gly
            100                 105                 110

Gly Gly Ser Val Glu Cys Pro Pro Cys Pro Ala Pro Pro Val Ala Gly
        115                 120                 125

Pro Ser Val Phe Leu Phe Pro Pro Lys Pro Lys Asp Thr Leu Met Ile
    130                 135                 140

Ser Arg Thr Pro Glu Val Thr Cys Val Val Val Asp Val Ser His Glu
145                 150                 155                 160

Asp Pro Glu Val Gln Phe Asn Trp Tyr Val Asp Gly Val Glu Val His
                165                 170                 175

Asn Ala Lys Thr Lys Pro Arg Glu Glu Gln Phe Asn Ser Thr Phe Arg
            180                 185                 190

Val Val Ser Val Leu Thr Val Val His Gln Asp Trp Leu Asn Gly Lys
        195                 200                 205

Glu Tyr Lys Cys Lys Val Ser Asn Lys Gly Leu Pro Ala Pro Ile Glu
    210                 215                 220

Lys Thr Ile Ser Lys Thr Lys Gly Gln Pro Arg Glu Pro Gln Val Tyr
225                 230                 235                 240

Thr Leu Pro Pro Ser Arg Glu Glu Met Thr Lys Asn Gln Val Ser Leu
                245                 250                 255

Thr Cys Leu Val Lys Gly Phe Tyr Pro Ser Asp Ile Ala Val Glu Trp
            260                 265                 270
```

-continued

```
Glu Ser Asn Gly Gln Pro Glu Asn Asn Tyr Lys Thr Thr Pro Pro Met
        275                 280                 285
Leu Asp Ser Asp Gly Ser Phe Phe Leu Tyr Ser Lys Leu Thr Val Asp
        290                 295                 300
Lys Ser Arg Trp Gln Gln Gly Asn Val Phe Ser Cys Ser Val Met His
305                 310                 315                 320
Glu Ala Leu His Asn His Tyr Thr Gln Lys Ser Leu Ser Leu Ser Pro
                325                 330                 335
Gly Lys

<210> SEQ ID NO 96
<211> LENGTH: 1014
<212> TYPE: DNA
<213> ORGANISM: Homo sapiens
<220> FEATURE:
<221> NAME/KEY: CDS
<222> LOCATION: (1)..(1014)
<220> FEATURE:
<221> NAME/KEY: modified_base
<222> LOCATION: (6)..(9)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (42)..(42)
<223> OTHER INFORMATION: a, c, t, g, unknown or other
<220> FEATURE:
<221> NAME/KEY: modified_base
<222> LOCATION: (46)..(48)
<223> OTHER INFORMATION: a, c, t, g, unknown or other
<220> FEATURE:
<221> NAME/KEY: modified_base
<222> LOCATION: (51)..(51)
<223> OTHER INFORMATION: a, c, t, g, unknown or other
<220> FEATURE:
<221> NAME/KEY: modified_base
<222> LOCATION: (58)..(60)
<223> OTHER INFORMATION: a, c, t, g, unknown or other
<220> FEATURE:
<221> NAME/KEY: modified_base
<222> LOCATION: (63)..(63)
<223> OTHER INFORMATION: a, c, t, g, unknown or other
<220> FEATURE:
<221> NAME/KEY: modified_base
<222> LOCATION: (66)..(66)
<223> OTHER INFORMATION: a, c, t, g, unknown or other
<220> FEATURE:
<221> NAME/KEY: modified_base
<222> LOCATION: (70)..(72)
<223> OTHER INFORMATION: a, c, t, g, unknown or other
<220> FEATURE:
<221> NAME/KEY: modified_base
<222> LOCATION: (81)..(81)
<223> OTHER INFORMATION: a, c, t, g, unknown or other
<220> FEATURE:
<221> NAME/KEY: modified_base
<222> LOCATION: (94)..(96)
<223> OTHER INFORMATION: a, c, t, g, unknown or other
<220> FEATURE:
<221> NAME/KEY: modified_base
<222> LOCATION: (99)..(99)
<223> OTHER INFORMATION: a, c, t, g, unknown or other
<220> FEATURE:
<221> NAME/KEY: modified_base
<222> LOCATION: (111)..(114)
<223> OTHER INFORMATION: a, c, t, g, unknown or other
```

-continued

```
<220> FEATURE:
<221> NAME/KEY: modified_base
<222> LOCATION: (118)..(120)
<223> OTHER INFORMATION: a, c, t, g, unknown or other
<220> FEATURE:
<221> NAME/KEY: modified_base
<222> LOCATION: (124)..(129)
<223> OTHER INFORMATION: a, c, t, g, unknown or other
<220> FEATURE:
<221> NAME/KEY: modified_base
<222> LOCATION: (132)..(132)
<223> OTHER INFORMATION: a, c, t, g, unknown or other
<220> FEATURE:
<221> NAME/KEY: modified_base
<222> LOCATION: (135)..(135)
<223> OTHER INFORMATION: a, c, t, g, unknown or other
<220> FEATURE:
<221> NAME/KEY: modified_base
<222> LOCATION: (144)..(144)
<223> OTHER INFORMATION: a, c, t, g, unknown or other
<220> FEATURE:
<221> NAME/KEY: modified_base
<222> LOCATION: (147)..(147)
<223> OTHER INFORMATION: a, c, t, g, unknown or other
<220> FEATURE:
<221> NAME/KEY: modified_base
<222> LOCATION: (156)..(156)
<223> OTHER INFORMATION: a, c, t, g, unknown or other
<220> FEATURE:
<221> NAME/KEY: modified_base
<222> LOCATION: (165)..(165)
<223> OTHER INFORMATION: a, c, t, g, unknown or other
<220> FEATURE:
<221> NAME/KEY: modified_base
<222> LOCATION: (187)..(189)
<223> OTHER INFORMATION: a, c, t, g, unknown or other
<220> FEATURE:
<221> NAME/KEY: modified_base
<222> LOCATION: (201)..(201)
<223> OTHER INFORMATION: a, c, t, g, unknown or other
<220> FEATURE:
<221> NAME/KEY: modified_base
<222> LOCATION: (204)..(204)
<223> OTHER INFORMATION: a, c, t, g, unknown or other
<220> FEATURE:
<221> NAME/KEY: modified_base
<222> LOCATION: (207)..(207)
<223> OTHER INFORMATION: a, c, t, g, unknown or other
<220> FEATURE:
<221> NAME/KEY: modified_base
<222> LOCATION: (219)..(219)
<223> OTHER INFORMATION: a, c, t, g, unknown or other
<220> FEATURE:
<221> NAME/KEY: modified_base
<222> LOCATION: (225)..(225)
<223> OTHER INFORMATION: a, c, t, g, unknown or other
<220> FEATURE:
<221> NAME/KEY: modified_base
<222> LOCATION: (246)..(246)
<223> OTHER INFORMATION: a, c, t, g, unknown or other
<220> FEATURE:
<221> NAME/KEY: modified_base
<222> LOCATION: (262)..(264)
<223> OTHER INFORMATION: a, c, t, g, unknown or other
<220> FEATURE:
<221> NAME/KEY: modified_base
<222> LOCATION: (270)..(270)
<223> OTHER INFORMATION: a, c, t, g, unknown or other
<220> FEATURE:
<221> NAME/KEY: modified_base
<222> LOCATION: (276)..(276)
<223> OTHER INFORMATION: a, c, t, g, unknown or other
<220> FEATURE:
<221> NAME/KEY: modified_base
<222> LOCATION: (279)..(279)
<223> OTHER INFORMATION: a, c, t, g, unknown or other
<220> FEATURE:
<221> NAME/KEY: modified_base
<222> LOCATION: (285)..(285)
```

```
<223> OTHER INFORMATION: a, c, t, g, unknown or other
<220> FEATURE:
<221> NAME/KEY: modified_base
<222> LOCATION: (288)..(288)
<223> OTHER INFORMATION: a, c, t, g, unknown or other
<220> FEATURE:
<221> NAME/KEY: modified_base
<222> LOCATION: (291)..(291)
<223> OTHER INFORMATION: a, c, t, g, unknown or other
<220> FEATURE:
<221> NAME/KEY: modified_base
<222> LOCATION: (294)..(294)
<223> OTHER INFORMATION: a, c, t, g, unknown or other
<220> FEATURE:
<221> NAME/KEY: modified_base
<222> LOCATION: (300)..(300)
<223> OTHER INFORMATION: a, c, t, g, unknown or other
<220> FEATURE:
<221> NAME/KEY: modified_base
<222> LOCATION: (303)..(303)
<223> OTHER INFORMATION: a, c, t, g, unknown or other
<220> FEATURE:
<221> NAME/KEY: modified_base
<222> LOCATION: (312)..(312)
<223> OTHER INFORMATION: a, c, t, g, unknown or other
<220> FEATURE:
<221> NAME/KEY: modified_base
<222> LOCATION: (315)..(315)
<223> OTHER INFORMATION: a, c, t, g, unknown or other
<220> FEATURE:
<221> NAME/KEY: modified_base
<222> LOCATION: (318)..(318)
<223> OTHER INFORMATION: a, c, t, g, unknown or other
<220> FEATURE:
<221> NAME/KEY: modified_base
<222> LOCATION: (321)..(321)
<223> OTHER INFORMATION: a, c, t, g, unknown or other
<220> FEATURE:
<221> NAME/KEY: modified_base
<222> LOCATION: (324)..(324)
<223> OTHER INFORMATION: a, c, t, g, unknown or other
<220> FEATURE:
<221> NAME/KEY: modified_base
<222> LOCATION: (327)..(327)
<223> OTHER INFORMATION: a, c, t, g, unknown or other
<220> FEATURE:
<221> NAME/KEY: modified_base
<222> LOCATION: (330)..(330)
<223> OTHER INFORMATION: a, c, t, g, unknown or other
<220> FEATURE:
<221> NAME/KEY: modified_base
<222> LOCATION: (333)..(333)
<223> OTHER INFORMATION: a, c, t, g, unknown or other
<220> FEATURE:
<221> NAME/KEY: modified_base
<222> LOCATION: (336)..(336)
<223> OTHER INFORMATION: a, c, t, g, unknown or other
<220> FEATURE:
<221> NAME/KEY: modified_base
<222> LOCATION: (339)..(339)
<223> OTHER INFORMATION: a, c, t, g, unknown or other
<220> FEATURE:
<221> NAME/KEY: modified_base
<222> LOCATION: (342)..(345)
<223> OTHER INFORMATION: a, c, t, g, unknown or other
<220> FEATURE:
<221> NAME/KEY: modified_base
<222> LOCATION: (348)..(348)
<223> OTHER INFORMATION: a, c, t, g, unknown or other
<220> FEATURE:
<221> NAME/KEY: modified_base
<222> LOCATION: (357)..(357)
<223> OTHER INFORMATION: a, c, t, g, unknown or other
<220> FEATURE:
<221> NAME/KEY: modified_base
<222> LOCATION: (360)..(360)
<223> OTHER INFORMATION: a, c, t, g, unknown or other
<220> FEATURE:
<221> NAME/KEY: modified_base
```

-continued

```
<222> LOCATION: (366)..(366)
<223> OTHER INFORMATION: a, c, t, g, unknown or other
<220> FEATURE:
<221> NAME/KEY: modified_base
<222> LOCATION: (369)..(369)
<223> OTHER INFORMATION: a, c, t, g, unknown or other
<220> FEATURE:
<221> NAME/KEY: modified_base
<222> LOCATION: (372)..(372)
<223> OTHER INFORMATION: a, c, t, g, unknown or other
<220> FEATURE:
<221> NAME/KEY: modified_base
<222> LOCATION: (375)..(375)
<223> OTHER INFORMATION: a, c, t, g, unknown or other
<220> FEATURE:
<221> NAME/KEY: modified_base
<222> LOCATION: (378)..(378)
<223> OTHER INFORMATION: a, c, t, g, unknown or other
<220> FEATURE:
<221> NAME/KEY: modified_base
<222> LOCATION: (381)..(381)
<223> OTHER INFORMATION: a, c, t, g, unknown or other
<220> FEATURE:
<221> NAME/KEY: modified_base
<222> LOCATION: (384)..(384)
<223> OTHER INFORMATION: a, c, t, g, unknown or other
<220> FEATURE:
<221> NAME/KEY: modified_base
<222> LOCATION: (387)..(390)
<223> OTHER INFORMATION: a, c, t, g, unknown or other
<220> FEATURE:
<221> NAME/KEY: modified_base
<222> LOCATION: (393)..(393)
<223> OTHER INFORMATION: a, c, t, g, unknown or other
<220> FEATURE:
<221> NAME/KEY: modified_base
<222> LOCATION: (399)..(399)
<223> OTHER INFORMATION: a, c, t, g, unknown or other
<220> FEATURE:
<221> NAME/KEY: modified_base
<222> LOCATION: (405)..(405)
<223> OTHER INFORMATION: a, c, t, g, unknown or other
<220> FEATURE:
<221> NAME/KEY: modified_base
<222> LOCATION: (408)..(408)
<223> OTHER INFORMATION: a, c, t, g, unknown or other
<220> FEATURE:
<221> NAME/KEY: modified_base
<222> LOCATION: (414)..(414)
<223> OTHER INFORMATION: a, c, t, g, unknown or other
<220> FEATURE:
<221> NAME/KEY: modified_base
<222> LOCATION: (423)..(423)
<223> OTHER INFORMATION: a, c, t, g, unknown or other
<220> FEATURE:
<221> NAME/KEY: modified_base
<222> LOCATION: (426)..(426)
<223> OTHER INFORMATION: a, c, t, g, unknown or other
<220> FEATURE:
<221> NAME/KEY: modified_base
<222> LOCATION: (433)..(438)
<223> OTHER INFORMATION: a, c, t, g, unknown or other
<220> FEATURE:
<221> NAME/KEY: modified_base
<222> LOCATION: (441)..(441)
<223> OTHER INFORMATION: a, c, t, g, unknown or other
<220> FEATURE:
<221> NAME/KEY: modified_base
<222> LOCATION: (444)..(444)
<223> OTHER INFORMATION: a, c, t, g, unknown or other
<220> FEATURE:
<221> NAME/KEY: modified_base
<222> LOCATION: (450)..(450)
<223> OTHER INFORMATION: a, c, t, g, unknown or other
<220> FEATURE:
<221> NAME/KEY: modified_base
<222> LOCATION: (453)..(453)
<223> OTHER INFORMATION: a, c, t, g, unknown or other
<220> FEATURE:
```

-continued

```
<221> NAME/KEY: modified_base
<222> LOCATION: (459)..(459)
<223> OTHER INFORMATION: a, c, t, g, unknown or other
<220> FEATURE:
<221> NAME/KEY: modified_base
<222> LOCATION: (462)..(462)
<223> OTHER INFORMATION: a, c, t, g, unknown or other
<220> FEATURE:
<221> NAME/KEY: modified_base
<222> LOCATION: (465)..(465)
<223> OTHER INFORMATION: a, c, t, g, unknown or other
<220> FEATURE:
<221> NAME/KEY: modified_base
<222> LOCATION: (471)..(474)
<223> OTHER INFORMATION: a, c, t, g, unknown or other
<220> FEATURE:
<221> NAME/KEY: modified_base
<222> LOCATION: (486)..(486)
<223> OTHER INFORMATION: a, c, t, g, unknown or other
<220> FEATURE:
<221> NAME/KEY: modified_base
<222> LOCATION: (492)..(492)
<223> OTHER INFORMATION: a, c, t, g, unknown or other
<220> FEATURE:
<221> NAME/KEY: modified_base
<222> LOCATION: (510)..(510)
<223> OTHER INFORMATION: a, c, t, g, unknown or other
<220> FEATURE:
<221> NAME/KEY: modified_base
<222> LOCATION: (516)..(516)
<223> OTHER INFORMATION: a, c, t, g, unknown or other
<220> FEATURE:
<221> NAME/KEY: modified_base
<222> LOCATION: (519)..(519)
<223> OTHER INFORMATION: a, c, t, g, unknown or other
<220> FEATURE:
<221> NAME/KEY: modified_base
<222> LOCATION: (525)..(525)
<223> OTHER INFORMATION: a, c, t, g, unknown or other
<220> FEATURE:
<221> NAME/KEY: modified_base
<222> LOCATION: (534)..(534)
<223> OTHER INFORMATION: a, c, t, g, unknown or other
<220> FEATURE:
<221> NAME/KEY: modified_base
<222> LOCATION: (540)..(540)
<223> OTHER INFORMATION: a, c, t, g, unknown or other
<220> FEATURE:
<221> NAME/KEY: modified_base
<222> LOCATION: (546)..(549)
<223> OTHER INFORMATION: a, c, t, g, unknown or other
<220> FEATURE:
<221> NAME/KEY: modified_base
<222> LOCATION: (565)..(567)
<223> OTHER INFORMATION: a, c, t, g, unknown or other
<220> FEATURE:
<221> NAME/KEY: modified_base
<222> LOCATION: (570)..(570)
<223> OTHER INFORMATION: a, c, t, g, unknown or other
<220> FEATURE:
<221> NAME/KEY: modified_base
<222> LOCATION: (574)..(576)
<223> OTHER INFORMATION: a, c, t, g, unknown or other
<220> FEATURE:
<221> NAME/KEY: modified_base
<222> LOCATION: (579)..(579)
<223> OTHER INFORMATION: a, c, t, g, unknown or other
<220> FEATURE:
<221> NAME/KEY: modified_base
<222> LOCATION: (582)..(585)
<223> OTHER INFORMATION: a, c, t, g, unknown or other
<220> FEATURE:
<221> NAME/KEY: modified_base
<222> LOCATION: (588)..(588)
<223> OTHER INFORMATION: a, c, t, g, unknown or other
<220> FEATURE:
<221> NAME/KEY: modified_base
<222> LOCATION: (591)..(591)
<223> OTHER INFORMATION: a, c, t, g, unknown or other
```

```
<220> FEATURE:
<221> NAME/KEY: modified_base
<222> LOCATION: (594)..(594)
<223> OTHER INFORMATION: a, c, t, g, unknown or other
<220> FEATURE:
<221> NAME/KEY: modified_base
<222> LOCATION: (597)..(597)
<223> OTHER INFORMATION: a, c, t, g, unknown or other
<220> FEATURE:
<221> NAME/KEY: modified_base
<222> LOCATION: (600)..(600)
<223> OTHER INFORMATION: a, c, t, g, unknown or other
<220> FEATURE:
<221> NAME/KEY: modified_base
<222> LOCATION: (615)..(615)
<223> OTHER INFORMATION: a, c, t, g, unknown or other
<220> FEATURE:
<221> NAME/KEY: modified_base
<222> LOCATION: (621)..(621)
<223> OTHER INFORMATION: a, c, t, g, unknown or other
<220> FEATURE:
<221> NAME/KEY: modified_base
<222> LOCATION: (642)..(645)
<223> OTHER INFORMATION: a, c, t, g, unknown or other
<220> FEATURE:
<221> NAME/KEY: modified_base
<222> LOCATION: (654)..(654)
<223> OTHER INFORMATION: a, c, t, g, unknown or other
<220> FEATURE:
<221> NAME/KEY: modified_base
<222> LOCATION: (657)..(657)
<223> OTHER INFORMATION: a, c, t, g, unknown or other
<220> FEATURE:
<221> NAME/KEY: modified_base
<222> LOCATION: (660)..(660)
<223> OTHER INFORMATION: a, c, t, g, unknown or other
<220> FEATURE:
<221> NAME/KEY: modified_base
<222> LOCATION: (663)..(663)
<223> OTHER INFORMATION: a, c, t, g, unknown or other
<220> FEATURE:
<221> NAME/KEY: modified_base
<222> LOCATION: (666)..(666)
<223> OTHER INFORMATION: a, c, t, g, unknown or other
<220> FEATURE:
<221> NAME/KEY: modified_base
<222> LOCATION: (678)..(678)
<223> OTHER INFORMATION: a, c, t, g, unknown or other
<220> FEATURE:
<221> NAME/KEY: modified_base
<222> LOCATION: (682)..(684)
<223> OTHER INFORMATION: a, c, t, g, unknown or other
<220> FEATURE:
<221> NAME/KEY: modified_base
<222> LOCATION: (690)..(690)
<223> OTHER INFORMATION: a, c, t, g, unknown or other
<220> FEATURE:
<221> NAME/KEY: modified_base
<222> LOCATION: (696)..(696)
<223> OTHER INFORMATION: a, c, t, g, unknown or other
<220> FEATURE:
<221> NAME/KEY: modified_base
<222> LOCATION: (702)..(705)
<223> OTHER INFORMATION: a, c, t, g, unknown or other
<220> FEATURE:
<221> NAME/KEY: modified_base
<222> LOCATION: (711)..(711)
<223> OTHER INFORMATION: a, c, t, g, unknown or other
<220> FEATURE:
<221> NAME/KEY: modified_base
<222> LOCATION: (717)..(717)
<223> OTHER INFORMATION: a, c, t, g, unknown or other
<220> FEATURE:
<221> NAME/KEY: modified_base
<222> LOCATION: (723)..(723)
<223> OTHER INFORMATION: a, c, t, g, unknown or other
<220> FEATURE:
<221> NAME/KEY: modified_base
<222> LOCATION: (726)..(726)
```

-continued

```
<223> OTHER INFORMATION: a, c, t, g, unknown or other
<220> FEATURE:
<221> NAME/KEY: modified_base
<222> LOCATION: (729)..(729)
<223> OTHER INFORMATION: a, c, t, g, unknown or other
<220> FEATURE:
<221> NAME/KEY: modified_base
<222> LOCATION: (732)..(738)
<223> OTHER INFORMATION: a, c, t, g, unknown or other
<220> FEATURE:
<221> NAME/KEY: modified_base
<222> LOCATION: (750)..(750)
<223> OTHER INFORMATION: a, c, t, g, unknown or other
<220> FEATURE:
<221> NAME/KEY: modified_base
<222> LOCATION: (762)..(765)
<223> OTHER INFORMATION: a, c, t, g, unknown or other
<220> FEATURE:
<221> NAME/KEY: modified_base
<222> LOCATION: (768)..(768)
<223> OTHER INFORMATION: a, c, t, g, unknown or other
<220> FEATURE:
<221> NAME/KEY: modified_base
<222> LOCATION: (771)..(771)
<223> OTHER INFORMATION: a, c, t, g, unknown or other
<220> FEATURE:
<221> NAME/KEY: modified_base
<222> LOCATION: (777)..(777)
<223> OTHER INFORMATION: a, c, t, g, unknown or other
<220> FEATURE:
<221> NAME/KEY: modified_base
<222> LOCATION: (780)..(780)
<223> OTHER INFORMATION: a, c, t, g, unknown or other
<220> FEATURE:
<221> NAME/KEY: modified_base
<222> LOCATION: (786)..(786)
<223> OTHER INFORMATION: a, c, t, g, unknown or other
<220> FEATURE:
<221> NAME/KEY: modified_base
<222> LOCATION: (795)..(798)
<223> OTHER INFORMATION: a, c, t, g, unknown or other
<220> FEATURE:
<221> NAME/KEY: modified_base
<222> LOCATION: (807)..(807)
<223> OTHER INFORMATION: a, c, t, g, unknown or other
<220> FEATURE:
<221> NAME/KEY: modified_base
<222> LOCATION: (810)..(810)
<223> OTHER INFORMATION: a, c, t, g, unknown or other
<220> FEATURE:
<221> NAME/KEY: modified_base
<222> LOCATION: (820)..(822)
<223> OTHER INFORMATION: a, c, t, g, unknown or other
<220> FEATURE:
<221> NAME/KEY: modified_base
<222> LOCATION: (828)..(828)
<223> OTHER INFORMATION: a, c, t, g, unknown or other
<220> FEATURE:
<221> NAME/KEY: modified_base
<222> LOCATION: (834)..(834)
<223> OTHER INFORMATION: a, c, t, g, unknown or other
<220> FEATURE:
<221> NAME/KEY: modified_base
<222> LOCATION: (852)..(852)
<223> OTHER INFORMATION: a, c, t, g, unknown or other
<220> FEATURE:
<221> NAME/KEY: modified_base
<222> LOCATION: (855)..(855)
<223> OTHER INFORMATION: a, c, t, g, unknown or other
<220> FEATURE:
<221> NAME/KEY: modified_base
<222> LOCATION: (858)..(858)
<223> OTHER INFORMATION: a, c, t, g, unknown or other
<220> FEATURE:
<221> NAME/KEY: modified_base
<222> LOCATION: (861)..(861)
<223> OTHER INFORMATION: a, c, t, g, unknown or other
<220> FEATURE:
<221> NAME/KEY: modified_base
```

-continued

```
<222> LOCATION: (867)..(867)
<223> OTHER INFORMATION: a, c, t, g, unknown or other
<220> FEATURE:
<221> NAME/KEY: modified_base
<222> LOCATION: (871)..(873)
<223> OTHER INFORMATION: a, c, t, g, unknown or other
<220> FEATURE:
<221> NAME/KEY: modified_base
<222> LOCATION: (879)..(882)
<223> OTHER INFORMATION: a, c, t, g, unknown or other
<220> FEATURE:
<221> NAME/KEY: modified_base
<222> LOCATION: (891)..(891)
<223> OTHER INFORMATION: a, c, t, g, unknown or other
<220> FEATURE:
<221> NAME/KEY: modified_base
<222> LOCATION: (895)..(897)
<223> OTHER INFORMATION: a, c, t, g, unknown or other
<220> FEATURE:
<221> NAME/KEY: modified_base
<222> LOCATION: (903)..(903)
<223> OTHER INFORMATION: a, c, t, g, unknown or other
<220> FEATURE:
<221> NAME/KEY: modified_base
<222> LOCATION: (906)..(906)
<223> OTHER INFORMATION: a, c, t, g, unknown or other
<220> FEATURE:
<221> NAME/KEY: modified_base
<222> LOCATION: (909)..(909)
<223> OTHER INFORMATION: a, c, t, g, unknown or other
<220> FEATURE:
<221> NAME/KEY: modified_base
<222> LOCATION: (916)..(921)
<223> OTHER INFORMATION: a, c, t, g, unknown or other
<220> FEATURE:
<221> NAME/KEY: modified_base
<222> LOCATION: (933)..(933)
<223> OTHER INFORMATION: a, c, t, g, unknown or other
<220> FEATURE:
<221> NAME/KEY: modified_base
<222> LOCATION: (939)..(939)
<223> OTHER INFORMATION: a, c, t, g, unknown or other
<220> FEATURE:
<221> NAME/KEY: modified_base
<222> LOCATION: (943)..(945)
<223> OTHER INFORMATION: a, c, t, g, unknown or other
<220> FEATURE:
<221> NAME/KEY: modified_base
<222> LOCATION: (949)..(951)
<223> OTHER INFORMATION: a, c, t, g, unknown or other
<220> FEATURE:
<221> NAME/KEY: modified_base
<222> LOCATION: (954)..(954)
<223> OTHER INFORMATION: a, c, t, g, unknown or other
<220> FEATURE:
<221> NAME/KEY: modified_base
<222> LOCATION: (966)..(966)
<223> OTHER INFORMATION: a, c, t, g, unknown or other
<220> FEATURE:
<221> NAME/KEY: modified_base
<222> LOCATION: (969)..(969)
<223> OTHER INFORMATION: a, c, t, g, unknown or other
<220> FEATURE:
<221> NAME/KEY: modified_base
<222> LOCATION: (984)..(984)
<223> OTHER INFORMATION: a, c, t, g, unknown or other
<220> FEATURE:
<221> NAME/KEY: modified_base
<222> LOCATION: (991)..(993)
<223> OTHER INFORMATION: a, c, t, g, unknown or other
<220> FEATURE:
<221> NAME/KEY: modified_base
<222> LOCATION: (996)..(999)
<223> OTHER INFORMATION: a, c, t, g, unknown or other
<220> FEATURE:
<221> NAME/KEY: modified_base
<222> LOCATION: (1002)..(1005)
<223> OTHER INFORMATION: a, c, t, g, unknown or other
<220> FEATURE:
```

```
<221> NAME/KEY: modified_base
<222> LOCATION: (1008)..(1008)
<223> OTHER INFORMATION: a, c, t, g, unknown or other
<220> FEATURE:
<221> NAME/KEY: modified_base
<222> LOCATION: (1011)..(1011)
<223> OTHER INFORMATION: a, c, t, g, unknown or other

<400> SEQUENCE: 96 gar acn nnn gcn tgy ath tay tay aay gcn aay tgg gar ytn gar nnn      48
Glu Thr Arg Ala Cys Ile Tyr Tyr Asn Ala Asn Trp Glu Leu Glu Arg
1               5                   10                  15 acn aay car nnn ggn ytn gar nnn tgy gar ggn gar car gay aar nnn      96
Thr Asn Gln Ser Gly Leu Glu Arg Cys Glu Gly Glu Gln Asp Lys Arg
            20                  25                  30 ytn cay tgy tay gcn nnn tgg nnn aay nnn nnn ggn acn ath gar ytn     144
Leu His Cys Tyr Ala Ser Trp Arg Asn Ser Ser Gly Thr Ile Glu Leu
        35                  40                  45 gtn aar aar ggn tgy tgg ytn gay gay tty aay tgy tay gay nnn car     192
Val Lys Lys Gly Cys Trp Leu Asp Asp Phe Asn Cys Tyr Asp Arg Gln
50                  55                  60 gar tgy gtn gcn acn gar gar aay ccn car gtn tay tty tgy tgy tgy     240
Glu Cys Val Ala Thr Glu Glu Asn Pro Gln Val Tyr Phe Cys Cys Cys
65                  70                  75                  80 gar ggn aay tty tgy aay gar nnn tty acn cay ytn ccn gar gcn ggn     288
Glu Gly Asn Phe Cys Asn Glu Arg Phe Thr His Leu Pro Glu Ala Gly
                85                  90                  95 ggn ccn gar gtn acn tay gar ccn ccn ccn acn gcn ccn acn ggn ggn     336
Gly Pro Glu Val Thr Tyr Glu Pro Pro Pro Thr Ala Pro Thr Gly Gly
            100                 105                 110 ggn ggn nnn gtn gar tgy ccn ccn tgy ccn gcn ccn gtn gcn ggn         384
Gly Gly Ser Val Glu Cys Pro Pro Cys Pro Ala Pro Val Ala Gly
        115                 120                 125 ccn nnn gtn tty ytn tty ccn ccn aar ccn aar gay acn ytn atg ath     432
Pro Ser Val Phe Leu Phe Pro Pro Lys Pro Lys Asp Thr Leu Met Ile
130                 135                 140 nnn nnn acn ccn gar gtn acn tgy gtn gtn gtn gay gtn nnn cay gar     480
Ser Arg Thr Pro Glu Val Thr Cys Val Val Val Asp Val Ser His Glu
145                 150                 155                 160 gay ccn gar gtn car tty aay tgg tay gtn gay ggn gtn gar gtn cay     528
Asp Pro Glu Val Gln Phe Asn Trp Tyr Val Asp Gly Val Glu Val His
                165                 170                 175 aay gcn aar acn aar ccn nnn gar gar car tty aay nnn acn tty nnn     576
Asn Ala Lys Thr Lys Pro Arg Glu Glu Gln Phe Asn Ser Thr Phe Arg
            180                 185                 190 gtn gtn nnn gtn ytn acn gtn gtn cay car gay tgg ytn aay ggn aar     624
Val Val Ser Val Leu Thr Val Val His Gln Asp Trp Leu Asn Gly Lys
        195                 200                 205 gar tay aar tgy aar gtn nnn aay aar ggn ytn ccn gcn ccn ath gar     672
Glu Tyr Lys Cys Lys Val Ser Asn Lys Gly Leu Pro Ala Pro Ile Glu
210                 215                 220 aar acn ath nnn aar acn aar ggn car ccn nnn gar ccn car gtn tay     720
Lys Thr Ile Ser Lys Thr Lys Gly Gln Pro Arg Glu Pro Gln Val Tyr
225                 230                 235                 240 acn ytn ccn ccn nnn nnn gar gar atg acn aar aay car gtn nnn ytn     768
Thr Leu Pro Pro Ser Arg Glu Glu Met Thr Lys Asn Gln Val Ser Leu
                245                 250                 255 acn tgy ytn gtn aar ggn tty tay ccn nnn gay ath gcn gtn gar tgg     816
Thr Cys Leu Val Lys Gly Phe Tyr Pro Ser Asp Ile Ala Val Glu Trp
            260                 265                 270 gar nnn aay ggn car ccn gar aay aay tay aar acn acn ccn ccn atg     864
Glu Ser Asn Gly Gln Pro Glu Asn Asn Tyr Lys Thr Thr Pro Pro Met
```

```
Glu Ser Asn Gly Gln Pro Glu Asn Asn Tyr Lys Thr Thr Pro Pro Met
            275                 280                 285 ytn gay nnn gay ggn nnn tty tty ytn tay nnn aar ytn acn gtn gay    912
Leu Asp Ser Asp Gly Ser Phe Phe Leu Tyr Ser Lys Leu Thr Val Asp
            290                 295                 300 aar nnn nnn tgg car car ggn aay gtn tty nnn tgy nnn gtn atg cay    960
Lys Ser Arg Trp Gln Gln Gly Asn Val Phe Ser Cys Ser Val Met His
305                 310                 315                 320 gar gcn ytn cay aay cay tay acn car aar nnn ytn nnn ytn nnn ccn   1008
Glu Ala Leu His Asn His Tyr Thr Gln Lys Ser Leu Ser Leu Ser Pro
                325                 330                 335 ggn aar                                                            1014
Gly Lys

<210> SEQ ID NO 97
<211> LENGTH: 338
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Ala, Phe, Gln, Val, Ile, Leu, Met, Lys, His,
      Trp or Tyr

<400> SEQUENCE: 97

Glu Thr Arg Xaa Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr Gly Gly
            100                 105                 110

Gly Gly Ser Val Glu Cys Pro Pro Cys Pro Ala Pro Pro Val Ala Gly
        115                 120                 125

Pro Ser Val Phe Leu Phe Pro Pro Lys Pro Lys Asp Thr Leu Met Ile
    130                 135                 140

Ser Arg Thr Pro Glu Val Thr Cys Val Val Val Asp Val Ser His Glu
145                 150                 155                 160

Asp Pro Glu Val Gln Phe Asn Trp Tyr Val Asp Gly Val Glu Val His
                165                 170                 175

Asn Ala Lys Thr Lys Pro Arg Glu Glu Gln Phe Asn Ser Thr Phe Arg
            180                 185                 190

Val Val Ser Val Leu Thr Val Val His Gln Asp Trp Leu Asn Gly Lys
        195                 200                 205

Glu Tyr Lys Cys Lys Val Ser Asn Lys Gly Leu Pro Ala Pro Ile Glu
    210                 215                 220

Lys Thr Ile Ser Lys Thr Lys Gly Gln Pro Arg Glu Pro Gln Val Tyr
225                 230                 235                 240

Thr Leu Pro Pro Ser Arg Glu Glu Met Thr Lys Asn Gln Val Ser Leu
                245                 250                 255
```

-continued

Thr Cys Leu Val Lys Gly Phe Tyr Pro Ser Asp Ile Ala Val Glu Trp
            260                 265                 270

Glu Ser Asn Gly Gln Pro Glu Asn Asn Tyr Lys Thr Thr Pro Pro Met
        275                 280                 285

Leu Asp Ser Asp Gly Ser Phe Phe Leu Tyr Ser Lys Leu Thr Val Asp
    290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335

Gly Lys

<210> SEQ ID NO 98
<211> LENGTH: 367
<212> TYPE: PRT
<213> ORGANISM: Homo sapiens
<220> FEATURE:
<221> NAME/KEY: MOD_RES
<222> LOCATION: (64)..(64)
<223> OTHER INFORMATION: Ala or Arg

<400> SEQUENCE: 98

Met Thr Ala Pro Trp Val Ala Leu Ala Leu Leu Trp Gly Ser Leu Trp
1               5                   10                  15

Pro Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Xaa
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Gly Gly Gly Ser Val Asp Lys Thr His
    130                 135                 140

Thr Cys Pro Pro Cys Pro Ala Pro Glu Leu Leu Gly Gly Pro Ser Val
145                 150                 155                 160

Phe Leu Phe Pro Pro Lys Pro Lys Asp Thr Leu Met Ile Ser Arg Thr
                165                 170                 175

Pro Glu Val Thr Cys Val Val Val Asp Val Ser His Glu Asp Pro Glu
            180                 185                 190

Val Lys Phe Asn Trp Tyr Val Asp Gly Val Glu Val His Asn Ala Lys
        195                 200                 205

Thr Lys Pro Arg Glu Glu Gln Tyr Asn Ser Thr Tyr Arg Val Val Ser
    210                 215                 220

Val Leu Thr Val Leu His Gln Asp Trp Leu Asn Gly Lys Glu Tyr Lys
225                 230                 235                 240

Cys Lys Val Ser Asn Lys Ala Leu Pro Ala Pro Ile Glu Lys Thr Ile
                245                 250                 255

Ser Lys Ala Lys Gly Gln Pro Arg Glu Pro Gln Val Tyr Thr Leu Pro
            260                 265                 270

```
Pro Ser Arg Asp Glu Leu Thr Lys Asn Gln Val Ser Leu Thr Cys Leu
        275                 280                 285

Val Lys Gly Phe Tyr Pro Ser Asp Ile Ala Val Glu Trp Glu Ser Asn
        290                 295                 300

Gly Gln Pro Glu Asn Asn Tyr Lys Thr Thr Pro Pro Val Leu Asp Ser
305                 310                 315                 320

Asp Gly Ser Phe Phe Leu Tyr Ser Lys Leu Thr Val Asp Lys Ser Arg
                325                 330                 335

Trp Gln Gln Gly Asn Val Phe Ser Cys Ser Val Met His Glu Ala Leu
                340                 345                 350

His Asn His Tyr Thr Gln Lys Ser Leu Ser Leu Ser Pro Gly Lys
                355                 360                 365

<210> SEQ ID NO 99
<211> LENGTH: 392
<212> TYPE: PRT
<213> ORGANISM: Homo sapiens
<220> FEATURE:
<221> NAME/KEY: MOD_RES
<222> LOCATION: (64)..(64)
<223> OTHER INFORMATION: Ala or Arg

<400> SEQUENCE: 99

Met Thr Ala Pro Trp Val Ala Leu Ala Leu Leu Trp Gly Ser Leu Trp
1               5                   10                  15

Pro Gly Ser Gly Arg Gly Glu Ala Glu Thr Arg Glu Cys Ile Tyr Tyr
                20                  25                  30

Asn Ala Asn Trp Glu Leu Glu Arg Thr Asn Gly Ser Gly Leu Glu Arg
            35                  40                  45

Cys Glu Gly Glu Gln Asp Lys Arg Leu His Cys Tyr Ala Ser Trp Xaa
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Gly Pro Trp Ala Ser
        115                 120                 125

Thr Thr Ile Pro Ser Gly Gly Pro Glu Ala Thr Ala Ala Ala Gly Asp
130                 135                 140

Gln Gly Ser Gly Ala Leu Trp Leu Cys Leu Glu Gly Pro Ala His Glu
145                 150                 155                 160

Gly Gly Gly Gly Ser Val Asp Lys Thr His Thr Cys Pro Pro Cys Pro
                165                 170                 175

Ala Pro Glu Leu Leu Gly Gly Pro Ser Val Phe Leu Phe Pro Pro Lys
            180                 185                 190

Pro Lys Asp Thr Leu Met Ile Ser Arg Thr Pro Glu Val Thr Cys Val
        195                 200                 205

Val Val Asp Val Ser His Glu Asp Pro Glu Val Lys Phe Asn Trp Tyr
    210                 215                 220

Val Asp Gly Val Glu Val His Asn Ala Lys Thr Lys Pro Arg Glu Glu
225                 230                 235                 240

Gln Tyr Asn Ser Thr Tyr Arg Val Val Ser Val Leu Thr Val Leu His
                245                 250                 255
```

-continued

```
Gln Asp Trp Leu Asn Gly Lys Glu Tyr Lys Cys Lys Val Ser Asn Lys
            260                 265                 270

Ala Leu Pro Ala Pro Ile Glu Lys Thr Ile Ser Lys Ala Lys Gly Gln
        275                 280                 285

Pro Arg Glu Pro Gln Val Tyr Thr Leu Pro Pro Ser Arg Asp Glu Leu
    290                 295                 300

Thr Lys Asn Gln Val Ser Leu Thr Cys Leu Val Lys Gly Phe Tyr Pro
305                 310                 315                 320

Ser Asp Ile Ala Val Glu Trp Glu Ser Asn Gly Gln Pro Glu Asn Asn
                325                 330                 335

Tyr Leu Thr Thr Pro Pro Val Leu Asp Ser Asp Gly Ser Phe Phe Leu
            340                 345                 350

Tyr Ser Lys Leu Thr Val Asp Lys Ser Trp Gln Gln Gly Asn Val Phe
        355                 360                 365

Ser Cys Ser Val Met His Glu Ala Leu His Asn His Tyr Thr Gln Lys
    370                 375                 380

Ser Leu Ser Leu Ser Pro Gly Lys
385                 390
```